US010883114B2

(12) United States Patent
Bovet

(10) Patent No.: US 10,883,114 B2
(45) Date of Patent: Jan. 5, 2021

(54) PLANTS WITH REDUCED ASPARAGINE CONTENT

(71) Applicant: PHILIP MORRIS PRODUCTS S.A., Neuchatel (CH)

(72) Inventor: Lucien Bovet, La Chaux-de-Fonds (CH)

(73) Assignee: Philip Morris Products S.A., Neuchatel (CH)

(*) Notice: Subject to any disclaimer, the term of this patent is extended or adjusted under 35 U.S.C. 154(b) by 49 days.

(21) Appl. No.: 15/758,200

(22) PCT Filed: Sep. 6, 2016

(86) PCT No.: PCT/EP2016/070972
§ 371 (c)(1),
(2) Date: Mar. 7, 2018

(87) PCT Pub. No.: WO2017/042162
PCT Pub. Date: Mar. 16, 2017

(65) Prior Publication Data

US 2019/0169628 A1 Jun. 6, 2019

(30) Foreign Application Priority Data

Sep. 9, 2015 (EP) .................................... 15184528

(51) Int. Cl.
*C12N 15/82* (2006.01)
*A01H 5/12* (2018.01)
(Continued)

(52) U.S. Cl.
CPC ........... *C12N 15/8251* (2013.01); *A01H 5/12* (2013.01); *A24B 3/12* (2013.01); *A24B 15/20* (2013.01);
(Continued)

(58) Field of Classification Search
CPC ........ A01H 5/12; A24B 3/12; C12N 15/8251; C12N 15/8216; C12N 15/8243;
(Continued)

(56) References Cited

U.S. PATENT DOCUMENTS 9,756,871 B2 9/2017 Duan
2007/0074304 A1 3/2007 Rommens
2013/0068240 A1* 3/2013 Elliott .................... A24B 15/20
131/352

FOREIGN PATENT DOCUMENTS

AU 2013200664 4/2015
CN 101313070 11/2008
(Continued)

OTHER PUBLICATIONS

Reddy, Thamalampudi Venkata, Samresh Dwivedi, and Navin Kumar Sharma. "Development of TILLING by sequencing platform towards enhanced leaf yield in tobacco." Industrial Crops and Products 40 (2012): 324-335. (Year: 2012).*
(Continued)

*Primary Examiner* — Weihua Fan
(74) *Attorney, Agent, or Firm* — Mueting Raasch Group

(57) ABSTRACT

There is described herein a mutant, non-naturally occurring or transgenic plant or part thereof having reduced expression or activity of asparagine synthetase, said asparagine synthetase comprising, consisting or consisting essentially of: (i) a polynucleotide sequence comprising, consisting or consisting essentially of a sequence having at least 90% sequence identity to SEQ ID NO:1 or at least 72% sequence identity to SEQ ID NO:3 or SEQ ID NO:5 or SEQ ID NO:7; or (ii) a polypeptide encoded by the polynucleotide set forth in (i); or (iii) a polypeptide having at least 78% sequence identity to SEQ ID NO:2 or SEQ ID NO:4 or SEQ ID NO:6 or SEQ ID NO:8; wherein the expression or activity of the
(Continued)

asparagine synthetase set forth in (i), (ii) or (iii) is reduced as compared to a control plant.

37 Claims, 22 Drawing Sheets

Specification includes a Sequence Listing.

(51) Int. Cl.
*A24B 3/12* (2006.01)
*A24B 15/20* (2006.01)
*C12N 9/00* (2006.01)

(52) U.S. Cl.
CPC .......... *C12N 9/93* (2013.01); *C12N 15/8218* (2013.01); *C12N 15/8243* (2013.01)

(58) Field of Classification Search
CPC .......... C12N 15/8241; C12N 15/8213; C12N 15/00; C12N 15/113; C12N 2310/141
See application file for complete search history.

(56) References Cited

FOREIGN PATENT DOCUMENTS

| | | | | |
|---|---|---|---|---|
| CN | 102121018 | | 7/2011 | |
| CN | 104168759 | | 11/2014 | |
| CN | 104884626 | | 9/2015 | |
| JP | 2008-161159 | | 7/2008 | |
| JP | 2009-508526 | | 3/2009 | |
| KR | 2012 0039175 | | 4/2012 | |
| RU | 2324737 | | 5/2008 | |
| WO | WO 2007/035752 | | 3/2007 | |
| WO | WO-2007035752 | A2 * | 3/2007 | ............ A23L 19/18 |
| WO | WO -2007035752 | A2 * | 3/2007 | ......... C12N 15/8245 |
| WO | WO 2010/076756 | | 7/2010 | |
| WO | WO 2013/043853 | | 3/2013 | |
| WO | WO 2014/018729 | | 1/2014 | |
| WO | WO 2014/144094 | | 9/2014 | |

OTHER PUBLICATIONS

Sierro, Nicolas, et al. "The tobacco genome sequence and its comparison with those of tomato and potato." Nature communications 5 (2014): 3833 (Year: 2014).*

Hovenkamp-Hermelink, J. H. M., et al. "Isolation of an amylose-free starch mutant of the potato (*Solanum tuberosunn* L.)." Theoretical and Applied Genetics 75.1 (1987): 217-221. (Year: 1987).*

Rommens, Caius M., et al. "Low-acrylamide French fries and potato chips." Plant Biotechnology Journal 6.8 (2008): 843-853. (Year: 2008).*

Office Action issued in Korea for Application No. 10-2018-7007060 dated May 5, 2019 (9 pages). English translation included.

Beato et al., "A Tobacco Asparagine Synthetase Gene Responds to Carbon and Nitrogen Status and its Root Expression is Affected Under Boron Stress", *Plant Science,* vol. 178, No. 3, Mar. 1, 2010, pp. 289-298.

Canales et al., "Novel insights into regulation of asparagine synthetase in conifers", *Plant Science,* vol. 3, Article 100, May 2012.

Chakrabarti et al., "CYP82E4-Mediated Nicotine to Nornicotine Conversion in Tobacco is Regulated by a Senescence-Specific Signaling Pathway", *Plant Mol Biol.* (2008) Mar.;66(4):415-27.

Cheng et al., "In Vitro Cellular & Developmental Biology-Plant", *In Vitro Cell Dev. Biol.,* 39 595 604.

Cooperation Centre for Scientific Research Relative to Tobacco Recommended (CORESTA) Method No. 62, Determination of nicotine in tobacco and tobacco products by gas chromatographic analysis (Feb. 2005).

Gaufichon et al., "*Arabidopsis thaliana* ASN2 Encoding Asparagine Synthetase is Involved in the Control of Nitrogen Assimilation and Export During Vegetative Growth", *Plant Cell Environ.* Feb. ;36(2):328-42.

Halford et al., "The acrylamide problem: a plant and agronomic science issue", *J. Exp. Bot.* 63: 2841-2851.

Lam et al., "Overexpression of the ASN1 Gene Enhances Nitrogen Status in Seeds of *Arabidopsis", Plant Physiol.* Jun. 2003;132(2):926-35).

Lewis et al., "Three nicotine demethylase genes mediate nornicotine biosynthesis in *Nicotiana tabacum* L.: functional characterization of the CYP82E10 gene", *Phytochemistry* 71: 17-18.

Lineback et al., "Acrylamide in Foods: A Review of the Science and Future Considerations", *Annu Rev Food Sci Technol.* 3:15-35.

Martin et al. "Design of a Tobacco Exon Array with Application to Investigate the Differential Cadmium Accumulation Property in Two Tobacco Varieties", *BMC Genomics* 2012, 13:674.

Masclaux-Daubresse et al, "Glutamine synthetase-glutamate synthase pathway and glutamate dehydrogenase play distinct roles in the sink-source nitrogen cycle in tobacco", *Plant Physiol.* 140:444-56, 2006.

Masclaux-Daubresse et al., "Nitrogen Uptake, Assimilation and Remobilation in Plants: Challenges for Sustainable and Production Agriculture", *Ann Bot.* Jun. 2010;105(7): 1141-57.

McCallum et al. "Targeted Screening for Induced Mutations", *Biotechnol* 18: 455-457.

Moldoveanu et al., "Human Male Genital Tract Secretions: Both Mucosal and Systemic Immune Compartments Contribute to the Humoral Immunity", *The Journal of Immunology,* 175:4127-4136, 2005.

Moldoveanu, Serban C., "Analysis of Protein Amino Acids in Tobacco Using Microwave Digestion of Plant Material", *Contributions to Tobacco Research,* 21: 451-465.

Naufal et al, "Differential exposure biomarker levels among cigarette smokers and smokeless tobacco consumers in the National Health and Nutrition Examination Survey 1999-2008" *Biomarkers* 16:222-235.

Ono et al., "Analysis of acrylamide by LC-MS/MS and GC-MS in processed Japanese foods" *Food Additives & Contaminants,* 20: 215-220, 2003.

Onoa et al, "Identifying Kinetic Barriers to Mechanical Unfolding of the T. Thermophila Ribozyme", *Science,* vol. 299, Mar. 21, 2003.

Ori et al., "Leaf Senescence is Delayed in Tobacco Plants Expresing the Maize Homeobox Gene Knotted1 Under the Control of a Senescence-Activated Promoter", *Plant Cell.* (1999) Jun.;11(6):1073-80.

Papousek et al., "Determination of Acrylamide and Acrolein in Smoke from Tobacco and E-Cigarettes", *Chromatographia* 77: 1145-1151, 2014.

Romagni et al, "Measuring Asparagine Synthetase Activity in Crude Plant Extracts", *J Agric Food Chem.* May;48(5):1692-6, 2000.X.

Sierro et al, The tobacco genome sequence and its comparison with those of tomato and potato. Nat Commun. 5:3833, 2014.

Smith et al., "Total Silencing by Intronspliced Hairpin RNAs", *Nature,* 407, 319-320, 2000.

Stemple, Derek L., "TILLING—A High-Throughput Harvest for Functional Genomics", *Nat Rev Genet* 5(2): 145-50, 2004.

Thompson et al, "CLUSTAL W: Improving the Sensitivity of Progressive Multiple Sequence Alignment Through Sequence Weighting, Position-Specific Gap Penalties and Weight Matrix Choice", *Nucleic Acids Research* (1994) 22, 4673-4680.

Thompson et al, "The CLUSTAL_X Windows Interface: Flexible Strategies for Multiple Sequence Alignment Aided by Quality Analysis Tools", *Nucleic Acids Research* (1997), 24, 4876-4882.

United States Environmental Protection Agency Method 8032A—Acrylamide by Gas Chromatography, Revision 1, Dec. 1996.

Wen et al., "A Novel Approach Obtaining Intron-Containing Hairpin RNA Constructs", *Bioscience, Biotechnology, and Biochemistry* (2008) 72, 2, 615-617.

Wernsman, et al.,"Tobacco" In: *Cultivar Development. Crop Species.* W. H. Fehr (ed.), MacMillan Publishing Co, Inc., New York, N. Y 761 pp.

Wesley et al, "Construct Design for Efficient, Effective and High-Throughput Gene Silencing in Plants", *Plant J.,* 27, 581-590, 2001.

European Search Report for Application No. 15184528.6 dated Feb. 23, 2016 (7 pages).

(56) References Cited

OTHER PUBLICATIONS

PCT Search Report and Written Opinion for PCT/EP2016/070972 dated Nov. 4, 2016 (16 pages).
Database Uniport [Online], May 27, 2015, SubName: Full-Uncharacterized Protein [ECO:0000313 EnsemblPlants:Solyc06g007180.2.1} XP002763747, retrieved from EBI accession No. UNIPROT:K4C3A1 Database Accession No. K43A1.
Office Action issued in China for Application No. 201680050837.4 dated Apr. 30, 2020 (16 pages). English translation included.
“Predicted” Asparagine Synthetase, XP 009792170.
“Predicted: Asparagine Synthetase”, XP006344055.1.
Pakula A. et al. (1989). Genetic analysis of protein stability and function. Anna. Rev. Genet, vol. 23, pp. 289-310.
Keskin et al., A new, structurally nonredundant, diverse data set of protein—protein interfaces and its implications, Protein Sci., 2004, vol. 13, N. 4, 1043-1055 (cm.1043-1044).
Peihong, Wang et al. (1995). Plant Biochemistry. China Agricultural Press (6 pages).
Jinting, Wang et al. (2014). An Introduction to Life Science. Huazhong University of Science and Technology Press (11 pages).
Office Action issued in Japan for Application No. 2018-512365 dated Jan. 21, 2019 (12 pages). English translation included.
Office Action issued in Europe for Application No. 16760735.7 dated Feb. 28, 2019 (9 pages).
Office Action issued in Russia for Application No. 2018112407 dated Feb. 25, 2020 (8 pages). English translation included.
Office Acton issued in China for Application No. 201680050837.4 dated Apr. 30, 2020 (16 pages). English translation included.
Database Uniport [Online], May 27, 2015, SubName: Full-Uncharacterized Protein [ECO:0000313 EnsemblPlants:Solyc06g007180.2.1} XP002763747, retrieved from EBI accession No. UNIPROT:K4C3A1 Database Accession No. K4C3A1.

* cited by examiner

FIGURE 3

Aspartate + Glutamine + ATP → Asparagine + Glutamate + AMP + PPi

SEQUENCE LISTING

<160> NUMBER OF SEQ ID NOS: 24

<210> SEQ ID NO 1
<211> LENGTH: 3646
<212> TYPE: DNA
<213> ORGANISM: Nicotiana tabacum

<400> SEQUENCE: 1
atgtgcggga tcttggctgt tttgggttgt tctgatgatt ctcaggccaa aagggttcgt 60
gttctcgagc tctctcgcag gtaaattata tttcccttct tttctgtatt gttaatgtta 120
ttgtgttgcg ttattatatt gattcttttt atgagaaagt agtttcctga acgtttgcat 180
tttagaataa aagaagacta aagcttaaga tagattatat atttagatat tcttgacgtg 240
gacctatatc ttagattcac aatataattt tctcggacca actgttttag catgacttgt 300

-continued

```
aaatgatgtt gatatgaaaa gctgtgattt aattagtagg agtaattcat ttccatgtta    360
caattactta tctttctcct ccttgtgttc ttgccactgc tagaggcaga tctataattc    420
ctacttagag tattgaacac attgtacttt tgaaattgta agtgtgcagt ttaatatttg    480
ttaaaatttt gaaggttttt ttaattacat gtatatcgtg acgttatata gcctctctac    540
ccgcataagg taggggtaat gtctgcgtac aaataggctg atttcactct gtgttcagtt    600
gaatcaatat atgcggcatc caccactgtt tgcaaatgca tgggaatgga aaagtcatgc    660
ctcatcactg tcacacatga tttttattta tttatttatt atatatgatt ctttaaatct    720
attagtgggt actgaatctt gctaactgat cgattgatga aacaggttga agcatcgtgg    780
accagattgg agtgggctgt atcaacatgg ggactgttac ttggcacatc agcgtctagc    840
tattgttgat cctgcttccg gtgatcaacc tctgtttaac gaagataaga cgattgttgt    900
tacggtgggt gcttttaatt tcatgtttac tctcatttct tgctcagttt actgatgaaa    960
acgaaactaa tgctgataac tatcaaccaa tcaaccacat acaagtaggg gtcgactata   1020
tgattcatta tatcctttcc tctattcaaa tagttgatga ttaatttcat gccaaaaatt   1080
tcaggtaaat ggagagatct acaatcacga gcaacttcgt aagcaaatgc ctaatcataa   1140
gttccggact ggcagtgact gtgatgtcat tgcacaccta gtgagtactc atcttccaac   1200
ttaggaaaca tgtatgtata tgtaaaatta ttccctgatt atattatgta cattaatcag   1260
tatgaagaac atggagaaga ttttgtggac atgctggatg ggatcttcgc ttttgtgtta   1320
ttggatactc gagataacag ctttcttgtt gctcgtgatg ccattggaat tacttccctt   1380
tatattggtt ggggacttga tggtaagatt ccatatgatt ttctcactta gattttgtta   1440
ttgcaaatga atatgttgaa tccttatatg tactaattgt tgtaattctg ttccttctca   1500
gggtctgtat ggatatcatc tgagcttaag ggcttgaatg atgactgcga acattttgaa   1560
gttttcccac cagggcactt gtactctagc aagaatggcg gctttaggag gtggtacaat   1620
cctccttggt tctctgaggc cattccttcc actcgttatg atcccttagt tctcaggcgt   1680
gcctttgaaa atgtgagtta atattgttgt tgttgaaatg gatccaacat gttggtttta   1740
aggctatata tcattttgca ggctgttatc aaaaggttga tgactgatgt ccccttttggt   1800
gttctcctct ccgggggact cgattcatcc ttggttgctt cgattactgc tcgctacttg   1860
gctggtacaa aggctgccaa gcagtgggga gcacagcttc attccttctg tgttggcctt   1920
gaggtcagat aatcttgaga cttgtgtgat tacaacatta ataacgacaa cacctcattc   1980
acaagctagt aaggtcagct atatgaaatc tgataccgat ttgcttgctt tcaccgaaca   2040
gggctcaccg gatctcaagg ctgcaagaga agttgctgac tacttgggaa ccgttcacca   2100
cgagtttcac ttcaccgttc aggttttgat ggagcaactc tattttcact tgatctatca   2160
tcctcttcgt ttctcctttg tttacctgat ggcaaatgac atgtgttgta tttgcaggat   2220
ggaattgatg caattgaaga tgttatttac catattgaga catacgatgt aacgacaatc   2280
agagcaagca ctcctatgtt ccttatgtcg cgtaagatta agtcactagg agtgaagatg   2340
gtcatatctg gggaaggatc tgatgaagtg tttggtggct acttgtactt tcacaaggct   2400
cccaacaagg aagagttcca caaggaaaca tgtcgcaagg tataagaaag tgcttccagt   2460
tcctagttta aataggacaa ggagttgaga aaatgttgat tttttcccta tgcagattaa   2520
agcgcttcac caatatgact gcttaagagc aaataagtca acatctgcat ggggtttaga   2580
agctagagtc cctttcctag ataaggagtt catcaatgtt gccatgagta ttgatccaga   2640
```

-continued

```
gtggaagttg gtaagtagtt gacccccaat tgttgatcga ataaacaatc aactgtccct   2700

aaaactatgt atttattcat ttcagattaa accagagcaa aggaggattg aaaagtgggc   2760

tctaaggagg gcctttgatg atgaggagca tccttatctc ccaaaggtgt actaaatcgc   2820

cattttcaaa ctgatttgca aatgattttg aatgttatat tattaatcaa actaacaatt   2880

tactcattac attccttgca gcacatcctg tataggcaaa aagaacaatt cagtgatggc   2940

gtgggctata gttggataga tggactcaaa gcacatgctg aacaacatgt gcgtttcaat   3000

gactaatcaa cgactttcta ctgctcttat ttatcttcca atgcttgttt gttttaaagc   3060

tgaccgagga aacaaatttt ttcctttaat aggtgaccaa taggatgatg tttaatgctt   3120

cacatatatt ccctcataac acacccatta caaaggaagc atactactat aggatgattt   3180

tcgagcgctt tttcccacag gtaatttgtt cagataatag tgagaattta tgataaatgg   3240

actaatttac gtttgttgtc gattttgcaa ccttccaaca gtgtgagcaa gctcacataa   3300

tcggaatttt ttgttcaaat aataatgcat tggaaatcat aatgctaaat tgagatttac   3360

ttttaaccat gttcctctac catttttggt tctgcagaat tcagctgggc taaccgttcc   3420

tggaggagca agtgtggcgt gtagcacagc taaagctgta gagtgggatg cttcttggtc   3480

aaagaacctt gatccttcag gcagggctgc tattggtgta cataactcgg cttatgagaa   3540

tcatgtacct gctatggcta atgggaattt gaccaaaaaa atcattggtc gtgtgccttc   3600

tatggtagaa gttggtgctg ctcccgagct cacaataaag agttag                 3646
```

```
<210> SEQ ID NO 2
<211> LENGTH: 590
<212> TYPE: PRT
<213> ORGANISM: Nicotiana tabacum

<400> SEQUENCE: 2

Met Cys Gly Ile Leu Ala Val Leu Gly Cys Ser Asp Asp Ser Gln Ala
1               5                   10                  15

Lys Arg Val Arg Val Leu Glu Leu Ser Arg Arg Leu Lys His Arg Gly
            20                  25                  30

Pro Asp Trp Ser Gly Leu Tyr Gln His Gly Asp Cys Tyr Leu Ala His
        35                  40                  45

Gln Arg Leu Ala Ile Val Asp Pro Ala Ser Gly Asp Gln Pro Leu Phe
    50                  55                  60

Asn Glu Asp Lys Thr Ile Val Val Thr Val Asn Gly Glu Ile Tyr Asn
65                  70                  75                  80

His Glu Gln Leu Arg Lys Gln Met Pro Asn His Lys Phe Arg Thr Gly
                85                  90                  95

Ser Asp Cys Asp Val Ile Ala His Leu Tyr Glu Glu His Gly Glu Asp
            100                 105                 110

Phe Val Asp Met Leu Asp Gly Ile Phe Ala Phe Val Leu Leu Asp Thr
        115                 120                 125

Arg Asp Asn Ser Phe Leu Val Ala Arg Asp Ala Ile Gly Ile Thr Ser
    130                 135                 140

Leu Tyr Ile Gly Trp Gly Leu Asp Gly Ser Val Trp Ile Ser Ser Glu
145                 150                 155                 160

Leu Lys Gly Leu Asn Asp Asp Cys Glu His Phe Glu Val Phe Pro Pro
                165                 170                 175

Gly His Leu Tyr Ser Ser Lys Asn Gly Gly Phe Arg Arg Trp Tyr Asn
            180                 185                 190

Pro Pro Trp Phe Ser Glu Ala Ile Pro Ser Thr Arg Tyr Asp Pro Leu
```

```
        195                 200                 205

Val Leu Arg Arg Ala Phe Glu Asn Ala Val Ile Lys Arg Leu Met Thr
    210                 215                 220

Asp Val Pro Phe Gly Val Leu Leu Ser Gly Gly Leu Asp Ser Ser Leu
225                 230                 235                 240

Val Ala Ser Ile Thr Ala Arg Tyr Leu Ala Gly Thr Lys Ala Ala Lys
                245                 250                 255

Gln Trp Gly Ala Gln Leu His Ser Phe Cys Val Gly Leu Glu Gly Ser
            260                 265                 270

Pro Asp Leu Lys Ala Ala Arg Glu Val Ala Asp Tyr Leu Gly Thr Val
        275                 280                 285

His His Glu Phe His Phe Thr Val Gln Asp Gly Ile Asp Ala Ile Glu
    290                 295                 300

Asp Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Glu Gly Ser Asp Glu Val Phe Gly Gly Tyr
            340                 345                 350

Leu Tyr Phe His Lys Ala Pro Asn Lys Glu Glu Phe His Lys Glu Thr
        355                 360                 365

Cys Arg Lys Ile Lys Ala Leu His Gln Tyr Asp Cys Leu Arg Ala Asn
    370                 375                 380

Lys Ser Thr Ser Ala Trp Gly Leu Glu Ala Arg Val Pro Phe Leu Asp
385                 390                 395                 400

Lys Glu Phe Ile Asn Val Ala Met Ser Ile Asp Pro Glu Trp Lys Leu
                405                 410                 415

Ile Lys Pro Glu Gln Arg Arg Ile Glu Lys Trp Ala Leu Arg Arg Ala
            420                 425                 430

Phe Asp Asp Glu Glu His Pro Tyr Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Ala His Ala Glu Gln His Val Thr Asn Arg Met Met Phe Asn
465                 470                 475                 480

Ala Ser His Ile Phe Pro His Asn Thr Pro Ile Thr Lys Glu Ala Tyr
                485                 490                 495

Tyr Tyr Arg Met Ile Phe Glu Arg Phe Phe Pro Gln Asn Ser Ala Gly
            500                 505                 510

Leu Thr Val Pro Gly Gly Ala Ser Val Ala Cys Ser Thr Ala Lys Ala
        515                 520                 525

Val Glu Trp Asp Ala Ser Trp Ser Lys Asn Leu Asp Pro Ser Gly Arg
    530                 535                 540

Ala Ala Ile Gly Val His Asn Ser Ala Tyr Glu Asn His Val Pro Ala
545                 550                 555                 560

Met Ala Asn Gly Asn Leu Thr Lys Lys Ile Ile Gly Arg Val Pro Ser
                565                 570                 575

Met Val Glu Val Gly Ala Ala Pro Glu Leu Thr Ile Lys Ser
            580                 585                 590


<210> SEQ ID NO 3
<211> LENGTH: 4564
<212> TYPE: DNA
<213> ORGANISM: Nicotiana tabacum
```

<220> FEATURE:
<221> NAME/KEY: misc_feature
<222> LOCATION: (3137)..(3137)
<223> OTHER INFORMATION: n is a, c, g, or t

<400> SEQUENCE: 3

```
atgtgcggga tcttggctgt tttgggttgt tctgatgatt ctcaggccaa aagggttcgt     60
gttctcgagc tctctcgcag gtaaattata ttcccttctt ttctctattg ttaatgttat    120
tgtgttgcat gcgttattaa ttctttttat gagaaagtag tttcctgagc gtttggagct    180
gctactgatt gcttgcattt tagaataaaa cttaagatgg attatatatt tagatattct    240
tgacgtggac ctatatctta gattcacaat tttctcggac caactgtttt agcatgactt    300
gtatatgatg ttgatatgaa aagctgtggt ttagtaattc atttccatgt tacaattact    360
aatctttctc ctatctgtgt tcttgccact gctagaggca gatctataat tcgtaattag    420
agtattgaac acattgtact tttcaaaatt ataagtgcgc aatttaatat ttgttaaaat    480
tttgaaggct tttttaatta catgtatatc gtgtctcgta tagcctctct acccatgtaa    540
ggtctgcgta cacattaccc gccccatgcc ctcccgtgaa attttactgg ggtttgctgt    600
tgttgttggt atcgtgtgtc gcatatactt tgttctgttg aatcaatata tgcgtcatct    660
gccactgttt gcaaatgcat ggaatggaaa agtcatgcct catcactgtc acacaggatt    720
tttatttatt tatttattta ttatatatga ttctttttct tgatgtgaaa tctattagtg    780
ggtactgaat ctggctaact gactaatgaa acaggttgaa gcatcgtgga ccagattgga    840
gtgggctgta tcaacatggg gactgttact tggcacatca gcgtctagct attgttgatc    900
ctgcttccgg tgatcaacct ctgtttaacg aagataagac gattgttgtt acggtgggtg    960
cttttaattt catgtttact ctcatttctt gctcagttta ctgatgaaca tgaaactaat   1020
gactatcaat cagccaatca accacgctta attccataca agtaggggtc gactatatga   1080
ttcattatat cctttcctct attccggttc ctttttattc aaatagttga tgattaattt   1140
catgccaaaa atttcaggta aatggagaga tctacaatca cgagcaactt cgcaagcaaa   1200
tgcctgatca taagttccgg actggaagtg actgtgatgt cattgcacac ctagtgagta   1260
atctagatta ctcatcttcc aacttaggaa acatgtatgt attcccctga ttatttcatc   1320
atctttatgt acattaatca gtatgaagaa catggagaag attttgtgga catgctggat   1380
gggatcttcg cttttgtgtt actggatact cgagataaca gctttcttgt tgctcgtgat   1440
gccattggaa ttacttccct ttatattggt tggggacttg atggtaagat tccatattat   1500
tttctcactt agattttgtt attgcaaatg aatatgttga atctttatat gtagtaactg   1560
ttgtaatttg gttccttctc agggtctgta tggatatcat ctgagcttaa gggcttgaat   1620
gatgactgcg aacattttga agttttccca ccaggacact tgtactctag caagaatggc   1680
ggctttagga ggtggtacaa tcctctttgg ttctctgagg ctattccttc cactccttat   1740
gatcccttag ttctcaggcg cgcctttgaa aatgtgagtt attattgttg ttgttgaaat   1800
ggatccaaca tgttggttct aaggctggat atcattgtgc aggctgttat caaaaggttg   1860
atgactgatg tccctttggg tgttctgctc tccgggggac tcgattcatc cttggttgct   1920
tcgattactg cccgctactt ggctggcaca aaggctgcca agcagtgggg agcacagctt   1980
cattccttct gtgttggcct tgaggtcaga taatcttgag atttctgtga ttacaacatt   2040
aataacgacc acacctcatt cacaagctag taaggtcagc tatatgaatc tgataccgat   2100
ttgcttgctt tcaaacgaac agggatcacc ggatctcaag gctgcaagag aagttgctga   2160
```

-continued

```
ctacttggga accgttcacc acgagtttca cttcaccgtt caggtattga tggagcaact   2220
ctattttgac ttgatctatc atcctctgcg ttccctttttg tttacctgat ggcaaatgac   2280
atgtgtcgta tttgcaggat ggaattgatg caattgaaga tgttatttac catattgaga   2340
catacgatgt aacgacaatc agagcaagca ctcctatgtt ccttatgtcg cgtaagatta   2400
agtcactagg agtgaagatg gttatatctg gggaaggctc tgatgaagtg tttggtggct   2460
acttgtactt tcacaaggct cccaacaagg aagagttcca caaggaaaca tgtcgcaagg   2520
tataaaaaag tgtttccagt tccttgttta aaaccttatt taaataggat aagcaacaac   2580
aacaacaaca acccagtata atcccactag tggggtctga ggagggtatt gtgtatgcag   2640
accttacccc taccctgggg tagagaggct gtttcagata gaaactcgac tccctccctc   2700
caaaaacctt atttaaatag gacaaggagt tgagaaaatg ttgatctttt tcctccatct   2760
ctatgcagat taaagcactt caccaatatg actgtttaag agcaaataag tcaacatctg   2820
catggggctt agaagctaga gtgcctttcc tagataagga gttcatcaat gttgccatga   2880
gtattgatcc agagtggaag ttggtaagta gttgaacccc aattgttgat cgaataaacg   2940
atcaactgtc cctaaaacct tgtattctat ccatttcaga ttaaaccaga gcaaaggagg   3000
attgagaagt gggctctaag gagggccttt gatgatgagg agcatcccta tctcccaaag   3060
gtggtactaa atcgcccttt tcaaactgat ttgcaagtga tttcgaatgt tatattgtta   3120
accaaactaa caatttnaag gctctgatga agtgtttggt ggctacttgt actttcacaa   3180
ggctcccaac aaagaagagt tccacaagga aacatgtcgc aaggtataaa aaagtgtttc   3240
cagttccttg tttaaaacct tatttaaata ggataagcaa caacaacaac aacaacccag   3300
tataatccca ctagtggggt ctgaggaggg tattgtgtat gcagacctta cccctaccct   3360
ggggtagaga ggctgtttca gatagaaact cgactccctc cctccaaaaa ccttatttaa   3420
ataggacaag gagttgagaa aatgttgatc tttttcctcc atctctatgc agattaaagc   3480
acttcaccaa tatgactgtt taagagcaaa taagtcaaca tctgcatggg gcttagaagc   3540
tagagtgcct ttcctagata aggagttcat caatgttgcc atgagtattg atccagagtg   3600
gaagttggta agtagttgaa ccccaattgt tgatcgaata aacgatcaac tgtccctaaa   3660
accttgtatt ctatccattt cagattaaac cagagcaaag gaggattgag aagtgggctc   3720
taaggagggc ctttgatgat gaggagcatc cctatctccc aaaggtggta ctaaatcgcc   3780
cttttcaaac tgatttgcaa gtgatttcga atgttatatt gttaaccaaa ctaacaattt   3840
actcattaca tttcctgcag cacatcctat acaggcagaa agaacaattc agtgatggcg   3900
taggctatag ttggatagat ggactcaaag cacatgctga acaacatgtg cgtttcaatg   3960
actaatcaac aactttctaa tgttcttatt tatcttccaa tgtttgtttg ttttaaagct   4020
gacttggaat tttttgttt cctttaatag gtgaccaata ggatgatgct taatgcttca   4080
catatattcc ctcataacac accgattaca aaggaagcat actattatag gatgattttc   4140
gagcgctttt tcccacaggt aatttgttca tgtattgtga ggattcatga taaattagct   4200
aacttatgct ggttttcaac cttgcaacct tccgataagt cacattgttg gagtttgttg   4260
ttcaaatgcg agatttactt ttaaccatgt tcctctggta tttttggttc tgcagaattc   4320
agctgggcta accgttcctg gaggagcgag tgtggcgtgt agcacagcta aagctgtaga   4380
gtgggatgct tcttggtcaa agaaccttga tccttcagga agggctgcta ttggtgtaca   4440
taactcagct tatgagaatc atgaacctgc tatggctaat gggaatttgg ccacaaaaat   4500
cattggccgt gcgccgtcta tggtagaagt tggtgctgct catgagctca caataaggag   4560
```

```
ttag                                                                    4564


<210> SEQ ID NO 4
<211> LENGTH: 590
<212> TYPE: PRT
<213> ORGANISM: Nicotiana tabacum

<400> SEQUENCE: 4

Met Cys Gly Ile Leu Ala Val Leu Gly Cys Ser Asp Asp Ser Gln Ala
1               5                   10                  15

Lys Arg Val Arg Val Leu Glu Leu Ser Arg Arg Leu Lys His Arg Gly
            20                  25                  30

Pro Asp Trp Ser Gly Leu Tyr Gln His Gly Asp Cys Tyr Leu Ala His
        35                  40                  45

Gln Arg Leu Ala Ile Val Asp Pro Ala Ser Gly Asp Gln Pro Leu Phe
    50                  55                  60

Asn Glu Asp Lys Thr Ile Val Val Thr Val Asn Gly Glu Ile Tyr Asn
65                  70                  75                  80

His Glu Gln Leu Arg Lys Gln Met Pro Asp His Lys Phe Arg Thr Gly
                85                  90                  95

Ser Asp Cys Asp Val Ile Ala His Leu Tyr Glu Glu His Gly Glu Asp
            100                 105                 110

Phe Val Asp Met Leu Asp Gly Ile Phe Ala Phe Val Leu Leu Asp Thr
        115                 120                 125

Arg Asp Asn Ser Phe Leu Val Ala Arg Asp Ala Ile Gly Ile Thr Ser
    130                 135                 140

Leu Tyr Ile Gly Trp Gly Leu Asp Gly Ser Val Trp Ile Ser Ser Glu
145                 150                 155                 160

Leu Lys Gly Leu Asn Asp Asp Cys Glu His Phe Glu Val Phe Pro Pro
                165                 170                 175

Gly His Leu Tyr Ser Ser Lys Asn Gly Gly Phe Arg Arg Trp Tyr Asn
            180                 185                 190

Pro Leu Trp Phe Ser Glu Ala Ile Pro Ser Thr Pro Tyr Asp Pro Leu
        195                 200                 205

Val Leu Arg Arg Ala Phe Glu Asn Ala Val Ile Lys Arg Leu Met Thr
    210                 215                 220

Asp Val Pro Phe Gly Val Leu Leu Ser Gly Gly Leu Asp Ser Ser Leu
225                 230                 235                 240

Val Ala Ser Ile Thr Ala Arg Tyr Leu Ala Gly Thr Lys Ala Ala Lys
                245                 250                 255

Gln Trp Gly Ala Gln Leu His Ser Phe Cys Val Gly Leu Glu Gly Ser
            260                 265                 270

Pro Asp Leu Lys Ala Ala Arg Glu Val Ala Asp Tyr Leu Gly Thr Val
        275                 280                 285

His His Glu Phe His Phe Thr Val Gln Asp Gly Ile Asp Ala Ile Glu
    290                 295                 300

Asp Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Glu Gly Ser Asp Glu Val Phe Gly Gly Tyr
            340                 345                 350

Leu Tyr Phe His Lys Ala Pro Asn Lys Glu Glu Phe His Lys Glu Thr
        355                 360                 365
```

```
Cys Arg Lys Ile Lys Ala Leu His Gln Tyr Asp Cys Leu Arg Ala Asn
    370                 375                 380

Lys Ser Thr Ser Ala Trp Gly Leu Glu Ala Arg Val Pro Phe Leu Asp
385                 390                 395                 400

Lys Glu Phe Ile Asn Val Ala Met Ser Ile Asp Pro Glu Trp Lys Leu
                405                 410                 415

Ile Lys Pro Glu Gln Arg Arg Ile Glu Lys Trp Ala Leu Arg Arg Ala
            420                 425                 430

Phe Asp Asp Glu Glu His Pro Tyr Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Ala His Ala Glu Gln His Val Thr Asn Arg Met Met Leu Asn
465                 470                 475                 480

Ala Ser His Ile Phe Pro His Asn Thr Pro Ile Thr Lys Glu Ala Tyr
                485                 490                 495

Tyr Tyr Arg Met Ile Phe Glu Arg Phe Phe Pro Gln Asn Ser Ala Gly
            500                 505                 510

Leu Thr Val Pro Gly Gly Ala Ser Val Ala Cys Ser Thr Ala Lys Ala
        515                 520                 525

Val Glu Trp Asp Ala Ser Trp Ser Lys Asn Leu Asp Pro Ser Gly Arg
    530                 535                 540

Ala Ala Ile Gly Val His Asn Ser Ala Tyr Glu Asn His Glu Pro Ala
545                 550                 555                 560

Met Ala Asn Gly Asn Leu Ala Thr Lys Ile Ile Gly Arg Ala Pro Ser
                565                 570                 575

Met Val Glu Val Gly Ala Ala His Glu Leu Thr Ile Arg Ser
            580                 585                 590
```

<210> SEQ ID NO 5
<211> LENGTH: 5276
<212> TYPE: DNA
<213> ORGANISM: Nicotiana tabacum

<400> SEQUENCE: 5

```
atgtgtggaa tcttggcttt gttgggttgt tcagatgatt ctcaggccaa aagggttcga      60

gttcttgagc tctctcgcag gcaatttccc ctttcttttc tcttttattt tattactcca     120

tcatataatt attctacttt cacctttttt gtttttaat ttcgatttgt ttgctttttg      180

ctttcttcat ttaatgttct tgcattgctc tagctcctat acgaataata ggagctaaag     240

taatagagtg aaggattatt ttggagcaac ggtaaagtta tttttgtata gttcacaggt     300

tggagccgta aaagcagtta ctagtgtttg cattagggta agttgtctat caggaaagat     360

atttgtagca attgaccacc ctttggcaaa aaattatgcg taaaatatta ctacttgtta     420

ttgattcaaa aaatatgact ttgaacatcc ttgtatagcc tagtggcaaa gggtgttcaa     480

aatttttgaa cacctttatt gaattttctg gtttcgtcgt tgctgtctac aacacactct     540

cgaagtgcgg ccttccctca aaccctacgt gaatatggaa cgcctagtgt gccgggatgc     600

cctttaggct gagtaataga gtactatgtt gatataccta aaatacggaa ctggcacgag     660

agataaattc agaatttata gcttaattat ttaaaattta tcatttgatt tatttcaacc     720

agagttcatt ctagtagagt ttatgttgca tatttgtctg atttgcacca tttgttttaa     780

tgttcttgca ttactctaat ttatttatga ataataagct aaactaattg agtttatgtt     840
```

```
gatgtaactg acctgagttg gcagtgatgt ttggctactt gaatttaaaa caagattaag    900
acttgtgagt tggcagtaat tgtttggata cttgaattta gaacaagaat aaaacaagat    960
taattaagga tacattattc ctaacccgga ccctaattct atagattgat tattaaattt   1020
ttcttggacc aaccgtcacc gtgacctgtt catgatggtg atggcaaaag ccataataca   1080
cttgatttct gttttcaatt tttaaggttc ttattattat acttattata tactttgaaa   1140
attatgggtc aaaattttaa tatttgttat tccttccgta tgtttgactc aacttggagt   1200
tcatgaaaaa aaaaaaaaat ttttttaaac ttgtggtctt aaacaagtca tcgatatatg   1260
tgtggttgtg aatcgcctcg ttaggataaa gtagaaattt taaagttaaa ctatttcgaa   1320
ataaaaaagt atgatagtgt ttttgggaca tactaaaaag gaaataacac ataaaatgga   1380
acaaagaagt atattttagt gatttttcac atatatatca gtattttgta tcaaaaatgc   1440
tggttcagtt gaactcattg aactgggtgc tccatccacc tccgagtact gcaacatgtg   1500
accggtggca gatgcaaccc ttacgtacca gggtcatctg aacctagtat aaatatattt   1560
gtgaaaaatc cctaaaattt caataattag tagatttaaa accttaattt taaaactaca   1620
atgagttcag ttttaaaatc tttatatgtc aaacctatca agattaaatc ctggatccac   1680
cttttgcatg tgacagtaca atagcctttt gtaattgaaa caaatatttg aattttggta   1740
actatttgat cacataggtt gaagcatcgt ggaccagatt ggagtgggat atatcaacat   1800
ggtgattttt acttagcaca tcaacgttta gcaattatcg atcctgcttc tggtgatcag   1860
cctctgttta atcaagataa gacgattgtt gttacagtga gtgcctctaa tttacctctt   1920
tttttttctt ttttttttt acgatcgcgt tgtttagatt atttatggat gaaaatttgt   1980
atatttgatt attgattgtg tgctaaattt tgcaggtcaa tggagagatt tacaatcatg   2040
agaaacttcg taatcttatg cctaatcaca agttcagaac tggaagtgat tgtgatgtta   2100
ttgcacatct tgtgagttag tttacttttc tcattgacca acttaggcca gtgaattata   2160
ttaggaattt cgggtgtttg gatatggtca aattagctta taagcactta ttatcaattt   2220
taacattttt atccatacac gtaactgttc attcataaag tcattttagc acttgatgct   2280
catcaaccta tgttgttggg actcttcgaa aatgtcagcc cgatagcatt tcggagagtc   2340
cgagcaacat agcaatcaac tacttttaat cagttaaacg aacatgctca tagtgataac   2400
ctctggaaaa tatgttatag taaattagaa aaatttatac gatgtctcac tatcggtatg   2460
tattgatcag tatgaagaat atggagaaaa ttttgtggac atgttggatg gggtgttctc   2520
ttttgtattg ttggatacgc gcgataacag ctttcttgct gctcgtgatg caattggaat   2580
tactccccta tatattggtt ggggacttga tggtaagatt ttctatacaa ttttccagtt   2640
agaaattaaa actgaagcta ttcctattta ctattgaaga atcttgatac atgttatttg   2700
gtatttcgtc gtgttgttat gtctcaggct ctgtgtggat ttcatctgag ctaaaaggat   2760
taaatggtga ctgtgaacat tttgaagttt tccctcccgg tcacttgtac tcgagcaaga   2820
atggcgggtt taggagatgg tacaatcctc aatggttctc tgaggctatt ccatcaaatc   2880
cttacgaccc cttagttttg agacgtgcct tcgaaaatgt gaggcttgtt aatgaatcta   2940
gtgtacaatc ttggatgttt ttctctcgac tttggtttta gcactcaaaa agttgtctgt   3000
acaaacgatc ttggctataa ggagtggtgg ttaattttgc aggctgttat caaacgattg   3060
atgaccgatg tcccctttgg tgttctgctc tccgggggac ttgattcgtc tttggttgct   3120
tctgtcactg ctcgctactt ggctggaaca aaagctgcta agcaatgggg agcacagctt   3180
cattccttct gtgttggtct cgaggtcaga ctatcaatcc tgagcggaga catatttggg   3240
```

```
gcgggttctg tgggttcaac tgaacccatt gcttttggtt cgaaccatat atacaaatcc   3300
aagaaaatat aagatgtgta catataatat gacactcatt ctgagcctac tgacgctaga   3360
tactggactc gcctttggtc ttgagacttt ataatagaaa atagatattc aataccaatt   3420
tctgtttttc ttttctgact gacagggctc accagatctc aaggctgcaa gagaagttgc   3480
tgactatttg ggaaccgttc accacgagtt caccttcaca gttcaggttt gtaaatcgtg   3540
ttgctactcc gatttattca tgtgagtctc ttctgttttc ctcctagaaa gcaacaagtg   3600
ttcatgtttt gcaggatgga attgatgcta ttgaagatgt tatttaccat atcgagacat   3660
acgatgtaac aacgatcaga gcaagcactc ctatgttcct tatgtcgcgt aagattaaat   3720
cactgggagt taagatggtc atatcagggg aaggctcaga tgaactgttt ggcggctatt   3780
tgtacttcca caaggctccg aacaaggaag aattccatgt ggagacatgt cacaaggtaa   3840
taaaacacgt cggctccctt ggcaagtctg attctccttg tcattgtttg tctcgggttg   3900
gaataaattg ctataattcg agaagaaatg ttaatcctgc tctttcactc gcatgcagat   3960
aaaagcgctt caccaatacg actgtttgag agcaaataag gcaacatcag catggggctt   4020
agaagctaga gtaccatttc tggataaaga gttcatcaac gttgctatga gtatcgatcc   4080
tgaatggaag atggtaacaa aactgagctc caattgtcaa tgagatgaga agcataactg   4140
aatatgcacg ttctctaaaa cttgtttttc atccgtttca gattaaacac gatcatggta   4200
ggatcgagaa gtgggttctt aggaaggctt ttgatgatga ggagcaaccc tatctcccaa   4260
aggtccacaa agtcatgttt ttcctactga tttgccgatt agtatggatc aaaactaaca   4320
tgttttgttc ttttatgtac tctgcagcat attctgtacc ggcagaaaga acaattcagt   4380
gatggcgtag gctatagttg gatcgatgga ctcaaagcac atgctgaaca acatgtgagc   4440
ttctaaataa atccagaact attacatcgt tatcgtccaa ttttcgtttg ttttgctgtc   4500
agctgatctt ggaaacaatt cttttctctc aggtgactga taggatgatg cttaatgctg   4560
cacatatctt ccctcacaac actccaacta caaaggaagc atactattac aggatgattt   4620
tcgagaggtt cttcccacag gtacttatag cgcgagacta gaatcatata tctcttaaat   4680
ggaaacatga aaaataaagg aggtgttttt tctccttgga aaaagtattt actactgatt   4740
aaagcacctt cattcaccca tcttgctact tcgcgtactt tactaagttg tggttctaaa   4800
aaagaagatt tagcttggta tattccatca cgaggaagcc acaaaaagat tctacttata   4860
agaagttgga tacttttaat ggtgtgagac cttttgggaa aaaccatgcg ggcttggccc   4920
aaagccgaca atatcacacc atgttaagag tatctttgct tcgttttagc caaacagtac   4980
aataagtcaa tttttaaacc atgttgttac tattgttgga tttgcagaat tcagcaaggc   5040
taactgttcc tggaggaccg agtatagctt gcagcacagc taaagctatt gagtgggatg   5100
cttcgtggtc gaacaacctt gatccttccg gtagggctgc aatcggtgta cataactcgg   5160
cttatgacga tcatctcccc gatgttggta atgggaattt ggacacaacg atcatcgata   5220
atgtgccgag gatggtagga gtgggtgctg ctgcagagct cacaataagg agctag         5276
```

<210> SEQ ID NO 6
<211> LENGTH: 590
<212> TYPE: PRT
<213> ORGANISM: Nicotiana tabacum

<400> SEQUENCE: 6

```
Met Cys Gly Ile Leu Ala Leu Leu Gly Cys Ser Asp Asp Ser Gln Ala
1               5                   10                  15
```

-continued

```
Lys Arg Val Arg Val Leu Glu Leu Ser Arg Arg Leu Lys His Arg Gly
        20                  25                  30

Pro Asp Trp Ser Gly Ile Tyr Gln His Gly Asp Phe Tyr Leu Ala His
    35                  40                  45

Gln Arg Leu Ala Ile Ile Asp Pro Ala Ser Gly Asp Gln Pro Leu Phe
    50                  55                  60

Asn Gln Asp Lys Thr Ile Val Val Thr Val Asn Gly Glu Ile Tyr Asn
65                  70                  75                  80

His Glu Lys Leu Arg Asn Leu Met Pro Asn His Lys Phe Arg Thr Gly
                85                  90                  95

Ser Asp Cys Asp Val Ile Ala His Leu Tyr Glu Glu Tyr Gly Glu Asn
            100                 105                 110

Phe Val Asp Met Leu Asp Gly Val Phe Ser Phe Val Leu Leu Asp Thr
        115                 120                 125

Arg Asp Asn Ser Phe Leu Ala Ala Arg Asp Ala Ile Gly Ile Thr Pro
    130                 135                 140

Leu Tyr Ile Gly Trp Gly Leu Asp Gly Ser Val Trp Ile Ser Ser Glu
145                 150                 155                 160

Leu Lys Gly Leu Asn Gly Asp Cys Glu His Phe Glu Val Phe Pro Pro
                165                 170                 175

Gly His Leu Tyr Ser Ser Lys Asn Gly Gly Phe Arg Arg Trp Tyr Asn
            180                 185                 190

Pro Gln Trp Phe Ser Glu Ala Ile Pro Ser Asn Pro Tyr Asp Pro Leu
        195                 200                 205

Val Leu Arg Arg Ala Phe Glu Asn Ala Val Ile Lys Arg Leu Met Thr
    210                 215                 220

Asp Val Pro Phe Gly Val Leu Leu Ser Gly Gly Leu Asp Ser Ser Leu
225                 230                 235                 240

Val Ala Ser Val Thr Ala Arg Tyr Leu Ala Gly Thr Lys Ala Ala Lys
                245                 250                 255

Gln Trp Gly Ala Gln Leu His Ser Phe Cys Val Gly Leu Glu Gly Ser
            260                 265                 270

Pro Asp Leu Lys Ala Ala Arg Glu Val Ala Asp Tyr Leu Gly Thr Val
        275                 280                 285

His His Glu Phe Thr Phe Thr Val Gln Asp Gly Ile Asp Ala Ile Glu
    290                 295                 300

Asp Val Ile Tyr His Ile Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Ile Ser Gly Glu Gly Ser Asp Glu Leu Phe Gly Gly Tyr
            340                 345                 350

Leu Tyr Phe His Lys Ala Pro Asn Lys Glu Glu Phe His Val Glu Thr
        355                 360                 365

Cys His Lys Ile Lys Ala Leu His Gln Tyr Asp Cys Leu Arg Ala Asn
    370                 375                 380

Lys Ala Thr Ser Ala Trp Gly Leu Glu Ala Arg Val Pro Phe Leu Asp
385                 390                 395                 400

Lys Glu Phe Ile Asn Val Ala Met Ser Ile Asp Pro Glu Trp Lys Met
                405                 410                 415

Ile Lys His Asp His Gly Arg Ile Glu Lys Trp Val Leu Arg Lys Ala
            420                 425                 430
```

```
Phe Asp Asp Glu Glu Gln Pro Tyr Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Ala His Ala Glu Gln His Val Thr Asp Arg Met Met Leu Asn
465                 470                 475                 480

Ala Ala His Ile Phe Pro His Asn Thr Pro Thr Thr Lys Glu Ala Tyr
                485                 490                 495

Tyr Tyr Arg Met Ile Phe Glu Arg Phe Phe Pro Gln Asn Ser Ala Arg
            500                 505                 510

Leu Thr Val Pro Gly Gly Pro Ser Ile Ala Cys Ser Thr Ala Lys Ala
        515                 520                 525

Ile Glu Trp Asp Ala Ser Trp Ser Asn Asn Leu Asp Pro Ser Gly Arg
    530                 535                 540

Ala Ala Ile Gly Val His Asn Ser Ala Tyr Asp Asp His Leu Pro Asp
545                 550                 555                 560

Val Gly Asn Gly Asn Leu Asp Thr Thr Ile Ile Asp Asn Val Pro Arg
                565                 570                 575

Met Val Gly Val Gly Ala Ala Ala Glu Leu Thr Ile Arg Ser
            580                 585                 590


<210> SEQ ID NO 7
<211> LENGTH: 5926
<212> TYPE: DNA
<213> ORGANISM: Nicotiana tabacum

<400> SEQUENCE: 7

atgacgtagt ttagcttgtt cgtccacggc ataaaaacgc ctataaattc ggtggtcatt      60

ttggttcatt tacagaatcc cacgatcatc ttttgtgtat tatcattttg ccttctttac     120

gtgttcttct ctcccaaaat cctgcaaatc tttaactatc ttcccatatt tctctccctc     180

tttctctttc tttttgttat ctactttact acttctatta gtagagcttt atccaattaa     240

agtcatctat attggatata gtttttacta ctactttatc ttgtttggga aagaaaagaa     300

taaaaaatta gagtgtctat attaagtata aaaaggtgaa aaataaaaaa gtagtgatca     360

atcatgtgtg ggatcttggc tttgttgggt tgtccagatg attctcaagc caaaagggtt     420

cgagttcttg agctctctcg caggcaattc ccctttcttt tctcttttat tttattactc     480

catcatatta ttcaactata atttcacctt ttttgttttt caattaatat ttgtctgctt     540

ttgctttctt catttaatgt tcttgcattg ctctagttcc tttatgaata ataggctaaa     600

gtaatagagt gaaggagtag agtcggagca acggtgaagc tgtctttaca tgatctatag     660

ctcacgggtt caccatagaa gcagccaatg gcgaagctag aaaattcaat aagggtgttc     720

tttcctttgc cagtgggcta tgcaagggtg ttcaaagtct atttttaatc aataacaagt     780

aatattttat cttatagtga aagcaaccac taatacttgc atttaggtaa ttagctgtct     840

atcaagggaa gttatgtgtg gtaagtagtg gcggagccag aattttcgtt aaggggtgtc     900

aaaatatata aaagtaaaca taccaggaaa ttaaggggag tcaatacata gtatatatac     960

atataattta tttttttacc tagctataca gtatattttt tccgcgaagt gacacccctt    1020

cctataaggt ggctccgcca ctggtggtaa gggtggtcaa ttgaacaccc ttcgccgaaa    1080

aattatactc tggatggtgt aaaatattac tacttgttac tgattcaata aataaatttt    1140

gaaaaccctt gcatagtcta gtagcaaaga gtgttcaaaa ttttgaacac atttattgaa    1200

ttctctggtt tcgccactgc tgtctacatc acatccctta aggtgcgatc ttttttcgaa    1260
```

```
tcatgtgtga atacgggatg ccttgtgttc caggctgccc ctttaggcta aagtaataga   1320
gtacgtctta attcttatgt tgatcatata cctgaaactc ggaactggca cgagagatat   1380
aaattcagaa tttatagcaa atttatcatt atgttgcatt tgttttaatg ttcttgcatt   1440
actctaattt ttttatgaat aataagctaa actaattgag tttatgttga tgtaactgac   1500
ctgagtttgg ctacttgaaa gttaaaacaa gattaagact tgtgagttgg cagcgattgt   1560
ttggatactt gaacacgttt aaaacaagat taagacatta tgatggatac attattccta   1620
acctgggtgg gacctaattc tatggattca ttattaaaat ttcttggaca aaccatcacc   1680
atgatctgtt catgatgttt atggcaaaag ccataataca ctttatttct gtatcacaac   1740
tactttatac acatgttata gagttttaaa attattttaa tatttgttat tccttgagtc   1800
tcctgatatt tgactccgca tgaaattcaa gaaaaaaaaa agaagatttt taaaatttat   1860
agtcgaaaac aagccatcga tatatgtgtg gttgttaata acctcgttag gcgtaaagta   1920
gaaattttaa agttaaacta tttctaaata agaaaatatg atattgtttt tgcatagact   1980
aataaggaaa gtatgacaag taaaataaaa caaagaagta tattttaatg attttttccg   2040
tgtcaaaaat gtcagtttag ttgaacttga actcattgaa actggtgacc agtggtggat   2100
gcaaacctta ggtacggagg tcatccgaac ctagtatagt tatatttgtg aaaaatcact   2160
aaaatttcaa taattactag atatgaaacc ttaattttaa aactacaatg agtgcagttt   2220
taaaatcttt aaatgtcaaa ccgatcaaga ttaaattatg gatccacctt taaatgtcaa   2280
accgacagta caatagcctt ttgcaattga aacaaatata aacattacat ttattaaact   2340
agttttaatt ttggttacta tttgattaca taggttgaag catcgtggac cagattggag   2400
tgggatatat caacatggtg atttttactt agcacatcaa cgtttagcaa ttatcgatcc   2460
tacttctggt gatcagcctc tgtttaatca agataagact attgttgtta cagtgagtgc   2520
ctctaattta ccctttttttt tgtggacgaa tgcgttgttt agattacttt aattatggct   2580
gaaaatttgt atatttgatt attgattgtg tgccaaatgt tgcaggtcaa tggagaaatt   2640
tacaatcatg agaaacttcg taatcttatg cctaatcaca agttcagaac cggaagtgat   2700
tgtgatgtta ttgcacatct tgtgagttag tttactttac tcatcaacca acttaggcta   2760
gtgaattcaa aggcggagct agaattttga gtatatgagt tctggaattt aggacaagat   2820
aagttactgg gttcggatag attatttaga catattaagt agatttctta acacaaatac   2880
acggcccgag ccgaagctat tgggttctgc cgaacccgta gctagacttg tagctccgcc   2940
attgagtgaa ttatataagg aatttcgggt gtttgggtaa acttataagc tggtcaaatt   3000
agcttataag cacttattat caatttcaac atttctatcc aaacacgtaa ctattcattc   3060
gattttagca cttgatgctt atcgactact tttaatcagt taaacgaaca ggctcatagt   3120
gacaaactct agaaaatatg gtattgtaaa ttagtagaag aatttatacg atgtctcact   3180
atcgatatgt attgatcagt atgaagaata tggagaaaat tttgtggaca tgttggatgg   3240
ggtgttctct tttgtattgt tggatacgcg cgataacagc tttcttgctg ctcgtgatgc   3300
gattggaatt actcccctct atattggttg gggacttgat ggtaagattt tctatacaat   3360
tttccaagta gaaattaaaa ctgaagccat tccaatttgc tattgtagaa tcttgatata   3420
tgttatttgg tatttcaggc tctgtgtgga tttcatctga gttaaagggc ttaaatgatg   3480
attgtgaaca ttttgaagtt ttccctcccg ggcacttgta ctcgagcaag aatggcgggt   3540
ttaggagatg gtacaatcct caatggttct ctgaggctgt tccatcaaat ccttatgacc   3600
```

-continued

```
ccttagttct gaggcgtgcc ttcgaaaatg tgagaaatga atctaggagg tttccctctc   3660
gactttggac ttagcactct aaaaatttgt ctgtacaaac gatcttggct ataaggagtg   3720
gttgttaatt tcgcaggctg ttattaaacg gttgatgacc gatgtaccct ttggtgttct   3780
gctctccggg ggacttgatt cgtctttggt tgcttctgtc actgctcgct acttggctgg   3840
aacaaaagct gctaagcaat ggggagcgca gcttcattcc ttctgtgttg gtctcgaggt   3900
cagtcaatca atcttgagta gaaaaaattt agggtcggtt ctgtgggttt aacttaactc   3960
attgcttttg gctcgaacca tatatgcaaa tccaaaaaga tttaagatgt atacatataa   4020
tataacactc attctgagcc tactgacgct agatactgga ctgtgccttt ggtcttgaga   4080
cttttgtaat agaaaattga tattcaatac caatttctgt tcttttgtga ctaacagggc   4140
tcaccagatc tcaaggctgc aagagaagtt gctgactatt tgggaaccgt tcaccacgag   4200
ttcaccttca cagttcaggt ttgtaaatcg cgatgctact tcaatttatt catgtgaggc   4260
tcttctgttt tcctactaga aagcaacatg tgtgcatgtt ttggcaggac ggaattgatg   4320
ctattgaaga tgttatttac catatcgaga cgtatgatgt aacaacgatc agagcaagca   4380
cccctatgtt ccttatgtcg cgtaagatta aatcacttgg agtgaagatg gtcatatcag   4440
gggaaggctc agatgaactg tttggtggct acttgtactt ccacaaggct cccaacaagg   4500
aagaattcca cacggagaca tgtcacaagg taataaaaca catcggcaag tctgattctc   4560
cttgtcattg tttgtctcgg gttggaataa attgctataa ttcgagatat ggaatgagtt   4620
aagaaatgtt aatcatgttt ttccattcgc atgcagataa aagcgcttca ccaatacgac   4680
tgtttgagag caaataaggc aacatcagca tggggcttag aagctagagt accatttctg   4740
gataaagagt tcatcaatat tgctatgagt atcgatcctg aatggaagat ggtaagaaaa   4800
ctgagctcca attgtcaatg agacgagaag cataactgaa tatgcgcgtt ctctaaaacc   4860
tgtttttcat ccgtttcaga ttaaacacga tcaaggtagg atcgagaagt gggttcttag   4920
gaaggctttt gatgatgagg agcaccccta tctcccaaag gtccacaaac tcatattttt   4980
cctactgatt tgccaataat tatggatcaa aactaacatg tttgttctgt tatgtgctct   5040
gcagcatatt ttgtaccggc agaaagaaca attcagcgat ggtgtaggct atagttggat   5100
cgatgggctc aaagcacatg ctgaacaaca tgtgagcttc cttaataaat ccagaactaa   5160
tgcagcgtta tcgtccaatt tttgtttgtt ttactatcaa ctaattttag tcatgttagt   5220
atgtttacct taggtactat gtttttaagg agtttttagt cgtgtcaaga atttattcgc   5280
tggtaaaaaa tagattgaac ttccagtatt ttctactttt attatgcata tgattggact   5340
gagatgaggt taaatggaac aacatggttg aggattaata taaccaattc caacttggtt   5400
ggaattgagg cgtcgtagtt gttgttagat ctcagaaaca attcttttct ctcaggtgac   5460
tgataggatg atgcttaatg cttcacatat cttccctcac aacactccaa ctacaaagga   5520
agcatactat tacaggatga tttttgagag gttctttcca caggtaatat tagtgagaga   5580
ttaaaatcta tagattttgt ttatggctga ggtttaaatc atagatttct taagctcaaa   5640
aactaaaacc atgtccctgc tactgttgga tttgcagaat tcagcaaggc taactgttcc   5700
tggaggaccg agtatagctt gcagcacggc taaagctatt gagtgggacg cttcttggtc   5760
gaacaacctt gatccttccg gtagggctgc tatcggtgta cataactcag cttatgacga   5820
tcatctaccc gatgttagta atgggaattt ggacacaacg atcatcgata atgtgccaag   5880
gatggtagga gtgggtgctt ctgcagagct cacaataagg agctag                  5926
```

<210> SEQ ID NO 8
<211> LENGTH: 565
<212> TYPE: PRT
<213> ORGANISM: Nicotiana tabacum

<400> SEQUENCE: 8

```
Met Thr Leu Lys His Arg Gly Pro Asp Trp Ser Gly Ile Tyr Gln His
1               5                   10                  15

Gly Asp Phe Tyr Leu Ala His Gln Arg Leu Ala Ile Ile Asp Pro Thr
            20                  25                  30

Ser Gly Asp Gln Pro Leu Phe Asn Gln Asp Lys Thr Ile Val Val Thr
        35                  40                  45

Val Asn Gly Glu Ile Tyr Asn His Glu Lys Leu Arg Asn Leu Met Pro
    50                  55                  60

Asn His Lys Phe Arg Thr Gly Ser Asp Cys Asp Val Ile Ala His Leu
65                  70                  75                  80

Tyr Glu Glu Tyr Gly Glu Asn Phe Val Asp Met Leu Asp Gly Val Phe
                85                  90                  95

Ser Phe Val Leu Leu Asp Thr Arg Asp Asn Ser Phe Leu Ala Ala Arg
            100                 105                 110

Asp Ala Ile Gly Ile Thr Pro Leu Tyr Ile Gly Trp Gly Leu Asp Gly
        115                 120                 125

Ser Val Trp Ile Ser Ser Glu Leu Lys Gly Leu Asn Asp Asp Cys Glu
    130                 135                 140

His Phe Glu Val Phe Pro Pro Gly His Leu Tyr Ser Ser Lys Asn Gly
145                 150                 155                 160

Gly Phe Arg Arg Trp Tyr Asn Pro Gln Trp Phe Ser Glu Ala Val Pro
                165                 170                 175

Ser Asn Pro Tyr Asp Pro Leu Val Leu Arg Arg Ala Phe Glu Asn Ala
            180                 185                 190

Val Ile Lys Arg Leu Met Thr Asp Val Pro Phe Gly Val Leu Leu Ser
        195                 200                 205

Gly Gly Leu Asp Ser Ser Leu Val Ala Ser Val Thr Ala Arg Tyr Leu
    210                 215                 220

Ala Gly Thr Lys Ala Ala Lys Gln Trp Gly Ala Gln Leu His Ser Phe
225                 230                 235                 240

Cys Val Gly Leu Glu Gly Ser Pro Asp Leu Lys Ala Ala Arg Glu Val
                245                 250                 255

Ala Asp Tyr Leu Gly Thr Val His His Glu Phe Thr Phe Thr Val Gln
            260                 265                 270

Asp Gly Ile Asp Ala Ile Glu Asp Val Ile Tyr His Ile Glu Thr Tyr
        275                 280                 285

Asp Val Thr Thr Ile Arg Ala Ser Thr Pro Met Phe Leu Met Ser Arg
    290                 295                 300

Lys Ile Lys Ser Leu Gly Val Lys Met Val Ile Ser Gly Glu Gly Ser
305                 310                 315                 320

Asp Glu Leu Phe Gly Gly Tyr Leu Tyr Phe His Lys Ala Pro Asn Lys
                325                 330                 335

Glu Glu Phe His Thr Glu Thr Cys His Lys Ile Lys Ala Leu His Gln
            340                 345                 350

Tyr Asp Cys Leu Arg Ala Asn Lys Ala Thr Ser Ala Trp Gly Leu Glu
        355                 360                 365

Ala Arg Val Pro Phe Leu Asp Lys Glu Phe Ile Asn Ile Ala Met Ser
    370                 375                 380
```

```
Ile Asp Pro Glu Trp Lys Met Ile Lys His Asp Gln Gly Arg Ile Glu
385                 390                 395                 400

Lys Trp Val Leu Arg Lys Ala Phe Asp Asp Glu Glu His Pro Tyr Leu
                405                 410                 415

Pro Lys His Ile Leu Tyr Arg Gln Lys Glu Gln Phe Ser Asp Gly Val
            420                 425                 430

Gly Tyr Ser Trp Ile Asp Gly Leu Lys Ala His Ala Glu Gln His Val
        435                 440                 445

Thr Asp Arg Met Met Leu Asn Ala Ser His Ile Phe Pro His Asn Thr
    450                 455                 460

Pro Thr Thr Lys Glu Ala Tyr Tyr Tyr Arg Met Ile Phe Glu Arg Phe
465                 470                 475                 480

Phe Pro Gln Asn Ser Ala Arg Leu Thr Val Pro Gly Gly Pro Ser Ile
                485                 490                 495

Ala Cys Ser Thr Ala Lys Ala Ile Glu Trp Asp Ala Ser Trp Ser Asn
            500                 505                 510

Asn Leu Asp Pro Ser Gly Arg Ala Ala Ile Gly Val His Asn Ser Ala
        515                 520                 525

Tyr Asp Asp His Leu Pro Asp Val Ser Asn Gly Asn Leu Asp Thr Thr
    530                 535                 540

Ile Ile Asp Asn Val Pro Arg Met Val Gly Val Gly Ala Ser Ala Glu
545                 550                 555                 560

Leu Thr Ile Arg Ser
                565


<210> SEQ ID NO 9
<211> LENGTH: 21008
<212> TYPE: DNA
<213> ORGANISM: Nicotiana tabacum
<220> FEATURE:
<221> NAME/KEY: misc_feature
<222> LOCATION: (18072)..(18072)
<223> OTHER INFORMATION: n is a, c, g, or t
<220> FEATURE:
<221> NAME/KEY: misc_feature
<222> LOCATION: (19355)..(19462)
<223> OTHER INFORMATION: n is a, c, g, or t
<220> FEATURE:
<221> NAME/KEY: misc_feature
<222> LOCATION: (19541)..(19541)
<223> OTHER INFORMATION: n is a, c, g, or t
<220> FEATURE:
<221> NAME/KEY: misc_feature
<222> LOCATION: (19714)..(19786)
<223> OTHER INFORMATION: n is a, c, g, or t
<220> FEATURE:
<221> NAME/KEY: misc_feature
<222> LOCATION: (20035)..(20035)
<223> OTHER INFORMATION: n is a, c, g, or t

<400> SEQUENCE: 9

atgtgtggaa tactagctgt ttttggttgc attgataact ctcaggccaa gcgttcccga      60

atcatcgaac tttccagaag gtttcttctt tttattgctt tccgattttc tacagcattc     120

ttattcttct ggggtgtcaa tggtatgcat gtgttttgga tttgctattc gtgaacttgt     180

tcgctttctc gtggtcttcg atttattttt gtcaatttat aatcagcgtt ttttgtatgg     240

atttctcttt tgaatctctc aaatatatga catttgattt cctcgagaaa atttggcatt     300

tttatggttc ttatgatatg tggttaaccc ctcgctctgc atcgcttcag cgctttaaaa     360

cacgaagtga tggctattag taatactgct agagtggtta ttgaattaca ttaaataacg     420

ggttgctagt agatcaaatt cagaatgaca gtgaaatatc tctggaaact tgaatccccg     480
```

-continued

```
ttcgattcgc tggtaaaacc tggctaaaaa atagctttat ctcaaaggag agtatgtcac    540
tgtgaaattg gtggtatgtg ttgtttaagg catgatatgc tgctcttagg tgatgtcaag    600
atgataatac catccttttc acactagact cagctttgta gcacttacat ctcagttaat    660
cgatggagga aaatctagtc tgctttgggg catattatac caaatgtctt ccttttgttt    720
tctagtgttg tttctcaaga attgaaaaac caatctacaa tatagtgata taattaacta    780
gttaactctt cctgtgtttt ctgaaaattt ccaataattg agaagtgttt actggtcaat    840
tagtaaaggg agaacggaat atttttttcc tctaaagaac ttctcttttt ccatacagaa    900
tgactttcta tacaaggcct aagtctaatt tagtgtctgc gattaagcat cttctgggaa    960
cttcacactt gaaagaagta gaactaggag ggggcaggtc tagaaagata attgcttcag   1020
tcatttctca taaaaaacat tgcttcagtc attatgtgca ttcatataga gttggtcaag   1080
ctgctaagct gagctaatag tatgatagct gtgactctcg acaaagtagg ttgcctctta   1140
gggctttatc ctttggctcc gtaaagaatt tctttgggag ggctccagag tgggtaggat   1200
tgttctcatg gtaagctgta acaccaacga aacaagcctt tgtagctgtg gaagtccgag   1260
ggggtggtgg tggtggtggt ggtgtgagag ttagagtggt ggaggagagg ggaggagtga   1320
agagaagttt atattttaaa gaatagggcc ttgagaactt ttagtagtga gcatgcatta   1380
ttattattgt tattgttatt attattatta ttattattat tattattata ttattattat   1440
tattatatta ttgttatgta attacttagc taatgaggtt tttccaactg tttccaaatt   1500
aggaaatgtg ttgaaagcat agttaagtat ataaaagcgt gttctttcta atatccttag   1560
cttttagagc agataatcac aaaatttatc atgataatat agcagacaat ttttcctagt   1620
tcaaatctca tgccaccctt cataaaaaat ttccacgtgc ttggctggca tgttagggga   1680
cgtcttggca taattaaaca aatagaattg tccctttcta acagcttaag cttttagatg   1740
aggcggtcaa caattcaaca atttgcattt gtttgataag aagatattaa aagaacctta   1800
aaaggtgtca gtatgtgaac aaactcaagg ggtagactaa ctagaagtca atttaaattt   1860
tctgcttgtc tgtgttttac ttcttttgca ctatagaaat tgcatttcca gcattccgaa   1920
agctgcttcc tttgcatata gacttcacat ttccagcgtt tctgataagc gttcttgctt   1980
attcctgtcc ttctacttgg ttgattctcc tctcacttag ttcactatct tcttgcacgc   2040
attttcaaat tgttttatca attctcttgc tttcttttca tctgacccca caaaatacct   2100
cccaaaagcc tttctgcttt tccgagtctg aaattatctg cttattactg cctttcaagt   2160
attctgatgc gttgactgtt tttttccctt gtagtaatgc atggttcgct gtccaatctc   2220
tattttgttt tttgtgaacc actattcttt gttgcttctg tttcgtcatc ctcagttccc   2280
catcttctca gtttgatttt cctcatttaa aaagcgtgtg ccccttttct tgtgctaccc   2340
tctaaaaaat cagttgctgt catctcgttt gatctgtcat gatcccagtt gatgccacat   2400
gtttagttct ttacctctgg acaactttta cttcctgaga accacgattt cttttcctga   2460
agaaattctt agaaattggt tatgtaaagg aaattcccag caatcaccat ttggcctcta   2520
cctggcttgc ttttcaactt accgacacgt gttcatcccc ttttaacaga tgctgaccat   2580
tatcttctgc ttgttggggc atacttctta cccatggtgt taaccctgat ctttcgtatc   2640
acatttttca actcttaatt ctcacatgta aagtgcctat ctttgcctct ttagttgatc   2700
ttgggttggg ctgttaatcc aaattctctg ggctttgctt tgaagtatga taagcggtag   2760
ctttactaca gtaccatatt ctacattgct acagacgtga aattatcctg atttgtcttt   2820
```

-continued

```
gatgtgatgt ctggcaagtg tagattacgc cacagaggac ctgattggag tggattgcat   2880
agccatgatg actgttatct tgctcatcaa cggttggcaa tagtagaccc aacttctgga   2940
gatcagccac tttacaacga ggacaagacc attgttgtcg cggtatggaa atatttatta   3000
tatttttct tagatattac cggtacatgg actttggaca atatttgtgc gttttgatct   3060
tctatagtac aaacttttct cgtaggataa atttcctcta ctttgaatgg atcttaacag   3120
gaaaatcgga ataaacaatt tgtgatttcg aaatttttag ttcttacata tttggaacat   3180
atgcggtaaa gtaactaggc gattgactag gtgaatacgg agaatttcct ctactgttat   3240
caatatttac tcagctcatt tgaaagatct ctgggtcgtc tagcagtaca gctatttagg   3300
caacttaacc aaatcccctt cccatgtgtt tcactttctt gacttatttt atattttgac   3360
attttgcaat gccgaaaata aattgttttt ccattttatg acctttaaaa tgttgaggtg   3420
aagggctagg cggtacttta attgacttat cagcaacaat gtattagata cagagcacaa   3480
acttgtttgg gtgcctaatt tggtattttt tgagaacgat ggagtaaatg gaaatatgaa   3540
ttagcaaaat attgaaatag tagatctgaa aaatgaatga ctgaatttag aggaggacct   3600
tttcttcttt ccttgctgaa gtggttataa gagaattatg tgaagaacat gtaagcttta   3660
gggtagtgtt acaccataac agtcatgctt tccctcaact attagtgtag ctgatgaatg   3720
ctttcagaaa tgtggctgtt tttttgctgc gtattttatg tctttcatca tctcaaaatt   3780
tattgtgttt taacactgct tggaaggcct agagtcttcc gaaaatagta ggttgagaaa   3840
acatgagtaa gcaaatttct tcctgctggc aattaatcgt tttatatgag gtgaagccac   3900
acaatctaac atggtcttag acataaaaat attatttttg acatagagca gacagaaatc   3960
ttgggtctag ttgctatctc ccttcctaat aagatgccct ctatcctcat tgctatatcc   4020
caaaacagat tcacactaga atgaataaat ctctccttgc agccacattt atattaataa   4080
gtagtgtaac accaaaacat ttgtgcttct gcaaagtctg ttgaagtgga cgattaagta   4140
ataaattgtg tgagtttgac tgaagagaaa gtaataaatt gggtgagctt ctcacatttt   4200
tcaggataat gtcaattcat ctgattgaac tttttgaagg acatctcctt ttctaaaagt   4260
ttttgttcac ttcctgaaaa tggttgcttt cccaaattta ttctcctgta ttttccttgt   4320
gctttttttt tttaccagga tgactctggc cttccctttt gcaaatagtg acttcattac   4380
cttttaacaa aagaccaaat agcctttgta tgcttgaaat cgaagcagaa tttacggctc   4440
aatttctcta ggagatgtgt agcagtaaca taaaacgtgg ttaaagcaac ttgtaagcac   4500
tgccactgtc caatttgaca tgactctatt actatttaga gtgtcaaata gtgtttcttt   4560
tgactaccaa tttttcaatt tctttttat accttttttc tttgactgtg acttatagta   4620
tattttatgt agtttcagaa tatatatttt agtttttaaa gaattgatgt ctgaaagtac   4680
agccaattag atggtttcac cctcgtactt taaatcttat aagttgtctt aggttaaagg   4740
aataatatgc atgattacat tgtttggatt gatattcaga agatcaaatg tgccggacaa   4800
aagcttgcag aagatataat tctgtcattt tgttgtttag ataaactacc cttgtcaaat   4860
acctaaaact aattcatact tttcaggatc cttcttgatt ggactactct gatcttcttc   4920
catatattga tatcctattc tttttgcttt taggttaacg gggagatata taaccataga   4980
gacttacggg aaaagctgaa gtcccaccag tttcgaactg gcagtgactg tgaagttatt   5040
gcacatcttg taagtacttt cagaatatat ttagataact atacatgact tctcagtttc   5100
tgtgcgcaga atgatttcaa aataccatga ctcaaatttt tcatcaaaag cgaaaaaggt   5160
ggattgtagt aggagaatga gatttttgt cataatttct ttcttatggt acttgaactc   5220
```

-continued

```
cgcaatctac ctatcgcagt atgaagacta tggagaagac ttcgttcaca tgttggatgg   5280
aatgttctcc tttgtgcttc ttgacacccg tgataaaagt ttcattgctg ctcgggatgc   5340
aattggcatt acacccccttt atatgggatg gggtcttgat ggtatgtaat tgttccattt   5400
cataattttt ggtatattgt ccttttaata aatagcccgt gagctatatg aagttccttt   5460
gttgtttcct tgttttttat ttgactgatg tatctttgtt gttttgccta ctattagggg   5520
tgtcaatggt tcggttcggc cggttatttt ataaaatttg taccatacca atttttaggt   5580
tattctatta tgtataacca aaattagact ttttgaaacc gtcccaatca tgtcggtttc   5640
tcttcggtat cggtacggtt cggttaattt tcggtatttt ttaatatcat gtaaaattca   5700
ccagtagaag tagaattgca ataacataca ttcttttata ggacttagca aaactctcta   5760
gatattttta ctgtttaaag ggtgatgaat taaaaaaaaa gaaaagaaag atggctagaa   5820
tatagatcca tcaactatta tacaacagcg taaaagaaat caaacaaaga caaagaaaat   5880
attaatcaca cgagttgaaa gatataccaa ggtaggactc aagaataaag tctatagaag   5940
attaaatatt caaaaagata aatctaaatt atatgaaagg aaacatattc aattcattgt   6000
agtttgctac tcataatcgc tagaatactt tgtgtcttgc taataaagat acttgaaata   6060
atttagttta agtagaagta gcataatagg ttttatgaat tagtattttg agtttaatta   6120
cttgttggct tgtaataatt ttcataattc caaggctcaa agaaaattta ttgcattatt   6180
atttttaaac ttactaaata aatatatttt ctacatgtaa aatttattcg gtatggttct   6240
gtatttttc ggtttatttt tataaaataa aaaacctacc ctaattatcg gtgcggttgt   6300
agatttatat aaaaacctac ggtttcttaa aaagaaagct aaaaatcggt tcggtgcggt   6360
acggttcggt cggtttagtc gattttcgaa tatccattga cacccctacc tactataatg   6420
ctggtctcat gctgttgtta caaacaaatg atgtataata gtgcatagta catgttttct   6480
tgccgctgta gatcaacaat gtaccaagaa catctgtctt agctagttca acctaatctt   6540
cagttatcta tcattccagt gaataacaca tatagagtta ggccgacatt acctaaggcc   6600
aactatacaa cattgtgagg tgcgactaag gaactctgaa cactgatcgg gagaaaaagc   6660
aacttatccg tgtttgtttt gaagtactat gaggaggcag caaccttgct ggatttatca   6720
cttgacagta aatgtcaatg gttgaggaac atttttaatg accggaggag aaacagagaa   6780
gagaagaaat aattgatttt aaaaaagcag aatagaaaat tttgtgaagt cgtatgttaa   6840
tttcaatgaa gaggatcaac aggtgcaata tttgacttgg cacctagcat gtagaagttt   6900
ctggttgggg ttgagcatgg taggcactgt tgcttttaca actgtcatta gagtcggaaa   6960
catattgtat tcttgaggga gcgttgctat ggataaaaaa ggcctatcta ctacttgata   7020
tttgggcatt cagaactagt tgtctaggag gaagaaaagg atttaaaatg gtgagtattg   7080
taggctttct ttgccgtcca ggatgcctgg gctagttccc tgaattggga tactggtgga   7140
ggatttcctg aaattgatca tggccctgat atgttagggg ataagaacat tgaaggatcg   7200
aaggaaggtg ccggcgctaa gttttgctag aaatgaacag ttccattatg gcttttgtca   7260
aagatgggaa tggaattggc cccaacttct aggcatctcc atccatcgtc aggtgaacta   7320
aagtaaggtt acactggtag aatttttcat tatttcatat taagtaaggt gaagccgtca   7380
acaatcattg cgtgagaagg aaccaggaac aaaatctaga agatgtctac taaagtgcta   7440
atagataatc tgcaaaattt agcacggtaa ggctagtgta gatctggttc aaattttaaa   7500
ttggtccaaa atgcgttaat aaatgtcggg cctcgttttg gtcccccgaa aggttgctaa   7560
```

-continued

```
ataaagactt gacaaagaaa caggtgaagg agaagcccaa acatttgaac aaactacacc   7620
tagcctaaac aaagtgattg tttgcgagga ggaaaagcga gcatgcggag agagcctcaa   7680
acacaaaaaa tggcctagtc ttgtaatgag tctagccaaa tcatgtaagc tccgactttc   7740
aagagagatc aacagaaaac ttcgtcaatc cggataaatc aagaaaatta tgataatgga   7800
aaggaggctg gacattctac tgccgacgca acccctggtt ttggagtcag tgagacaagt   7860
ggaactaaag aagaatatgg atcaaaagag tttatccagt tgacacctga tagactcact   7920
acatcagttt tcagttcaag aacatttcaa ttcttgctga taaagatagt tgccgataaa   7980
gataggcaaa ctgttaccta ccaatcaaag gaggttgttt caattgagtt agaggtatca   8040
aaggaggagc cagtatatat agagcaagtt ttgatgaagg gagttgcctc tatttgagac   8100
caccaggtac tcaagtgctt cccgtagttc ctaggcattt tatgatggat atgatagaga   8160
aatgtcttat tgacaagaat atactagggc tacagggata atagggttgg gaaggtgagg   8220
acttctttgg ttgctgtcag gaacttggaa acaaagggag aaaggggttg gaatcaaagg   8280
ttttgatttc gtttttgatt tataaggaaa taatgggtag tggatggagt cgaggatagg   8340
aaagaggttt accagttgca ccattgaata tgtaattaga gacactatcc tcttgttagg   8400
gaacacgact atcacaagca cgtaagggtg agtgaaagct ccgacatgga cgtggtttat   8460
tcgggtatgt tggcacgaag ccttcgtgtc taggtttggt gttgggttaa gtgcaactcc   8520
ttaggaaggc aaataaactt gggacagatt tgatagttgt cggaagttgc acaatgatga   8580
tattttcttt atccaaacgc tacgaatgat tgcacatata gtaactagag ttatttctca   8640
tttgagcttt tatatgtaag aatcaaataa aatgattgat gaaatgcatg aaagctcaaa   8700
tgagaaataa ctagttgtga gaatgcacgg gggaaaaata tattatattg attaaagtgt   8760
tgtacaaccc tatttagata cagtaattac ataataatag gtatctactt cccgatgtgg   8820
gacactagac atgactaact acttaacaat ccccctcaag ccggtgcata taaatcatat   8880
gtatcgagct tgttacagat gtaactaata cgagaaccag taagagactt agtgaaaata   8940
tctgctagct aatcattcga ctttacaaac tttgtaacaa tatctcttga gagtattttt   9000
tctctaacaa agtgacagtc gatctcaatg tgtttagtcc tttcatagaa caccggattt   9060
gacgcaatat gaagagcagc ttgattatca cacaccagtt ccatcttgct gatttctccg   9120
aacttcaact ccttgagcaa ctgcttgatc caaactagaa tcacacgttg ccacaaccat   9180
ggcccgatat tcggcttcgg cgctagatcg agcaactaca ttctgtttct tgctcttcca   9240
agagactaaa ttacctccta ctagaacaca atatccagac gtagaacgtc aatcagcagg   9300
taatcctgcc caatcagcat ctgtgtaccc aacaatctgc tcgtggcctc gatcctcaaa   9360
tcgtaaccct ttgcctggag ctgactttat ataccgaaga atgcgaacaa ctgcatccca   9420
gtgactatca cagggagaaa ccataaacta acttgcaaca ctcaccggaa aagaaatatt   9480
aggtctagtc actgtgtggt aatttaattt gccaaccaac ctcctctatc tcgtaggatc   9540
tctaagatgc tccccctgtc catgcagaag cttagcattc ggatccatag aagtgtcaac   9600
tggtctacaa cccatcattc cagtctcctc aagaatgtct aaggcatatt tccgctgtga   9660
aataacaata cctgagctag actgagcgac ctcaatacct agaaaatact tcaatctgcc   9720
cagatcctta gtctggaagt gctgaaagag atgctgcttc agattagtaa taccatcttg   9780
atcattgcca ataataataa tatcatcaac ataccactca actttggcat ttctatctca   9840
atttggctgg aatatcctgg acaatgccca ataacactgc gtctcttctc agtagctgga   9900
acaatggagg ggcaaatatt aaacagaaga aatggtggaa agtagttcct gcttgtatct   9960
```

-continued

```
ggtgggtcat gtggaaggaa aagaatgcag agtttttgaa gataggccta gctcttagcc  10020
tcttaccaga aaattaagct taattgtttt ttgttatttc atttttggtg caaagagagc  10080
tatagggagg atgtacattc tttactagat ttgctagaag aaatgtaatc gattagaata  10140
ggcaaggcag ttgcagatct tttggggtct gattgtggct tacactatct cctgtaaata  10200
tttttaatct tttatataat ttgttaccat tctaaaaaaa aacataaacc accagataaa  10260
tatacagatt aggagcagaa tgtcgataaa gcacagagtg atccgcttca ctacgagtca  10320
tgccgaactc ctgaataatt atgctgaact taccaaacca agctcgaggg aactgtttca  10380
aaccatatag tgacctgcgc aatcggcata caagaccact agacttccct taagcaacaa  10440
aaccaggtga ttgctccata taaatttctt cctcaagatc accgtggagg aaagcattct  10500
tagtgtctaa ctgataaaga ggtcattgac gtacaacaac catgaacaag aagagacaac  10560
cgatgctact ttagccacgg gagagagtgt cactataatc aagcccaaaa atctgagtgt  10620
atccttttgc aacaagacga gccttaagac gatcaacttg gccatccggg ctgactttga  10680
ctgcataaac ccaacgataa ccaacaatag acttacttga aggaagagga acaagcttcc  10740
aagtgccact cacatgtaaa gcagacatct cctcaatcat agtttgtcgc catcctggat  10800
gagatagtgc ctcacctgta gactttggga tagaaacaat tgacaaagat gatataaaag  10860
cataatgagg tgatgacaga cgatgataac ttaaatcgac ataatgagga ttaagattaa  10920
gagtggatca tacacctttc cgaagtgcaa tcggtgtact aggaagagac aagtccgcag  10980
taggagcagg gtcaagtgta ggatgtgaat cagttgggcc tgatgctggg tgcggacgac  11040
gatgatatgt caagagtggt gttccggtgg cggggaatct aggaggagcc acactagact  11100
ccccaacggt tggaatgggt aagacttatg tggcggaagg tgaaggagga gctatagtaa  11160
gctctttaaa ggtcggtata ggtaagacct cagatatatc aaggtggtca gaagaggtaa  11220
agaaaggttt agactcaaaa aatgtgacgt cagatgacat aaagtaatta cgaaaatcaa  11280
gtgagtaaca acgatatccc ttttgaacac gagaataacc aaggaagaca tacttgagag  11340
tacgaggagc taacttatct ttcctagggg ctaaattatg aacgaaacaa gagctcccca  11400
aaacacgagg aggaacagag tataagggtg actgggaaac aatactgcat acggaatctg  11460
attctggatg ggagatgaag gcattcgatt aaccaaataa caagctgtga gaactgtatc  11520
gcctaaaaaa cgcaacggaa catgagattc aaagagaagt gtgcgagcag tttcaatgat  11580
gtgcctattc tttctctctg caaccccatt ttgctgaggg gtataaggac aagaggtctg  11640
atgaataatt ccttgagaag tcataaagtg ctaaaattga gaggataact attctaaggc  11700
attatcactg cgaaaagtgc gaatagaaac accaaattga tttttaattt catcacaaaa  11760
attctggaat atagaaaaca actcagaacg atctttcatt aagaaaatcc aagtacatct  11820
tgaatgatca tcaatgaaac tatcaaacta acgaaatccc aaggttgagt tgactctact  11880
atgaccctat atatcagaat gaactaaaga aaaaacagac tatgcatgac tctcaatact  11940
acgaggaaag gaggctcagg tatgtttccc gagctgacat gactcacact ctaatgtaga  12000
taaactaggc actatcttct gaagcttgga tgtcctaaac atctgtgaat taggtccgga  12060
ggatctgtaa ctagacatgc cttggaggaa ttgagtgggt taaggtagta aaggccttct  12120
aattcaagtc ctgttccaat cgtctgtccg tactgcggtc ctgcataata aaagaatcat  12180
taataaaata tataccacaa tggagggcac aagtcaaacg actaacagat gcaagattaa  12240
aaggacaacc agggacataa agaacggaat ctagagtgac agagggtagg ggattcgctt  12300
```

-continued gtccaactcc ttttgcttca gtttgagacc cgttggctaa agtaacagtg gaaagagact 12360
gtgaatacgc aatatttgac aaaagtgatt tattaccaga gatatgatca gaagcggttg 12420
agtccacaac ccattgtcca agagtactag actgggaaac acaagcaaaa gaattaccag 12480
caacaaaagc atcagtctga gcaacagagg ctacttgtgg agatgtctgc ttacttgctc 12540
gatactgaag gaacttatta tactcccctt ccgataaaga aaatacccgg ttacctatag 12600
tctcggtctg agcaacataa gcatttttgg gtggacgacc atgtaaagaa tagcacacgt 12660
cacgagtgtg tccaagttta tgacaataag agcacttggg tctagatctt ccaaaacgac 12720
ctcctcctcg tctattctcc atagtttgag atgcccgatt gttcacttac tgggatacga 12780
gaacagatga gtcaggtctc tgtgatgagc tcactgggtg acttggtgct gcagcaaggc 12840
gaagtaatcg agagaataat tcatcaactg tggggacagt cggactagcc aaaatctggt 12900
cacgtactga atcaaggtca ttagggagtc catcaagtgt aagaactaga aacatcttct 12960
gtcgttgctc ttgttgcttt ttaatactag cagaaactgg catcaacgtc tcaaattctt 13020
ccatgattgc ctgtacttgt cccctagtaa gtagacatat ccaattcctg tttcttcaag 13080
cttgtcattc gcgatattac atcatagaaa cgagatatgt cattagtgta taaattacga 13140
gccttttccc aaactaaata acatgtctgg aatggacgga acaagggcat caacttggaa 13200
tcaatagatc gccacaggat actacataac tgagcatcga ccttcttcaa aagtgttttg 13260
gccttttcat caccttcgct agcctttttt gttaaatgat cttgaactcc ttgaccttta 13320
caacacaact cgacagacga agcccaagct aagtagtttg aacttctcat taaaggttct 13380
gaggtaatca taatagcaga acttccagaa ctcgtgtttt tagacccaaa tacatccact 13440
cccaaagaca ttattggatt gaaaagagat ctagcaaatt agcaccaaat aaaacaaaga 13500
atcaactgtg gttgcccaaa aactgccgga aaactactgt agttgccgga aaattttcaa 13560
agtgctcgga atcaaaaaat aaaaatatgg gcaggctcgg aatggtagag cgatcagact 13620
aacctaaagg agtttttctg aaaaaattga cggaacgggc tccatgcgct ggtgcgtgga 13680
gtagatctcg ccggagaaga ctgtctccga tcggcgcgtg gcggtgcgtg aggcggctta 13740
tgacggaggt gttcgctggg gtttggtcgc cggaagttgg gggaccttgt ggtggtgttg 13800
gtttttgcac aacaccgatg gaattggttt tgacgaaaaa tagccctaaa aggtcaccgg 13860
aattgaagca cggcgacggc tggttttttt tttccccgga tgttttctca ctgccgctct 13920
gataccatgt gagaatgcac gggagaaaaa tatattatat tgattaaagt gttgtacaac 13980
cctatttata tacagtaatt acataataat aggtatctac ttcccgatgt gggacactaa 14040
acatgactaa ctacttaaca ctagtaacct catggttctc atcctacttc attgaccact 14100
tggccacatc cttgggtgcc tgcactgtag ttgtagctgt aatgaagata gttttttttc 14160
ttttctggat actcttatat tgtgacaatt tttctctatt tgctgttaat ggatgaggtt 14220
atgtgactct ccggtggtga gaatgttaat gaacatcaag ctcacatgtc atttcatttt 14280
ctgattgatc ttgctcttca ctctttacga gtttaatgtg ttagtccttc caagttctgt 14340
ccatctatct ttctggtgtg cttaacccat gtatattgga ccacactttg tattcatgct 14400
gattgcaaca aagcctgact gatcctgaac tcctccttta tgccttaggt agaaattttg 14460
tgtgtttagt gttacatgtt tcgcttcaaa ggaaaaaggg agaaacttaa ggtagaatcc 14520
tgctccttga cctttggatc cttgcacatt gaagtggaca gacatgtttg ctttgctttg 14580
atgagttgtt ttagtagtcg gtctaaacaa ctgctgatgt attctgcttt attgtaagtg 14640
tctataattt ttatctttcc acaatttgct ttcagctctt tctgcatgta gagaaaataa 14700

-continued

```
cagaagcttc tatttgatca tgtaatattg actgcgcaag ttcagtttta aacaactttg  14760
gctatgcata tgcaagcaat gacctgaaat aaatattatt ttttatgcag ggtctgtatg  14820
gttttcttca gagatgaaag ccttaagtga tgactgtgaa cgatttgtta gtttccttcc  14880
cggtcacatt tattcaagca aaaatggtat gcccatacga agctcatttc tgagcttgtg  14940
cttcatttat gttgatagtt gatcatgttt cctatacgat cagcgtactt ttgctattta  15000
tttcagattt actttaggac cctgtcggaa acagtcttga aacccttatt gatggtgtaa  15060
ttgttatctc ttgatcaacc aaaggagtaa ttacatgtaa ttattacaaa tttgcaataa  15120
aataactttt aggataacca gtggagctta atgaatcttt taggatattt gggatgctag  15180
agtgatgtac ttttgataat gtcggttaat ataaaatcct ctgactttgt actgatgtac  15240
tggctgagca gattttatat tactttctag tccctctgca aataaaaaaa ttgtgagact  15300
gcaatataac accatttttt aatgcattta caatgtttaa acttgatgta gcagtgaaga  15360
acatgtcgac cttaaacaga ggttctattt gtcctagata aaggaacatc agcgtaatga  15420
aacattacag gagagaagct ctattgagtt tttgttaatc tagagggagc ccgtaaatag  15480
aacaccaatt catctgttat atgacttctt tttcattttg gaacgtttta aaagtttgac  15540
aacatttttt gatctccgta cactaaactt tttgatgtat taaactaact atttccacta  15600
ctttaatatt ttcttcctta aacaactcat gttagcatct taaactgtgt gtgttcaata  15660
ccctcataaa aaattaaacg agtatttttt tatatttgct tatgcccttg gagattggga  15720
tggggaagtt catcatttga ggtgaaaggt aaattctttt ggatggacaa aaagtgaacc  15780
tcgtctttgg catggaggga ctatttaaat cgtcatcatt accaaagtca tcctttcaaa  15840
tgtttacttt caagaactat tcatgctatt tctcaagtat attatgggtg caggaggact  15900
cagaagatgg tacaacccac catggtactc agaaaccatt ccttctactc catatgatca  15960
ccttgtctta cggaaagctt ttgagaaggt cattctattt tggatgtcgc ttgtttctga  16020
gttgtacata atatttaggt gccactttgt tatattttga acttcatcaa aagcctttgg  16080
ttttttgagg acacatatcc ccttgactga ctgggcgctg aatttccttg atgtattgtg  16140
cttattttga ttgtcctctt ctttgtaata ctcttgccta taaataaacc ttctttatca  16200
aaagaaaatg ataaaatgtt aataacactt tgtgatatat gttgaagggg agtcttggca  16260
taactggtaa agttgctgcc atgtgaccag gaggtcacgg gttcaagccg tggaaacagc  16320
ctcttgcaga aatgtagggt aaggctgcat acaatcgacc cttgtggtcc gacccttccc  16380
cggaccccgc gcataacggg agcttagtgc accgggctgt ccttttttttt tgcatagact  16440
ttacatgata ttttatttca atctttatca attctttttt accttcacat gcaaattata  16500
ctaccgtatg tgaaatatgc aatagttttt cccgcaattt tcatctttca tgtacctctc  16560
tctactatcc ttgtattact actgatttgg tgcattagat gttaatttta ttcccaacct  16620
ttactttatg caggctgtag tcaagcgact tatgacggat gtaccatttg gtgtgcttct  16680
ctcaggtgga ctagattctt cacttgttgc tgcagtggcc aaccgttatt tggctgatac  16740
tgaagctgcg cgacaatggg gatcacagtt gcataccttt tgcgtaggct tgaaggtggt  16800
gatgctccct tttgtaaact tgctctgatt agggaattgc tagctgtatc atcccaattc  16860
acatggaagt tctagaccat tattgctgtt tcttttccat atatagggat tttctgaaaa  16920
tagtaaaaag gaaatggaat ttctcattat taaagatacc aaatgccttt ttgggaaatg  16980
atcttacagt tgaatctgaa atttcctttt gacattgtga ttaattctga tatgaatttg  17040
```

```
gtccatcctg gctttccttc tcttgattgt agattttttt tctctttttg caattatatg  17100
cctttgtatt tcatatctct tattatgcta ttattttatt atgcattttt atggtactaa  17160
tatatcggct cctgttgctt tttttgagcc gagattttgt ttatttctgc tatcacgtcc  17220
tcctgaaaaa gtgctactat cttgtattca tgcgggagtt tgaaatttgc aagtgtataa  17280
ctttacaaaa tgattcgaac tgatcacagt tcattgctaa taaactttta taaaaagcag  17340
gtattgttgt gatataatgt gacacttaaa taaatttaaa cctacatcct ttcgaaatct  17400
ctaatagctt cactaatatt tcttgtgcta aattcttcca acacctctta tcgatgccaa  17460
atttggcaga ccttagtgca attgaaagtg tttagtgttc tttatgcagt aggtatgtta  17520
ttgtccaaaa tgacagaaat aaagttagag atttgttgaa aagccacttg gtgtgattga  17580
gcagttcgga gatgagtgat ttatccatct ttttatactt ttagtgtttt gttttctttt  17640
atattgtttt ctcttttgct tttgtcattg taattaaggt tgtcttttgt ttgactttag  17700
ggttctcctg atctgaaagc tgccagagag gtggcagact accttggaac tcgtcaccat  17760
gagtttcact ttactgtgca ggtaactttc ttcataaaga catcctatgc tgattttcct  17820
tataggagta taactgctta agtcaaattg gctatctact tctttctatt gctacatcag  17880
gaaggaattg atgcactaga tgaagtcatt tatcatgttg aaacatatga tgtgaccact  17940
atcagagcca gtacaccaat gtttctcatg tctcggaaga taaagtcctt gggtgtgaaa  18000
atggttctat ctggtgaagg ttctgatgaa atttttggcg gttatttata tttccacaag  18060
gcacccaaca antttacaca aaaatgacac aagttatgca gaaaaaatag tcctcaatgt  18120
catgggagac cagggttcaa atctgaggtt aaaaaaaata ctaggtgaac tcttctaatc  18180
cgtttaagcc ttggtagata gagttaacta gtatatgagc tagttagagc tagcaggtac  18240
ctggtagatt agtgcaggtg cacacgagct gactcaaaac caccattatt aaaaaataag  18300
aaagttttca atgttgttcc accgtgaatt catgatgtgc cgactttcct gtgtttatct  18360
ctggatagat gaagagtgtt tttggatctt gattaattct gtttggcccc tttgaggttc  18420
tgcaagctat ttctagactc aaacttgctg cgatctatgt taggtctaga gaatatctgc  18480
caaataaaac aatggaaggt acactcaagt attttatctc catattacaa gtcagtgtta  18540
gttgaatggg tctgatatat gggacagaaa atggcttcat acccataacc tcattaaaat  18600
gttgctgatg tgctgatctc atctgtacat ctagtataat cctaattaca aattaatgca  18660
tctctttgcg gtgactatag tatgctgaag aacttttctt gaaacattgc agatcagacc  18720
tgatctcgga agaatagaaa agtgggttct acgcaatgct tttgacgatg atcagaatcc  18780
ttatctgcca aaggtttgtt tgttttcttg tatcaggtcc aaaatcaaaa tctttgttta  18840
ttcatttgca taaacaggca gtagactccc aatacattgt gtacacttat gcacaaatgt  18900
atgagatgtg tattatatgt gtcacatata agggtatttc cacatggtgt ttattgatct  18960
agagaaagcg tacgacaggg ttcctaggga ggtcctatgg agatgcctag aggttaaagg  19020
ggtcccggtt gactgcatta gggtgattaa agacatgtat gatggagcta agactcgaat  19080
taggacagta ggaggcaact ccgaccattt tccggttgtt acggggttgc atcaagggtc  19140
tgcgttcaac cctttcctat ttgccttggt gatggatgct ataaccgcat catattcaag  19200
gggaggtgcc atggtgcatg ttatttgctg atgacatagt cctaattgac gagacacgac  19260
gcggcgtcaa cgagaggcta gaggtttgga gacatgccct tgagtctaaa ggtttcaggc  19320
tgagcaggac gaagacggaa tatctcgagt gcaannnnnn nnnnnnnnnn nnnnnnnnnn  19380
nnnnnnnnnn nnnnnnnnnn nnnnnnnnnn nnnnnnnnnn nnnnnnnnnn nnnnnnnnnn  19440
```

```
nnnnnnnnnn nnnnnnnnnn nnatcgtata tgggtagggt ggatgaagtg gaggttagca  19500
acgggagtct tgtgtgacaa gaaagtgtca ccgttactaa ntctcgagtg caactttggg  19560
gccgagccga tggaagcatg agtggaagtg aggctcgact cacaagtcat ccctaagagg  19620
ggtagtttca agtaccttgg gtcagttatt caggggaccg gggagatcga cgaggatgtc  19680
acacatcgta taggggtggg gtggatgaag tggnnnnnnn nnnnnnnnnn nnnnnnnnnn  19740
nnnnnnnnnn nnnnnnnnnn nnnnnnnnnn nnnnnnnnnn nnnnnnatag gggtagggtg  19800
gatgaagtgg aggttagcaa cgggagtctt gtgtgacaag aaagtgtcac cgttactaaa  19860
aggtaagttt tacagagcag tggttaggcc tgctatgttg catgggaccg agtgttggcc  19920
ggttaaaaat tcacacatct agaagatgaa agtagcagag atgaggatgc tgaggtggat  19980
gtgcgggcat acaaggatgg acaagattag gaatgaagtt attcgagaga aggtnttgag  20040
ccgagggtct cctggaaaca gcctctctgc ccctcggggt aggggtaagg tctgcgtaca  20100
tactaccctc cccagacccc attggtggga ttatactggg atgttgttgt tgttgttgtt  20160
gttgttgtac atataagggt attatatgta cacactcctc ccacctttca cttatatatt  20220
cacgtaaaac acatgcatgt gtaaaaccta tatatgtgtg tgtgatatat ataataaaat  20280
gatgtttgaa aagacattat gatcaagtag ttgatcttca tctgctttcc gtttttagca  20340
tatcttgtat aggcagaagg aacagttcag tgatggagtt ggctacagtt ggattgatgg  20400
tttgaaggat cacgcaagca gactggtgag ctttttagtt gttttctctt ccctcctctt  20460
ccattcttta tcccttcctt tgtggttttg ttgaacacat ctcgtatatt tggtccaggt  20520
ttctgattct atgttagcga atgcaagttt cgtttacccg cataacacac ccacgacaaa  20580
ggaaggatac tactatagaa ctatttttga gcgatatttc cccaaggtgg gtcttagata  20640
gtcttctttt ccttgttatt catgttcaat tttgatattt ttgtcccaaa caatgttttc  20700
tttttcttcc ttctgttaac aaggtcgctt ctatcttcat atttgttgat aaaggtaatc  20760
acattgataa ctattatttg gagcagaatg ctgcgaggga aacagttcca ggtggtccaa  20820
gtgtggcatg cagcactgca aaagcagtag aatgggacgc agcttggtcc aagaatctag  20880
atccatctgg acgagctgca ctcggtgttc atgcagctgc ttatgaggat gcatcagagg  20940
ttaaaaccac agtcgcaaca gatacccctc agaaacttga agttgataaa gctgcagtag  21000
ctgtttga                                                          21008
```

<210> SEQ ID NO 10
<211> LENGTH: 581
<212> TYPE: PRT
<213> ORGANISM: Nicotiana tabacum

<400> SEQUENCE: 10

```
Met Cys Gly Ile Leu Ala Val Phe Gly Cys Ile Asp Asn Ser Gln Ala
1               5                   10                  15

Lys Arg Ser Arg Ile Ile Glu Leu Ser Arg Arg Leu Arg His Arg Gly
            20                  25                  30

Pro Asp Trp Ser Gly Leu His Ser His Asp Asp Cys Tyr Leu Ala His
        35                  40                  45

Gln Arg Leu Ala Ile Val Asp Pro Thr Ser Gly Asp Gln Pro Leu Tyr
    50                  55                  60

Asn Glu Asp Lys Thr Ile Val Val Ala Val Asn Gly Glu Ile Tyr Asn
65                  70                  75                  80

His Arg Asp Leu Arg Glu Lys Leu Lys Ser His Gln Phe Arg Thr Gly
```

-continued

```
                85                  90                  95

Ser Asp Cys Glu Val Ile Ala His Leu Tyr Glu Asp Tyr Gly Glu Asp
            100                 105                 110

Phe Val His Met Leu Asp Gly Met Phe Ser Phe Val Leu Leu Asp Thr
        115                 120                 125

Arg Asp Lys Ser Phe Ile Ala Ala Arg Asp Ala Ile Gly Ile Thr Pro
    130                 135                 140

Leu Tyr Met Gly Trp Gly Leu Asp Gly Ser Val Trp Phe Ser Ser Glu
145                 150                 155                 160

Met Lys Ala Leu Ser Asp Asp Cys Glu Arg Phe Val Ser Phe Leu Pro
                165                 170                 175

Gly His Ile Tyr Ser Ser Lys Asn Gly Gly Leu Arg Arg Trp Tyr Asn
            180                 185                 190

Pro Pro Trp Tyr Ser Glu Thr Ile Pro Ser Thr Pro Tyr Asp His Leu
        195                 200                 205

Val Leu Arg Lys Ala Phe Glu Lys Ala Val Val Lys Arg Leu Met Thr
    210                 215                 220

Asp Val Pro Phe Gly Val Leu Leu Ser Gly Gly Leu Asp Ser Ser Leu
225                 230                 235                 240

Val Ala Ala Val Ala Asn Arg Tyr Leu Ala Asp Thr Glu Ala Ala Arg
                245                 250                 255

Gln Trp Gly Ser Gln Leu His Thr Phe Cys Val Gly Leu Lys Gly Ser
            260                 265                 270

Pro Asp Leu Lys Ala Ala Arg Glu Val Ala Asp Tyr Leu Gly Thr Arg
        275                 280                 285

His His Glu Phe His Phe Thr Val Gln Glu Gly Ile Asp Ala Leu Asp
    290                 295                 300

Glu Val Ile Tyr His Val Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Leu Ser Gly Glu Gly Ser Asp Glu Ile Phe Gly Gly Tyr
            340                 345                 350

Leu Tyr Phe His Lys Ala Pro Asn Lys Glu Glu Phe His Gln Glu Thr
        355                 360                 365

Cys Arg Lys Ile Lys Ala Leu His Leu Tyr Asp Cys Leu Arg Ala Asn
    370                 375                 380

Lys Ser Thr Ser Ala Trp Gly Val Glu Ala Arg Val Pro Phe Leu Asp
385                 390                 395                 400

Lys Glu Phe Val Asn Val Ala Met Asn Met Asp Pro Glu Ser Lys Met
                405                 410                 415

Ile Arg Pro Asp Leu Gly Arg Ile Glu Lys Trp Val Leu Arg Asn Ala
            420                 425                 430

Phe Asp Asp Asp Gln Asn Pro Tyr Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Asp His Ala Ser Arg Leu Val Ser Asp Ser Met Leu Ala Asn
465                 470                 475                 480

Ala Ser Phe Val Tyr Pro His Asn Thr Pro Thr Thr Lys Glu Gly Tyr
                485                 490                 495

Tyr Tyr Arg Thr Ile Phe Glu Arg Tyr Phe Pro Lys Asn Ala Ala Arg
            500                 505                 510
```

```
Glu Thr Val Pro Gly Gly Pro Ser Val Ala Cys Ser Thr Ala Lys Ala
        515                 520                 525

Val Glu Trp Asp Ala Ala Trp Ser Lys Asn Leu Asp Pro Ser Gly Arg
    530                 535                 540

Ala Ala Leu Gly Val His Ala Ala Ala Tyr Glu Asp Ala Ser Glu Val
545                 550                 555                 560

Lys Thr Thr Val Ala Thr Asp Thr Pro Gln Lys Leu Glu Val Asp Lys
                565                 570                 575

Ala Ala Val Ala Val
            580


<210> SEQ ID NO 11
<211> LENGTH: 17971
<212> TYPE: DNA
<213> ORGANISM: Nicotiana tabacum
<220> FEATURE:
<221> NAME/KEY: misc_feature
<222> LOCATION: (1389)..(1389)
<223> OTHER INFORMATION: n is a, c, g, or t

<400> SEQUENCE: 11

atgtgtggaa tactagcagt tttcggttgc attgataatt ctcaggccaa gcgttcccga     60

atcatcgaac tttctagaag gtagaatttt tttaaaaaaa aaattgcatt ccaatttttc    120

tacagcattc ttattctttg gggtgacaat ggtatgcatg tgttttggat ttgctattcg    180

tggacttgtt cgctttctcg tggtcttcga tttgtttttg ttaatttata atcagtgttt    240

ttatatggat ttcttttttg aatctctcaa atatatgaca tttgatttcc acgagaaaat    300

ttggcatttt tatggttctt atgatatgcg gttaaccctt cgccttgcat cgcttcagcg    360

ctttaaaaga cgaaatgatg gctattagta atactgctag agtggttatt gaattacatt    420

aaataacaga ttgctagtag atcaaattca gaatgacagt gaaatatctc tggaaacttg    480

aatccccgtt caattcgctg gtaaaacctg gcaaaaaaat agctttatct caaaggagag    540

tatgtcactg tgaaattggt ggtatgtgtt gtttaagctt taaggcatga tatgctgctc    600

ttaggtgatg tcaggatgat aataccatcc ttttcacact agactcagct ttgaagcact    660

ttcatctcag ttaatcggtg gaggaaaatc tagtttgctt tgggcataat ataccaaatg    720

tcttcctttt gttttctagt gttgtttctc aagaattgaa aaaccaacct acaatatagt    780

gatataatta actagttagc tcttcctgtt tttctgaaaa tttccaataa ttgagaagcg    840

tttacaggtc aattagtaaa gggagaacgg aacatttttt tcctctaaag aacttctctt    900

tttccataca gaatgacttt ctatacaagg cctaagtctg ctttagtgtc tgcgattaag    960

catcttctgg gaaacttcac acttgaaaga agtagaacta ggagggggca ggtctagcaa   1020

gataattgct tcagtcattt ctcataaaaa aacattgttt cattcattat gtgcattcat   1080

atagagttgg ttaagctgct aagctgagct aatagtatga tagctatgaa tctcgacaaa   1140

gtaggttgct tcttagggct ttattctttg gctccgtaaa gaatttcttt tggaagggct   1200

tcagagtggg taggactgtt ctgatgataa gctgtaacac caacgaaaca agcctttgta   1260

gctgtggaag tccgaggggg tggtggtggt ggtggtggtg tgagagttag agtggtggag   1320

gagaggggag gagtgaagag aagtttatat tttaaagaat agggccttga gaacttttag   1380

tagtgagcng gggggggggg ggggcagagg ggaggagtga agagaagtat atattttaaa   1440

gaatagggcc ttgagaactt atagtagtaa gcatgcatta ttattattgt tgttattatt   1500

attattatta ttatttttat tattatgtaa gatgtaatta cttagctaat gaggtttttc   1560
```

```
caactatttc caaattgtga aatgtgttga aagcataatt aagtatataa aagcgtgttc   1620
tttctaatat ctttagcttt aagaggagat aatcacaaaa tttatcttga taatatagca   1680
gacaattttt cctagttcaa atctcacgtc acccttcata aaaaatttcc acgtgcttgg   1740
cttgcatgtt aggggacgtc ttgacataat taaacaaata taattgtccc tctctaacag   1800
cttaagcttt tagatgaggc ggtcaacaat tcaacaattt gcatttgttt gataagaagt   1860
tatattaaaa gaacacttaa aaggtgtcag tatgtgcaca aactcaaggt gtagactaac   1920
tagaagtcaa ttcaaatttt ctgcttgttc tctctgtttt acttcttttg cactatagaa   1980
attgcatttc cagcattccc gaaagctgct tcctttgcat atagacatca catttccagc   2040
gtgtctgata agcgttcttg cttattcctg tccctctact tggttgattt tcctctcact   2100
tagttcactg tcttcttgca cgcattatca aattgtgttc tcaattctct tgccttcttt   2160
tcatctgacc ccacaaaata cctcccaaaa agcctttagt ttctgctttt ccgagtctga   2220
aattatctgc ttattactgc ctttcaagta ttctgatacg ttgaccattg ttttccccag   2280
tagtaatgca ttgttctctg tccaatctct attttttttt ttgtgaacca ctattctttg   2340
ttgcttctgt ttcgtcatcc tcagttcccc atcttctcaa tttgattttc ctcatttaaa   2400
aagcgtgtgc cccttttctt gtgctaccct ctcaaaaatc agttgctgtc atctcgtttg   2460
atctgtcatg aacccagttg atgccacatg tttagttctt tacctctgga caacttttac   2520
ttcctgagaa ccacaatttc ctttccttaa gaaattctta gaaattggtt atgtaaactg   2580
taaagggaaa atttcccagc aatcaccatt tggcctctac gtggcttgct tttcaactta   2640
ccgacacgtg ttcatcccct tttaacaaat gctgaccatt atcttctgct tgttggggca   2700
tgcttcttac ccatggtgtt aaccctgatc tttcgtatca catttttcaa ctcttaattc   2760
tcatcttata aagtgcatat ccttgcctct ttagttgatc ttgggttggg ctgttaatcc   2820
aaattccatg ggctttgctt tgaagtatga taagcattag ctttactaca gtagcatatt   2880
ctacgttgct acagacatga aattttcctg atttgtcttt gatgtgatgt ctggcaagtg   2940
tagattacgc cacagaggac ctgactggag tggattgcat agccatgatg actgttatct   3000
tgctcatcaa cggttggcaa tagtagaccc aacttctgga gatcagccac tttacaatga   3060
ggacaagacc attgttgtcg cggtagggaa atatttatta tatcatttct tagatagtta   3120
agtattttac cagtacatgg actttggaca atatttgtgc gttttgatct tctatagcac   3180
aaacttttct cgtaggataa atttcctcta ctttgagtga atcttaacag gaaaatcgga   3240
ataaacaatt tgtgatttcg aaatttttag ttcttacata tttgaaacat gtgcggtgaa   3300
gtaactaggc gcttgactag gtgaatacgg agaatttcct ctactgttat cgatattttc   3360
tcagttcatt tgaaagatct ctgggtcgtc tagcagtaca actatttagg caacttaatc   3420
aaatcccctt cccatgagtt tcactttctt gacttgtttt atattttgac attttgcaat   3480
gccgaaaata aattgttttt ccattttatg acctttaaaa tgttgaggtg aagggctagg   3540
cggtacttta atcgacttat cggcaacaat gtattagata cagagcacaa acttgtttgg   3600
gtgcctaaat tgatattttt gaaaagtcga tggagtaaat ggaaatatgg attagcaaaa   3660
atattgaaat agtagatcta aacaatggat gactgaattt agaggaggac cttttcttct   3720
ttccttgttg aagtggttat aagagaatta ttggaagaaa atgtaagctt tagggtagtg   3780
ttgcaccata acagtcatgc tttccctcaa ttattagtgt agctgatgaa tgcttttgga   3840
aaggtggctg attttttgct gcgtatttta tgtctttcat catctcaaaa tttgttgtgt   3900
```

-continued

```
tttaacagtg cttggaaggc ctagagtctt ctgaaaaaag taggctgaga aaacatgagt   3960
aagcaaattt cttcctgctg gcaattaatc tttgtatatg aggtgaagcc acataatcta   4020
acatggtatt agacatataa atattatttt tgacatagag cagacagaaa tcttgggtct   4080
agttgctatc tcccttccta ataagatgcc ctcattgcta tatcccaaaa cagattcacc   4140
ctagaacgaa taaatctctc cttgcagcca catatatatt aataagtagt gtaacactaa   4200
aacatttgtg cttctgcaaa gtctgttgaa gtgggcgatt aagtaataaa ttgtgtgagt   4260
ttgactgaag agaaagtaat aaattgtgtg agcttctcac attttcatga taatgtcaat   4320
tcatctgatt gaacttttg aaggacatct ccttttctaa aagtttttgt tcacttcctg   4380
aaaatggttg ctttcccaaa tgtattctcc tgtattttcc ttgtgcttta tgttgaccag   4440
gatgactctg gccttccctt tttcaaatgg tgacttcatt acctttttaac aaaagatcaa   4500
atagcctttg tatgcttgaa atcgaagcag aatttagggc tcaatttctc taggagatgt   4560
gtagcagtaa cataacacgt ggttaaagca acttttaagc actgccactg tcaaatttga   4620
tatgacgcta ttactattta gagtgtcaaa tagtatttct tttgactacc aatttttcaa   4680
tatcttttt atacctttt tctttgactg tgacttatag tatattttat gtagtttcag   4740
aatatatatt ttagttttta aagaattgat gtctgaaagt acagccaatt agatggtttc   4800
acccttgtac ttcaaatctt ataagttgtt taggttaaag gaataatatg catgattaca   4860
ttgtttggat tgaaattcag aagatcaaat gtgcaggcaa aaagcttgcg gaagatataa   4920
ttctgtcatt ttgttgttta gattaacttc ccctgtcaaa tagctaaaac taattcatac   4980
tttctcagga tccttcttga ttggactact ctgatcttct tccatatatt gatatatcat   5040
attccttttg cttttaggtt aacggggaga tatataacca tagagaatta cgggaaaagc   5100
tgaagtccca ccagtttcga actggcagtg actgtgaagt tattgcacat cttgtaagta   5160
ctttcagaat atattcaaat aaatatacat gacttctcag tttctgtgcg aagaatgatt   5220
tcaaaatacc atgactcaaa tttctcatca aaagagaaaa aggtggattg tagtaagaga   5280
atgagatttt ttgtcataat ttctttctta tggtatttga actccacgat ctacctatcg   5340
cagtatgaag actttggaga agacttcgtt cacatgttgg atggaatgtt ctcctttgtg   5400
cttcttaaca cccgtgataa aagtttcatt gctgctcggg atgcaattgg cattacgccc   5460
ctttatatgg gatggggtct tgatggtatg taatttttcc atttcataat ttttggtata   5520
ttgccctttt aataaatagc ctgtgagtta tgtgaagttc ctttgttgtt tccttgtttt   5580
ttatttgcct gatgcatctt tgttgttttg cctactataa tgctggtttc atgctgttgt   5640
tacaaacaaa tgatgtataa tagtgaacag tacatgtttt cttgccgctg tagatcaaca   5700
atgtaccaag aacatctgtc ttaagctagt tcaacctaat cttcagttat ctatcattcc   5760
agcgaataac acatgtagag ttaaccggac attacctaag gccagctata caacattgtg   5820
aggtgtgact aaggaactct gaacactgtt tggagaaatg gaaagcaaca tatccgtgtt   5880
tgttttgaag tactataagg aggcagcaac cttgctggat ttatcacttg acagcaaatg   5940
tcaatggttg aggaacattt tttatggctg gaggagaaac agagaagaga aaaaataatt   6000
gattttaaaa aacagaggag aaaattttgt gaagtcgtat gttaatttca atggctggag   6060
gtgcaatatt tgacttggca actagcgtgt agaagtttct ggttggggtt gagcatggaa   6120
gacactgttg cttttacaac tgtcattaga gtcggaaaca tattgtattc ttgagggagc   6180
gttgcaatgg ataaaaaagt cctacctact acttgatatt tgggcattca gaactggttg   6240
tctaaagctg agaaggaaga aaaggattta aaatggtgag tattgtaggc tttcttttct   6300
```

```
gtccagggtg cctggactag ttccctgaat tgggatactg gtggaggatt tcctgaaatt   6360
gatcatggcc aaagagatat gtcaggggat aagaacattg aaggatcaaa ggaaggtgct   6420
gcgctaagtt ttgctagaaa tgaacagttc cactatggct tttgtcaaag atgggaattg   6480
aattggcccc aacttctggg catctccatc catcgtcagg tgaacaaaag taaggttaca   6540
atggtagaat ttttcattat ttcaaacaag taaggtgaag tcgtcagcaa tcattgcctg   6600
agaaggaacc aggaacaaaa tctagaagat gtctgctaaa gtgctaatag ataatctgcc   6660
aaatttagca cggtaaggct agtgcagatc tggttcaaat tttaaattgg tccaaaatgc   6720
tttaataaat gtcggacctc gttttggtcc cccaaaaggt tgctatataa agacttgaca   6780
aagaaacagg tgaaggagaa gcccaaacaa ttgaacaaac tacacctagc ctaaagaaag   6840
tggttgatag tttggtcgga ggaggaagag cgagcctgcg gagagagcct caaacataaa   6900
aaatgaccta gtcttgtaat gagtctggcc aaatcaagta agctctgact ttcaagagag   6960
atcaacagaa aacttcgtca gtctagataa atcaagaaaa ttatgataat gaaaaggagg   7020
ctggacattc tactgccgac caaccctggt tttggtgtca gtgagacaag tggaactaaa   7080
gaagaatatg gatcaaaaga gtttatccgg ttgacacctg ataaactcac tacatcagtt   7140
ttcagttcaa aaacatttca attcttgctg ataaagacag gcaaactgtc acctaccaat   7200
caaaggaggt tgtttcaatt gagttagagg tatcaaagga ggcggcagta tatatggagc   7260
aagttttgat gaagggagtt gcttctattg gagaccacca ggtactcaag tgcttcccgt   7320
agttcctagg cattttataa ttgatatgac agagaaatgt cttattgaca agaatagact   7380
aggactacag ggataatagt gttgggaagg tgaggacttc tttggttgct gtcaggaact   7440
tggaaacaaa gggagaaagg ggttggaatc aaaggttttg atttcatttt tgatttatga   7500
ggaaataatg ggtagtggat ggagtcgagg atgggaaaga ggtttaccaa ttgcaccatt   7560
gaatatgtaa ttagagacac tatcctctta tttgggaaca cgactagggt gagggaacgc   7620
tccgacaggg atgtggttta ttcgggtatg ttggcacgaa gcttttgtgt ctaggtttgg   7680
tgttggctta agtgcaacac cttaggaaga caaacaaact taggacagat ttgatagttg   7740
tcggaaattg cacagtgatg atattttctt cttccaaacg ttgggaatga ttgcacatgt   7800
agtaactaga gttatttctc atttaagctt ttatatgtaa gaatcaaata aaataattga   7860
tgaaatgcat gaaagcaact gtcttacgcc tgaatgcttt taaaaggcat gctttacaaa   7920
gtttttggta catctatctg acatgacaca ctaacattca ctcttatatg tgtacatatt   7980
taactaagtc caagcctaac tatctaactg gagatatcaa agttcttagc tctttaaagc   8040
tttcttaact ttaggaagat cctgcagtgt tgttttttta taaccgtggt atccaggcta   8100
gcttgcacac atctcgacta attccaccgg gtgcttgcta tctcccacca acacagatta   8160
cctggtaact catgggaaga aatcacctat tgttttgagt ctgctggcat ttgaagtttt   8220
ggactactaa cctcatggtt ctcatcccac ttcattgacc acttggccac atccttgggt   8280
gcctgcactg tagctgtaac gaagatagtt ttttttccg ggatactctt atattgtgat    8340
aatttttttg tattcgctgt taatggatga ggttatgtga ctctccggtg gtgagagtgt   8400
taatgaacat caagctcata tgtcatttca ttttctgatt gatcttgctc ttcactcttt   8460
acgagtttaa tgtgttagtc cttcccagtt ttttttaaga gcgagaagcg caaaaaaagcg  8520
acaagggctc gcctcgcttc aaaagcgaag cgcaaagcga agcgcacact ttattaaagt   8580
gaagcgcaat tcttaaaaaa cataatgtaa accttgcaaa gacacaatat aaaattataa   8640
```

```
ataatcaaaa agttcaaatt gtcaaaatca aagctactaa attactagaa tcaacctctt   8700
attcttctac tcttcttgtt cttcttcaag attgtcaaaa tcttgaattc ctctattatc   8760
ttcatattgc tcgtcatctt cctcctcccc ctcctcttcc tcttcatgat cactttcatc   8820
ttcatcaatt agggataggg atcgacttgt agtagccaca ctttttccct tcctaatcga   8880
gcttgaactt gaagtattcc cccttaaacc ataaggattc tccccaactc cactagcaac   8940
cgcaacatca ccccaagtga aattagaatc gccttcaaat acttcttcat cttcacaatt   9000
ttcggggact ccggttagcc actcattagc ctcatcaata ttgtccaaaa gaattggatc   9060
aattagattg cggtggttgt agcgacgcct caatgctcta ttgtatttta tgaacactag   9120
attatggagg cgcttcaagg ttagtcgatt cctcttcttt gtatgaatct gcaaacaaga   9180
tgtgtcaact aattagtagg agttgggaca attgagatat aatttacttt atctcaaaac   9240
acgaaataat tctttttatt tctcacgtgt tcaaaaacgc tccagttcct ttcacatccg   9300
gatgagctac aagttaaact tagaactctg atggcgaaag tctgtaaatt cggagtctct   9360
acaccatatt ggtcccacca ctcaactata gaagtgaaaa aaaaaaattc aagagttaat   9420
aagtataaaa aatacattaa agttagagct ataaaatata gaagcacttg gtcacctggc   9480
gatttcgtct ttctttgttt aatagcaagt cggagcttaa aaagtccctc agctgccttg   9540
taaatagcaa gctgatctac tatcttttct tgcatgtctt catctggggt caacttgata   9600
acaacctcat ggaatcctgt ccacacttct ctagccaatg aattattctc atgctgatca   9660
taaaagagtg acgggttcag aataagtcca gctgcatgca aaggtctatg aagttgctca   9720
ctccatcttg catcaatgat ctgaaagacc tttgcatatt tctgctcatc agtgaatgat   9780
gcttgaatag cctccttggc cctatccata gcttcataga ggtagcccat tggtggtttt   9840
tgctccccat ccaccaaacg gagtacttta accaaagggc caccaatttt aagagcatga   9900
aggacattat tccaaaaaga ataagaaaga ataatgcgtg caacatcttt ccctgcactt   9960
tcctttgcaa atttactctt gctccattcc tctgaagtga acaactttct caaattggat  10020
ttttgcaagt ggatactatg taaagtcaag aaagcagtgg cgaaccttgt cttgcccggt  10080
ttcaccaaat ttttttgtcc ggtgaatctt ctcatcatat tcaataacaa gggccgctga  10140
gaaatataag aatgtaccct aacgccctgg ccaaaaactg tagagaaggg tttttccttg  10200
aaaatgtccc cgaagattaa gttgatacaa tgagccgcac atggagtcca atagacattc  10260
ttgtacgctc cttccaccat gccacccgct ttcacatttt cactcgcatt atcagtgacc  10320
acttgaacaa ctttgcttgg gccaatcttt tcaatggtgt tctgaaacaa ggtgaacatt  10380
ttgatgtggt cagtggatga gtcgctagca tcaatggact caagaaacaa acttcccttg  10440
ggagaattca ccaacacgtt aataatcatt ttcccagttc ttgccgtcca cttatccatc  10500
ataatggagc agccatactt gttccacgca actttatgtt cctccacaat tttattagtc  10560
tcctccactt ccttatttag ataaggacct ctgatttcat gataagtggg aggcttcatt  10620
ccaggtccgt attgaccaac ggcctcaata aagtctccaa aagtgtcagt atagttgaca  10680
caattgaagg ggagcccagc atcatagacc catcgtgcaa aagctctaac tgcacgatcc  10740
ctcaaaatgt ccttagcaat tttttgtaca tcttttccac cgctctttcc ttccggcttc  10800
tttgggaaat agcaatctat aggaccttta gtcctactcg tacccgtcga tccatggctt  10860
gaagagattg catctcttcc ccgttttgtt ggaagtgaca attcttcaat atcatcatca  10920
ccatcatcat caagattggt caccaatggt tgatgactca tttgattttt ttgctccttc  10980
ttcttctcaa caaaattctt tatttcatcc ctcacctccg gtggacattt cggacaactt  11040
```

-continued

```
gtgacgtttc tatcgccacc aataagatgg aatttaaagc gataaattcc acccgttgta  11100
atcttgttac aaaacttgca tacaatattt gtattcttct cattaactct atcgccatat  11160
cgccaagccg ggtctttatc tttcgatctt tgagacattt tgaaatccct attaagatat  11220
aagaaaatac ataatcaaat aaactgaaaa tacatataat atatataata attaatttta  11280
taaaccgaaa tacacattaa aaaaatcaaa taaactaaaa tataacatat ataattttct  11340
aaattgaaat acatataaaa ttaatcaaat aaactgaaaa cataacatat atataataat  11400
taattttata tactgaaaaa tgcattaaga aaatcaaata aactgaaaaa tataacatat  11460
ataaataata attaatttta tatactgaaa taaaaatcaa ataaactaaa atataacata  11520
tatatataat aattaatttt ctaaaatgaa atacatataa aattaatcaa ataaactgaa  11580
aatataacat atataaataa taattaatat tatatactga aatatacatt aaaaaatcaa  11640
ataaactgaa aaatataaca tatataaata ataattaatt ttatatgctg aaatatacat  11700
taaaaaaatc aaataaactg aaaaatataa catatataaa taataattaa ttttataaac  11760
taaaatacat attaaaagta ataaataaga agaataaagg ggggaaaaaa acaaaatggg  11820
ttagagataa aaggaagaag aagacgctga agtctgaaca gtgcaaactg gactgtcaga  11880
gtctcagaga taaacgaaga agaagaagga agaaagaagg aaaaagaaag aaaaaaaagc  11940
agaatctgac gggaccaaga agaagaaaga aagaagaaag aaaaaaaaga gaagaagaaa  12000
attacctgga ctggtcagca atgtcaatga agttgaaccc taggctttgg tcgacctcga  12060
tcgaagaaga gagaagaaga aatggccatt ttttgtcaat ttagggtctg ttttgtataa  12120
tagaaaaaca gacccaaagt ttttttaaa aaaaaaaggg cctgcgcttt tttaacaaaa  12180
gcgatcgctt cgtcgcttcc tccgttgaag cgtgcgcttc cctcggtcga gtcgcctcag  12240
gcagctagaa gcgacactga gtcgcgtcgc gtcgcttcgc gctttaagcg cgaagcgatc  12300
gcttttctaa acactggtcc ttccaagttc tgtccatctt tctggtgtgc ttaacccatg  12360
tatattggac cacactttgt attcatgctg attgcaacaa agcctgactg atcctgaact  12420
cctccttttt gccttgggta gaattatttt tgtgttttta gtgttacata tttcaattta  12480
aaggaaaaag ggagaagctt aaggtagaat cctgctcctt gacctttgga tccttacaca  12540
ttgaagtgga cagacatgtt tgctttgctt tgctttgatg agttgtttta gtagtcagtc  12600
taagcaactg ctgatgtatt ctgctttatt gtaagtgtct ataattttta tctttccaca  12660
atttgctttc agctctttct gcatataaga gaaaataaca gaagcttcta ttcgatcatg  12720
taatattgac tgcacaagtg catatttaaa caactttggc tatgcgtatg caagcaataa  12780
taaatattac tttttatgca gggtctgtat ggttttcttc agagatgaaa gccttaagtg  12840
atgactgtga acgatttgtt agtttccttc ccggtcatat ttattcaagc aaaaatggta  12900
tgcccatacg aagctcattt ctgagcttgc gcttcattta tgatcagcgt acttttccta  12960
tttatttcag atttacttta ggaccctgtt ggaaacagtc ttgaaccctt attgatggtg  13020
taattattat ctcttgatca accaaaggag taattacatg taattattac aaatttgcaa  13080
caaaatcttt taggataatc agtggagctt catgaatctt ttaggatagt tgggatgcta  13140
gagtgatgta cttttgataa tgtcggttaa cataaatcct ctgactttgt actgatgtac  13200
tggctgagca gattttatat tactttctaa tccctctaca aataaaaaaa ttgtgagact  13260
gcaatataac accatttttt taatgcattt acaatgttta aacttgattt agcaacgtag  13320
aacatgtcga ccttaaacag aggttctatt tgtcctagat aaaggaagat cagcataatg  13380
```

-continued

```
aaacattaca ggagaggagc tctattgagt ttttgttaat ctagagggag cccgtaaata  13440
gtacaccaat tcatctctta tatgacttct ttttcatttt ggaacgtttt aaaagtttga  13500
ctacattttt tgatctccgt acactaaact ttttgatgta ttaaactaac tatttccact  13560
actttaatat tttcttcctt aaacaactcc tgttagcatc ttaaactctg tgtgttcaat  13620
accctcatat aaaattatac gagtattttt tttatatttg cttatgtcct tggagtttgg  13680
gatggggaag ctcatcattt gaggcgaaag gtaaattctt ttgaatggac aaaaagtgaa  13740
cctcggtctt tggcatggag ggactattta agtcgccatc attaccaaag tcatcctttc  13800
aagtgtttgc tttcaagaac tattcatgct atgtctcaag tatattatgt gtgcaggagg  13860
actcagaaga tggtacaacc caccatggta ctcagaaacc attccttcta ctccatatga  13920
tcaccttgtc ttacggaaag cttttgagaa ggtcattcta ttttggaagt cgcttgtttc  13980
tgagttgtat ataatattta ggtgccactt tgttatattt taaacttcat caaaagcctt  14040
tggattcttt gaggacacat atccccttga ctgactggga gctgaatttc cttgatgtat  14100
agtgcttatt ttgattgtcc tctcctttgt aatactcttg cctataaata aaccttcctt  14160
atcaaaagaa aatgataaaa tgttaaaaat actttgtgat agatgttgac tatagacttt  14220
aaatgatatt ttatctcaat ctttatcaat tcttttttac cttcacatgc aaattatact  14280
acagtatgtg aaatatgcaa tagtttgtcc tgcaattttc atctttcatg tacctctctc  14340
tactatccgt gtattactac tgatttgatg cattaaatgc taattttatt cccaaccttt  14400
actttatgca ggctgtagtc aagcgactta tgacggatgt accatttggt gtgcttctct  14460
caggcggact agattcttca cttgttgctg cagtggccaa ccgctatttg gctgatactg  14520
aagctgcgcg acaatgggga tcacagttgc ataccttttg cgtaggcttg aaggtggtga  14580
tgctcctttt tgtaaacttg ctctgatttg ggaattgcta gctgtatcat cccaatttac  14640
atggaagttc tagaccatta ttgctgtttc ttttccatat atagggattt tctgaaaata  14700
gtaaaaagga aatggaattt ctctttatta aagataccga atgccttttt gggaaatgat  14760
cttacagttc tgaatcgaaa atttcctttt gacattgtga ttaattctga tatgaatttg  14820
gtccatcctg gctttccttc tcttgattgt agattttcct tctcttgtta caattatatg  14880
cctgtctttt tgtcttactc tctgagacag gcaatgtaac tccagttgca aggtttggta  14940
atattgactt gtttatttct gttatcacat cctcctgaaa aagtgctact agcttgtatt  15000
catgcgggaa tttgaaattt tcaagtgtat agctttacaa aatgatcaga actgatcaca  15060
gtcattgctc taaataaaat tttctaaaaa gcaggtattg ttgtgatata atgtgacact  15120
taaataaatt taaacctaca tcctttcgaa atctgtaata gctccactaa tatttcttgt  15180
gctaaactat tccaacacct cttatcgatg ccaattttga cagaccttag tgcacttaaa  15240
agtgtttagt gttctttatg cagtaggtat gttattgtcc aaaatgacag aaataaagtt  15300
agagatttgt tgaaagccac ttggtgtgat tgagcagttc ggagatgagt gatttatcca  15360
ttttatatac ttgtagtgtt ttgttttctt ttgcttttgt cattgtaatt aaggttgtct  15420
tttgtttgac attagggttc tcctgatctg aaagctgcca gagaggtggc agactacctt  15480
ggaacccgtc accatgagtt tcactttaca gtgcaggtaa ctttccacaa agacatccta  15540
ccatgtgacc aggaggtcac gggtttgagc tgtggaaaca accttttgca gaaatgcagc  15600
gtaaggttgc gtacaataga cccttgtggt ccggcccttc cccgaccccg cacatagcgg  15660
gagcttagtg caccgggctg cccatcctaa gctgattttc cttataggag tataaccgct  15720
taagtcaaat tggctatcta cttctttcta ttgctacatc aggaaggaat tgatgcacta  15780
```

```
gatgaagtca tttatcatgt tgaaacatat gatgtgacca ctatcagagc cagtacacca  15840
atgtttctca tgtctcggaa gataaagtct ttgggtgtga aaatggttct atctggtgaa  15900
ggttctgatg aaatttttgg cggttattta tatttccaca agggacccaa caaagaggag  15960
tttcaccaag aaacttgtag aaaggtggat ctcattgtca tttcttcagt cattcaggat  16020
tattggaagt aactgtattt ttactagaat acttctttga actatttcta gctctgatgg  16080
acgctttgat gttaatccag attaaagcac ttcatcttta tgattgcttg agggccaaca  16140
aatctacttc agcttggggt gttgaagctc gtgtaccttt cttggataaa gaatttatca  16200
atgttgcaat gaacattgat ccagagtgga aaatggtaac ctacagtgct tccgtctcat  16260
ttctccaccc cccacccccc caaaaaaaag aacagaaaag aattgaaaag agagattctt  16320
ttcttccttc aaggaagaag gggtaacaa aagaatagct gcaagttatg cagaaaaaat  16380
agtcttccat gtcatgggag accagggttc aaatctgatt gttaaaaaaa acactaggtg  16440
aactcttcta atctgtttaa gccttggtgg acatagttaa ctagtatatg agctagttag  16500
agctgactcg aaaccaccat tattcaaaaa attaagaaag tcttcaatgt tgttccaccg  16560
tgaattcatg atgtgtcgac tttcatgtgt ttatctctgg atagatgaag agttttttg  16620
gatcttgatt aattctgttt ggcccctttg aggttctgca cgctatttct agactcaaac  16680
ttgctgcgac ctatgttagg tctagagaat atctgcctaa taaaacaatg gaagttacat  16740
tcaagtattt tacctccata ttacaagtca gtgttagtta aatgggtctg atatatggga  16800
tagaaaatgg cttcataccc ataacctcgt taaaatgttg ctgatgtgct gatctcatct  16860
gtacatctag tataatccta attacaaatt aatgcatctc tttgcggtga ctatagtatg  16920
ctgaagaacc tgtcttgaaa cattgcagat cagacctgat ctcggaagaa tagaaaagtg  16980
ggttctacgc aatgcttttg acgatgatca gaatccttat ctgccaaagg tttgtttgtt  17040
ttcttgtatc aggtccaata atcataatct ttgtttattc atttgcataa aaggcagtag  17100
actcccaata cattgtgtac gcttatgcac aaatgtatga gatgtgtatt atatgtgtca  17160
catataaggg tattatatgt acacactcct cccaccttcc acatatatta tgtgtgtgtg  17220
tgtgtgtgta taatgaaatg atgtttgaaa agacattatg atcaagtagt tgatcctcat  17280
ctgctttctg tttttagcat atcttgtata ggcagaagga acagttcagt gatggagttg  17340
gctacagttg gattgatggc ttgaaggatc acgcaagcag tctggtgagc tctttagttg  17400
ttttctcttc cctcctcttc cattctttat cccttccttt tgtggttttg ttgaacacat  17460
ctcatatact tggtccaggt ttctgattct atgttagcga atgcaagttt tgtttacccg  17520
cataacacac ccacgacaaa ggaaggatac tattatagaa ctatttttga gcgatatttc  17580
cccaaggtgg gtcttacata gtcttctttt ccttgttatt catgttcagt ttatgatatt  17640
ttgtcccaaa caatgttttc tttttcttcc tttttctgtt aacaagatcg cttctatctt  17700
cgtatttgtt gataaagtta atcacattgt taactattat ttggagcaga atgctgcgag  17760
ggaaacagtt ccaggtggtc caagtgtggc atgcagcact gcaaaagcag tagaatggga  17820
cgcagcttgg tccaagaatc tagatccatc tggtcgagct gcactcggtg ttcatgcagc  17880
tgcttatgag gatgcatcag aggttaaaac cacagtcgcg acagatactg ctcagaaact  17940
tgacgttgat aaagctgcag tagctgtttg a                                 17971
```

<210> SEQ ID NO 12
<211> LENGTH: 581
<212> TYPE: PRT

<213> ORGANISM: Nicotiana tabacum

<400> SEQUENCE: 12

```
Met Cys Gly Ile Leu Ala Val Phe Gly Cys Ile Asp Asn Ser Gln Ala
1               5                   10                  15

Lys Arg Ser Arg Ile Ile Glu Leu Ser Arg Arg Leu Arg His Arg Gly
            20                  25                  30

Pro Asp Trp Ser Gly Leu His Ser His Asp Asp Cys Tyr Leu Ala His
        35                  40                  45

Gln Arg Leu Ala Ile Val Asp Pro Thr Ser Gly Asp Gln Pro Leu Tyr
    50                  55                  60

Asn Glu Asp Lys Thr Ile Val Val Ala Val Asn Gly Glu Ile Tyr Asn
65                  70                  75                  80

His Arg Asp Leu Arg Glu Lys Leu Lys Ser His Gln Phe Arg Thr Gly
                85                  90                  95

Ser Asp Cys Glu Val Ile Ala His Leu Tyr Glu Asp Tyr Gly Glu Asp
            100                 105                 110

Phe Val His Met Leu Asp Gly Met Phe Ser Phe Val Leu Leu Asp Thr
        115                 120                 125

Arg Asp Lys Ser Phe Ile Ala Ala Arg Asp Ala Ile Gly Ile Thr Pro
    130                 135                 140

Leu Tyr Met Gly Trp Gly Leu Asp Gly Ser Val Trp Phe Ser Ser Glu
145                 150                 155                 160

Met Lys Ala Leu Ser Asp Asp Cys Glu Arg Phe Val Ser Phe Leu Pro
                165                 170                 175

Gly His Ile Tyr Ser Ser Lys Asn Gly Gly Leu Arg Arg Trp Tyr Asn
            180                 185                 190

Pro Pro Trp Tyr Ser Glu Thr Ile Pro Ser Thr Pro Tyr Asp His Leu
        195                 200                 205

Val Leu Arg Lys Ala Phe Glu Lys Ala Val Val Lys Arg Leu Met Thr
    210                 215                 220

Asp Val Pro Phe Gly Val Leu Leu Ser Gly Gly Leu Asp Ser Ser Leu
225                 230                 235                 240

Val Ala Ala Val Ala Asn Arg Tyr Leu Ala Asp Thr Glu Ala Ala Arg
                245                 250                 255

Gln Trp Gly Ser Gln Leu His Thr Phe Cys Val Gly Leu Lys Gly Ser
            260                 265                 270

Pro Asp Leu Lys Ala Ala Arg Glu Val Ala Asp Tyr Leu Gly Thr Arg
        275                 280                 285

His His Glu Phe His Phe Thr Val Gln Glu Gly Ile Asp Ala Leu Asp
    290                 295                 300

Glu Val Ile Tyr His Val Glu Thr Tyr Asp Val Thr Thr Ile Arg Ala
305                 310                 315                 320

Ser Thr Pro Met Phe Leu Met Ser Arg Lys Ile Lys Ser Leu Gly Val
                325                 330                 335

Lys Met Val Leu Ser Gly Glu Gly Ser Asp Glu Ile Phe Gly Gly Tyr
            340                 345                 350

Leu Tyr Phe His Lys Ala Pro Asn Lys Glu Glu Phe His Gln Glu Thr
        355                 360                 365

Cys Arg Lys Ile Lys Ala Leu His Leu Tyr Asp Cys Leu Arg Ala Asn
    370                 375                 380

Lys Ser Thr Ser Ala Trp Gly Val Glu Ala Arg Val Pro Phe Leu Asp
385                 390                 395                 400
```

-continued

```
Lys Glu Phe Val Asn Val Ala Met Asn Met Asp Pro Glu Ser Lys Met
                405                 410                 415

Ile Arg Pro Asp Leu Gly Arg Ile Glu Lys Trp Val Leu Arg Asn Ala
            420                 425                 430

Phe Asp Asp Asp Gln Asn Pro Tyr Leu Pro Lys His Ile Leu Tyr Arg
        435                 440                 445

Gln Lys Glu Gln Phe Ser Asp Gly Val Gly Tyr Ser Trp Ile Asp Gly
    450                 455                 460

Leu Lys Asp His Ala Ser Arg Leu Val Ser Asp Ser Met Leu Ala Asn
465                 470                 475                 480

Ala Ser Phe Val Tyr Pro His Asn Thr Pro Thr Thr Lys Glu Gly Tyr
                485                 490                 495

Tyr Tyr Arg Thr Ile Phe Glu Arg Tyr Phe Pro Lys Asn Ala Ala Arg
            500                 505                 510

Glu Thr Val Pro Gly Gly Pro Ser Val Ala Cys Ser Thr Ala Lys Ala
        515                 520                 525

Val Glu Trp Asp Ala Ala Trp Ser Lys Asn Leu Asp Pro Ser Gly Arg
    530                 535                 540

Ala Ala Leu Gly Val His Ala Ala Ala Tyr Glu Asp Ala Ser Glu Val
545                 550                 555                 560

Lys Thr Thr Val Ala Thr Asp Thr Pro Gln Lys Leu Glu Val Asp Lys
                565                 570                 575

Ala Ala Val Ala Val
            580


<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13

tcacatatat tccctcataa cacac                                          25


<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14

aagaagcatc ccactctaca gctt                                           24


<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15

atatcttccc tcacaacact ccaact                                         26


<210> SEQ ID NO 16
<211> LENGTH: 22
<212> TYPE: DNA
<213> ORGANISM: Artificial Sequence
<220> FEATURE:
<223> OTHER INFORMATION: Primer
```

<400> SEQUENCE: 16

```
ctaccggaag gatcaaggtt gt                                              22
```

<210> SEQ ID NO 17
<211> LENGTH: 330
<212> TYPE: DNA
<213> ORGANISM: Nicotiana tabacum

<400> SEQUENCE: 17

```
tcacatatat tccctcataa cacacccatt acaaaggaag catactacta taggatgatt     60

ttcgagcgct ttttcccaca gaattcagct gggctaaccg ttcctggagg agcaagtgtg    120

gcgtgtagca cagctaaagc tgtagagtgg gatgcttctt ggtcaaagaa ccttgatcct    180

tcaggcaggg ctgctattgg tgtacataac tcggcttatg agaatcatgt acctgctatg    240

gctaatggga atttgaccaa aaaaatcatt ggtcgtgtgc cttctatggt agaagttggt    300

gctgctcccg agctcacaat aaagagttag                                     330
```

<210> SEQ ID NO 18
<211> LENGTH: 364
<212> TYPE: DNA
<213> ORGANISM: Nicotiana tabacum

<400> SEQUENCE: 18

```
gaccagattg gagtgggata tatcaacatg gtgatttta  cttagcacat caacgtttag     60

caattatcga tcctacttct ggtgatcagc ctctgtttaa tcaagataag actattgttg    120

ttacagtcaa tggagaaatt tacaatcatg agaaacttcg taatcttatg cctaatcaca    180

agttcagaac cggaagtgat tgtgatgtta ttgcacatct ttatgaagaa tatggagaaa    240

attttgtgga catgttggat ggggtgttct cttttgtatt gttggatacg cgcgataaca    300

gctttcttgc tgctcgtgat gcgattggaa ttactcccct ctatattggt tggggacttg    360

atgg                                                                 364
```

<210> SEQ ID NO 19
<211> LENGTH: 1815
<212> TYPE: DNA
<213> ORGANISM: Nicotiana tabacum

<400> SEQUENCE: 19

```
atgtgcggga tcttggctgt tttgggttgt tctgatgatt ctcaggccaa aagggttcgt     60

gttctcgagc tctctcgcag gtaggttgaa gcatcgtgga ccagattgga gtgggctgta    120

tcaacatggg gactgttact tggcacatca gcgtctagct attgttgatc ctgcttccgg    180

tgatcaacct ctgtttaacg aagataagac gattgttgtt acggtaggta aatggagaga    240

tctacaatca cgagcaactt cgtaagcaaa tgcctaatca taagttccgg actggcagtg    300

actgtgatgt cattgcacac ctagtagtat gaagaacatg gagaagattt tgtggacatg    360

ctggatggga tcttcgcttt tgtgttattg gatactcgag ataacagctt tcttgttgct    420

cgtgatgcca ttggaattac ttccctttat attggttggg gacttgatgg tagggtctgt    480

atgaatatca tctgagctta agggcttgaa tgatgactgc gaacattttg aagttttccc    540

accagggcac ttgtactcta gcaagaatgg cggctttagg aggtggtaca atcctccttg    600

gttctctgag gccattcctt ccactcgtta tgatccctta gttctcaggc gtgcctttga    660

aaatgtaggc tgttatcaaa aggttgatga ctgatgtccc ctttggtgtt ctcctctccg    720
```

```
ggggactcga ttcatccttg gttgcttcga ttactgctcg ctacttggct ggtacaaagg    780

ctgccaagca gtggggagca cagcttcatt ccttctgtgt tggccttgag gtagggctca    840

ccggatctca aggctgcaag agaagttgct gactacttgg gaaccgttca ccacgagttt    900

cacttcaccg ttcaggtagg atggaattga tgcaattgaa gatgttattt accatattga    960

gacatacgat gtaacgacaa tcagagcaag cactcctatg ttccttatgt cgcgtaagat   1020

taagtcacta ggagtgaaga tggtcatatc tggggaagga tctgatgaag tgtttggtgg   1080

ctacttgtac tttcacaagg ctcccaacaa ggaagagttc cacaaggaaa catgtcgcaa   1140

ggtagattaa agcgcttcac caatatgact gcttaagagc aaataagtca acatctgcat   1200

ggggtttaga agctagagtc cctttcctag ataaggagtt catcaatgtt gccatgagta   1260

ttgatccaga gtggaagttg agattaaacc agagcaaagg aggattgaaa agtgggctct   1320

aaggagggcc tttgatgatg aggagcatcc ttatctccca aaggtagcac atcctgtata   1380

ggcaaaaaga acaattcagt gatggcgtgg gcatagttgg atagatggac tcaaagcaca   1440

tgctgaacaa catgtaggtg accaatagga tgatgtttaa tgcttcacat atattccctc   1500

ataacacacc cattacaaag gaagcatact actataggat gattttcgag cgctttttcc   1560

cacaggtaga attcagctgg gctaaccgtt cctggaggag caagtgtggc gtgtagcaca   1620

gctaaagctg tagagtggga tgcttcttgg tcaaagaacc ttgatccttc aggcagggct   1680

gctattggtg tacataactc ggcttatgag aatcatgtac ctgctatggc taatgggaat   1740

ttgaccaaaa aaatcattgg tcgtgtgcct tctatggtag aagttggtgc tgctcccgag   1800

ctcacaataa agagt                                                    1815
```

<210> SEQ ID NO 20
<211> LENGTH: 155
<212> TYPE: PRT
<213> ORGANISM: Nicotiana tabacum

<400> SEQUENCE: 20

```
Met Cys Gly Ile Leu Ala Val Leu Gly Cys Ser Asp Asp Ser Gln Ala
1               5                   10                  15

Lys Arg Val Arg Val Leu Glu Leu Ser Arg Arg Leu Lys His Arg Gly
            20                  25                  30

Pro Asp Trp Ser Gly Leu Tyr Gln His Gly Asp Cys Tyr Leu Ala His
        35                  40                  45

Gln Arg Leu Ala Ile Val Asp Pro Ala Ser Gly Asp Gln Pro Leu Phe
    50                  55                  60

Asn Glu Asp Lys Thr Ile Val Val Thr Val Asn Gly Glu Ile Tyr Asn
65                  70                  75                  80

His Glu Gln Leu Arg Lys Gln Met Pro Asn His Lys Phe Arg Thr Gly
                85                  90                  95

Ser Asp Cys Asp Val Ile Ala His Leu Tyr Glu Glu His Gly Glu Asp
            100                 105                 110

Phe Val Asp Met Leu Asp Gly Ile Phe Ala Phe Val Leu Leu Asp Thr
        115                 120                 125

Arg Asp Asn Ser Phe Leu Val Ala Arg Asp Ala Ile Gly Ile Thr Ser
    130                 135                 140

Leu Tyr Ile Gly Trp Gly Leu Asp Gly Ser Val
145                 150                 155
```

<210> SEQ ID NO 21
<211> LENGTH: 1818

-continued

<212> TYPE: DNA
<213> ORGANISM: Nicotiana tabacum

<400> SEQUENCE: 21
atgtgcggga tcttggctgt tttgggttgt tctgatgatt ctcaggccaa aagggttcgt 60
gttctcgagc tctctcgcag gtaggttgaa gcatcgtgga ccagattgga gtgggctgta 120
tcaacatggg gactgttact tggcacatca gcgtctagct attgttgatc ctgcttccgg 180
tgatcaacct ctgtttaacg aagataagac gattgttgtt acggtaggta aatggagaga 240
tctacaatca cgagcaactt cgcaagcaaa tgcctgatca taagttccgg actggaagtg 300
actgtgatgt cattgcacac ctagtagtat gaagaacatg gagaagattt tgtggacatg 360
ctggatggga tcttcgcttt tgtgttactg gatactcgag ataacagctt tcttgttgct 420
cgtgatgcca ttggaattac ttccctttat attggttggg gacttgatgg tagggtctgt 480
atgaatatca tctgagctta agggcttgaa tgatgactgc gaacattttg aagttttccc 540
accaggacac ttgtactcta gcaagaatgg cggctttagg aggtggtaca atcctctttg 600
gttctctgag gctattcctt ccactcctta tgatccctta gttctcaggc gcgcctttga 660
aaatgtaggc tgttatcaaa aggttgatga ctgatgtccc ttttggtgtt ctgctctccg 720
ggggactcga ttcatccttg gttgcttcga ttactgcccg ctacttggct ggcacaaagg 780
ctgccaagca gtggggagca cagcttcatt ccttctgtgt tggccttgag gtagggatca 840
ccggatctca aggctgcaag agaagttgct gactacttgg gaaccgttca ccacgagttt 900
cacttcaccg ttcaggtagg atggaattga tgcaattgaa gatgttattt accatattga 960
gacatacgat gtaacgacaa tcagagcaag cactcctatg ttccttatgt cgcgtaagat 1020
taagtcacta ggagtgaaga tggttatatc tggggaaggc tctgatgaag tgtttggtgg 1080
ctacttgtac tttcacaagg ctcccaacaa ggaagagttc cacaaggaaa catgtcgcaa 1140
ggtagattaa agcacttcac caatatgact gtttaagagc aaataagtca acatctgcat 1200
ggggcttaga agctagagtg cctttcctag ataaggagtt catcaatgtt gccatgagta 1260
ttgatccaga gtggaagttg gtagattaaa ccagagcaaa ggaggattga gaagtgggct 1320
ctaaggaggg cctttgatga tgaggagcat ccctatctcc caaaggtagc acatcctata 1380
caggcagaaa gaacaattca gtgatggcgt aggctatagt tggatagatg gactcaaagc 1440
acatgctgaa caacatgtag gtgaccaata ggatgatgct taatgcttca catatattcc 1500
ctcataacac accgattaca aaggaagcat actattatag gatgattttc gagcgctttt 1560
tcccacaggt agaattcagc tgggctaacc gttcctggag gagcgagtgt ggcgtgtagc 1620
acagctaaag ctgtagagtg ggatgcttct tggtcaaaga accttgatcc ttcaggaagg 1680
gctgctattg gtgtacataa ctcagcttat gagaatcatg aacctgctat ggctaatggg 1740
aatttggcca caaaaatcat tggccgtgcg ccgtctatgg tagaagttgg tgctgctcat 1800
gagctcacaa taaggagt 1818

<210> SEQ ID NO 22
<211> LENGTH: 155
<212> TYPE: PRT
<213> ORGANISM: Nicotiana tabacum

<400> SEQUENCE: 22

Met Cys Gly Ile Leu Ala Val Leu Gly Cys Ser Asp Asp Ser Gln Ala
1 5 10 15

Lys Arg Val Arg Val Leu Glu Leu Ser Arg Arg Leu Lys His Arg Gly

```
            20                  25                  30

Pro Asp Trp Ser Gly Leu Tyr Gln His Gly Asp Cys Tyr Leu Ala His
        35                  40                  45

Gln Arg Leu Ala Ile Val Asp Pro Ala Ser Gly Asp Gln Pro Leu Phe
    50                  55                  60

Asn Glu Asp Lys Thr Ile Val Val Thr Val Asn Gly Glu Ile Tyr Asn
65                  70                  75                  80

His Glu Gln Leu Arg Lys Gln Met Pro Asp His Lys Phe Arg Thr Gly
                85                  90                  95

Ser Asp Cys Asp Val Ile Ala His Leu Tyr Glu Glu His Gly Glu Asp
            100                 105                 110

Phe Val Asp Met Leu Asp Gly Ile Phe Ala Phe Val Leu Leu Asp Thr
        115                 120                 125

Arg Asp Asn Ser Phe Leu Val Ala Arg Asp Ala Ile Gly Ile Thr Ser
    130                 135                 140

Leu Tyr Ile Gly Trp Gly Leu Asp Gly Ser Val
145                 150                 155


<210> SEQ ID NO 23
<211> LENGTH: 1818
<212> TYPE: DNA
<213> ORGANISM: Artificial Sequence
<220> FEATURE:
<223> OTHER INFORMATION: DNA sequence of ASN5-S stop mutant: ASN5-S_Q66*
<220> FEATURE:
<221> NAME/KEY: mutation
<222> LOCATION: (199)..(201)

<400> SEQUENCE: 23

atgtgtggaa tcttggcttt gttgggttgt tcagatgatt ctcaggccaa aagggttcga     60

gttcttgagc tctctcgcag gcaggttgaa gcatcgtgga ccagattgga gtgggatata    120

tcaacatggt gatttttact tagcacatca acgtttagca attatcgatc ctgcttctgg    180

tgatcagcct ctgtttaatt aagataagac gattgttgtt acagtaggtc aatggagaga    240

tttacaatca tgagaaactt cgtaatctta tgcctaatca caagttcaga actggaagtg    300

attgtgatgt tattgcacat cttgtagtat gaagaatatg gagaaaattt tgtggacatg    360

ttggatgggg tgttctcttt tgtattgttg gatacgcgcg ataacagctt tcttgctgct    420

cgtgatgcaa ttggaattac tcccctatat attggttggg gacttgatgg taggctctgt    480

gtggatttca tctgagctaa aaggattaaa tggtgactgt gaacattttg aagttttccc    540

tcccggtcac ttgtactcga gcaagaatgg cgggtttagg agatggtaca atcctcaatg    600

gttctctgag gctattccat caaatcctta cgacccctta gttttgagac gtgccttcga    660

aaatgtaggc tgttatcaaa cgattgatga ccgatgtccc ctttggtgtt ctgctctccg    720

ggggacttga ttcgtctttg gttgcttctg tcactgctcg ctacttggct ggaacaaaag    780

ctgctaagca atggggagca cagcttcatt ccttctgtgt tggtctcgag gtagggctca    840

ccagatctca aggctgcaag agaagttgct gactatttgg gaaccgttca ccacgagttc    900

accttcacag ttcaggtagg atggaattga tgctattgaa gatgttattt accatatcga    960

gacatacgat gtaacaacga tcagagcaag cactcctatg ttccttatgt cgcgtaagat   1020

taaatcactg ggagttaaga tggtcatatc aggggaaggc tcagatgaac tgtttggcgg   1080

ctatttgtac ttccacaagg ctccgaacaa ggaagaattc catgtggaga catgtcacaa   1140

ggtagataaa agcgcttcac caatacgact gtttgagagc aaataaggca acatcagcat   1200
```

-continued

```
ggggcttaga agctagagta ccatttctgg ataaagagtt catcaacgtt gctatgagta   1260

tcgatcctga atggaagatg gtagattaaa cacgatcatg gtaggatcga gaagtgggtt   1320

cttaggaagg cttttgatga tgaggagcaa ccctatctcc caaaggtagc atattctgta   1380

ccggcagaaa gaacaattca gtgatggcgt aggctatagt tggatcgatg gactcaaagc   1440

acatgctgaa caacatgtag gtgactgata ggatgatgct taatgctgca catatcttcc   1500

ctcacaacac tccaactaca aaggaagcat actattacag gatgattttc gagaggttct   1560

tcccacaggt agaattcagc aaggctaact gttcctggag gaccgagtat agcttgcagc   1620

acagctaaag ctattgagtg ggatgcttcg tggtcgaaca accttgatcc ttccggtagg   1680

gctgcaatcg gtgtacataa ctcggcttat gacgatcatc tccccgatgt tggtaatggg   1740

aatttggaca caacgatcat cgataatgtg ccgaggatgg taggagtggg tgctgctgca   1800

gagctcacaa taaggagc                                                  1818


<210> SEQ ID NO 24
<211> LENGTH: 65
<212> TYPE: PRT
<213> ORGANISM: Artificial Sequence
<220> FEATURE:
<223> OTHER INFORMATION: Amino acid sequence of ASN5-S stop mutant:
      ASN5-S_Q66*

<400> SEQUENCE: 24

Met Cys Gly Ile Leu Ala Leu Leu Gly Cys Ser Asp Asp Ser Gln Ala
1               5                   10                  15

Lys Arg Val Arg Val Leu Glu Leu Ser Arg Arg Leu Lys His Arg Gly
            20                  25                  30

Pro Asp Trp Ser Gly Ile Tyr Gln His Gly Asp Phe Tyr Leu Ala His
        35                  40                  45

Gln Arg Leu Ala Ile Ile Asp Pro Ala Ser Gly Asp Gln Pro Leu Phe
    50                  55                  60

Asn
65
```

PLANTS WITH REDUCED ASPARAGINE CONTENT

This application is a U.S. National Stage Application of International Application No. PCT/EP2016/070972, filed Sep. 6, 2016, which was published in English on Mar. 16, 2017, as International Publication No. WO 2017/042162 A1. International Application No. PCT/EP2016/070972 claims priority to European Application No. 15184528.6 filed Sep. 9, 2015.

FIELD OF THE INVENTION

The present invention discloses the polynucleotide sequences of genes encoding asparagine synthetase from *Nicotiana tabacum* and variants, homologues and fragments thereof. The polypeptide sequences encoded thereby and variants, homologues and fragments thereof are also disclosed. The modification of the expression of the one or more genes or the activity of the protein(s) encoded thereby to modulate the levels of asparagine in a plant is disclosed.

BACKGROUND OF THE INVENTION

Acrylamide is a chemical compound of formula C3H5NO (IUPAC name is prop-2-enamide) and concerns have been raised regarding its potential toxicity. The origin of acrylamide in the aerosol of smoking articles comprising tobacco may be the amino acid asparagine which can be present in tobacco material used for the production of said smoking articles. It may therefore be desirable to reduce the levels of certain amino acids—such as asparagine—in plants, especially in those plants that are used for tobacco production.

US2013/0068240 describes genetically modified tobacco plants and tobacco products exhibiting a decrease in at least one amino acid such that upon heating and/or combusting the tobacco generates reduced levels of a compound derived from the at least one amino acid compared to a unmodified parent tobacco plant. Mutagenizing seeds with ethyl methane sulfonate (EMS) to obtain mutant tobacco lines with reduced levels of asparagine and reduced acrylamide levels in cigarette smoke is described. Various EMS mutants are described US2013/0068240. In flue cured upper stalk leaves, three EMS mutants, namely FC Up 10NH-5, FC Up 10NH-18 and FC-Up 10NH-23 showed: (i) a 71%, a 30% and a 62% reduction in asparagine, respectively; (ii) a 47%, a 42% and a 44% reduction in acrylamide in tobacco smoke, respectively; and (iii) a 38% decrease, a 111% increase and a 19% decrease in nicotine in flue cured upper stalk tobacco, respectively. Thus, the highest level of asparagine and acrylamide reduction of 71% and 47%, respectively, was achieved with the mutant FC Up 10NH-5. However, in this mutant, the nicotine levels showed a 38% decrease as compared to the control. In flue cured middle stalk leaves, three EMS mutants, namely FC Mid10NH-5, FC Up 10NH-18 and FC-Up 10NH-23 showed: (i) a 6 decrease, a 531% increase and a 29% decrease in asparagine, respectively; (ii) a 19 decrease, a 140% increase and a 200% increase in acrylamide in tobacco smoke, respectively; and (iii) a 36% decrease, a 113% increase and a 19% decrease in nicotine in flue cured middle stalk tobacco, respectively, Thus, the highest level of acrylamide reduction of 19% was achieved with FC Up 10NH-5 but the level of asparagine was reduced by only 6% and the level of nicotine decreased by 36%.

The highest level of asparagine and acrylamide reduction of 71% and 47%, respectively, is found in the flue cured upper stalk leaves of FC Up 10NH-5. However, in this mutant the nicotine levels showed a 38% decrease as compared to the control. In flue cured middle stalk leaves of FC Up 10NH-5, the level of acrylamide was reduced by only 19%, the level of asparagine was reduced by only 6% and there was again a decrease in nicotine levels (of 36%) as compared to the control.

Reduction in the level of nicotine is not desirable since a consumer of the tobacco product will need to consume more tobacco in order to receive the same level of nicotine. It is also clear from the results presented in US2013/0068240 that the levels of asparagine, acrylamide and nicotine vary widely and randomly between the various EMS mutants.

It is desirable to find alternative ways to reduce the levels of asparagine in a plant and thereby minimise the quantity of acrylamide in aerosol produced from a heated or combusted part of the plant. It is also desirable to find ways to further reduce the quantity of acrylamide to levels that are lower than those disclosed in US2013/0068240. It is also desirable to maintain the levels of nicotine in the plant. It is also desirable to develop methods that can consistently produce plants with these properties. The present invention seeks to address this need.

SUMMARY OF THE INVENTION

Six full-length asparagine synthetase genes have been identified in *Nicotiana tabacum* that are called NtASN1-S (SEQ ID NO: 1), NtASN1-T (SEQ ID NO: 3), NtASN3-S (SEQ ID NO: 9), NtASN3-T (SEQ ID NO: 11), NtASN5-S (SEQ ID NO: 5) and NtASN5-T (SEQ ID NO: 7). ASN3-S and ASN3-T genes were found to be only poorly expressed during curing, whereas it was surprisingly found that NtASN1-S, NtASN1-T, NtASN5-S and NtASN5-T are highly expressed during curing, for example during the first 10, 20, 30, 40, 50, 60, 70, 80, 90 or 100 hours of curing. Suitably, the ASN3-S or ASN3-T genes or the proteins encoded thereby are not used in the present disclosure. Reducing the expression of NtASN1 and/or NtASN5 or the activity of the protein(s) encoded thereby is shown herein to contribute to reduced levels of asparagine in cured leaves—such as cured mid-bottom stalk leaf. This in turn results in reduced levels of acrylamide in aerosol produced upon heating or combusting the cured leaf. In contrast to the results obtained in US2013/0068240, reducing the expression of NtASN1 or NtASN5 not only results in a reduction in asparagine in leaves, it also consistently results in a reduction in acrylamide in aerosol. This consistent reduction in asparagine and acrylamide levels is accompanied by levels of nicotine in cured leaves that are about the same as, if not higher than, a control plant. Advantageously, lower values of about 89% reduction in asparagine and about 70% reduction in acrylamide with substanitally, minimal or no impact on nicotine content can be obtained in certain embodiments of this disclosure.

Without wishing to be bound by theory, it has been further determined that acrylamide produced in tobacco aerosol is dependent on the pool of asparagine that is generated during leaf curing.

Accordingly, acrylamide levels in aerosol can be modulated (eg. decreased) by reducing the pool of asparagine generated during curing or drying by modulating (eg. decreasing) the expression or activity of asparagine synthetase that is active during the early phase of curing or drying. Plants are described that have a reduced content of asparagine and exhibit a reduced expression or function of asparagine synthetase. In embodiments, this is achieved using RNA interference or mutation of the asparagine synthetase coding sequences described herein that are expressed during curing or drying. Reducing asparagine levels reduces the amount of acrylamide present in aerosol. When applied to tobacco, this results in lower amounts of acrylamide present in aerosol that is inhaled by a consumer of a smoking article, including a heated or a combusted tobacco product. Further advantages of the present invention are described herein.

ASPECTS AND EMBODIMENTS OF THE INVENTION

Aspects and embodiments of the present invention are set forth in the accompanying claims.

In one aspect, there is provided a mutant, non-naturally occurring or transgenic plant or part thereof having reduced expression or activity of asparagine synthetase, said asparagine synthetase comprising, consisting or consisting essentially of: (i) a polynucleotide sequence comprising, consisting or consisting essentially of a sequence having at least 72% or at least 90% sequence identity to SEQ ID NO:1 or at least 72% sequence identity to SEQ ID NO:3 or SEQ ID NO:5 or SEQ ID NO:7; or (ii) a polypeptide encoded by the polynucleotide set forth in (i); or (iii) a polypeptide having at least 78% sequence identity to SEQ ID NO:2 or SEQ ID NO:4 or SEQ ID NO:6 or SEQ ID NO:8; wherein the expression or activity of the asparagine synthetase set forth in (i), (ii) or (iii) is reduced as compared to a control plant.

Suitably, the plant comprises at least one genetic alteration in a regulatory region or in the coding sequence of the polynucleotide encoding the asparagine synthetase.

Suitably, the reduced expression or activity of the asparagine synthetase confers a reduction in the level of asparagine in cured or dried leaf derived from the mutant, non-naturally occurring or transgenic plant or part thereof as compared to the level of asparagine in cured or dried leaf derived from the control plant, suitably wherein the level of asparagine is reduced by at least about 17% as compared to the control plant.

Suitably, the reduced expression or activity of the asparagine synthetase confers a reduction in the level of acrylamide in aerosol produced upon heating or combusting the cured or dried leaf derived from the mutant, non-naturally occurring or transgenic plant or part thereof as compared to cured or dried leaf derived from the control plant, suitably, wherein the level of acrylamide in aerosol is reduced by at least 20% as compared to cured or dried leaf of the control plant.

Suitably, the level of asparagine in cured or dried leaf derived from the mutant, non-naturally occurring or transgenic plant or part thereof is at least about 22% lower and the amount of acrylamide in aerosol produced upon heating or combusting the cured or dried leaf derived from the mutant, non-naturally occurring or transgenic plant or part thereof is at least 24% lower than cured or dried leaf and aerosol of the control plant; suitably, wherein the level of asparagine in cured or dried leaf derived from the mutant, non-naturally occurring or transgenic plant or part thereof is at least about 44% lower and the amount of acrylamide in aerosol produced upon heating or combusting the cured or dried leaf derived from the mutant, non-naturally occurring or transgenic plant or part thereof is at least 66% lower as compared to cured or dried leaf and aerosol of the control plant; suitably, wherein the level of asparagine in cured or dried leaf derived from the mutant, non-naturally occurring or transgenic plant or part thereof is at least about 70% lower and the amount of acrylamide in aerosol produced upon heating or combusting the cured or dried leaf derived from the mutant, non-naturally occurring or transgenic plant or part thereof is at least about 88% lower as compared to cured or dried leaf and aerosol of the control plant.

Suitably, the level of nicotine in cured or dried leaf from the mutant, non-naturally occurring or transgenic plant or part thereof is substantially the same as the level of nicotine in cured or dried leaf of the control plant.

Suitably, the formation of glutamine, aspartic acid and glutamic acid is increased in cured or dried leaf derived from the mutant, non-naturally occurring or transgenic plant or part thereof as compared to cured or dried leaf of the control plant.

Suitably, the plant is selected form the group consisting of tobacco or tea (*Camellia sinensis*). Suitably, the tobacco plant is a *Nicotiana tabacum* tobacco plant, preferably, a Burley type *Nicotiana tabacum* tobacco plant.

Suitably, the plant comprises at least one mutation in each copy of the polynucleotide sequence encoding the asparagine synthetase set forth in (i), (ii) or (iii), suitably a stop mutation(s) and/or a gene fragment(s) that interferes with the translation of an RNA transcript encoding the asparagine synthetase.

Suitably, the asparagine synthetase nucleotide sequence comprises a nucleotide sequence encoding a stop mutation at a position equivalent to the location of the nucleotide sequence encoding the stop mutation in SEQ ID Nos. 19, 21 and 23, or wherein the asparagine synthetase comprises a nucleotide sequence encoding a stop codon at a position equivalent to the location of the stop codon in SEQ ID Nos. 20, 22 and 24.

Suitably, the asparagine synthetase comprises a nucleotide sequence selected from the group consisting of SEQ ID Nos. 19, 21 and 23, or is encoded by the nucleotide sequence selected from the group consisting of SEQ ID Nos. 19, 21 and 23, or comprises, consists or consists essentially of the polypeptide sequence set forth in SEQ ID Nos. 20, 22 and 24.

Suitably, the amount of leaf biomass from the mutant, non-naturally occurring or transgenic plant or part thereof plant is substantially the same as the amount of leaf biomass from the control plant.

Suitably, the leaf is air cured, suitably, wherein the air cured leaf is sun cured or fire cured.

Suitably, the leaf is air dried, suitably, wherein the air dried leaf is sun dried or fire dried.

In another aspect, there is provided plant material or cured or dried plant material from the plant of the present disclosure.

In another aspect, there is provided a plant product comprising at least a part of the plant or the plant material of the present disclosure.

In another aspect, there is provided a method of preparing plant material with reduced levels of asparagine and reduced levels of acrylamide in aerosol derived from said plant material as compared to plant material from a control plant, said method comprising the steps of: (a) providing a plant or part thereof comprising a polynucleotide comprising, consisting or consisting essentially of a sequence encoding an asparagine synthetase and having at least 72% or at least 90 sequence identity to SEQ ID NO:1 or at least 72% sequence identity to SEQ ID NO:3 or SEQ ID NO:5 or SEQ ID NO:7; (b) reducing the expression of the polynucleotide or the activity of the protein encoded thereby in the plant or part thereof; (c) harvesting plant material from the plant or part thereof; (d) drying or curing the plant material; (e) optionally, measuring the levels of asparagine in the plant or part thereof and/or measuring the levels of acrylamide in aerosol derived from the plant or part thereof; and (f) obtaining cured or dried plant material with reduced levels of asparagine and reduced levels of acrylamide in aerosol derived from said plant material, suitably, wherein the level of nicotine is substantially the same as the level of nicotine in the control plant; suitably, wherein the formation of glutamine, aspartic acid and glutamic acid is increased as compared to cured or dried leaf of the control plant.

Suitably, the plant material is cured or dried for at least about 3 days after harvesting.

Suitably, the plant material is air cured, suitably, wherein the air cured leaf is sun cured or fire cured.

Suitably, the plant material is air dried or sun dried or fire dried.

Plant material obtained or obtainable by this method is also disclosed.

In another aspect, there is provided a method for identifying one or more genetic alterations in a plant that correlates with reduced levels of asparagine in cured or dried plant material from the plant and reduced levels of acrylamide in aerosol derived from the cured or dried plant or part thereof as compared to a control plant that does not comprise the one or more genetic alterations, said method comprising the steps of: (a) identifying a cured or dried plant with reduced levels of asparagine in plant material from the plant and reduced levels of acrylamide in aerosol derived from the cured or dried plant material as compared to plant material from a control plant; (b) providing a nucleic acid sample from the plant identified in step (a); and (c) identifying in the nucleic acid sample from step (b) one or more genetic alterations in a polynucleotide sequence encoding asparagine synthetase and having at least 72% or at least 90% sequence identity to SEQ ID NO:1 or at least 72% sequence identity to SEQ ID NO:3 or SEQ ID NO:5 or SEQ ID NO:7.

In another aspect, there is provided a method for producing plant material with reduced levels of asparagine and reduced levels of acrylamide in aerosol derived from cured or dried plant material as compared to a control plant, said method comprising the steps of: (a) providing the plant or the plant material according to the present disclosure; (b) harvesting plant material from the plant; (c) curing or drying the plant material for a period of time; and (d) obtaining cured or dried plant material that has reduced levels of asparagine and reduced levels of acrylamide in aerosol derived from the cured or dried plant material, suitably, wherein the level of nicotine is substantially the same as the level of nicotine in the control plant; suitably, wherein the formation of glutamine, aspartic acid and glutamic acid is increased as compared to the control plant.

In another aspect, there is provided an isolated polynucleotide sequence comprising, consisting or consisting essentially of a sequence encoding asparagine synthetase and having at least 72% or at least 90% sequence identity to SEQ ID NO:1 or at least 72% sequence identity to SEQ ID NO:3 or SEQ ID NO:5 or SEQ ID NO:7 or comprising, consisting or consisting essentially of a sequence encoding asparagine synthetase and having at least 72% sequence identity to SEQ ID Nos 19, 21 and 23 with the proviso that the sequence with at least 72% sequence identity to SEQ ID Nos 19, 21 and 23 comprises a nucleotide sequence encoding a stop codon at a position equivalent to the location of the stop codon in SEQ ID Nos. 19, 21 and 23, preferably wherein said isolated polynucleotide is a synthetic polynucleotide or cDNA.

In another aspect, there is provided an isolated polypeptide encoded by the polynucleotide described herein.

In another aspect, there is provided an isolated polypeptide comprising, consisting or consisting essentially of a sequence encoding asparagine synthetase and having at least 78% sequence identity to SEQ ID NO:2 or SEQ ID NO:4 or SEQ ID NO:6 or SEQ ID NO:8 or SEQ ID NO: 20 or SEQ ID NO: 22 or SEQ ID NO: 24 or comprising, consisting or consisting essentially of a sequence encoding asparagine synthetase and having at least 78% sequence identity to SEQ ID NO:2 or SEQ ID NO:4 or SEQ ID NO:6 or SEQ ID NO:8 or SEQ ID NO: 20 or SEQ ID NO: 22 or SEQ ID NO: 24 with the proviso that the sequence with at least 78% sequence identity to SEQ ID NO: 20 or SEQ ID NO: 22 or SEQ ID NO: 24 comprises a stop codon at a position equivalent to the location of the stop codon in SEQ ID NO: 20 or SEQ ID NO: 22 or SEQ ID NO: 24, preferably wherein said isolated polynucleotide is a synthetic polynucleotide or cDNA.

In another aspect, there is provided a construct, vector or expression vector comprising the isolated polynucleotide described herein.

In another aspect, there is provided a mutant, non-naturally occurring or transgenic plant cell from the plant described herein.

In another aspect, there is provided cured or dried plant material comprising the cell described herein.

In another aspect, there is provided a tobacco product or a smoking article comprising the plant material described herein.

Combinations of one or more of the embodiments set forth is also disclosed.

Some Advantages

It is shown herein that asparagine is actively produced during curing. It is shown that this accumulation of asparagine leads to the formation of acrylamide in aerosol produced when the cured plant material is heated or combusted. Advantageously, NtASN1-S, NtASN1-T, NtASN5-S and NtASN5-T are highly expressed during curing, particularly from the onset of curing. Reducing the expression of one or more of these genes can result in lower levels of acrylamide in aerosol since the level of asparagine can be reduced throughout the curing process.

There is limited impact on levels of nicotine in the modified plants described herein, which is desirable when the modified plants are intended to be used for the production of tobacco plants.

The methods described herein consistently result in plants in which the accumulation of asparagine during curing or drying is reduced and the formation of acrylamide in aerosol is also reduced.

There is limited impact on leaf biomass and phenotype which is advantageous when using the modified plants described herein for commercial purposes.

The present disclosure allows non-genetically modified plants to be created which may be more acceptable to consumers.

The present disclosure is not restricted to the use of EMS mutant plants as in US2013/0068240. An EMS mutant plant can have less potential to bring improved properties to a crop after breeding. Once breeding is started, the desirable characteristic(s) of the EMS mutant plant can be lost for different reasons. For example, several mutations may be required, the mutation can be dominant or recessive, and the identification of a point mutation in a gene target can be difficult to reach. In contrast, the present disclosure exploits the use of certain genes that can be specifically manipulated and/or knocked out to produce plants with a desirable phenotype. The disclosure may be applied to other tobacco varieties or crops, thereby offering a desirable solution to reduce at least acrylamide.

BRIEF DESCRIPTION OF THE DRAWINGS

FIG. 3 shows the asparagine synthetase activity pathway.

DEFINITIONS

Figure 1:
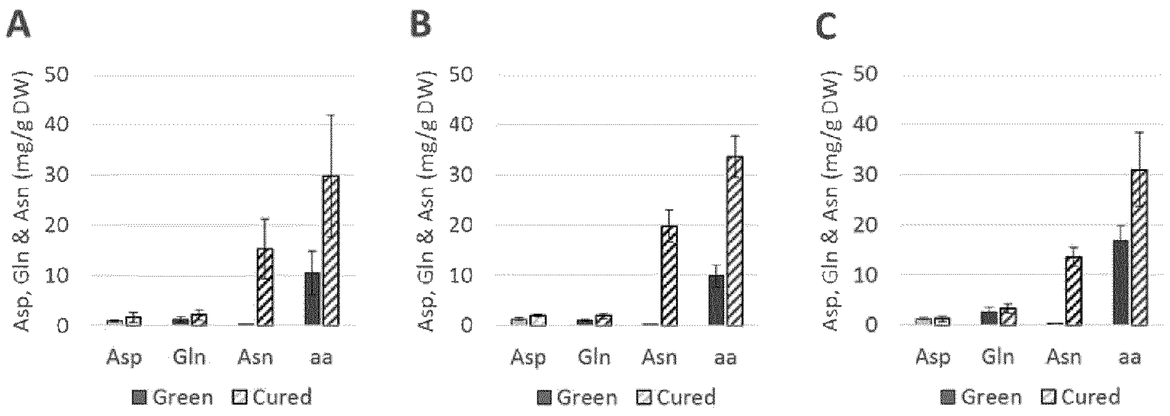
FIG. 1 shows the aspartate (Asp), glutamine (Glu), asparagine (Asn) and total free amino acid (aa) content in 3 different Burley tobacco cultivated in the same field (average of 5 plot replicates) and cured simultaneously. The three Burley are TN90 (A), Banket A1 (B) and Kentucky 14 (C).

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

An "expression vector" is a nucleic acid vehicle that comprises a combination of nucleic acid components for enabling the expression of nucleic acid. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment. The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (for example, BLOSUM62, PAM250, Gonnet etc.), and gap-penalty, for example, functional form and constants. Having made the alignment, there are different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance. The popular multiple alignment program ClustalW (Nucleic Acids Research (1994) 22, 4673-4680; Nucleic Acids Research (1997), 24, 4876-4882) is a suitable way for generating multiple alignments of polypeptides or polynucleotides. Suitable parameters for ClustalW maybe as follows: For polynucleotide alignments: Gap Open Penalty=15.0, Gap Extension Penalty=6.66, and Matrix=Identity. For polypeptide alignments: Gap Open Penalty=10. o, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment. Suitably, calculation of percentage identities is then calculated from such an alignment as (N/T), where N is the number of positions at which the sequences share an identical residue, and T is the total number of positions compared including gaps but excluding overhangs.

A "variant" means a substantially similar sequence. A variant can have a similar function or substantially similar function as a wild-type sequence. For asparagine synthetase, a similar function is at least about 50%, 60%, 70%, 80% or 90% of wild-type enzyme function of converting aspartate to asparagine from under the same conditions. For asparagine synthetase, a substantially similar function is at least about 90%, 95%, 96%, 97%, 98% or 99% of wild-type enzyme function of converting aspartate to asparagine under the same conditions. The variants can have one or more favourable mutations that result in the enzyme having a reduced level of asparagine synthetase activity as compared to the wild-type polypeptide. The variants can have one or more favourable mutations that result in their asparagine synthetase activity being knocked out (ie. a 100% inhibition, and thus a non-functional polypeptide). An exemplary variant of wild-type ASN1-S is ASN1-S_W156*(SEQ ID Nos 19 and 20) which has a favourable stop mutation that results in about a 17% reduction in asparagine as compared to the wild-type ASN1-S polypeptide. An exemplary variant of wild-type ASN1-T is ASN1-T_W156*(SEQ ID Nos 21 and 22) which has a favourable stop mutation that results in about a 83% reduction in asparagine as compared to the wild-type ASN1-S polypeptide. An exemplary variant of wild-type ASN5-S is ASN5-S_Q66*(SEQ ID Nos 23 and 24) which has a favourable stop mutation that results in about a 44% reduction in asparagine as compared to the wild-type ASN1-S polypeptide.

The term "plant" refers to any plant or part of a plant at any stage of its life cycle or development, and its progenies. In one embodiment, the plant is a "tobacco plant", which refers to a plant belonging to the genus *Nicotiana*. Preferred species of tobacco plant are described herein. Suitably, the plant is a mutant, non-naturally occurring or transgenic plant in which the expression of one or more genes or the activity of one or more proteins is modulated as compared to a control plant. Suitably, the alteration that renders the plant a mutant, non-naturally occurring or transgenic plant results in the modulation of the expression of one or more genes or the modulation of the activity of one or more proteins. In certain embodiments, the alteration is a genetic alternation or a genetic modification.

"Plant parts" include plant cells, plant protoplasts, plant cell tissue cultures from which a whole plant can be regenerated, plant calli, plant clumps and plant cells that are intact in plants or parts of plants such as embryos, pollen, anthers, ovules, seeds, leaves, flowers, stems, branches, fruit, roots, root tips and the like. Progeny, variants and mutants of regenerated plants are also included within the scope of the disclosure, provided that they comprise the introduced polynucleotides described herein. Leaves of plants are particularly preferred for use in the present disclosure.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant.

The term "plant material" refers to any solid, liquid or gaseous composition, or a combination thereof, obtainable from a plant, including biomass, leaves, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, stem, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term 'non-naturally occurring' as used herein describes an entity (for example, a polynucleotide, a genetic mutation, a polypeptide, a plant, and a plant cell and plant material) that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell.

The term "modulating" may refer to reducing, inhibiting, increasing or otherwise affecting the expression or activity of a polypeptide. The term may also refer to reducing, inhibiting, increasing or otherwise affecting the activity of a gene encoding a polypeptide which can include, but is not limited to, modulating transcriptional activity.

The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity and protein expression.

Transformation of a cell may be stable or transient. The term "transient transformation" or "transiently transformed" or variations thereof refers to the introduction of one or more exogenous polynucleotides into a cell in the absence of integration of the exogenous polynucleotide into the host cell's genome. In contrast, the term "stable transformation" or "stably transformed" refers to the introduction and integration of one or more exogenous polynucleotides into the genome of a cell. The term "stable transformant" refers to a cell which has stably integrated one or more exogenous polynucleotides into the genomic or organellar DNA. It is to be understood that an organism or its cell transformed with the nucleic acids, constructs and/or vectors of the present disclosure can be transiently as well as stably transformed. In certain embodiments, stable transformation is preferred.

The term "increase" or "increased" as used herein, refers to an increase of from about 5% to about 99%, or an increase of at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "substantially" as used herein and when used in the context of an amount means that the amount is at least about 10%, at least about 9%, at least about 8%, at least about 7%, at least about 6%, at least about 5%, at least about 4%, at least about 3%, at least about 2%, at least about 1%, or at least about 0.1% of the amount that it is being compared to.

The term "control" in the context of a control plant or control plant cell and the like means a plant or plant cell in which the expression or activity of the gene or protein of interest has not been modulated and so it can provide a comparison or reference with a plant or plant cell in which the expression or activity of the enzyme has been modified. Thus, in the context of the present invention, the control will not include the at least one genetic alteration which reduces the expression or activity of the asparagine synthetase. The control plant or pant cell may comprise an empty vector. The control plant or plant cell may correspond to a wild-type plant or wild-type plant cell and the like. In all such cases, the subject plant and the control plant are cultured and harvested using the same protocols for comparative purposes. Changes in levels, ratios, activity, or distribution of the genes or polypeptides described herein, or changes in plant phenotype, particularly reduced accumulation of asparagine and/or reduced accumulation of acrylamide and/or increased accumulation of glutamine, and/or increased accumulation of aspartic acid and/or increased accumulation of glutamic acid can be measured by comparing a subject plant to the control plant, suitably, where the subject plant and the control plant have been cultured and/or harvested using the same protocols. The control plant can provide a reference point for measuring changes in phenotype of the subject plant. The measurement of changes in phenotype can be measured at any time in a plant, including during plant development, senescence, or after curing. Measurement of changes in phenotype can be measured in plants grown under any conditions, including from plants grown in growth chamber, greenhouse, or in a field. Changes in phenotype can be measured by measuring asparagine content and/or glutamine content and/or aspartic acid content and/or glutamic acid content (as described in Moldoveanu (2005)) and/or acrylamide content (as described in Papousek et al., 2014 and/or Onoa et al., 2003 and/or United States Environmental Protection Agency Method 8032A—Acrylamide by Gas Chromatography, Revision 1, Dec. 1996 and/or nicotine content (using Cooperation Centre for Scientific Research Relative to Tobacco Recommended (CORESTA) Method Number 62, Determination of nicotine in tobacco and tobacco products by gas chromatographic analysis (February 2005)) can be monitored before and/or during and/or after curing or drying using methods that are well known in the art. Free amino acid analyses is performed using a method adapted from Moldoveanu (2005).

DETAILED DESCRIPTION

In one embodiment, there is provided an isolated polynucleotide comprising, consisting or consisting essentially of a polynucleotide sequence having at least 60% sequence identity to any of the sequences described herein, including any of polynucleotides shown in the sequence listing. Suitably, the isolated polynucleotide comprises, consists or consists essentially of a sequence having at least 60%, 61%, 62%, 63%, 64%, 65%, 66%, 67%, 68%, 69%, 70%, 71%, 72%, 73%, 74%, 75%, 78%, 80%, 85%, 87%, 88%, 89%, 90%, 91%, 92%, 93%, 94%, 95% 96%, 97%, 98%, 99% or 100% sequence identity thereto. More suitably, the isolated polynucleotide comprises, consists or consists essentially of a sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity thereto. Alignments of the sequences described herein are shown in Table 1.

In another embodiment, there is provided an isolated polynucleotide comprising, consisting or consisting essentially of a polynucleotide sequence having at least 60% sequence identity to SEQ ID NO:1 or SEQ ID NO:3 or SEQ ID NO:5 or SEQ ID NO:7 or SEQ ID NO:9 or SEQ ID NO:11. Suitably, the isolated polynucleotide SEQ ID NO:1 or SEQ ID NO:3 or SEQ ID NO:5 or SEQ ID NO:7 or SEQ ID NO:9 or SEQ ID NO:11 comprises, consists or consist essentially of a sequence having at least about 60%, 61%, 62%, 63%, 64%, 65%, 66%, 67%, 68%, 69%, 70%, 75%, 78% 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:1 or SEQ ID NO:3 or SEQ ID NO:5 or SEQ ID NO:7 or SEQ ID NO:9 or SEQ ID NO:11. More suitably, the isolated polynucleotide comprises, consists or consists essentially of a sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO:1 or SEQ ID NO:3 or SEQ ID NO:5 or SEQ ID NO:7 or SEQ ID NO:9 or SEQ ID NO:11.

More suitably, the isolated polynucleotide comprises, consists or consists essentially of a sequence having at least 90%, 91%, 92%, 93%, 94%, 95% 96%, 97%, 98%, 99% or 100% sequence identity to SEQ ID NO:1.

More suitably, the isolated polynucleotide comprises, consists or consists essentially of a sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO:3 or SEQ ID NO:5 or SEQ ID NO:7 or SEQ ID NO:9 or SEQ ID NO:11.

In another embodiment, there is provided an isolated polynucleotide comprising, consisting or consisting essentially of a polynucleotide sequence having at least 60% sequence identity to SEQ ID NO:19 or SEQ ID NO:21 or SEQ ID NO:23 with the proviso that said isolated polynucleotide comprises the mutation encoding the stop codon at a position equivalent to the position set forth in SEQ ID NO:19 or SEQ ID NO:21 or SEQ ID NO:23.

Suitably, the isolated polynucleotide comprises, consists or consist essentially of a sequence having at least about 60%, 61%, 62%, 63%, 64%, 65%, 66%, 67%, 68%, 69%, 70%, 75%, 78% 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:19 or SEQ ID NO:21 or SEQ ID NO:23. More suitably, the isolated polynucleotide comprises, consists or consists essentially of a sequence having at least 72%, 73%, 74%, 75%, 78%, 80%, 85%, 87%, 88%, 89%, 90%, 91%, 92%, 93%, 94%, 95% 96%, 97%, 98%, 99% or 100% sequence identity to SEQ ID NO:19 or SEQ ID NO:21 or SEQ ID NO:23.

In another embodiment, there is provided a polynucleotide comprising, consisting or consisting essentially of a polynucleotide with substantial homology (that is, sequence similarity) or substantial identity to SEQ ID NO:1 or SEQ ID NO:3 or SEQ ID NO:5 or SEQ ID NO:7 or SEQ ID NO:9 or SEQ ID NO:11.

In another embodiment, there is provided a polynucleotide comprising, consisting or consisting essentially of a polynucleotide with substantial homology (that is, sequence similarity) or substantial identity to SEQ ID NO:19 or SEQ ID NO:21 or SEQ ID NO:23 with the proviso that said isolated polynucleotide comprises the mutation encoding the stop codon at a position equivalent to the position set forth in SEQ ID NO:19 or SEQ ID NO:21 or SEQ ID NO:23.

In another embodiment, there is provided polynucleotide variants that have at least about 60%, 61%, 62%, 63%, 64%, 65%, 66%, 67%, 68%, 69%, 70%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:1 or SEQ ID NO:3 or SEQ ID NO:5 or SEQ ID NO:7 or SEQ ID NO:9 or SEQ ID NO:11. Suitably, there is provided polynucleotide variants that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:1 or SEQ ID NO:3 or SEQ ID NO:5 or SEQ ID NO:7 or SEQ ID NO:9 or SEQ ID NO:11.

Suitably, there is provided polynucleotide variants that have at least about 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:1.

Suitably, there is provided polynucleotide variants that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:3 or SEQ ID NO:5 or SEQ ID NO:7 or SEQ ID NO:9 or SEQ ID NO:11.

In another embodiment, there is provided polynucleotide variants that have at least about 60%, 61%, 62%, 63%, 64%, 65%, 66%, 67%, 68%, 69%, 70%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:19 or SEQ ID NO:21 or SEQ ID NO:23 with the proviso that said polynucleotide variants comprise the mutation encoding the stop codon at a position equivalent to the position set forth in SEQ ID NO:19 or SEQ ID NO:21 or SEQ ID NO:23. Suitably, there is provided polynucleotide variants that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:19 or SEQ ID NO:21 or SEQ ID NO:23 with the proviso that said polynucleotide variants comprise the mutation encoding the stop codon at a position equivalent to the position set forth in SEQ ID NO:19 or SEQ ID NO:21 or SEQ ID NO:23. In another embodiment, there is provided fragments of SEQ ID NO:1 or SEQ ID NO:3 or SEQ ID NO:5 or SEQ ID NO:7 or SEQ ID NO:9 or SEQ ID NO:11 with substantial homology (that is, sequence similarity) or substantial identity thereto that have at least about 60%, 61%, 62%, 63%, 64%, 65%, 66%, 67%, 68%, 69%, 70%, 78%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:1 or SEQ ID NO:3 or SEQ ID NO:5 or SEQ ID NO:7 or SEQ ID NO:9 or SEQ ID NO:11.

In another embodiment, there is provided fragments of SEQ ID NO:1 with substantial homology (that is, sequence similarity) or substantial identity thereto that have at least about 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragment of SEQ ID NO:1.

In another embodiment, there is provided fragments of SEQ ID NO:3 or SEQ ID NO:5 or SEQ ID NO:7 or SEQ ID NO:9 or SEQ ID NO:11 with substantial homology (that is, sequence similarity) or substantial identity thereto that have at least about 60%, 61%, 62%, 63%, 64%, 65%, 66%, 67%, 68%, 69%, 70%, 78%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:3 or SEQ ID NO:5 or SEQ ID NO:7 or SEQ ID NO:9 or SEQ ID NO:11.

Suitably, there is provided fragments of polynucleotide variants of SEQ ID NO:1 or SEQ ID NO:3 or SEQ ID NO:5 or SEQ ID NO:7 or SEQ ID NO:9 or SEQ ID NO:11 with substantial homology (that is, sequence similarity) or substantial identity thereto that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the corresponding fragments of SEQ ID NO:1 or SEQ ID NO:3 or SEQ ID NO:5 or SEQ ID NO:7 or SEQ ID NO:9 or SEQ ID NO:11.

Suitably, there is provided fragments of polynucleotide variants of SEQ ID NO:1 with substantial homology (that is, sequence similarity) or substantial identity thereto that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the corresponding fragments of SEQ ID NO:1.

Suitably, there is provided fragments of polynucleotide variants of SEQ ID NO:3 or SEQ ID NO:5 or SEQ ID NO:7 or SEQ ID NO:9 or SEQ ID NO:11 with substantial homology (that is, sequence similarity) or substantial identity thereto that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the corresponding fragments of SEQ ID NO:3 or SEQ ID NO:5 or SEQ ID NO:7 or SEQ ID NO:9 or SEQ ID NO:11.

In another embodiment, there is provided polynucleotide fragments of SEQ ID NO:19 or SEQ ID NO:21 or SEQ ID NO:23 with substantial homology (that is, sequence similarity) or substantial identity thereto that have at least about 60%, 61%, 62%, 63%, 64%, 65%, 66%, 67%, 68%, 69%, 70%, 78%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:19 or SEQ ID NO:21 or SEQ ID NO:23 with the proviso that said fragments comprise the mutation encoding the stop codon at a position equivalent to the position set forth in SEQ ID NO:19 or SEQ ID NO:21 or SEQ ID NO:23. Suitably, there is provided fragments of polynucleotide variants of SEQ ID NO:19 or SEQ ID NO:21 or SEQ ID NO:23 with substantial homology (that is, sequence similarity) or substantial identity thereto that have at least about 72%, 73%, 74%, 75%, 78%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8% or 99.9% sequence identity to the corresponding fragments of SEQ ID NO:19 or SEQ ID NO:21 or SEQ ID NO:23 with the proviso that said fragments comprise the mutation encoding the stop codon at a position equivalent to the position set forth in SEQ ID NO:19 or SEQ ID NO:21 or SEQ ID NO:23.

In another embodiment, there is provided polynucleotides comprising a sufficient or substantial degree of identity or similarity to SEQ ID NO:1 or SEQ ID NO:3 or SEQ ID NO:5 or SEQ ID NO:7 or SEQ ID NO:9 or SEQ ID NO:11 that encodes a polypeptide that functions as an asparagine synthetase. Suitably, the polynucleotide(s) described herein encode a protein with asparagine synthetase activity that is at least about 60%, 70%, 80%, 90%, 95%, 96%, 97%, 98%, 99% or 100% or more of the activity of the protein set forth in SEQ ID NO:2 or SEQ ID NO:4 or SEQ ID NO:6 or SEQ ID NO:8 or SEQ ID NO:10 or SEQ ID NO:12. To determine if a polypeptide is a functional asparagine synthetase, the assay described by Romagni & Dayan (2000) *J Agric Food Chem*. May; 48(5):1692-6 can be used. In another embodiment, there is provided polynucleotides comprising a sufficient or substantial degree of identity or similarity to SEQ ID NO:19 or SEQ ID NO:21 or SEQ ID NO:23 that encodes a polypeptide that functions as an asparagine synthetase with the proviso that said polynucleotides comprise the mutation encoding the stop codon at a position equivalent to the position set forth in SEQ ID NO:19 or SEQ ID NO:21 or SEQ ID NO:23. Suitably, the polynucleotide(s) described herein encode a protein with asparagine synthetase activity that is at least about 60%, 70%, 80%, 90%, 95%, 96%, 97%, 98%, 99% or 100% or more of the activity of the protein set forth in SEQ ID NO:19 or SEQ ID NO:21 or SEQ ID NO:23.

In certain embodiments, the expression of a polynucleotide comprising, consisting or consisting essentially of a sequence encoding asparagine synthetase and having at least 72% sequence identity to SEQ ID NO:1 and SEQ ID NO:3 and SEQ ID NO:5 and SEQ ID NO:7 is modulated.

In certain embodiments, the expression of a polynucleotide comprising, consisting or consisting essentially of a sequence encoding asparagine synthetase and having at least 90% sequence identity to SEQ ID NO:1 is modulated.

In certain embodiments, the expression of a polynucleotide comprising, consisting or consisting essentially of a sequence encoding asparagine synthetase and having at least 72% sequence identity to SEQ ID NO:3 and SEQ ID NO:5 and SEQ ID NO:7 is modulated.

In certain embodiments, the expression of a polynucleotide comprising, consisting or consisting essentially of a sequence encoding asparagine synthetase and having at least 72% sequence identity to SEQ ID NO:1 or SEQ ID NO:3 or SEQ ID NO:5 or SEQ ID NO:7 is modulated.

In certain embodiments, the expression of a polynucleotide comprising, consisting or consisting essentially of a sequence encoding asparagine synthetase and having at least 90% sequence identity to SEQ ID NO:1 is modulated.

In certain embodiments, the expression of a polynucleotide comprising, consisting or consisting essentially of a sequence encoding asparagine synthetase and having at least 72% sequence identity to SEQ ID NO:3 or SEQ ID NO:5 or SEQ ID NO:7 is modulated.

In certain embodiments, the expression of a polynucleotide comprising, consisting or consisting essentially of a sequence encoding asparagine synthetase and having at least 72% sequence identity to SEQ ID NO:1 and SEQ ID NO:3 is modulated. In certain embodiments, the expression of a polynucleotide comprising, consisting or consisting essentially of a sequence encoding asparagine synthetase and having at least 90% sequence identity to SEQ ID NO:1 and at least 72% sequence identity to SEQ ID NO:3 is modulated. In certain embodiments, the expression of a polynucleotide comprising, consisting or consisting essentially of a sequence encoding asparagine synthetase and having at least 72% sequence identity to SEQ ID NO:5 and SEQ ID NO:7 is modulated. In certain embodiments, the expression of a polynucleotide comprising, consisting or consisting essentially of a sequence encoding asparagine synthetase and having at least 72% sequence identity to SEQ ID NO:1 and SEQ ID NO:3 and SEQ ID NO:5 and/or SEQ ID NO:7 is modulated. In certain embodiments, the expression of a polynucleotide comprising, consisting or consisting essentially of a sequence encoding asparagine synthetase and having at least 90% sequence identity to SEQ ID NO:1 and at least 72% sequence identity to SEQ ID NO:3 and SEQ ID NO:5 and/or SEQ ID NO:7 is modulated. In certain embodiments, the expression of a polynucleotide comprising, consisting or consisting essentially of a sequence encoding asparagine synthetase and having at least 72% sequence identity to SEQ ID NO:1 and/or SEQ ID NO:3 and SEQ ID NO:5 and SEQ ID NO:7 is modulated. In certain embodiments, the expression of a polynucleotide comprising, consisting or consisting essentially of a sequence encoding asparagine synthetase and having at least 90% sequence identity to SEQ ID NO:1 and/or at least 72% sequence identity to SEQ ID NO:3 and SEQ ID NO:5 and SEQ ID NO:7 is modulated.

In certain embodiments, the expression of a polynucleotide comprising, consisting or consisting essentially of a sequence encoding asparagine synthetase and having at least 72% sequence identity to SEQ ID NO:19 and SEQ ID NO:21 and SEQ ID NO:23 is modulated with the proviso that said polynucleotides comprise the mutation encoding the stop codon at a position equivalent to the position set forth in SEQ ID NO:19 or SEQ ID NO:21 or SEQ ID NO:23.

In certain embodiments, the expression of a polynucleotide comprising, consisting or consisting essentially of a sequence encoding asparagine synthetase and having at least 72% sequence identity to SEQ ID NO:19 or SEQ ID NO:21 or SEQ ID NO:23 is modulated with the proviso that said polynucleotides comprise the mutation encoding the stop codon at a position equivalent to the position set forth in SEQ ID NO:19 or SEQ ID NO:21 or SEQ ID NO:23.

In certain embodiments, the expression of a polynucleotide comprising, consisting or consisting essentially of a sequence encoding asparagine synthetase and having at least 72% sequence identity to SEQ ID NO:19 and SEQ ID NO:21 is modulated with the proviso that said polynucleotides comprise the mutation encoding the stop codon at a position equivalent to the position set forth in SEQ ID NO:19 and SEQ ID NO:21.

In certain embodiments, the expression of a polynucleotide comprising, consisting or consisting essentially of a sequence encoding asparagine synthetase and having at least 72% sequence identity to SEQ ID NO:21 and SEQ ID NO:23 is modulated with the proviso that said polynucleotides comprise the mutation encoding the stop codon at a position equivalent to the position set forth in SEQ ID NO:21 and SEQ ID NO:23.

In certain embodiments, the expression of a polynucleotide comprising, consisting or consisting essentially of a sequence encoding asparagine synthetase and having at least 72% sequence identity to SEQ ID NO:19 and SEQ ID NO:21 and/or SEQ ID NO:23 is modulated with the proviso that said polynucleotides comprise the mutation encoding the stop codon at a position equivalent to the position set forth in SEQ ID NO:19, SEQ ID NO:21 and SEQ ID NO:23.

In certain embodiments, the expression of a polynucleotide comprising, consisting or consisting essentially of a sequence encoding asparagine synthetase and having at least 72% sequence identity to SEQ ID NO:19 and/or SEQ ID NO:21 and SEQ ID NO:23 is modulated with the proviso that said polynucleotides comprise the mutation encoding the stop codon at a position equivalent to the position set forth in SEQ ID NO: 19, SEQ ID NO:21 and SEQ ID NO:23.

A polynucleotide as described herein can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

A polynucleotide as described herein will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in nucleic acid hybridisation assays or primers for use in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide encoding a protein with asparagine synthetase activity or encoding an asparagine synthetase enzyme comprising the use of the probes or primers or both. Exemplary primers are set forth in SEQ ID NOs: 13 to 16. Accordingly, a further aspect, relates to an oligonucleotide primer comprising, consisting or consisting essential of a nucleotide sequence with at least 60%, 61%, 62%, 63%, 64%, 65%, 66%, 67%, 68%, 69%, 70%, 75%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 13, SEQ ID NO: 14, SEQ ID NO: 15 or SEQ ID NO: 16. Method of using these primers to detect a polynucleotide encoding a protein with asparagine synthetase activity and uses thereof are also disclosed.

The basic parameters affecting the choice of hybridization conditions for polynucleotides and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions can be readily determined by those having ordinary skill in the art based on, for example, the length or base composition of the polynucleotide. One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15 M sodium chloride, 10 mM sodium phosphate, and 1.25 mM Ethylenediaminetetraacetic acid, pH 7.4) can be substituted for Standard Sodium Citrate (1× Standard Sodium Citrate is 0.15 M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2 (number of A+T bases)+4 (number of G+C bases). For hybrids above 18 base pairs in length, melting temperature (° C.)=81.5+16.6 (log 10[Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction. Recombinant constructs provided herein can be used to transform plants or plant cells in order to modulate protein expression and/or activity levels. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which protein expression and/or activity levels are modulated can include mutant, non-naturally occurring, transgenic, man-made or genetically engineered plants or plant cells. Suitably, the plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. The plant can include a plant regenerated from an originally-transformed plant cell and progeny plants from later generations or crosses of a transformed plant. Suitably, the modification alters the expression or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available. The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent protein, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. The use of genome editing is also contemplated.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified protein operably linked, in the sense or antisense orientation, to regulatory sequences are joined to appropriate T-DNA sequences by conventional methods. These are introduced into protoplasts by polyethylene glycol techniques or by electroporation techniques, both of which are standard. Alternatively, such vectors comprising recombinant DNA molecules encoding the subject purified protein are introduced into live *Agrobacterium* cells, which then transfer the DNA into the plant cells. Transformation by naked DNA without accompanying T-DNA vector sequences can be accomplished via fusion of protoplasts with DNA-containing liposomes or via electroporation. Naked DNA unaccompanied by T-DNA vector sequences can also be used to transform cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Examples of promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Examples of promoters include constitutive promoters that can be activated in most cell types without requiring specific inducers. Examples of promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Examples of leaf-specific promoters include pyruvate, orthophosphate dikinase (PPDK) promoter from C4 plant (maize), cab-m1Ca+2 promoter from maize, the Arabidopsis thaliana myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Examples of senescence-specific promoters include a tomato promoter active during fruit ripening, senescence and abscission of leaves, a maize promoter of gene encoding a cysteine protease, the promoter of 82E4 and the promoter of SAG genes.

In certain embodiments, a senescence-specific promoter is preferred. Suitably, the promoter can be an E4 promoter. The E4 promoter has been reported as a suitable senescence promoter for tobacco using GUS as reporter gene in *Plant Mol Biol*. (2008) March; 66(4):415-27. Another exemplary promoter is the SAG12 promoter as described in *Plant Cell*. (1999) June; 11(6):1073-80. Anther-specific promoters are further examples. Root-preferred promoters known to persons skilled in the art may be selected. Seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nucic; and celA (cellulose synthase). Gama-zein is an endosperm-specific promoter. Glob-1 is an embryo-specific promoter. For dicots, seed-specific promoters include, but are not limited to, bean beta-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an Itp2 promoter, cim1 promoter, maize end1 and end2 promoters, nuc1 promoter, Zm40 promoter, eep1 and eep2; lec1, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids), or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter). In certain embodiments, a Mirabilis Mosaic Virus (MMV) promoter is preferred. In certain embodiments, a 35S promoter is preferred.

In another aspect, there is provided an isolated polypeptide comprising, consisting or consisting essentially of a polypeptide sequence having at least 60% sequence identity to any of the polypeptide sequences described herein, including any of the polypeptides shown in the sequence listing. Suitably, the isolated polypeptide comprises, consists or consists essentially of a sequence having at least 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity thereto.

In one embodiment, the isolated polypeptide comprises, consists or consists essentially of a sequence having at least 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:2 or SEQ ID NO:4 or SEQ ID NO:6 or SEQ ID NO:8 or SEQ ID NO:10 or SEQ ID NO:12. In another embodiment, the isolated polypeptide comprises, consists or consists essentially of a sequence having at least 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:2 or SEQ ID NO:4 or SEQ ID NO:6 or SEQ ID NO:8 or SEQ ID NO:10 or SEQ ID NO:12.

In one embodiment, the isolated polypeptide comprises, consists or consists essentially of a sequence having at least 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:20 or SEQ ID NO:22 or SEQ ID NO:24 with the proviso that said polypeptide comprises the stop codon mutation at a position equivalent to the position set forth in SEQ ID NO:20 or SEQ ID NO:22 or SEQ ID NO:24.

In another embodiment, the isolated polypeptide comprises, consists or consists essentially of a sequence having at least 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:20 or SEQ ID NO:22 or SEQ ID NO:24 with the proviso that said polypeptide comprises the stop codon mutation at a position equivalent to the position set forth in SEQ ID NO:20 or SEQ ID NO:22 or SEQ ID NO:24.1n another embodiment, there is provided a polypeptide variant comprising, consisting or consisting essentially of an amino acid sequence encoded by a polynucleotide variant with at least about 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% sequence identity to SEQ ID NO:2 or SEQ ID NO:4 or SEQ ID NO:6 or SEQ ID NO:8 or SEQ ID NO:10 or SEQ ID NO:12.

In another embodiment, there is provided a polypeptide variant comprising, consisting or consisting essentially of an amino acid sequence encoded by a polynucleotide variant with at least about 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95% 96%, 97%, 98%, 99%, 99.1%, 99.2%, 99.3%, 99.4%, 99.5%, 99.6%, 99.7%, 99.8%, 99.9% sequence identity to SEQ ID NO:20 or SEQ ID NO:22 or SEQ ID NO:24 with the proviso that said polypeptide comprises the stop codon mutation at a position equivalent to the position set forth in SEQ ID NO:20 or SEQ ID NO:22 or SEQ ID NO:24.1n another embodiment, there is provided fragments of the polypeptide of SEQ ID NO:2 or SEQ ID NO:4 or SEQ ID NO:6 or SEQ ID NO:8 or SEQ ID NO:10 or SEQ ID NO:12 or fragments of SEQ ID NO:2 or SEQ ID NO:4 or SEQ ID NO:6 or SEQ ID NO:8 or SEQ ID NO:10 or SEQ ID NO:12 that have at least about 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:2 or SEQ ID NO:4 or SEQ ID NO:6 or SEQ ID NO:8 or SEQ ID NO:10 or SEQ ID NO:12.

In another embodiment, there is provided fragments of the polypeptide of SEQ ID NO:20 or SEQ ID NO:22 or SEQ ID NO:24 or fragments of SEQ ID NO:20 or SEQ ID NO:22 or SEQ ID NO:24 that have at least about 60%, 61%, 62%, 63%, 64%, 65%, 66%, 67%, 68%, 69%, 70%, 75%, 76%, 77%, 78%, 79%, 80%, 85%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:20 or SEQ ID NO:22 or SEQ ID NO:24 with the proviso that said polypeptide comprises the stop codon mutation at a position equivalent to the position set forth in SEQ ID NO:20 or SEQ ID NO:22 or SEQ ID NO:24.1n certain embodiments, the activity of a polypeptide comprising, consisting or consisting essentially of a sequence encoding asparagine synthetase and having at least 78% sequence identity to SEQ ID NO:2 or SEQ ID NO:4 or SEQ ID NO:6 or SEQ ID NO:8 is modulated. In certain embodiments, the activity of a polypeptide comprising, consisting or consisting essentially of a sequence encoding asparagine synthetase and having at least 78% sequence identity to SEQ ID NO:2 and SEQ ID NO:4 and SEQ ID NO:6 and SEQ ID NO:8 is modulated. In certain embodiments, the activity of a polypeptide comprising, consisting or consisting essentially of a sequence encoding asparagine synthetase and having at least 78% sequence identity to SEQ ID NO:2 and SEQ ID NO:4 is modulated. In certain embodiments, the activity of a polypeptide comprising, consisting or consisting essentially of a sequence encoding asparagine synthetase and having at least 78% sequence identity to SEQ ID NO:6 and SEQ ID NO:8 is modulated. In certain embodiments, the activity of a polypeptide comprising, consisting or consisting essentially of a sequence encoding asparagine synthetase and having at least 78% sequence identity to SEQ ID NO:2 and SEQ ID NO:4 and SEQ ID NO:6 and/or SEQ ID NO:8 is modulated. In certain embodiments, the activity of a polypeptide comprising, consisting or consisting essentially of a sequence encoding asparagine synthetase and having at least 78% sequence identity to SEQ ID NO:2 and/or SEQ ID NO:4 and SEQ ID NO:6 and SEQ ID NO:8 is modulated.

In certain embodiments, the activity of a polypeptide comprising, consisting or consisting essentially of a sequence encoding asparagine synthetase and having at least 78% sequence identity to SEQ ID NO:20 or SEQ ID NO:22 or SEQ ID NO:24 is modulated with the proviso that said polypeptide comprises the stop codon mutation at a position equivalent to the position set forth in SEQ ID NO:20 or SEQ ID NO:22 or SEQ ID NO:24.

In certain embodiments, the activity of a polypeptide comprising, consisting or consisting essentially of a sequence encoding asparagine synthetase and having at least 78% sequence identity to SEQ ID NO:20 and SEQ ID NO:22 and SEQ ID NO:24 is modulated with the proviso that said polypeptide comprises the stop codon mutation at a position equivalent to the position set forth in SEQ ID NO:20 and SEQ ID NO:22 and SEQ ID NO:24.

In certain embodiments, the activity of a polypeptide comprising, consisting or consisting essentially of a sequence encoding asparagine synthetase and having at least 78% sequence identity to SEQ ID NO:20 and SEQ ID NO:22 is modulated with the proviso that said polypeptide comprises the stop codon mutation at a position equivalent to the position set forth in SEQ ID NO:20 and SEQ ID NO:22.

In certain embodiments, the activity of a polypeptide comprising, consisting or consisting essentially of a sequence encoding asparagine synthetase and having at least 78% sequence identity to SEQ ID NO:22 and SEQ ID NO:24 is modulated with the proviso that said polypeptide comprises the stop codon mutation at a position equivalent to the position set forth in SEQ ID NO:22 and SEQ ID NO:24.

In certain embodiments, the activity of a polypeptide comprising, consisting or consisting essentially of a sequence encoding asparagine synthetase and having at least 78% sequence identity to SEQ ID NO:20 and SEQ ID NO:24 is modulated with the proviso that said polypeptide comprises the stop codon mutation at a position equivalent to the position set forth in SEQ ID NO:20 and SEQ ID NO:24.

In certain embodiments, the activity of a polypeptide comprising, consisting or consisting essentially of a sequence encoding asparagine synthetase and having at least 78% sequence identity to SEQ ID NO:20 and SEQ ID NO:22 and/or SEQ ID NO:24 is modulated with the proviso that said polypeptide comprises the stop codon mutation at a position equivalent to the position set forth in SEQ ID NO:20 and SEQ ID NO:22 and/or SEQ ID NO:24.

In certain embodiments, the activity of a polypeptide comprising, consisting or consisting essentially of a sequence encoding asparagine synthetase and having at least 78% sequence identity to SEQ ID NO:20 and/or SEQ ID NO:22 and SEQ ID NO:24 is modulated with the proviso that said polypeptide comprises the stop codon mutation at a position equivalent to the position set forth in SEQ ID NO:20 and/or SEQ ID NO:22 and SEQ ID NO:24. The polypeptide can include fragments of sequences comprising a sufficient or substantial degree of identity or similarity to function as an asparagine synthetase. Fragments of the polypeptide(s) typically retain some or all of the activity of the full length sequence—such as at least about 95%, 96%, 97%, 98%, 99%, 99.1%, 99.2%, 99.3%, 99.4%, 99.5%, 99.6%, 99.7%, 99.8%, 99.9% or 100% of the activity.

As discussed herein, the polypeptides also include mutants produced by introducing any type of alterations (for example, insertions, deletions, or substitutions of amino acids; changes in glycosylation states; changes that affect refolding or isomerizations, three-dimensional structures, or self-association states), provided that they still have some or all of their function or activity as an asparagine synthetase. Suitably, the function or activity as an asparagine synthetase is modulated, reduced or inhibited. Suitably, the function or activity as an asparagine synthetase is inhibited such that the asparagine synthetase activity is not detectable.

Polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. The variant may have alterations which produce a silent change and result in a functionally equivalent protein. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| | | |
|---|---|---|
| ALIPHATIC | Non-polar | Gly Ala Pro Ile Leu Val |
| | Polar - uncharged | Cys Ser Thr Met Asn Gly |
| | Polar - charged | Asp Glu Lys Arg |
| AROMATIC | | His Phe Trp Tyr |

The polypeptide may be a mature protein or an immature protein or a protein derived from an immature protein. Polypeptides may be in linear form or cyclized using known methods.

Polypeptides typically comprise at least 10, at least 20, at least 30, or at least 40, or at least 50, or at least 100, or at least 200, or at least 300, or at least 400, or at least 500, or at least 600 contiguous amino acids.

A polypeptide encoded by SEQ ID NO:2 or SEQ ID NO:4 or SEQ ID NO:6 or SEQ ID NO:8 or SEQ ID NO:10 or SEQ ID NO:12 or SEQ ID NO: 20 or SEQ ID NO:22 or SEQ ID NO:24 that has 100% sequence identity thereto or a polypeptide comprising, consisting or consisting essentially of the sequence set forth in SEQ ID NO:2 or SEQ ID NO:4 or SEQ ID NO:6 or SEQ ID NO:8 or SEQ ID NO:10 or SEQ ID NO:12 or SEQ ID NO: 20 or SEQ ID NO:22 or SEQ ID NO:24 is also disclosed.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide, glutathione-5-transferase, his-tag or thioredoxin. Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as a "substantially purified polypeptide"; such purified polypeptides include polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

Isolated or substantially purified polynucleotides or protein compositions are disclosed. An “isolated” or “purified” polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an “isolated” polynucleotide is free of sequences (optimally protein encoding sequences) that naturally flank the polynucleotide (for example, sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with native polypeptides may possess biological properties in common therewith, including biological activity.

Differences in genetic background can be detected by phenotypic differences or by molecular biology techniques known in the art—such as nucleic acid sequencing, presence or absence of genetic markers (for example, microsatellite RNA markers).

Antibodies that are immunoreactive with the polypeptides described herein are also provided. The polypeptides, fragments, variants, fusion polypeptides, and the like, as set forth herein, can be employed as “immunogens” in producing antibodies immunoreactive therewith. Such antibodies may specifically bind to the polypeptide via the antigen-binding sites of the antibody. Specifically binding antibodies are those that will specifically recognize and bind with a polypeptide, homologues, and variants, but not with other molecules. In one embodiment, the antibodies are specific for polypeptides having an amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with a polypeptide, fragment, variant, or mutants thereof. Such host animals may include, but are not limited to, rabbits, mice, and rats, to name a few. Various adjutants may be used to increase the immunological response. Depending on the host species, such adjuvants include, but are not limited to, Freund’s (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Fragments of polynucleotides and polypeptides encoded thereby are also disclosed. Fragments of a polynucleotide may encode protein fragments that retain the biological activity of the native protein. Alternatively, fragments of a polynucleotide that are useful as hybridization probes or PCR primers generally do not encode fragment proteins retaining biological activity. Furthermore, fragments of the disclosed nucleotide sequences include those that can be assembled within recombinant constructs as discussed herein. Fragments of a polynucleotide sequence may range from at least about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides, or about 1500 nucleotides, about 2000 nucleotides, about 3000 nucleotides, about 4000 nucleotides, about 5000 nucleotides, about 6000 nucleotides, about 7000 nucleotides, about 8000 nucleotides, about 9000 nucleotides, about 10000 nucleotides, about 15000 nucleotides, about 20000 nucleotides, and up to the full-length polynucleotide encoding the polypeptides described herein. Fragments of a polypeptide sequence may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, about 600 amino acids, or up to the full-length polypeptide described herein.

It is to be understood that reducing the expression or activity of the asparagine synthetase(s) described herein may be achieved by various means. According to certain embodiments, reducing the expression of the asparagine synthetase (s) can be carried out at the genomic and/or the transcript level using a variety of molecules that interfere with transcription and/or translation including, but not limited to, antisense, siRNA, Ribozyme, or DNAzyme molecules. Inserting one or more mutations to the at least one gene, including deletions, insertions, site specific mutations, zinc-finger nucleases and the like can be also used. According to other embodiments, expression can be inhibited at the protein level using antagonists, or enzymes that cleave the polypeptide and the like.

In one aspect, a mutant plant or part thereof comprising at least one mutation and (i) a polynucleotide comprising, consisting or consisting essentially of a sequence encoding asparagine synthetase and having at least 72% sequence identity to SEQ ID NO:1 or SEQ ID NO:3 or SEQ ID NO:5 or SEQ ID NO:7; (ii) a polypeptide encoded by the polynucleotide set forth in (i); (iii) a polypeptide comprising, consisting or consisting essentially of a sequence encoding asparagine synthetase and having at least 78% sequence identity to SEQ ID NO:2 or SEQ ID NO:4 or SEQ ID NO:6 or SEQ ID NO:8; or (iv) a construct, vector or expression vector comprising the isolated polynucleotide set forth in (i), wherein the at least one mutation reduces the expression or activity of the asparagine synthetase as compared to a control plant which does not comprise the at least one mutation is described. In another aspect, a mutant plant or part thereof comprising at least one mutation and (i) a polynucleotide comprising, consisting or consisting essentially of a sequence encoding asparagine synthetase and having at least 90% sequence identity to SEQ ID NO:1 or at least 72% sequence identity to SEQ ID NO:3 or SEQ ID NO:5 or SEQ ID NO:7; (ii) a polypeptide encoded by the polynucleotide set forth in (i); (iii) a polypeptide comprising, consisting or consisting essentially of a sequence encoding asparagine synthetase and having at least 78% sequence identity to SEQ ID NO:2 or SEQ ID NO:4 or SEQ ID NO:6 or SEQ ID NO:8; or (iv) a construct, vector or expression vector comprising the isolated polynucleotide set forth in (i), wherein the at least one mutation reduces the expression or activity of the asparagine synthetase as compared to a control plant which does not comprise the at least one mutation is described.

The plant or plant cell can therefore comprise one or more mutations in NtASN1-S (SEQ ID NO: 1) and/or NtASN1-T (SEQ ID NO: 3) and/or NtASN3-S (SEQ ID NO: 9) and/or NtASN3-T (SEQ ID NO: 11) and/or NtASN5-S (SEQ ID NO: 5) and/or NtASN5-T (SEQ ID NO: 7) wherein said mutation results in reduced expression or reduced function of said gene or protein encoded thereby. A plant or plant cell can comprise one or more mutations in NtASN1-S (SEQ ID NO: 1) or NtASN1-T (SEQ ID NO: 3) or NtASN5-S (SEQ ID NO: 5) or NtASN5-T (SEQ ID NO: 7) as described, wherein said mutation results in reduced expression or reduced function of said the gene or protein encoded thereby. A plant or plant cell can comprise one or more mutations (for example, nonsense mutations or the like as described herein) in NtASN1-S (SEQ ID NO: 1) and NtASN1-T (SEQ ID NO: 3) or NtASN5-S (SEQ ID NO: 5) and NtASN5-T (SEQ ID NO: 7) as described, wherein said mutation results in reduced expression or reduced function of said the gene or protein encoded thereby. The expression or function of the mutant(s) may be modulated, inhibited or reduced. Aside from the one or more mutations described herein, the mutant plant or plant cell can have one or more further mutations in one or more other genes or polypeptides. In certain embodiments, the mutants can have one or more further mutations in one or more other genes or polypeptides. Mutants of NtASN1-S, NtASN1-T, NtASN5-S and ASN5-T are described herein. In certain embodiments, the one or more mutations are in the glutaminase domain.

Three stop mutations are identified in ASN1-S (ASN1-S_W156*-SEQ ID Nos 19 and 20), ASN1-T (ASN1-T_W156*-SEQ ID Nos 21 and 22) and ASN5-S (ASN5-S_Q66*-SEQ ID Nos 23 and 24) copies, but not in the ASN5-T copy. As no stop mutations were identified in ASN5-T, a non-stop mutation was identified as a potential candidate. There was a clear tendency for asparagine reduction in ASN1-S_W156*, ASN1-T_W156* and ASN5-S_Q66*compared to their corresponding WT segregants, but not for ASN5-T_G59D. The strongest reduction was observed for ASN1-T_W156*(83%), then for ASN5-S_Q66*(44%) and finally for ASN1-S_W156*(17%). The line ASN5-T_G59D showed a slight increase in asparagine. The stop mutations in ASN1-S and ASN5-S had no impact on plant biomass and size. According to Canales et al., 2012, the mutations in all Nt-ASN genes are located in the glutaminase domain releasing ammonia from glutamine, the synthetase domain being localized in Nt-ASN from amino acid R211 to D451 consensus region. Said mutant plant or plant cell can be heterozygous or homozygous for the mutation(s). Said mutant plant or plant cell can be heterozygous for at least one mutation and homozygous for at least one different mutation. Suitably, the mutant plant or plant cell is homozygous for the mutation(s).

The mutant can have a mutation (for example, a nonsense mutation that results in a stop codon) at a position equivalent to amino acid position 156 of SEQ ID NO: 2. An example of such a mutant is ASN1-S_W156* as described herein.

The mutant can have a mutation (for example, a nonsense mutation that results in a stop codon) at a position equivalent to amino acid position 156 of SEQ ID NO: 4. An example of such a mutant is ASN1-T_W156* as described herein.

The mutant can have a mutation (for example, a nonsense mutation that results in a stop codon) at a position equivalent to amino acid position 66 of SEQ ID NO: 6. An example of such a mutant is ASN5-S_Q66* as described herein.

Combinations of these mutations are also contemplated. Said combinations can include the combination of ASN1-S_W156* and ASN1-T_W156*; or the combination of ASN1-S_W156* and ASN5-S_Q66*; or the combination of ASN1-T_W156* and ASN5-S_Q66*; or the combination of ASN1-S_W156*, ASN1-T_W156* and ASN5-S_Q66*.

In another aspect, there is provided a method for reducing the level of asparagine in a plant or in plant material derived from the plant, said method comprising introducing into the genome of said plant one or more mutations that reduce the expression of at least one asparagine synthetase gene, wherein said at least one asparagine synthetase gene encodes NtASN1-S, NtASN1-T, NtASN5-S or Nt ASN5-T. Suitably, in addition to the mutation(s) in NtASN1-S, NtASN1-T, NtASN5-S or NtASN5-T, one or more mutations can also be introduced into at least one allele of at least one, two or three or more further asparagine synthetase genes. Mutations in NtASN1-S and NtASN1-T or NtASN5-S and NtASN5-T are also contemplated.

There is also provided a method for identifying a plant with reduced levels of asparagine, said method comprising screening a nucleic acid sample from a plant of interest for the presence of one or more mutations in NtASN1-S, NtASN1-T, NtASN5-S or ASN5-T. Suitably, said method further comprises screening said nucleic acid sample, or another nucleic acid sample from said plant of interest, for the presence of a mutation in NtASN1-S, the presence of a mutation in NtASN1-T, or the presence of a mutation in NtASN5-S, or the presence of a mutation in NtASN5-T.

There is also disclosed a plant or plant cell that is heterozygous or homozygous for one or more mutations in a gene encoding NtASN1-S, NtASN1-T, NtASN5-S or NtASN5-T, wherein said mutation(s) results in reduced expression of the gene or reduced function of the protein encoded thereby.

In some embodiments, the favourable mutation(s) is introduced into a plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded protein can be determined using methods that are well known in the art. Insertional mutations in gene exons usually result in null-mutants. Mutations in conserved residues can be particularly effective in inhibiting or reducing the metabolic function of the encoded protein.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Mutant polypeptide variants can be used to create mutant, non-naturally occurring or transgenic plants (for example, mutant, non-naturally occurring, transgenic, man-made or genetically engineered plants) or plant cells comprising one or more mutant polypeptide variants. Suitably, mutant polypeptide variants retain the activity of the unmutated polypeptide. The activity of the mutant polypeptide variant may be higher, lower or about the same as the unmutated polypeptide.

Mutations in the nucleotide sequences and polypeptides described herein can include man-made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man. By way of example, the process may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. By way of further example, the process may include one or more plant crossing steps.

The activity of one or more asparagine synthetase polypeptides in a plant is reduced or inhibited according to the present disclosure if the conversion activity is statistically lower than the conversion activity of the same asparagine synthetase polypeptide(s) in a plant that has not been modified to inhibit the conversion activity of that asparagine synthetase polypeptide and which has been cultured and harvested using the same protocols. The activity of asparagine synthetase polypeptide in a plant is considered to be eliminated when it is not detectable by the assay methods described herein. Methods of determining the activity of an asparagine synthetase polypeptide are described herein.

Other than mutagenesis, compositions that can modulate the expression or the activity of one or more of the polynucleotides or polypeptides described herein include, but are not limited to, sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more proteins; sequence-specific polynucleotides that can interfere with the enzymatic activity of one or more proteins or the binding activity of one or more proteins with respect to substrates or regulatory proteins; antibodies that exhibit specificity for one or more proteins; small molecule compounds that can interfere with the stability of one or more proteins or the enzymatic activity of one or more proteins or the binding activity of one or more proteins; zinc finger proteins that bind one or more polynucleotides; and meganucleases that have activity towards one or more polynucleotides. Gene editing technologies, genetic editing technologies and genome editing technologies are well known in the art.

One method of gene editing involves the use of transcription activator-like effector nucleases (TALENs) which induce double-strand breaks which cells can respond to with repair mechanisms. Non-homologous end joining reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) proteins to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of protein transcription factors.

Antisense technology is another well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into a plant cell and the antisense strand of RNA is produced.

The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA duplexes of 21-23 bp length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event. An example of a coding sequence from NtASN1-S that can be used to silence both NtASN1-S and NtASN1-T copies is shown in SEQ ID NO: 17. A further aspect therefore relates to the nucleotide sequence set forth in SEQ ID NO: 17 or a sequence having at least 72%, 73%, 74%, 75%, 80%, 85%, 87%, 88%, 89%, 90%, 91%, 92%, 93%, 94%, 95% 96%, 97%, 98%, 99% sequence identity thereto. An example of a coding sequence from NtASN5-T that can be used to silence both NtASN1-S and NtASN1-T copies is shown in SEQ ID NO: 18. A further aspect therefore relates to the sequence set forth in SEQ ID NO: 17. A further aspect therefore relates to the nucleotide sequence set forth in SEQ ID NO: 18 or a sequence having at least 72%, 73%, 74%, 75%, 80%, 85%, 87%, 88%, 89%, 90%, 91%, 92%, 93%, 94%, 95% 96%, 97%, 98%, 99% sequence identity thereto. Method of gene silencing using these coding sequences and uses thereof are also contemplated.

Figure 22:
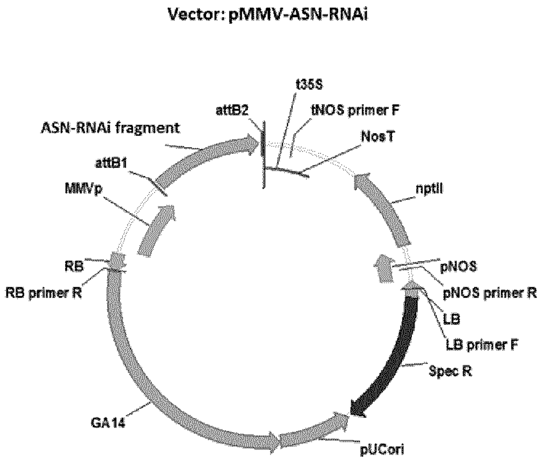
FIG. 22 shows examples of vectors used to generate ASN-RNAi plants.
Figure 22:
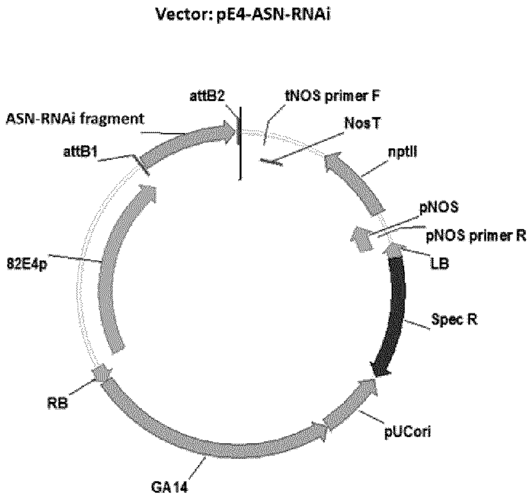

Interfering RNA expression vectors may comprise interfering RNA constructs encoding interfering RNA polynucleotides that exhibit RNA interference activity by reducing the expression level of mRNAs, pre-mRNAs, or related RNA variants. Exemplary constructs are shown in FIG. 22. The expression vectors may comprise a promoter positioned upstream and operably-linked to an Interfering RNA construct, as further described herein. Interfering RNA expression vectors may comprise a suitable minimal core promoter, an Interfering RNA construct of interest, an upstream (5) regulatory region, a downstream (3') regulatory region, including transcription termination and polyadenylation signals, and other sequences known to persons skilled in the art, such as various selection markers.

The polynucleotides can be produced in various forms, including as double stranded structures (that is, a double-stranded RNA molecule comprising an antisense strand and a complementary sense strand), double-stranded hairpin-like structures, or single-stranded structures (that is, a ssRNA molecule comprising just an antisense strand). The structures may comprise a duplex, asymmetric duplex, hairpin or asymmetric hairpin secondary structure, having self-complementary sense and antisense strands. The double stranded interfering RNA can be enzymatically converted to double-stranded small interfering RNAs. One of the strands of the small interfering RNA duplex can anneal to a complementary sequence within the target mRNA and related RNA variants. The small interfering RNA/mRNA duplexes are recognized by RNA-induced silencing complexes that can cleave RNAs at multiple sites in a sequence-dependent manner, resulting in the degradation of the target mRNA and related RNA variants.

The double-stranded RNA molecules may include small interfering RNA molecules assembled from a single oligonucleotide in a stem-loop structure, wherein self-complementary sense and antisense regions of the small interfering RNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active small interfering RNA molecule capable of mediating interfering RNA.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the small interfering RNA molecule is a double-stranded RNA or ssRNA molecule between about 15 and about 35 nucleotides in length. In another embodiment, the small interfering RNA molecule is a double-stranded RNA or ssRNA molecule between about 17 and about 30 nucleotides in length. In another embodiment, the small interfering RNA molecule is a double-stranded RNA or ssRNA molecule between about 19 and about 25 nucleotides in length. In another embodiment, the small interfering RNA molecule is a double-stranded RNA or ssRNA molecule between about 21 to about 23 nucleotides in length. In certain embodiments, hairpin structures with duplexed regions longer than 21 nucleotides may promote effective small interfering RNA-directed silencing, regardless of loop sequence and length. Exemplary coding sequences used for RNA interference are set forth in SEQ ID Nos: 17 and 18.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a small interfering RNA sequence designed) using computer software available commercially (for example, OligoEngine, Target Finder and the small interfering RNA Design Tool which are commercially available).

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the small interfering RNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotide sequences described herein.

The specific antisense sequence comprised by the small interfering RNA molecule can be identical or substantially identical to the complement of the target sequence. In one embodiment, the specific antisense sequence comprised by the small interfering RNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the small interfering RNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. Double-stranded RNA molecules, in which one or more nucleotide substitution occurs in the sense sequence, but not in the antisense strand, are also contemplated. When the antisense sequence of an small interfering RNA molecule comprises one or more mismatches between the nucleotide sequence of the small interfering RNA and the target nucleotide sequence, as described above, the mismatches may be found at the 3' terminus, the 5' terminus or in the central portion of the antisense sequence. In another embodiment, the small interfering RNA molecules comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature,* 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley et al. (2001) *Plant J.,* 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617). Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

When determining the percentage identity of the interfering RNA molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the small interfering RNA molecule.

The interfering RNA molecules can comprise one or more 5' or 3'-cap structures. The interfering RNA molecule can comprise a cap structure at the 3'-end of the sense strand, the antisense strand, or both the sense and antisense strands; or at the 5'-end of the sense strand, the antisense strand, or both the sense and antisense strands of the interfering RNA molecule. Alternatively, the interfering RNA molecule can comprise a cap structure at both the 3'-end and 5'-end of the interfering RNA molecule. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the activity, cellular distribution, cellular uptake, bioavailability or stability of the interfering RNA molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to an interfering RNA molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

The molecules and polynucleotides described herein may be prepared using well-known techniques of solid-phase synthesis. Any other means for such synthesis known in the art may additionally or alternatively be employed.

Figure 21:
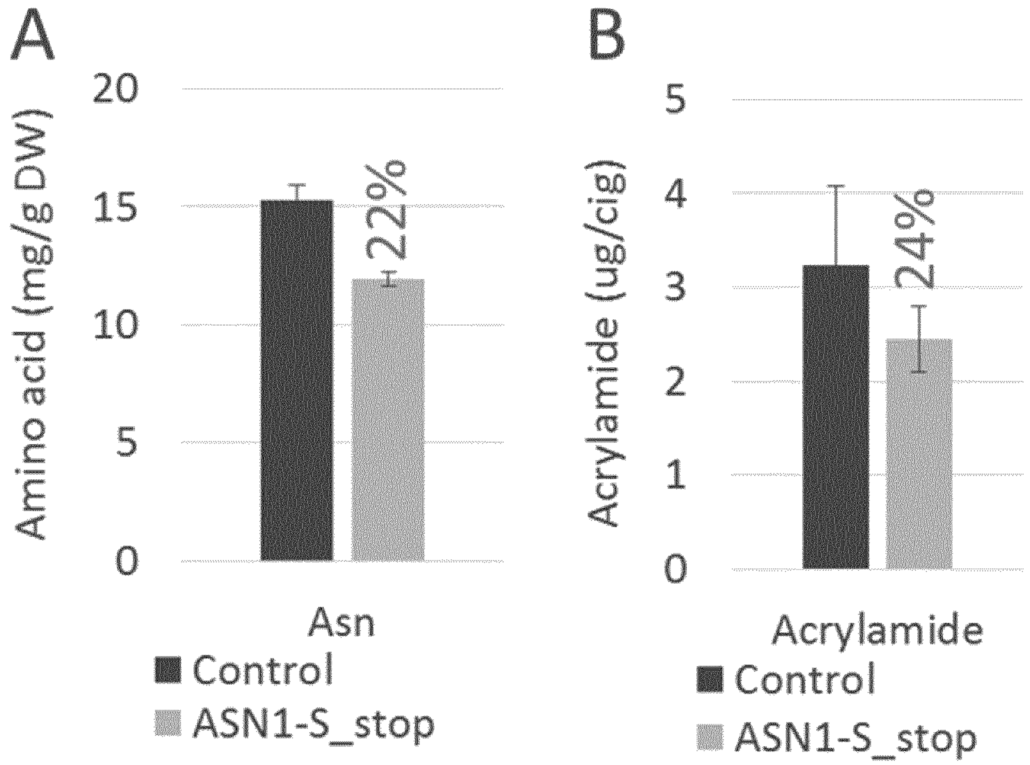
FIG. 21 shows the determination of acrylamide in the aerosol from an aerosol-generating article made of ASN1-S_stop mutant and control (WT out-segregant) leaves. Asparagine was determined in fine powder from ASN1-S_stop mutant and control leaves after blending with 50% Virginia tobacco (A). The tobacco blend was transformed into cast leaf and aerosol generated from the aerosol-forming article. Acrylamide in the aerosol was then determined (B).

Various embodiments are directed to expression vectors comprising one or more of the polynucleotides or one or more interfering RNA constructs described herein. Exemplary constructs are shown in FIG. 21.

Various embodiments are directed to expression vectors comprising one or more polynucleotides or one or more interfering RNA constructs encoding one or more interfering RNA polynucleotides described herein that are capable of self-annealing to form a hairpin structure, in which the construct comprises (a) one or more of the polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilised for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference activity can be enzymatically converted to small interfering RNAs to modulate RNA levels.

Thus, various embodiments are directed to expression vectors comprising one or more polynucleotides or interfering RNA constructs described herein encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the polypeptides described herein (or any combination thereof as described herein) by promoting co-suppression of gene expression. The phenomenon of co-suppression occurs as a result of introducing multiple copies of a transgene into a plant cell host. Integration of multiple copies of a transgene can result in modulated expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing, in which transcripts can be produced but enhanced rates of degradation preclude accumulation of transcripts. The mechanism for co-suppression by post-transcriptional gene silencing is thought to resemble RNA interference, in that RNA seems to be both an important initiator and a target in these processes, and may be mediated at least in part by the same molecular machinery, possibly through RNA-guided degradation of mRNAs.

Co-suppression of nucleic acids can be achieved by integrating multiple copies of the nucleic acid or fragments thereof, as transgenes, into the genome of a plant of interest. The host plant can be transformed with an expression vector comprising a promoter operably-linked to the nucleic acid or fragments thereof. Various embodiments are directed to expression vectors for promoting co-suppression of endogenous genes comprising a promoter operably-linked to a polynucleotide.

Various embodiments are directed to methods for modulating the expression level of one or more of the polynucleotide(s) described herein (or any combination thereof as described herein) by integrating multiple copies of the polynucleotide(s) into a plant genome, comprising: transforming a plant cell host with an expression vector that comprises a promoter operably-linked to a polynucleotide.

Various compositions and methods are provided for modulating the endogenous gene expression level by modulating the translation of mRNA. A host plant cell can be transformed with an expression vector comprising: a promoter operably-linked to a polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

Genes can also be targeted for inactivation by introducing transposons (for example, IS elements) into the genomes of plants of interest. These mobile genetic elements can be introduced by sexual cross-fertilization and insertion mutants can be screened for loss in protein activity. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, solanum nodiflorum mottle virus, and subterranean clover mottle virus. Various target RNA-specific ribozymes are known to persons skilled in the art.

As discussed herein, the expression of one or more polypeptides can be modulated by non-transgenic means—such as creating one or more mutations in one or more genes, as discussed herein. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis and targeting induced local lesions in genomes (TILLING), homologous recombination, oligonucleotide-directed mutagenesis, and meganuclease-mediated mutagenesis. In one embodiment, TILLING is used. This is a mutagenesis technology that can be used to generate and/or identify polynucleotides encoding polypeptides with modified expression and/or activity. TILLING also allows selection of plants carrying such mutants. TILLING combines high-density mutagenesis with high-throughput screening methods. Methods for TILLING are well known in the art (see McCallum et al., (2000) *Nat Biotechnol* 18: 455-457 and Stemple (2004) *Nat Rev Genet* 5(2): 145-50).

Some non-limiting examples of mutations are deletions, insertions and missense mutations of at least one nucleotide, single nucleotide polymorphisms and a simple sequence repeat. After mutation, screening can be performed to identify mutations that create premature stop codons or otherwise non-functional genes. After mutation, screening can be performed to identify mutations that create functional genes that are capable of being expressed at elevated levels. Screening of mutants can be carried out by sequencing, or by the use of one or more probes or primers specific to the gene or protein. Specific mutations in polynucleotides can also be created that can result in modulated gene expression, modulated stability of mRNA, or modulated stability of protein. Such plants are referred to herein as “non-naturally occurring” or “mutant” plants. Typically, the mutant or non-naturally occurring plants will include at least a portion of foreign or synthetic or man-made nucleic acid (for example, DNA or RNA) that was not present in the plant before it was manipulated. The foreign nucleic acid may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

The mutant or non-naturally occurring plants or plant cells can have any combination of one or more mutations in one or more genes which results in modulated protein levels. For example, the mutant or non-naturally occurring plants or plant cells may have a single mutation in a single gene;

multiple mutations in a single gene; a single mutation in two or more or three or more or four or more genes; or multiple mutations in two or more or three or more or four or more genes. Examples of such mutations are described herein. By way of further example, the mutant or non-naturally occurring plants or plant cells may have one or more mutations in a specific portion of the gene(s)—such as in a region of the gene that encodes an active site of the protein or a portion thereof. By way of further example, the mutant or non-naturally occurring plants or plant cells may have one or more mutations in a region outside of one or more gene(s)—such as in a region upstream or downstream of the gene it regulates provided that they modulate the activity or expression of the gene(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Mutagens that create primarily point mutations and short deletions, insertions, transversions, and or transitions, including chemical mutagens or radiation, may be used to create the mutations.

Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. Any method of plant nucleic acid preparation known to those of skill in the art may be used to prepare the plant nucleic acid for mutation screening.

Prepared nucleic acid from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to polynucleotide-specific amplification techniques, such as Polymerase Chain Reaction. Any one or more primers or probes specific to the gene or the sequences immediately adjacent to the gene may be utilized to amplify the sequences within the optionally pooled nucleic acid sample. Examples of oligonucleotide primers are set forth in SEQ ID NO: 13, SEQ ID NO: 14, SEQ ID NO: 15 and SEQ ID NO: 16. Suitably, SEQ ID NOs: 13 and SEQ ID NOs: 14 are used in combination to detect NtAsn-1. Suitably, SEQ ID NOs: 15 and SEQ ID NOs: 16 are used in combination to detect NtAsn-5. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art. Polymorphisms may be identified by means known in the art and some have been described in the literature.

In a further aspect there is provided a method of preparing a mutant plant. The method involves providing at least one cell of a plant comprising a gene encoding a functional polynucleotide described herein (or any combination thereof as described herein). Next, the at least one cell of the plant is treated under conditions effective to modulate the activity of the polynucleotide(s) described herein. The at least one mutant plant cell is then propagated into a mutant plant, where the mutant plant has a modulated level of polypeptide(s) described (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to create a mutation that is non-naturally occurring in that plant and to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. Plants showing a desired trait may be screened out of a pool of mutant plants. Suitably, the selection is carried out utilising the knowledge of the nucleotide sequences as described herein. Consequently, it is possible to screen for a genetic trait as compared to a control. Such a screening approach may involve the application of conventional nucleic acid amplification and/or hybridization techniques as discussed herein. Thus, a further aspect relates to a method for identifying a mutant plant comprising the steps of: (a) providing a sample comprising nucleic acid from a plant; and (b) determining the nucleic acid sequence of the polynucleotide, wherein a difference in the sequence of the polynucleotide as compared to the polynucleotide sequence of a control plant is indicative that said plant is a mutant plant. In another aspect there is provided a method for identifying a mutant plant which accumulates reduced levels of asparagine as compared to a control plant comprising the steps of: (a) providing a sample from a plant to be screened; (b) determining if said sample comprises one or more mutations in one or more of the polynucleotides described herein; and (c) determining at least the asparagine content of said plant. In another aspect there is provided a method for preparing a mutant plant which has reduced levels of asparagine as compared to a control plant comprising the steps of: (a) providing a sample from a first plant; (b) determining if said sample comprises one or more mutations in one or more of the polynucleotides described herein that result in reduced levels of asparagine; and (c) transferring the one or more mutations into a second plant. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant.

In another aspect there is provided a method for preparing a mutant plant which has reduced levels of asparagine as compared to a control plant comprising the steps of: (a) providing a sample from a first plant; (b) determining if said sample comprises one or more mutations in one or more of the polynucleotides described herein that results in reduced levels of asparagine; and (c) introgressing the one or more mutations from the first plant into a second plant. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar.

A further aspect relates to a mutant plant (including a cultivar or elite cultivar mutant plant) obtained or obtainable by the methods described herein. In certain embodiments, the "mutant plant" may have one or more mutations localised only to a specific region of the plant—such as within the sequence of the one or more polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of one or more of the polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the polynucleotide(s) described herein; or may not have one or more mutations in one or more, two or more, three or more, four or more or five or more introns of the polynucleotide(s) described herein; or may not have one or more mutations in a promoter of the polynucleotide(s) described herein; or may not have one or more mutations in the 3' untranslated region of the polynucleotide(s) described herein; or may not have one or more mutations in the 5' untranslated region of the polynucleotide(s) described herein; or may not have one or more mutations in the coding region of the polynucleotide(s) described herein; or may not have one or more mutations in the non-coding region of the polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a polynucleotide described herein comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding a polynucleotide described herein or a variant or a fragment thereof, wherein a difference in said sequence is indicative of one or more mutations therein.

Zinc finger proteins can also be used to modulate the expression or the activity of one or more of the polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more base pairs apart. Accordingly, zinc finger proteins that bind to polynucleotides are provided.

A zinc finger protein may be engineered to recognize a selected target site in a gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the target nucleic acid and that does not occur in the cell or organism comprising the nucleic acid which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a polynucleotide, and a second polynucleotide coding for a non-specific endonuclease such as, but not limited to, those of a Type IIS endonuclease. A fusion protein between a zinc finger protein and the nuclease may comprise a spacer consisting of two base pairs or alternatively, the spacer can consist of three, four, five, six, seven or more base pairs. In various embodiments, a zinc finger nuclease introduces a double stranded break in a regulatory region, a coding region, or a non-coding region of a genomic DNA sequence of a polynucleotide and leads to a reduction of the level of expression of a polynucleotide, or a reduction in the activity of the protein encoded thereby. Cleavage by zinc finger nucleases frequently results in the deletion of DNA at the cleavage site following DNA repair by non-homologous end joining.

In other embodiments, a zinc finger protein may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the disclosure provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger protein and zinc finger nuclease to a plant are similar to those described below for delivery of meganuclease.

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease proteins can be delivered into plant cells by a variety of different mechanisms known in the art.

The disclosure also encompass the use of meganucleases to inactivate a polynucleotide(s) described herein (or any combination thereof as described herein) in a plant cell or plant. Particularly, the disclosure provides a method for inactivating a polynucleotide in a plant using a meganuclease comprising: a) providing a plant cell comprising a polynucleotide as described herein; (b) introducing a meganuclease or a construct encoding a meganuclease into said plant cell; and (c) allowing the meganuclease to substantially inactivate the polynucleotide(s) Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the polynucleotide from the genome of the plant. Such applications are possible using a pair of engineered meganucleases, each of which cleaves a meganuclease recognition site on either side of the intended deletion. TAL Effector Nucleases (TALENs) that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

The genes that have been identified as being involved in the synthesis of asparagine during curing in the Burely variety of Nicotinia tabacum may be applicable to other plants and other varieties of plants. Therefore, the present disclosure is likely reproducible in other plants and applicable for breeding with variant lines.

Plants suitable for use in the present disclosure include, but are not limited to, monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*. Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), *Triticosecale* (tritic wheat times rye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea ycliseca* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (petunia), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), Sorghu56yclise56or (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant, non-naturally occurring or transgenic plants or plant cells modified to modulate gene expression levels thereby producing a plant or plant cell—such as a tobacco plant or tobacco plant cell—in which the expression level of a polypeptide is modulated within tissues of interest as compared to a control. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis subsp. hesperis, N. otophora, N. paniculata, N. pauciflora, N. petunioides, N. plumbaginifolia, N. quadrivalvis, N. raimondii, N. repanda, N. rosulata, N. rosulata subsp. ingulba, N. rotundifolia, N. setcheffii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides*, and *N. x sanderae*.

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation (s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Periqe' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H2O, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, P01, P02, P03, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpão Comum, HBO4P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

In one embodiment, the Burley type variety of *Nicotiana tabacum* is used.

Other plants suitable for use in the present disclosure include, but are not limited to, tea (*Camellia sinensis*).

Embodiments are also directed to compositions and methods for producing mutant plants, non-naturally occurring plants, hybrid plants, or transgenic plants that have been modified to modulate the expression or activity of a polynucleotide(s) described herein (or any combination thereof as described herein). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a nucleic acid conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

A still further aspect, relates to a cured plant material—such as cured leaf or cured tobacco—derived or derivable from a mutant, non-naturally occurring or transgenic plant or cell, wherein expression of one or more of the polynucleotides described herein or the activity of the protein encoded thereby is reduced and which results in reduced levels of asparagine therein.

Suitably the visual appearance of said plant (for example, leaf) is substantially the same as the control plant. Suitably, the plant is a tobacco plant.

Embodiments are also directed to compositions and methods for producing mutant, non-naturally occurring or transgenic plants or plant cells that have been modified to modulate the expression or activity of the one or more of the polynucleotides or polypeptides described herein which can result in plants or plant components (for example, leaves—such as cured or dried leaves) or plant cells with reduced levels of asparagine.

The mutant, non-naturally occurring or transgenic plants that are obtained according to the methods described herein may be similar or substantially the same in visual appearance to the control plants. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant. In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants. Suitably, the plant is a tobacco plant.

In another aspect, there is provided a method for modulating (eg. reducing) the amount of asparagine in at least a part of a plant (for example, the leaves—such as cured or dried leaves—or in tobacco), comprising the steps of: (i) modulating (eg. reducing) the expression or activity of an one or more of the polypeptides described herein, suitably, wherein the polypeptide(s) is encoded by the corresponding polynucleotide sequence described herein; (ii) measuring the asparagine content in at least a part (for example, the leaves—such as cured leaves) of the mutant, non-naturally occurring or transgenic plant obtained in step (i); and (iii) identifying a mutant, non-naturally occurring or transgenic plant in which the asparagine content therein has been reduced in comparison to a control plant. Suitably, the visual appearance of said mutant, non-naturally occurring or transgenic plant is substantially the same as the control plant. Suitably, the plant is a tobacco plant.

In another aspect, there is provided a method for reducing the amount of asparagine in at least a part of cured or dried plant material—such as cured or dried leaf—comprising the steps of: (i) reducing the expression or activity of an one or more of the polypeptides described herein, suitably, wherein the polypeptide(s) is encoded by the corresponding polynucleotide sequence described herein; (ii) harvesting plant material—such as one or more of the leaves—and curing or drying for a period of time; (iii) measuring the asparagine content in at least a part of the cured or dried plant material obtained in step (ii); and (iv) identifying cured or dried plant material in which the asparagine content therein has been reduced in comparison to a control plant.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or polynucleotide expression or polypeptide expression or a combination thereof.

A reduction in activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

Polynucleotides and recombinant constructs described herein can be used to modulate the expression of the enzymes described herein in a plant species of interest, suitably tobacco.

A number of polynucleotide based methods can be used to increase gene expression in plants and plant cells, for example. By way of example, a construct, vector or expression vector that is compatible with the plant to be transformed can be prepared which comprises the gene of interest together with an upstream promoter that is capable of overexpressing the gene in the plant or plant cell. Exemplary promoters are described herein. Following transformation and when grown under suitable conditions, the promoter can drive expression in order to modulate (for example, reduce) the levels of this enzyme in the plant, or in a specific tissue thereof. In one exemplary embodiment, a vector carrying one or more polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

Various embodiments are directed to methods for reducing the expression level of one or more polynucleotides described herein by integrating multiple copies of the polynucleotide into a plant genome, comprising: transforming a plant cell host with an expression vector that comprises a promoter operably-linked to one or more polynucleotides described herein. The polypeptide encoded by a recombinant polynucleotide can be a native polypeptide, or can be heterologous to the cell.

A plant carrying a mutant allele of one or more polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the disclosure.

In one embodiment, a method is provided for producing a non-naturally occurring plant comprising: (a) crossing a mutant or transgenic plant with a second plant to yield progeny tobacco seed; (b) growing the progeny seed, under plant growth conditions, to yield the non-naturally occurring plant. The method may further comprises: (c) crossing the previous generation of non-naturally occurring plant with itself or another plant to yield progeny seed; (d) growing the progeny seed of step (c) under plant growth conditions, to yield additional non-naturally occurring plants; and (e) repeating the crossing and growing steps of (c) and (d) multiple times to generate further generations of non-naturally occurring plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly plant breeding, are well known and can be used in the methods of the disclosure. The disclosure further provides non-naturally occurring plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing or drying. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other plants, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

In a breeding program, successful crosses yield F1 plants that are fertile. Selected F1 plants can be crossed with one of the parents, and the first backcross generation plants are self-pollinated to produce a population that is again screened for variant gene expression (for example, the null version of the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the nucleotide sequence information for the polynucleotide(s) described herein (or any combination thereof as described herein).

Hybrid varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or activity of the polypeptide(s) encoded thereby. Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression or activity of polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

Without limitation, the plants described herein may be modified for other purposes either before or after the expression or activity has been modulated according to the present disclosure. One or more of the following genetic modifications can be present in the mutant, non-naturally occurring or transgenic plants. In one embodiment, one or more genes that are involved in the conversion of nitrogenous metabolic intermediates is modified resulting in plants (such as leaves) that when cured, produces lower levels of at least one tobacco-specific nitrosamine than control plants. Non-limiting examples of genes that can be modified include, as described herein, genes encoding an asparagine synthetase, such as CYP82E4, CYP82E5 and CYP82E10 which participate in the conversion of nicotine to nornicotine and are described in WO2006091194, WO2008070274, WO2009064771 and PCT/US2011/021088 and as described herein. In another embodiment, one or more genes that are involved in heavy metal uptake or heavy metal transport are modified resulting in plants or parts of plants (such as leaves) having a lower heavy metal content than control plants or parts thereof without the modification(s). Non-limiting examples include genes in the family of multidrug resistance associated proteins, the family of cation diffusion facilitators (CDF), the family of Zrt-, Irt-like proteins (ZIP), the family of cation exchangers (CAX), the family of copper transporters (COPT), the family of heavy-metal P-type ATPases (for example, HMAs, as described in WO2009074325), the family of homologs of natural resistance-associated macrophage proteins (NRAMP), and the family of ATP-binding cassette (ABC) transporters (for example, MRPs, as described in WO2012/028309, which participate in transport of heavy metals, such as cadmium. The term heavy metal as used herein includes transition metals. Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from Arabidopsis. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided crylAc and crylC Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from Arabidopsis; genes coding mannitol dehydrogenase and sorbitol dehydrogenase which are involved in synthesis of mannitol and sorbitol improve drought resistance. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic plants from another cultivar or may be directly transformed into it. The introgression of the trait(s) into the mutant, non-naturally occurring or transgenic plants may be achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y. 761 pp.). Molecular biology-based techniques described above, in particular RFLP and microsatellite markers, can be used in such backcrosses to identify the progenies having the highest degree of genetic identity with the recurrent parent. This permits one to accelerate the production of varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic plants, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Various embodiments provide mutant plants, non-naturally occurring plants or transgenic plants, as well as biomass in which the expression level of a polynucleotide (or any combination thereof as described herein) is reduced to reduce the asparagine content therein.

Parts of such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured or dried tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion (or burning), a tobacco composition or another aerosol forming material is heated, for example, by one or more electrical heating elements or a carbon heat source to produce an aerosol. Typically in such heated smoking articles, an aerosol is generated by the transfer of heat from a heat source to a physically separate aerosol-forming substrate or material, which may be located within, around or downstream of the heat source. During smoking, volatile compounds are released from the aerosol-forming substrate by heat transfer from the heat source and entrained in air drawn through the smoking article. As the released compounds cool, they condense to form an aerosol that is inhaled by the user. Such devices include, for example, electrically heated aerosol-generating devices in which an aerosol is generated by the transfer of heat from of the aerosol-generating device to the aerosol-forming substrate of a heated smoking article. Suitably, during heating of the aerosol-forming substrate, combustion or burning of the tobacco does not occur. A suitable aerosol forming article is described in WO2013/098405 and comprises an aerosol-forming substrate for generating an inhalable aerosol when heated by an internal heating element of an aerosol-generating device. It can comprise an electrically heated aerosol-generating device comprising an internal heating element. It can further comprise, in a linear sequential arrangement, an aerosol-forming substrate, a support element located immediately downstream of the aerosol-forming substrate, an aerosol-cooling element located downstream of the support element, and an outer wrapper circumscribing the aerosol-forming substrate, the support element and the aerosol-cooling element. The support element can abut the aerosol-forming substrate. The aerosol-forming substrate is penetrable by the heating element of the aerosol-generating device.

As used herein, the term “combustion” refers to a redox chemical reaction where the reactant molecules, namely the fuel and the oxidant, mix and rearrange to become product molecules with the simultaneous release of heat. Combustion may be positively indicated by the presence of relevant amounts of nitrogen oxides in the gaseous products, not formed from the decomposition of nitrates present in the original reactant substrate, and the clear evidence of a simultaneous overall exothermic process. The evolution of relevant amounts of nitrogen oxides in the gaseous products for combustion may be determined by comparing the overall quantities of nitrogen oxides formed in the conditions of interest (for example, in air) and nitrogen oxides formed in the same conditions but in the absence of oxygen (for example, in a pure nitrogen or helium atmosphere). In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as combustible cigarettes, or by combusting an aerosol forming material.

In certain embodiments, heating without combusting or burning the plant material is preferred.

In one embodiment, there is also provided cured plant material from the mutant, transgenic and non-naturally occurring tobacco plants described herein. Processes of curing green tobacco leaves are known by those having ordinary skill in the art and include without limitation air-curing, fire-curing, flue-curing and sun-curing. The process of curing green tobacco leaves depends on the type of tobacco harvested. For example, Burley and certain dark strains are usually air-cured, and pipe tobacco, chewing tobacco, and snuff are usually fire-cured.

In another embodiment, there is also provided dried plant material from the mutant, transgenic and non-naturally occurring plants described herein. Processes of drying leaves are known by those having ordinary skill in the art and include without limitation air-drying and sun-drying. The exact process of drying leaves depends on the type of plant that is harvested. Suitably, the plant material is dried after harvesting. Thus, the use of dried material and post-harvested dried material is contemplated herein. The drying process may activate one or more senescence associated genes. The expression of activity of the genes and proteins described herein can be monitored during curing or drying. Likewise, the levels of asparagine, nicotine, glutamine, aspartic acid and glutamic acid can be monitored during curing or drying. By way example, measurements can be made after 0, 10, 20, 30, 40, 50, 60, 70, 80, 90 or 100 hours of curing or drying. By way of further example, measurements can be made after 0 days, 1 days, 2 days, 3 days, 4 days, 5 days or 10 days or more.

In another embodiment, there is described tobacco products including tobacco-containing aerosol forming materials comprising plant material—such as leaves, preferably cured or dried leaves—from the mutant tobacco plants, transgenic tobacco plants or non-naturally occurring tobacco plants described herein. The tobacco products described herein can be a blended tobacco product which may further comprise unmodified tobacco.

The amount of asparagine in the plant, part of the plant, plant material, plant product or tobacco product described herein after curing or drying (for example, 3 days curing or drying) is about 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—as compared to the control plant. Suitably, the amount of asparagine in the plant, part of the plant, plant material, plant product or tobacco product described herein after curing or drying (for example, 3 days curing or drying) is at least about 60%, 65%, 70%, 75%, 80%, 85%, 90%, 95%, 96%, 97%, 98%, 99%, and 100% lower—such as about 200% or 300% lower—as compared to the control, more suitably, at least about 80% lower or at least about 90% lower—as compared to the control.

The amount of asparagine in the plant, part of the plant, plant material, plant product or tobacco product described herein after curing or drying (for example, 3 days curing or drying) is about 40 mg/g dry weight leaves or less, more suitably about 35 mg/g dry weight leaves or less, more suitably about 30 mg/g dry weight leaves or less, more suitably about 25 mg/g dry weight leaves or less, more suitably about 20 mg/g dry weight leaves or less, more suitably, about 15 mg/g dry weight or less, more suitably about 12 mg/g dry weight, more suitably, about 10 mg/g dry weight dry weight leaves or less, or more suitably about 5 mg/g dry weight leaves or less. Suitably, the leaves are harvested from the bottom-mid stalk position of the plant.

The amount of acrylamide in aerosol derived from the plant, part of the plant, plant material, plant product or tobacco product after curing or drying and obtained by heating is at least about 70%, lower as compared to the control. By way of example, the amount of acrylamide in aerosol derived from the tobacco product after curing or drying and obtained by heating is about 1.5 μg per cigarette.

The amount of acrylamide in aerosol derived from the plant, part of the plant, plant material, plant product or tobacco product after curing or drying and obtained by combustion is at least about 55% lower as compared to the control. By way of example, the amount of acrylamide in aerosol derived from the tobacco product after curing or drying and obtained by combustion is about 2.5 μg per cigarette.

Suitably, the amount of acrylamide in aerosol derived from the plant, part of the plant, plant material, plant product or tobacco product after curing or drying and obtained by combustion or heating is at least about 55% to about 70% lower as compared to the control. By way of example, the amount of acrylamide in aerosol derived from the tobacco product after curing or drying and obtained by combustion or heating is between is about 1.5 μg per cigarette and 2.5 μg per cigarette.

The amount of nicotine in the plant, part of the plant, plant material, plant product, tobacco product or aerosol can be substantially the same as the amount of nicotine from plants, plant parts, plant materials, smokable articles, smokeless products and aerosols from the control plant. For example, the amount of nicotine can be within about 20%, 15%, 10%, 9%, 8%, 7%, 6%, 5%, 4%, 3%, 2% or 1% or less of the amount of nicotine that is present in the control plant. Suitably, the amount of nicotine is within about 10%, 9%, 8%, 7%, 6%, 5%, 4%, 3%, 2% or 1% or less of the amount of nicotine that is present in the control plant. The amount of nicotine is typically between about 15 and 20 mg/g dry weight biomass of leaves.

In one embodiment, the amount of asparagine in the plant, part of the plant, plant material, plant product or tobacco product after curing (for example, cured cast leaf) is at least about 20% lower (for example, at least about 22% lower) and the amount of acrylamide in aerosol derived from the plant, part of the plant, plant material, plant product or tobacco product after curing (for example, cured cast leaf) is at least about 25% lower (for example, at least about 24% or lower) than the control. In another embodiment, the amount of asparagine in the plant, part of the plant, plant material, plant product or tobacco product after curing (for example, cured cast leaf) is about 12 mg/g dry weight or less and the amount of acrylamide in aerosol derived from the plant, part of the plant, plant material, plant product or tobacco product after curing (for example, cured cast leaf) is about 2.5 μg/cigarette or less. Suitably, the level of nicotine is substantially the same as the level of nicotine in the control.

In another embodiment, the amount of asparagine in the plant, part of the plant, plant material, plant product or tobacco product after curing (for example, cured cast leaf) is at least about 70% lower (for example, at least about 66% lower) and the amount of acrylamide is aerosol derived from the plant, part of the plant, plant material, plant product or tobacco product after curing is at least about 45% lower (for example, at least about 44% lower) than the control. In another embodiment, the amount of asparagine in the plant, part of the plant, plant material, plant product or tobacco product after curing (for example, cured cast leaf) is about 12 mg/g dry weight or less and the amount of acrylamide is aerosol derived from the plant, part of the plant, plant material, plant product or tobacco product after curing is about 3 μg/cigarette or less. Suitably, the level of nicotine is substantially the same as the level of nicotine in the control.

In another embodiment, the amount of asparagine in the plant, part of the plant, plant material, plant product or tobacco product after curing (for example, cured cast leaf) is at least about 90% lower (for example, at least about 88% or lower) and the amount of acrylamide is aerosol derived from the plant, part of the plant, plant material, plant product or tobacco product after curing is at least about 70% lower than the control. In another embodiment, the amount of asparagine in the plant, part of the plant, plant material, plant product or tobacco product after curing (for example, cured case leaf) is about 5 mg/g dry weight or less and the amount of acrylamide is aerosol derived from the plant, part of the plant, plant material, plant product or tobacco product after curing is about 1.5 μg/cigarette or less. Suitably, the level of nicotine is substantially the same as the level of nicotine in the control.

In another embodiment, modulation of expression of NtASN1 via RNAi can: (i) decrease the amount of asparagine in the plant, part of the plant, plant material, plant product or tobacco product after curing or drying (for example, cured cast leaf) by between 24% and about 89% (for example, to between about 35 mg/g to about 5 mg/g); (ii) maintain the level of nicotine at about 20%, 15%, 10%, 9%, 8%, 7%, 6%, 5%, 4%, 3%, 2% or 1% or less of the amount of nicotine that is present in the control plant (for example, at about 15 and 20 mg/g dry weight biomass of leaves); and (iii) reduce the level of acrylamide in aerosol by at least about 70% to 1.5 3 μg/cigarette or less. The amount of leaf biomass is generally between about 300-400 g.

In another embodiment, modulation of expression of NtASN5 via RNAi can: (i) decrease the amount of asparagine in the plant, part of the plant, plant material, plant product or tobacco product after curing or drying (for example, cured cast leaf) by between about 35% and about 66% (for example, to between about 31 mg/g to about 18 mg/g); (ii) maintain the level of nicotine at about 20%, 15%, 10%, 9%, 8%, 7%, 6%, 5%, 4%, 3%, 2% or 1% or less of the amount of nicotine that is present in the control plant (for example, at about 15 and 20 mg/g dry weight biomass of leaves); and (iii) reduce the level of acrylamide in aerosol by at least about 44% to about 3 μg/cigarette or less. The amount of leaf biomass is generally between about 300-400 g.

In another embodiment, modulation of expression of NtASN1 via mutagenesis can: (i) decrease the amount of asparagine in the plant, part of the plant, plant material, plant product or tobacco product after curing or drying (for example, cured cast leaf) by between about 17% and about 83% (for example, to between about 19.4 mg/g to about 4.7 mg/g); and (iii) reduce the level of acrylamide in aerosol by at least about 24% to about 2.5 μg/cigarette or less.

In another embodiment, modulation of expression of NtASN5 via mutagenesis can decrease the amount of asparagine in the plant, part of the plant, plant material, plant product or tobacco product after curing or drying (for example, cured cast leaf) by between about 44% (for example, to about 14.5 mg/g). The mutant, non-naturally occurring or transgenic plants may have other uses in, for example, agriculture. For example, mutant, non-naturally occurring or transgenic plants described herein can be used to make animal feed and human food products.

The disclosure also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one of more primers for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the polynucleotide(s) described herein are disclosed. Said primers or probes may comprise or consist of about 15, 20, 25, 30, 40, 45 or 50 more contiguous polynucleotides that hybridise (for example, specifically hybridise) to the polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the polynucleotide(s). By way of specific example, two primers may be used in a polymerase chain reaction protocol to amplify a nucleic acid fragment encoding a nucleic acid—such as DNA or RNA. The polymerase chain reaction may also be performed using one primer that is derived from a nucleic acid sequence and a second primer that hybridises to the sequence upstream or downstream of the nucleic acid sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a polynucleotide(s) described herein (or any combination thereof as described herein) in a sample comprising the step of: (a) providing a sample comprising, or suspected of comprising, a polynucleotide; (b) contacting said sample with one of more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one of more primers or probes for specifically detecting at least a portion of the polynucleotide(s). Kits for detecting at least a portion of the polynucleotide(s) are also provided which comprise one of more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for determining at least the asparagine content and/or acrylamide aerosol content in plant material, cured or dried plant material or cured or dried leaves. In some embodiments, a kit may comprise instructions for one or more of the methods described.

The kits described may be useful for genetic identity determination, phylogenetic studies, genotyping, haplotyping, pedigree analysis or plant breeding particularly with co-dominant scoring.

The present disclosure also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present disclosure further provides a means to follow segregation of one or more genes or nucleic acids as well as chromosomal sequences genetically linked to these genes or nucleic acids using such techniques as AFLP analysis.

In one embodiment, there is also provided cured or dried plant material from the mutant, transgenic and non-naturally occurring plants described herein. For example, processes of curing or drying tobacco leaves are known by those having skills in the field and include without limitation air-curing, fire-curing, flue-curing and sun-curing. The process of curing green tobacco leaves depends on the type of tobacco harvested as described herein.

In another embodiment, there is described tobacco products including tobacco products comprising plant material—such as leaves, suitably cured plant material—such as cured or dried leaves—from the mutant, transgenic and non-naturally occurring plants described herein or which are produced by the methods described herein. The tobacco products described herein may further comprise unmodified tobacco.

In another embodiment, there is described tobacco products comprising plant material, preferably leaves—such as cured or dried leaves, from the mutant, transgenic and non-naturally occurring plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant, transgenic or non-naturally occurring plant which has modifications in one or more genes other than the genes disclosed herein.

The invention is further described in the Examples below, which are provided to describe the invention in further detail. These examples, which set forth a preferred mode presently contemplated for carrying out the invention, are intended to illustrate and not to limit the invention.

EXAMPLES

Example 1

Synthesis of Asparagine in Cured Tobacco Leaves

During the curing of tobacco leaf and especially leaf of Burley cultivars, asparagine is actively produced contributing to about 50% of the total amino acids present in the cured leaves. In FIG. 1, the increase of asparagine and total free amino acids is shown, mainly resulting from asparagine increase, in cured leaves of three Burley tobacco cultivars grown and air-cured in parallel in the same field and barn. Surprisingly, asparagine is the sole amino acid markedly accumulated during curing. Considering that asparagine is synthesized during the early curing phase, the reaction is then dependent on asparagine synthetase activities using glutamine and aspartate as substrate. However, in FIG. 1, Asp and Gln only show a small increase compared to asparagine, thereby suggesting that pools of Gln and Asp are likely varying during the long air-curing process (>2 months). No variation in the pool of glutamate was observed (data not shown).

Figure 2:
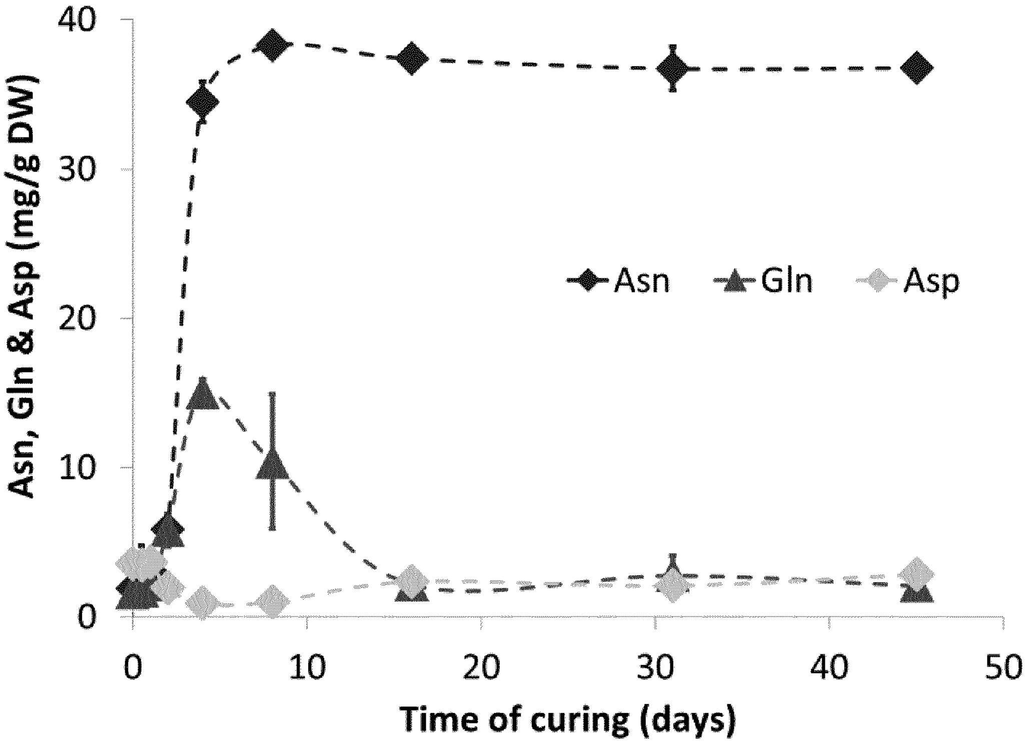
FIG. 2 shows the time-course of the asparagine, glutamine and aspartate evolution during curing of Burley leaves.

FIG. 2 indicates that Gln increases during the first 4 days of curing (96 h) and then decreases at the onset of asparagine accumulation. In contrast, the pool of aspartate remains mostly flat, although some fluctuation can be observed. Without wishing to be bound by any particular theory, the pool of glutamine observed could serve as substrate for asparagine synthetase(s) to generate asparagine during the first 4-5 days of curing (see FIG. 3).

Figure 4:
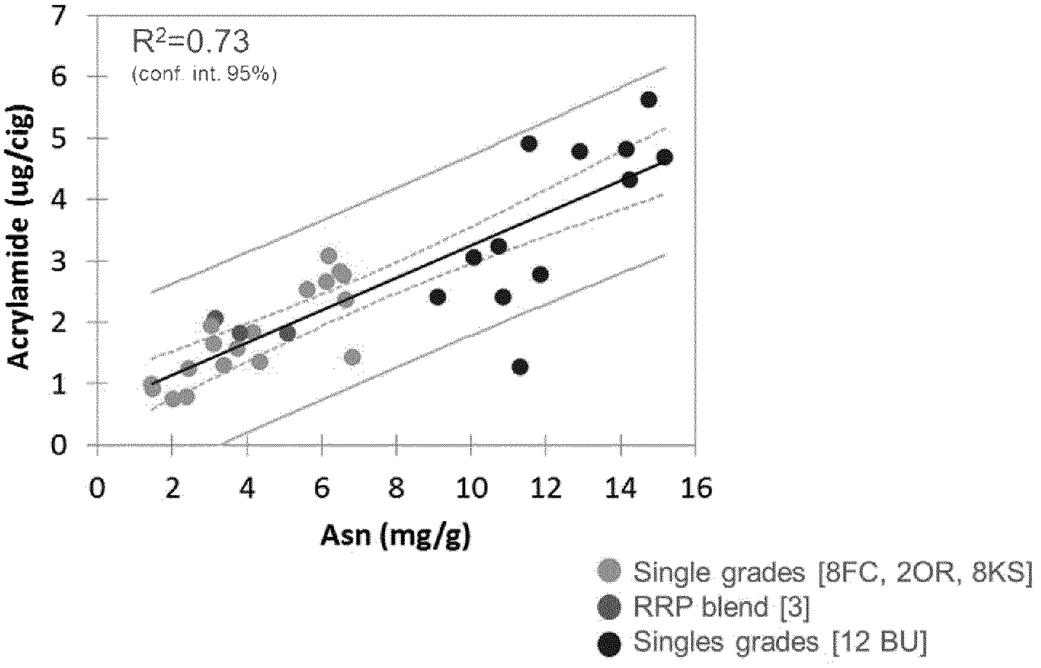
FIG. 4 shows the correlation existing between the presence of asparagine in tobacco single grades, Virginia (FC), Oriental (OR), Kasturi (KS) or Burley (BU) and a blend comprising a mixture of Virginia (FC), Kasturi (KS), and Oriental (OR) (referred to as RRP).
Figure 5:
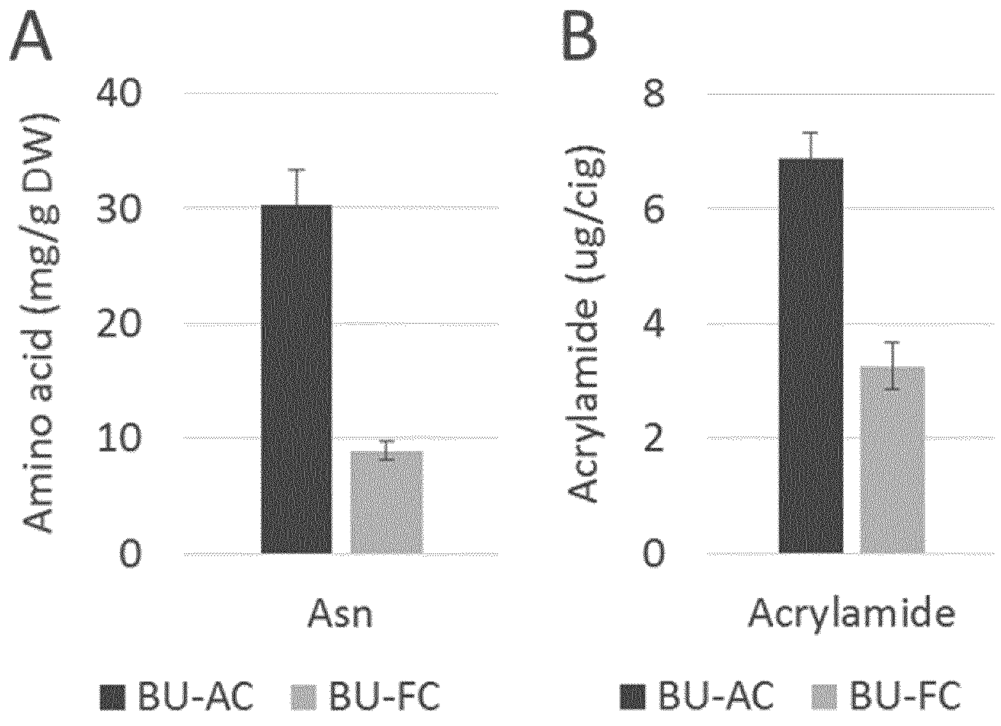
FIG. 5 shows the results obtained when Swiss Burley Stella was grown in Switzerland and cured either in an air-cured barn for 10 weeks (classical agricultural practices, BU-AC) or in a flue-cured oven, exactly like Swiss Virginia tobacco (BU-FC). After curing, leaf lamina was ground and subjected to asparagine determination (A). A homogenized powder of tobacco material (less than or equivalent to 200 micron) was made. The homogenized tobacco material was used in an aerosol-generating article essentially as described in WO2013098405 for use with an aerosol-generating device. The aerosol-generating article was smoked using a Health-Canada smoking regime to determine the content of acrylamide in aerosol (B).

As mentioned above, asparagine accumulation observed during curing could result from a specific activity of senescence-induced asparagine synthetase. Once heated or combusted, asparagine and reducing sugars have the potential to generate acrylamide in aerosol via a Maillard reaction. A good correlation exists between asparagine accumulated in cured tobacco leaf or tobacco blends and the acrylamide measured in aerosol (see FIG. 4). Without wishing to be bound by any particular theory, this suggests that the increase of acrylamide in aerosol is strictly dependent on the presence of asparagine. In addition, the presence of asparagine in leaf tissues is also related to the curing process used, as indicated in FIG. 5.

Example 2

Asparagine Synthetase Genes in Tobacco 6 full-length asparagine synthetase genes are identified in tobacco and called NtASN1-S, NtASN1-T, NtASN3-S, NtASN3-T, NtASN5-S and NtASN5-T. Interestingly, Arabidopsis has 3 genes related to asparagine synthetase AtASN1, AtASN2 and AtASN3 and Tomato only 2 full-length genes (Solyc06g007180 and Solyc04g055200). The phylogenetic analyses using the putative protein sequences derived from genomic sequences extracted from the tobacco genome (Sierro et al., 2014) suggests that during the evolution two groups of asparagine synthetases diverged (see FIG. 6). Indeed, one group comprising Solyc04g055200, AtASN2 & 3 is close to NtASN3-S and NtASN3-T. The gene product of AtASN2 belonging to this group is localized in the phloem and is apparently essential for nitrogen assimilation, distribution and remobilization in green tissues (Gaufichon et al., 2013 Plant Cell Environ. February; 36(2): 328-42.). This group belongs to the Dicot subclass of class II. The second group including Solyc06g007180, AtASN1, NtASN1-S, NtASN1-T, NtASN5-S and NtASN5-T belongs to the Dicot subclass of class I (Gaufichon et al., 2010 Ann Bot. 2010 June; 105(7):1141-57.). Overexpression of AtASN1 contributes to an increase of asparagine content in flowers and developing siliques and to an elevation of seed protein content, thereby attesting of an enhanced transport of asparagine from source to sink tissues. This suggests that the group of AtASN1 is more devoted to the translocation of the nitrogen source to the seeds to allow proper seed germination and high tolerance of seedlings to nitrogen-limiting substrate (Lam et al., 2003 Plant Physiol. 2003 June; 132 (2):926-35).

The percentage identity between the gene products revealed that NtASN3-S and NtASN3-T are identical, and very close to Solyc04g055200 and AtASN3 (85% identity) suggesting that this gene cluster was relatively well-conserved during the evolution, likely to maintain nitrogen assimilation in vegetative tissues (see above). Interestingly, each *N. sylvestris* and *N. tomemtosiformis* deduced protein copies of NtASN1-S/NtASN1-T, and NtASN5-S/NtASN5-T share both high percentage of identity close to 98%. It suggests that the gene function of both ASN1 and ASN5 copies is likely conserved between each tobacco ancestor and likely derived from one single common ancestor as found in Tomato and Arabidopsis. Furthermore, NtASN5-S shares 95% identity with Solyc06g007180 suggesting a similar function.

Knowing that asparagine rapidly increases during the air-curing process of Burley tobacco, the production of asparagine during the early phase of curing (see FIG. 1 and FIG. 2) may not directly result from proteolytic degradation of proteins or polypeptides but from denovo synthesis during curing. If so, and as mentioned above, asparagine synthesis can only originate from active asparagine synthetase(s).

Figure 7:
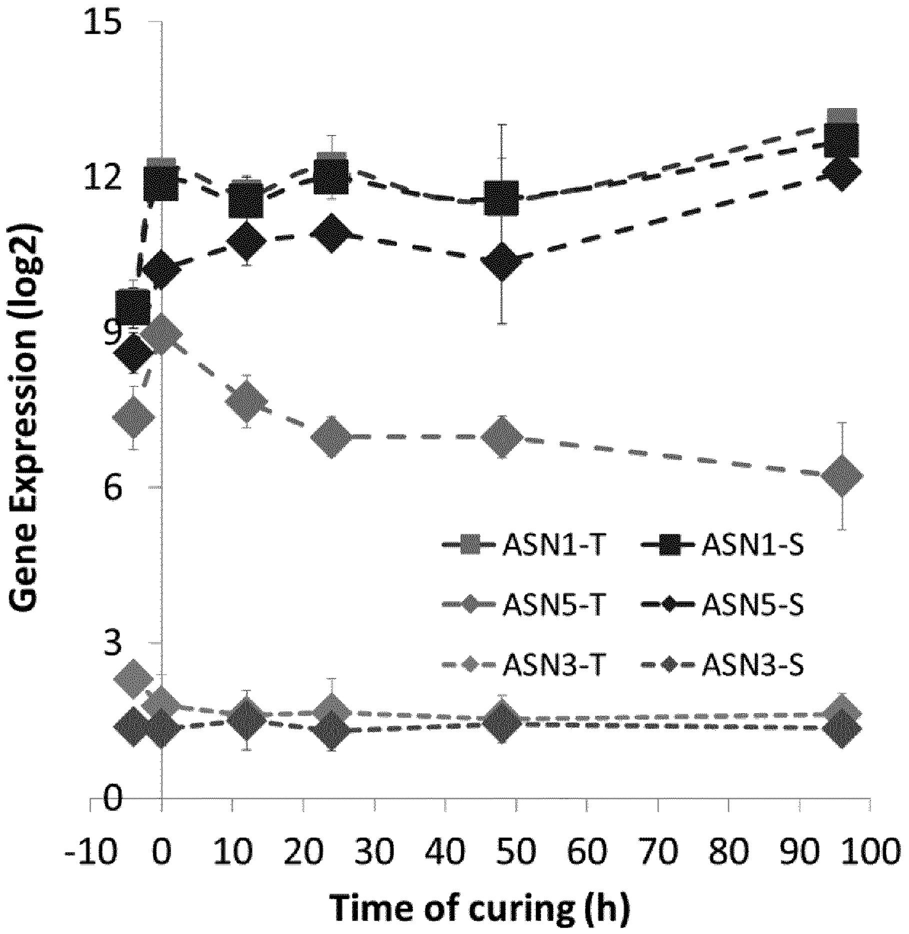
FIG. 7 shows the expression of the ASN genes during curing of Swiss Burley tobacco (Stella) grown in Switzerland in 2010. ARN were isolated from leaf samples (mid-stalk position) collected in a time-course manner in the field (−4 h) and in the air-curing barns till 96 h of curing. Gene expression on specific probes was determined by using microarray analyses with Affymetrix Tobarray chips.

To determine the expression of asparagine synthetase genes during curing, data collected from microarray analyses using Tobarray Affymetrix gene chips (Martin et al. *BMC Genomics* 2012, 13:674) is analysed. Leaf RNAs are isolated in a time-course manner during the first 96 h hours of curing. Specific probes (100% identity) matching with the six ASN coding sequences (NtPMla1g47375e1_st for ASN1-T; NtPMla1g31395e1_st for ASN1-S; NtPMla1g25255e1_st for ASN5-T; NtPMla1g57337e1_st for ASN5-S; NtPMla1g152348e1_st for ASN3-T and NtPMla1g121582e1_st for ASN3-S) are identified. For RNA preparation, leaves are collected at mid-stalk position of Stella (CH-Burley) directly in the field (−4 h), the time 0 being the moment when the leaves are hung in the air-curing barn. ASN3-S and ASN3-T are only poorly expressed in Burley leaves during air-curing. In contrast, ASN1-S, ASN1-T and ASN5-S are highly expressed at the beginning of curing (senescence, yellowing phase), whereas ASN5-T is up-regulated just after harvest and then constantly decreases during the first 96 h of curing (FIG. 7).

Figure 8:
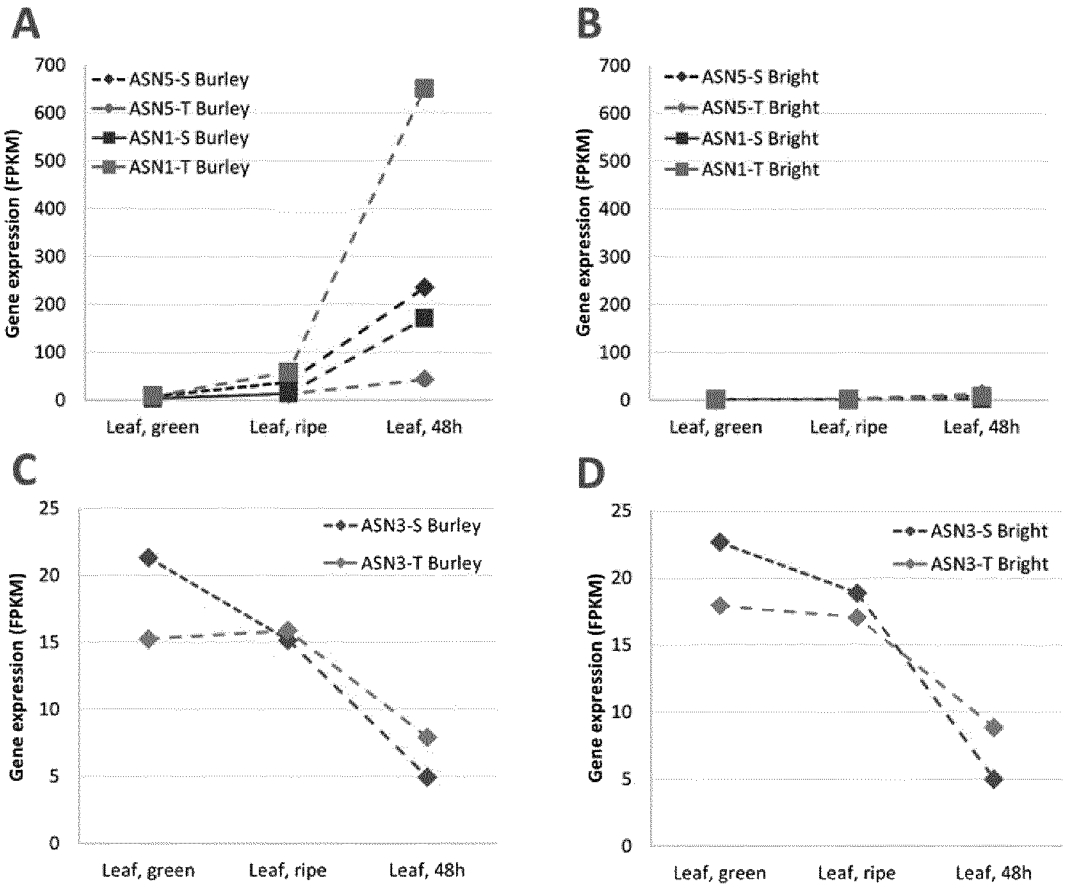
FIG. 8 shows the expression of ASN genes in Swiss Burley (Stella, A & C) and Swiss Virginia (Bright, ITB 683, B & B) tobacco after 48 h curing.

To check any cross-hybridization that may occur in microarray analyses particularly for genes sharing high sequence homology, the expression of ASN1-S/T and ASN5-S/T using RNAseq technology is analysed. The data are presented in FIG. 8. In Swiss Burley “Stella” (FIG. 8A), RNA-seq data confirm that ASN5-T is less induced during curing than the other three ASN1/5 copies (see FIG. 7), ASN1-T being the most intensively expressed gene after the two first air-curing days. Such an ASN gene activity does not occur with similar intensity in Swiss bright Virginia “ITB 683” classically cured in an oven. In such a tobacco the expression of ASN1-S/T and ASN5-S/T remains low after 48 h curing. In both tobacco, ASN3S/T expression is not induced by curing (FIGS. 8C&D), thus confirming the Affymetrix data presented in FIG. 7.

Figure 9:
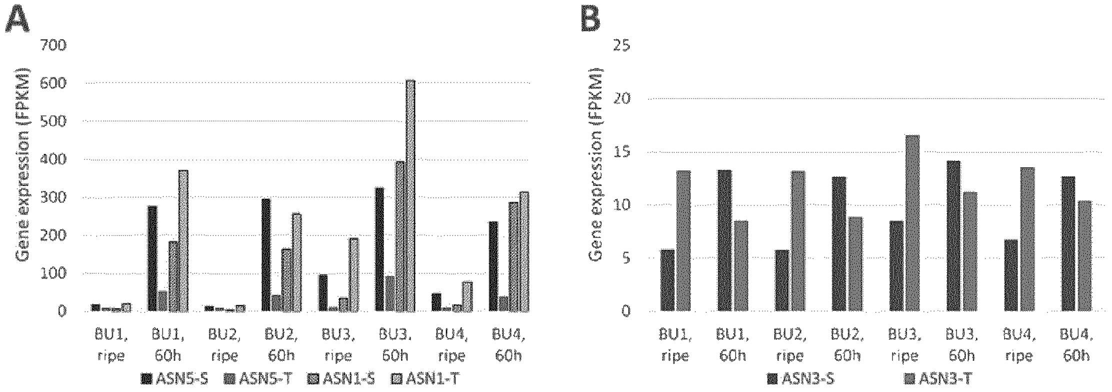
FIG. 9 shows the post-harvest expression of ASN1, ASN5 (A) and ASN3 (B) after 60 h air-curing in 4 different Burley leaves (lower stalk position) grown in Payerne field in 2013.

To test the robustness of the ASN gene induction during the early phase of Burley curing leaf RNA is isolated before and after 60 h curing in a barn from four different Burley accessions (BU1-4: Saplack, BanketA1, Stella and TN90) grown simultaneously in a Swiss field (2013). The time-point to isolate RNA is extended to 60 h, since TN90 need more time to start yellowing in Switzerland. The expression data (FIG. 9A) show that in all Burley leaves ASN1-T and ASN5-T are again the most and less expressed ASN genes during air-curing (except ASN1-T in BU2), respectively, confirming thus the data presented in FIG. 8. The transcripts ASN1-S and ASN5-S are constantly and solidly expressed during the early phase of curing in the leaves of the different Burley accession. FIG. 9B confirms that the two ASN3 copies originating from *N. tomentosiformis* and *N. sylvestris* are both not induced during curing, thereby indirectly confirming that these two copies which are closer to AtASN2 (see FIG. 6) are likely to have more basal function in vegetative plant tissues for maintaining physiological pools of asparagine.

Figure 10:
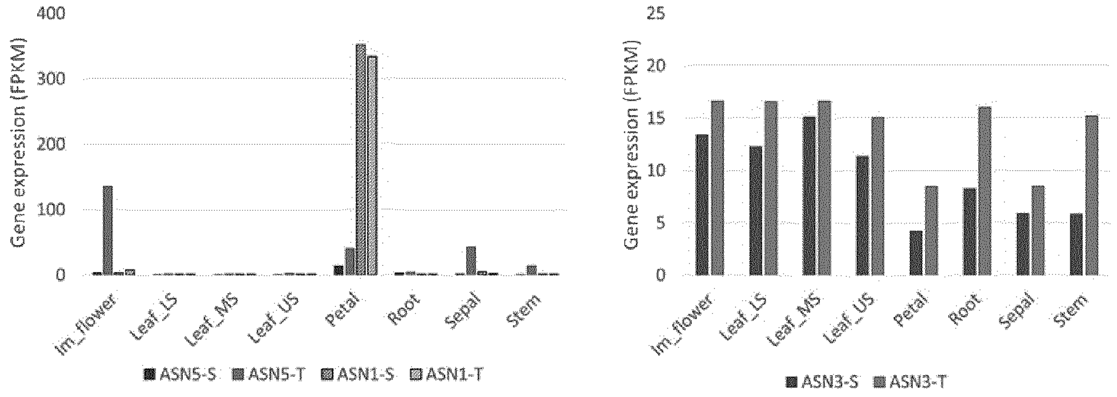
FIG. 10 shows the expression of ASN1, ASN5 (left panel) and ASN3 (right panel) in 8 tissues collected from mature Burley tobacco grown in the field (Immature flower (Im_ flower; Leaf at lower, _LS, mid,_MS and upper, _US, stalk positions; Petal, Root, Sepal and Stem).

The analyses of the corresponding transcripts in 8 tissues collected from TN90 plants at flowering stage and grown in the field suggests that ASN5-T is more active in flower than in leaves, the ASN5-T RNA copies being particularly found in immature flower, petal and sepal (see FIG. 10, left panel). In addition to being expressed in leaves, ASN1-T and ASN1-S are also strongly expressed in petal possibly to assimilate nitrate which is a function that has already been described in Arabidopsis (Lam et al., 2003 Plant Physiol. 2003 June; 132(2):926-35) for the orthologous gene AtASN1 (see FIG. 6). ASN3-S/T have low basal expression in all of these 8 tissues (see FIG. 10, right panel).

Example 3

ASN1 and ASN5 RNAi TN90e3 Lines

The silencing of ASN1-S/ASN1-T and ASN5-S/ASN5-T copies in Burley tobacco plants is investigated to determine if it contributes to reducing asparagine in cured Burley leaves. Specific DNA fragments are cloned between the strong constitutive MMV (Mirabilis Mosaic Virus) promoter or the senescence promoter E4 (asparagine synthetase). The ASN gene fragment is flanked between MMV or E4 and the 3' nos terminator sequence of the nopaline synthase gene of *Agrobacterium tumefaciens* (Cheng et al., 2003 In Vitro Cellular & Developmental Biology-Plant, 39 595 604). A diagram of the constructs used in this study is shown in FIG. 22. The Burley tobacco line TN90e4e5e10 (Zyvert) is transformed individually with each of the five constructs using standard *Agrobacterium*-mediated transformation protocols. TN90e4e5e10 (Zyvert) represents a selection from an ethylmethane sulfonate (EMS) mutagenized burley population that contains knockout mutations in CYP82E4, CYP82E5v2 and CYP82E10, the major asparagine synthetase genes of tobacco (Lewis et al., 2010), to prevent nornicotine production. Using such a background line can avoid potential complications when interpreting future TSNA data.

To enable the selection of plants that express the respective transgenes at a high level, at least 10 independent T0 plants for each construct are assayed by qPCR. Seeds are harvested from the three T0 lines of each construct that display the highest levels of ASN silencing events. To test whether the T1 progeny that inherited the RNAi gene fragment(s) perform efficient gene silencing, RNA is extracted from 4 plants of selected independent transformation events to get T2 seeds available for future field test (2016). TN90e4e5e10 (Zyvert) control lines are used as background to compare the efficiency of the transformation.

Three independent transformation events are selected in T0 ASN1-RNAi and ASN5-RNAi plants based on the level of ASN1 and ASN5 transcripts. ASN1-RNAi plants are generated to silence both ASN1-T and ASN1-S copies under the control of either the MMV promoter or the E4 promoter and ASN5-RNAi plants are generated to silence both ASN5-T and ASN5-S copies under the control of either the MMV promoter or the E4 promoter. Fifteen plants are selected on kanamycin for each transformation event and grown in the greenhouse. When mature, four leaves at mid-bottom position are collected from each plant and subjected to air-curing for 7 weeks.

Concentrations of amino acids and nicotine are determined by HPLC-MS: Aliquots (–30 mg) of ground tobacco are extracted with ethanol-water (1:1; 6 mL) for 45 minutes at 50° C. The centrifuged extracts are diluted 10-fold. Liquid chromatographic separation is performed on an amide column (Waters Acquity BEH amide, 2.1×150 mm, 1.7 μm) at 45° C. eluting with a gradient of 2 mM ammonium formate in water+0.25% formic acid (eluent A) and acetonitrile+0.1 formic acid (eluent B), applying an eluent gradient (0 min—10% A, 0.5 min—10% A, 4 min—60% A, 4.5 min—60% A, 4.6 min—10% A, 6.8 min—10% A; flow 0.5 ml/min). For mass spectrometric detection of the amino acids a Q Exactive instrument (Thermo Scientific) is used in positive electrospray mode acquiring full scan mass spectra. Nicotine concentrations in the extracts are calculated from its peak area in the 260 nm trace of a photodiode UV/VIS detector.

Asparagine is measured in cured leaf lamina. After 3 days of curing during the yellowing phase, a punch of lamina is extracted, RNA is isolated from each plant and qPCR is performed. In FIG. 11A, it is shown that the ASN1 RNAi gene fragment under the control of both MMV and E4 promoters affects the level of asparagine in cured leaf samples, the amount of asparagine varying in the different transformation events. E284-4 showed a reduction of asparagine of 24%, whereas E284-6 exhibited 89% of asparagine reduction compared to the background plants TN90e4e5e10 (Zyvert) grown in parallel. The asparagine content is correlated with the level of ASN1 RNA measured after 3 days of curing for both promoters MMV or E4 (FIG. 11B), confirming that asparagine is synthesized during curing and that ASN1-T and/or ASN1-S copies are involved in the asparagine production during the early phase of curing. Both a constitutive promoter, like MMV, and a senescence promoter, like E4, are active to silence ASN1. The efficiency of the E4 promoter attests that ASN1 genes are mainly active during senescence (yellowing) contributing to asparagine production in cured leaf, likely for the redistribution of nitrogen from source leaves to the seeds. After three days of curing, in parallel to the transcription analyses, asparagine is also measured, already showing a similar asparagine reduction profiles for the 6 tested lines, although about only one third of this amino acid was synthesized after this curing period (16.4 mg/g in the control TN90e4e5e10 (Zyvert), data not shown), this peak of asparagine being maximum after 9-10 days of air-curing following leaf harvest (see FIG. 2).

Asparagine synthetase is transferring the amine group from glutamine (Gln), the first amino acid fixing ammonia as the nitrogen form assimilated from nitrate stores in leaves, to aspartate (Asp). From this activity using ATP, it results in the formation of asparagine (asparagine) and glutamate (Glu, see also FIG. 3). Consequently we can speculate that silencing ASN1 will result in an increase of Gln and Asp and a decrease of Glu.

Figure 12:
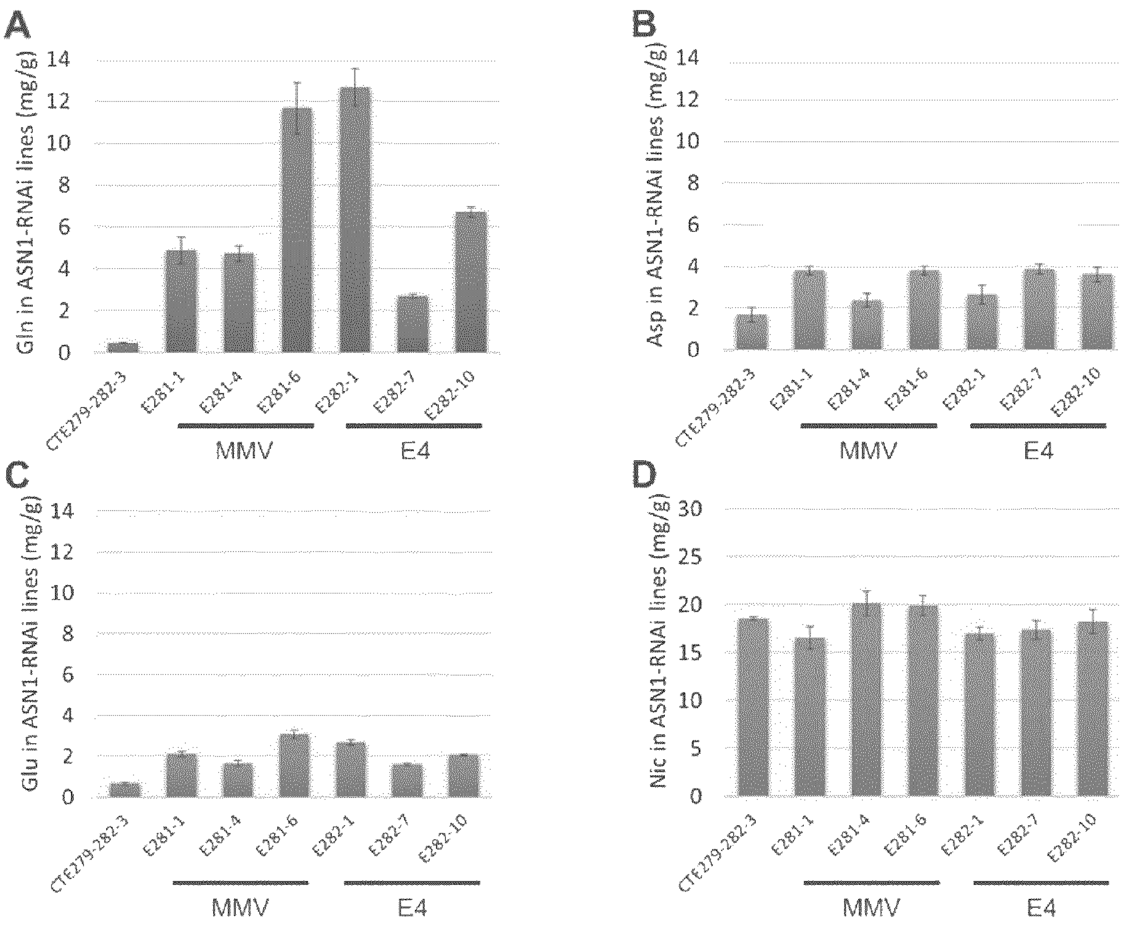
FIG. 12 shows the glutamine, aspartate, glutamate and nicotine content in ASN1-RNAi plants grown in the greenhouse under the control of MMV or E4 promoter. The amount of Gln (A), Asp (B), Glu (C) and nicotine (D) were measured in mid-bottom stalk leaf positions from 15 plants of each transformation event.

Therefore in the same samples the amount of Gln, Asp, Glu and nicotine is also analysed. A concomitant increase of Gln in the samples exhibiting a strong reduction of asparagine is seen i.e. E281-6 and E282-1 and in the opposite a lower Gln amount in the samples showing low asparagine i.e. E282-7 (FIG. 12A). For both Gln and asparagine, the amino acid balance resulting from the silencing of ASN1 genes is modified in the opposite way within the cured leaves. A similar effect is also observed for Asp and Glu, but less marked than for Gln. Both Asp and Glu show an increase (~1.5-3×) in all transformed lines exhibiting a similar Gln profiles (except for Asp in E282-7). Looking at the asparagine synthetase activity (see FIG. 3), an increase of Glu was not expected.

Nicotine content is not affected by the silencing of ASN1 silencing neither in MMV constructs nor in E4 constructs, confirming that the activity of ASN1-S and/or ASN1-T is not related to the nicotine synthesis pathway and is restricted to post-harvest leaf maturation during the early senescence program.

Figure 13:
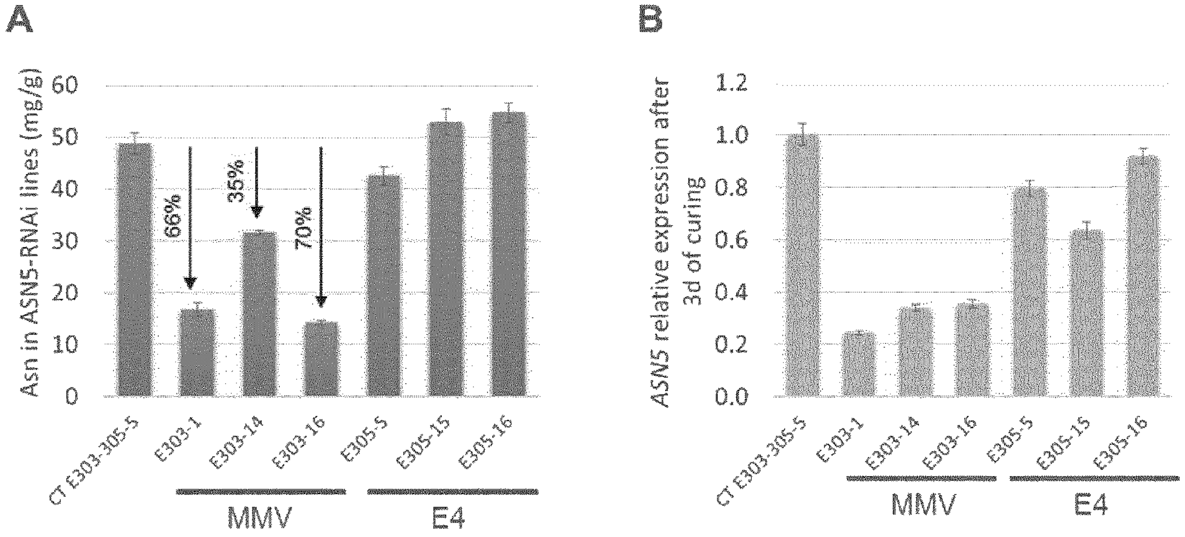
FIG. 13 shows the asparagine content in ASN5-RNAi plants grown in the greenhouse under the control of MMV or E4 promoter and ASN5 transcript levels determined after 3 days of curing. The amount of asparagine was measured in mid-bottom stalk leaf positions from 15 plants of each transformation event (A). The relative expression of ASN5 transcript was estimated by qPCR using RNA collected after 3 days of curing in 15 plants from each transformation event (B).

A similar experiment is performed to silence ASN5-S and ASN5-T using RNAi transgenic lines. The data shows that asparagine is efficiently reduced especially in two lines when the ASN5 RNAi fragment is expressed under the control of the constitutive promoter MMV, and not or only slightly under the control of the E4 promoter (FIG. 13A). Interestingly, the data are only partially correlated with the level of ASN5 mRNA estimated by qPCR after 3 days of curing (FIG. 13B). First, transformant events under the control of the E4 promoter show more abundant ASN5 mRNA than under the control of MMV, confirming that the E4 promoter is less efficient than the MMV promoter for silencing ASN5, possibly indicating that the ASN5 protein synthesis program occurs faster and earlier than the production of ASN1 protein after leaf harvest (FIG. 7). In certain lines, the percentage of asparagine is not correlated with the mRNA level, compare for instance E303-14 with E303-16 or E305-5 with E305-15. This may be due to the fact that the ASN5-T copy is involved in activities not present or only slightly present in cured leaf (FIG. 9) but rather within the flowering tissues (FIG. 10). After three days of curing, asparagine is also measured, showing a similar asparagine reduction profiles for the 6 lines (data not shown) as for ASN1 transgenic lines (see text above).

Figure 14:
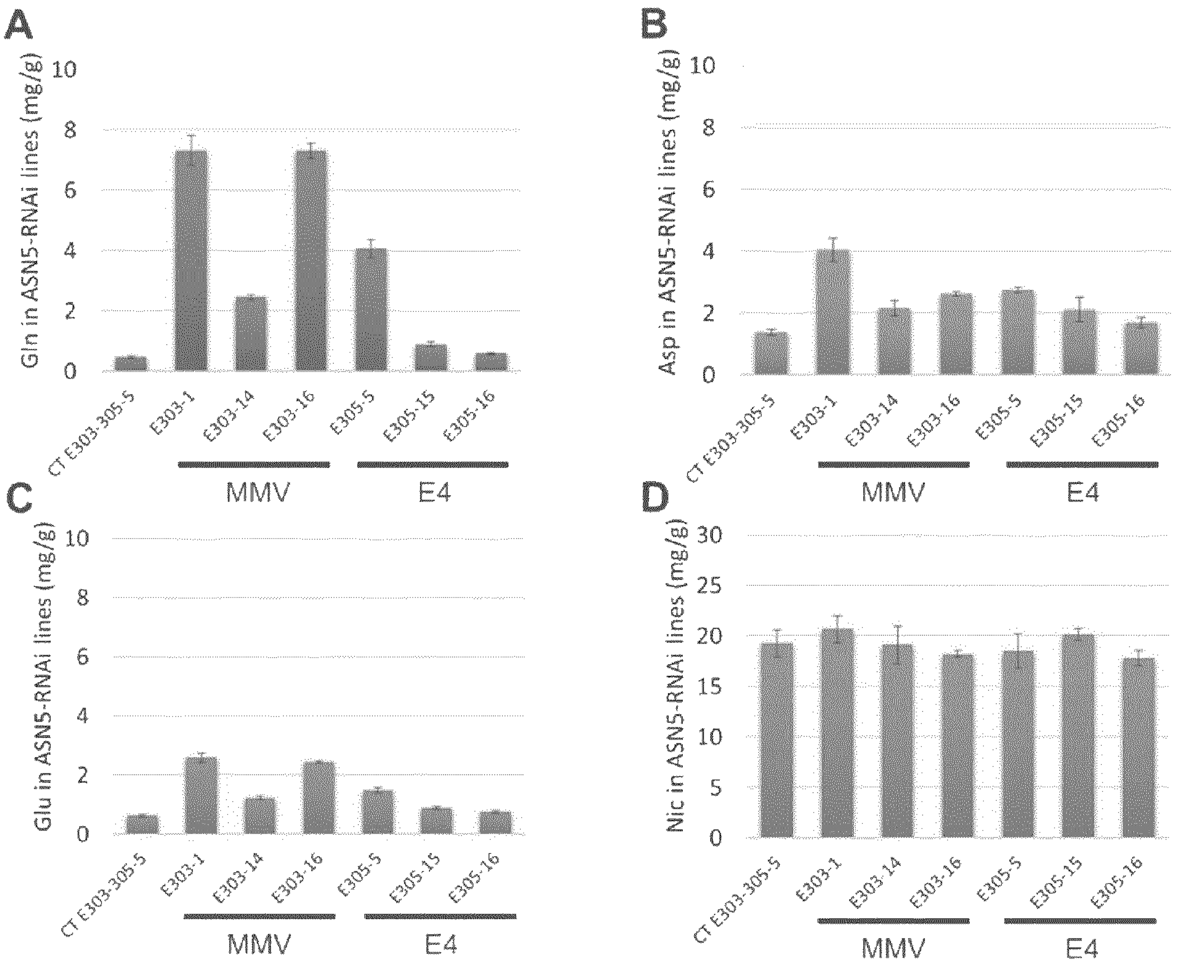
FIG. 14 shows the glutamine, aspartate, glutamate and nicotine content in ASN5-RNAi plants grown in the greenhouse under the control of MMV or E4 promoters. The amount of Gln (A), Asp (B), Glu (C) and nicotine (D) were measured in mid-bottom stalk leaf positions from 15 plants of each transformation event.

The amount of Gln, Asp, Glu and nicotine is also measured in ASN5-RNAi lines (FIG. 14). In ASN1-RNAi lines, a concomitant increase of Gln is seen in the samples showing a strong reduction of asparagine i.e. E303-1 and E303-16 and in the opposite a lower Gln amount in the samples exhibiting higher asparagine content, i.e. E303-14 and E-305-16. E305-5 shows less than 10% asparagine reduction and increased Gln, Asp and Glu as compared to the control and the sister lines E-305-15 and E305-16, suggesting that in certain case the E4 promoter can partially silence the ASN5 copies. The line E303-1 shows the highest mRNA reduction (FIG. 13B), a strong asparagine reduction (66%, FIG. 13A) and a relevant increase of Gln (14×), Asp (3×) and Glu (3×) compared to the control (FIGS. 14A, B and C). Thus, as for ASN1-RNAi plants, silencing ASN5 results in a marked decrease of asparagine and an increase of Gln, Asp and Glu. Nicotine level is not varying in ASN5-RNAi plants (FIG. 14D), as observed for ASN1-RNAi lines, suggesting that the reaction is disconnected from the nicotine pathway.

Figure 15:
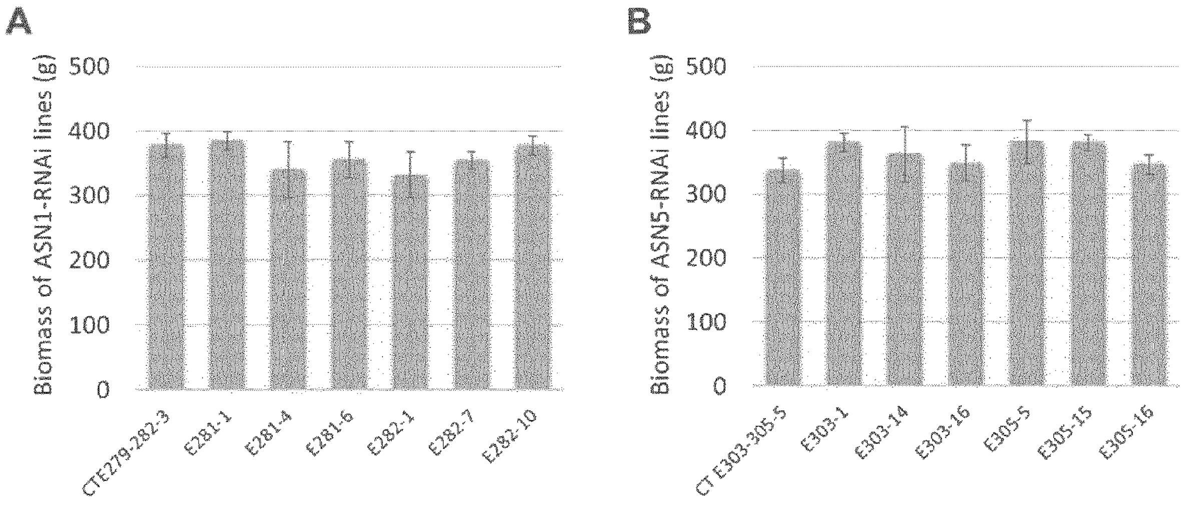
FIG. 15 shows the leaf biomass of ASN1- and ASN5-RNAi lines. Four leaves were collected at mid-stalk position from 4 plants of each transformation event, randomly selected and weighed. Weight average and standard deviation are shown.
Figure 16:
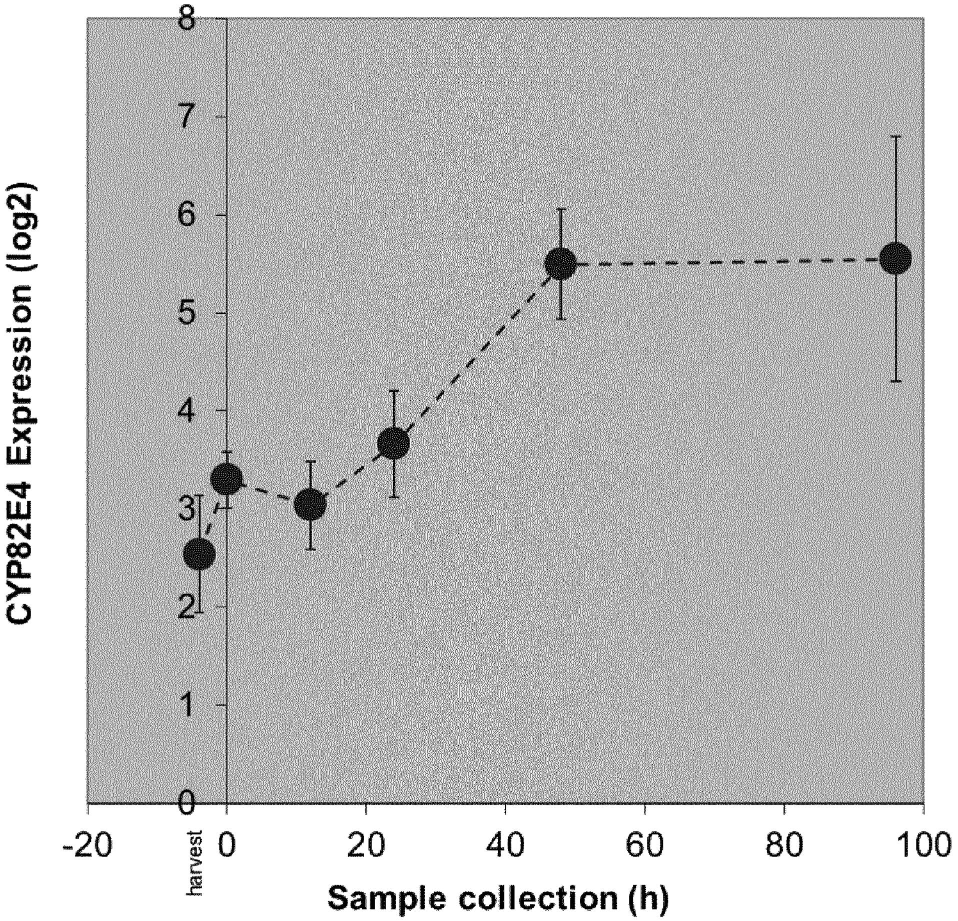
FIG. 16 shows the expression of CYP82E4 during the early steps of Swiss Burley (Stella) air-curing. Transcripts were determined using Tobarray Affymetrix chips based on the specific probe NtPMIa1g2e2_st for cytochrome P450 monooxygenase CYP82E4.

Leaves at mid-stalk position are weighted in each transformation event and control lines. The data show no major variation in leaf biomass, when ASN1- and ASN5-RNAi plants are grown in a controlled environment such as the greenhouse (FIG. 15).

In conclusion, both ASN1 and ASN5 gene families are silenced in the corresponding MMV RNAi lines, thereby indicating that ASN1 and ASN5 gene copies are both involved in the synthesis of asparagine during Burley curing.

Figure 6:
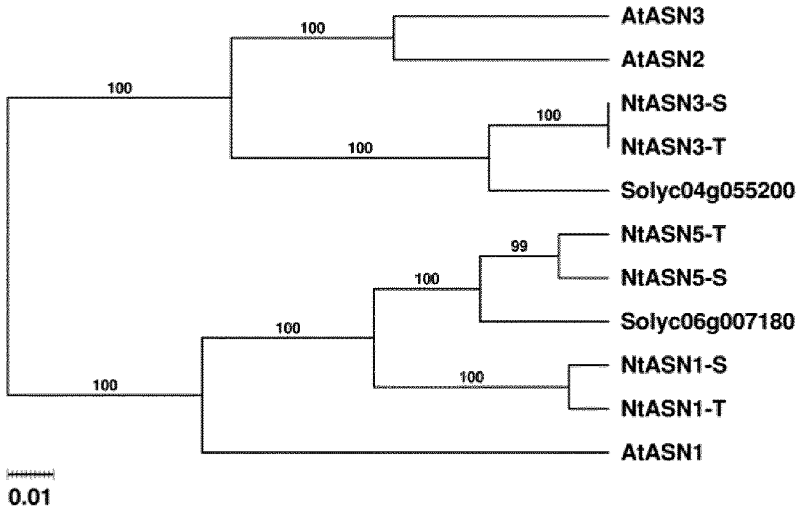
FIG. 6 shows the phylogenetic tree of the amino acid sequences deduced from the tobacco genes corresponding to NtASN1-S, NtASN1-T, NtASN3-S, NtASN3-T, NtASN5-S, NtASN5-T compared with the Arabidopsis proteins AtASN1 (At3g47340), AtASN2 (At5g65010) and AtASN3 (At5g10240) and tomato proteins Solyc06g007180 and Solyc04g055200.

Cross-qPCR analyses to determine whether both ASN1 and ASN5 transcript families are silenced in the corresponding ASN1-RNAi and ASN5-RNAi plants controlled under the MMV promoter is performed. In Table 2, the data show that in ASN5-RNAi plants both ASN1 and ASN5 transcripts are silenced, but this is less clear in ASN1-RNAi plants, particular for lines ASN1-1 and ASN1-2. This observation is likely due to the fact that both ASN5 and ASN1 (S&T) genes are very similar, belonging to the same gene cluster (FIG. 6). However this may also indicate that it is sufficient to only inactivate the ASN1 gene cluster to alter asparagine synthesis in cured leaves.

The analysis of the expression of CYP82E4 during Burley curing indicates that the E4 promoter becomes fully active only after 48 h curing, thereby suggesting that all the transgenic constructs or gene fragments under the control of the E4 promoter are expressed lately in the early curing phase (>48 h). Therefore, based on the data presented in FIG. 11 and FIG. 13, it is predicted that ASN1-T and -S are activated later during the first phase of the curing process, since the ASN1 silencing can be equally driven by MMV and the E4 promoters. The E4 promoter is weakly controlling the silencing of ASN5, thereby suggesting that ASN1 genes are controlled by a sequence of events related to the induced leaf-senescence program.

Example 4

ASN Variant (EMS Mutant) Lines

ASN EMS-mutants for the two ASN1-S and -T copies and the two ASN5-S and -T copies are identified. Specific mutations are screened on genomic DNA in the predicted exon sequences.

Three stop mutations are identified in ASN1-S (ASN1-S_W156*), ASN1-T (ASN1-T_W156*) and ASN5-S (ASN5-S_Q66*) copies, but not in the ASN5-T copy. As no stop mutations are identified in ASN5-T, a non-stop mutation is selected exhibiting a SIFT score of 0.0004 as a potential candidate that could replace a stop codon (ASN5-T_G59D).

From the M2 parents, offspring seeds harbouring mutations (variants) or being non-mutated in the selected genes (VVT out-segregants) are genotyped, identified and planted in the field. 10 plants of each selected variant are grown on the side of 10 plants of their corresponding WT out-segregant in individual plots to prevent any impact of the field variability (i.e. non-homogenous nitrate fertilization and soil variation). Four mid-bottom stalk leaves are collected at harvest time and hung on string for 2 months in an air-cured barn. Leaves are stripped and lamina ground in fine powder. Asparagine (mg/g) is determined in each leaf pool. Although some variations can be observed due to plot-by-plot variability, a clear tendency for asparagine reduction in ASN1-S_W156*, ASN1-T_W156* and ASN5-S_Q66*compared to their corresponding WT segregants is visible, but not for ASN5-T_G59D (see Table 3).

Figure 17:
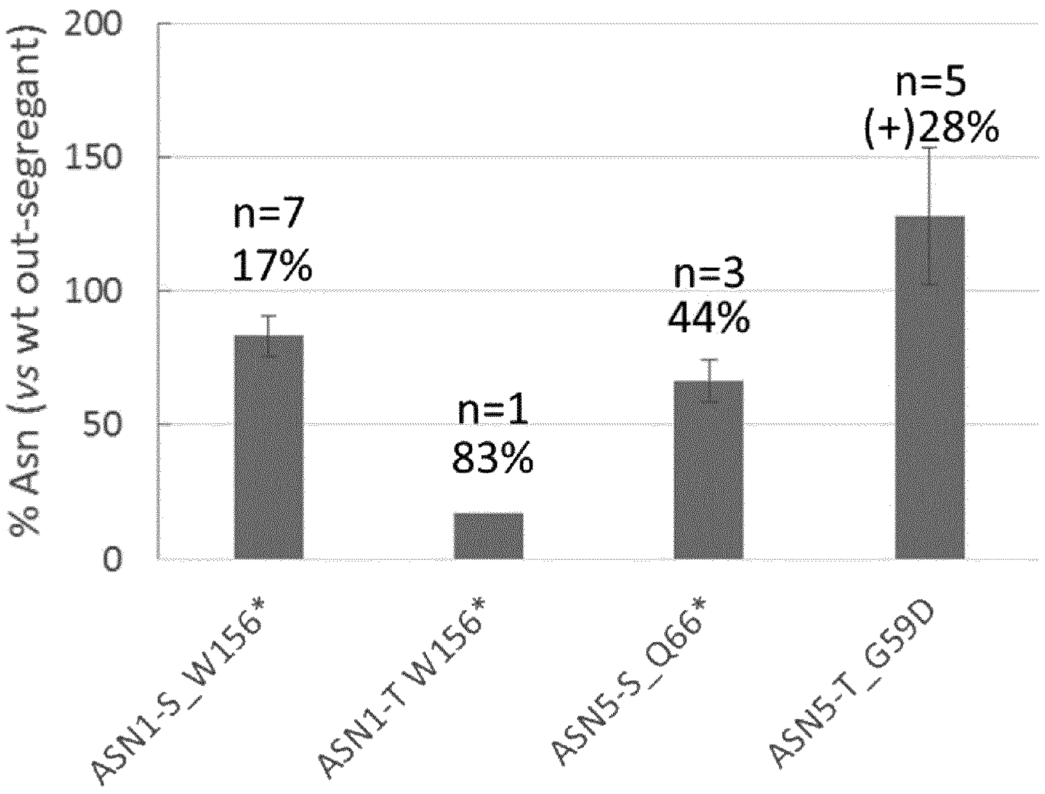
FIG. 17 shows the percentage of asparagine reduction in ASN variants. Percentage values are calculated versus VVT out-segregants for each variant line.

The percentage of asparagine reduction is shown in FIG. 17. The strongest reduction is observed for ASN1-T_W156* (83%), then for ASN5-S_Q66*(44%) and finally for ASN1-S_W156*(17%). The line ASN5-T_G59D showed a slight increase in asparagine. The content of asparagine in ASN variants is correlated with the level of gene activation during curing. Indeed, ASN1-T is more expressed during curing than ASN5-S and ASN1-S after 48 h and 60 h of curing (see FIG. 8 and FIG. 9). However this observation should still be taken with caution, since the data for ASN1-T_W156* results from only one plot in the field and both ASN1-T_W156* and the WT out-segregants plants for this line exhibited a strong reduction of biomass in this field experiment (see FIG. 18).

Figure 18:
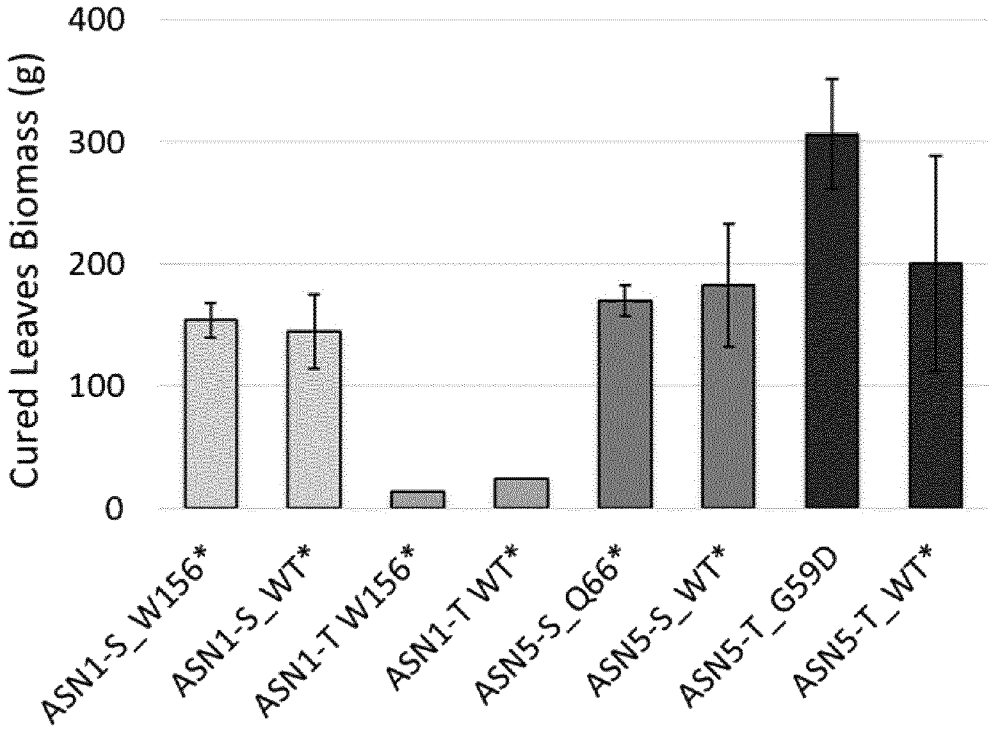
FIG. 18 shows the biomass of cured leaves (4) harvested at Mid-Bottom stalk position.

The reduction of biomass in both ASN1-T_W156* and its corresponding WT out-segregants ASN1-T_WT* likely results from another mutation(s) still present in both variant lines. Indeed, transgenic experiments with ASN1/5-RNAi lines tend to indicate that ASN1-T and any other ASN1 and ASN5 copies have no impact on plant height and biomass phenotype (see FIG. 15). Crossings with the background variety AA37 and subsequent plant selfing will allow us to conclude about any effect of ASN1-T stop mutation on the plant size. FIG. 18 also shows that stop mutations in ASN1-S and ASN5-S have no impact on plant biomass. This is also valid for the G59D point mutation in ASN5-T which is likely according to the expression data (FIG. 7 and FIG. 8) preferentially involved in other tissues, like flower (see FIG. 10).

A second field test is run with the similar stop mutants for ASN1-T (6 plots including 10 out-segregant plants and 10 stop mutant plants), ASN1-S (6 plots including 10 out-segregant plants and 10 stop mutant plants) and ASN5-S (9 plots including 10 out-segregant plants and 10 stop mutant plants). After leaf curing (6 leaves at mid-stalk position), ASN1-T stop mutant plants exhibit an asparagine reduction of 19% compared to out-segregants in the leaf lamina, ASN1-S stop mutant plants exhibit an asparagine reduction of 23% compared to out-segregants in the leaf lamina and finally, ASN5-S stop mutant plants exhibit an asparagine reduction of about 10% compared to out-segregants in the leaf lamina. These results confirm the previous results shown in Table 3, attesting that the selected stop-mutants are efficient to reduce asparagine in cured leaves. When compared with the asparagine data from ASN-RNAi lines, the combination of the three stop mutants ASN1-T_W156*, ASN1-S_W156* and ASN5-S_Q66* should provide similar asparagine reduction in the lamina of cured leaves.

We conclude from these data that ASN1-S, ASN1-T and ASN5-S are involved in the formation of asparagine during leaf air-curing of Burley tobacco.

Example 5

Impact of Asparagine Reduction in ASN Transgenic Lines on Acrylamide Formation

Figure 19:
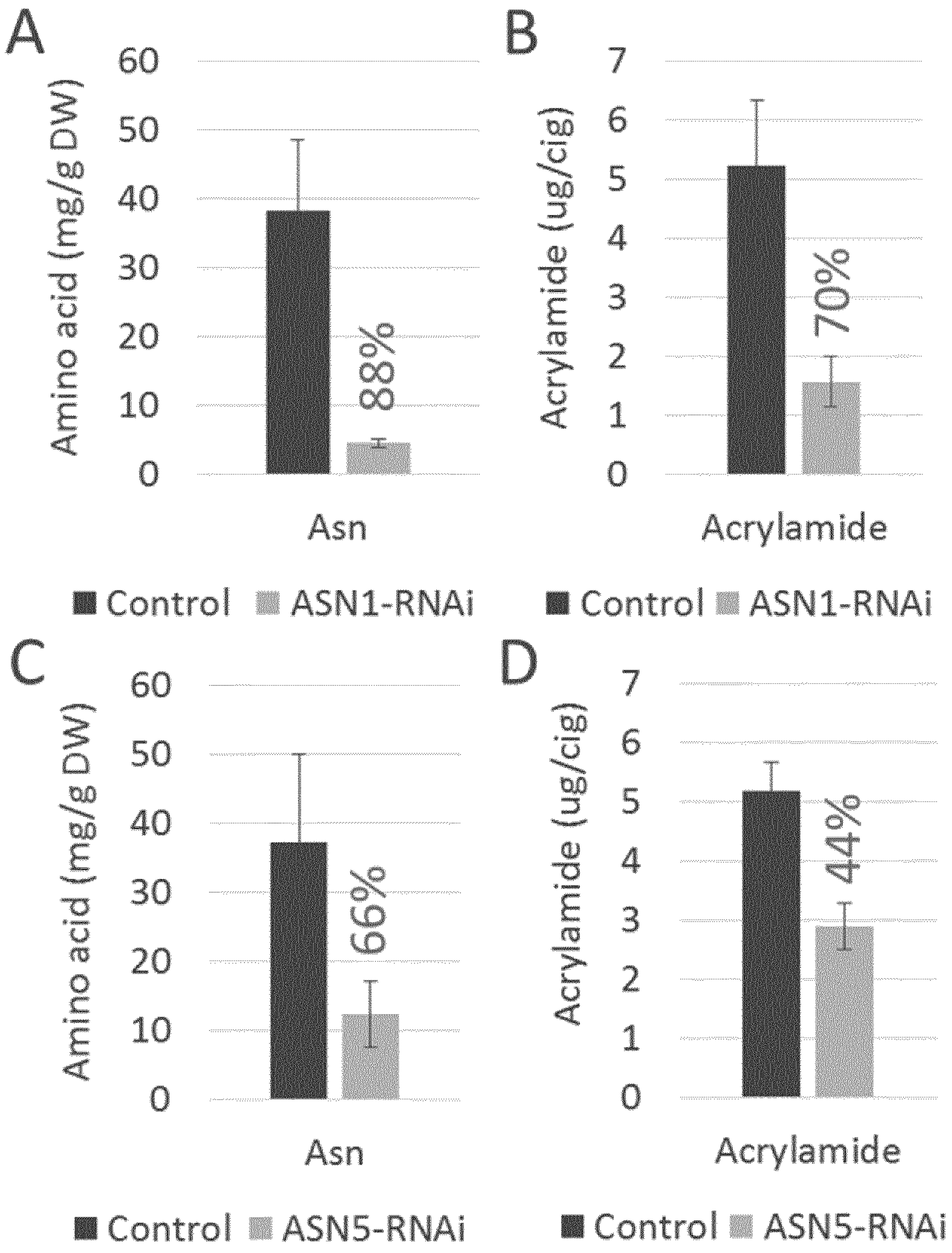
FIG. 19 shows the determination of acrylamide in the aerosol generated from heating an aerosol forming article, as described in WO2013/098405, made of ASN1-RNAi, ASN5-RNAi and their respective control leaves. Asparagine was determined in fine powder from ASN1-RNAi, ASN5-RNAi and control leaves (see FIG. 11 and FIG. 13) after blending with 50% Virginia tobacco (A, C). Tobacco blend was transformed in cast leaf and heated within an aerosol forming article. Acrylamide was then determined in the aerosol (B, D).

Lamina powder from leaf of the transgenic lines MMV-ASN1-RNAi (line E281-6 and its respective control, see FIG. 11) and MMV-ASN5-RNAi (line E303-1 and its respective control, see FIG. 13) is blended with 50% Virginia tobacco powder to make a slurry and cast leaf material according to manufacturing specification. Aerosol-forming articles were produced and the aerosol generated by heating them were subjected to analyses (Health Canada regime) to measure acrylamide. The data are shown in FIG. 19. Asparagine exhibiting 88% reduction in ASN1-RNAi lines transferred into a reduction of 70% acrylamide compared to the corresponding tobacco control. Similar data are obtained with the second transgenic lines, asparagine exhibiting 66% reduction in leaves of ASN5-RNAi lines for an acrylamide reduction of 40% in the aerosol compared to the tobacco control.

Figure 20:
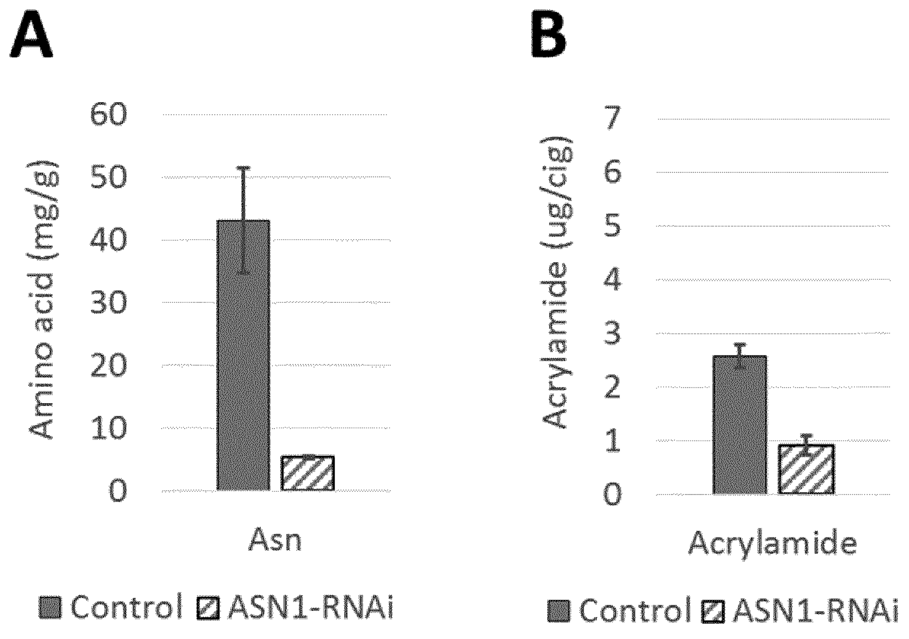
FIG. 20 shows the determination of acrylamide in smoke of combustible cigarette made from cut-filler of ASN1-RNAi and their respective control mid-stalk leaf lamina (panel B). Asparagine (panel A) was determined in cut-filler prepared from ASN1-RNAi and control leaves. The combustible cigarettes are smoked and acrylamide analysed in the smoke.

Acrylamide is a biological marker (Naufal et al., 2011) for smokers. The production of acrylamide is also analyzed in combustible cigarette smoke (FIG. 20). Combustible cigarettes are prepared from mid-stalk cured leaves of ASN1-RNAi plants using the following procedure. Tobacco leaf is conditioned at 22° C. and 60% ambient humidity. Cut-filler is prepared from leaf lamina after mid-rib removal. The cigarettes are hand-made, filled with an electric cigarette injector machine "Powermatic 2" using standard cigarette tubes. The weight of cut-filler inserted into the cigarette varied (around 800 mg) to obtain Resistance To Draw corresponding to 120 to 140 mm water gauge. Each cigarette is then controlled by hand for firmness (hardness). Once the parameters are determined for a set of cut-filler, they are maintained for the series of each cigarette stick made (200 per sample).

Figure 11:
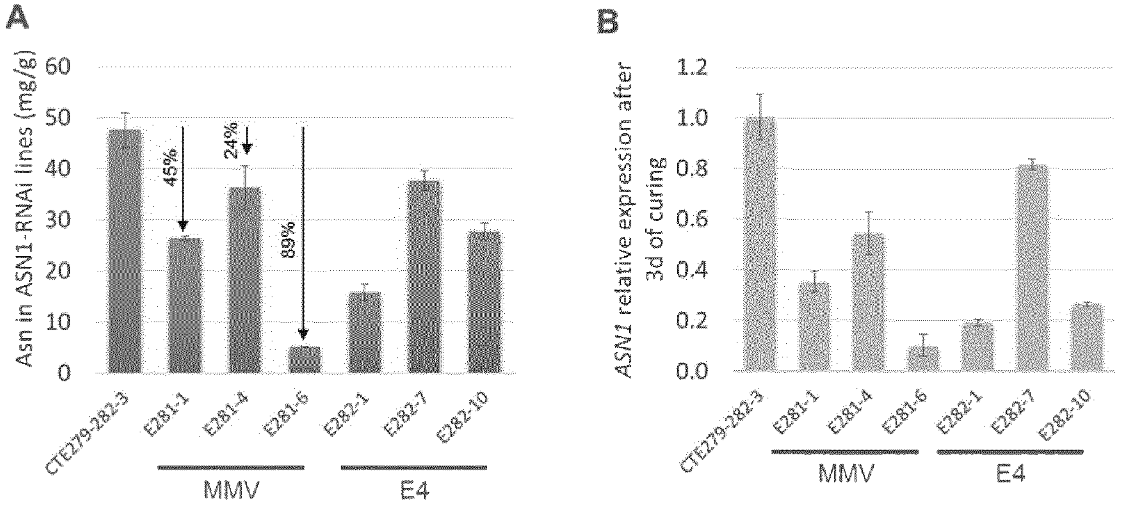
FIG. 11 shows the asparagine content in ASN1-RNAi plants grown in the greenhouse under the control of MMV or E4 promoter and ASN1 transcript levels determined after 3 days of curing. The amount of asparagine was measured in mid-bottom stalk leaf positions from 15 plants of each transformation event (A). The relative expression of ASN1 transcript was estimated by qPCR using RNA collected after 3 days of curing in 15 plants from each transformation event (B).

In the controlled plants, the content of asparagine within the tobacco cut-filler (FIG. 20) was comparable to the content of asparagine measured in the blend powder for cast-leaf (see FIG. 19) and about 10% lower compared to the amount measured in FIG. 11. Such a difference is due to the leaf stalk position at harvest time, asparagine being more abundant in lower stalk leaf than upper stalk leaves after Burley curing. However, the reduction of asparagine in ASN-RNAi compared to wild type plants was similar to the data presented in FIG. 11 and FIG. 19. Interestingly, the reduction of acrylamide was less effective in combustible cigarette smoke (57%) than in aerosol generating article aerosol (70%), possibly indicating that the Maillard reaction leading to the formation of asparagine is more efficient in heated than combusted or burnt tobacco products.

The reduction of acrylamide is also efficient in the aerosol from aerosol forming articles made of lamina from ASN1-S stop mutant (FIG. 21). However, in this case this reduction is limited due to the limited impact of the sole ASN1-S as a contributor for asparagine synthesis in cured leaf compared to ASN1-T for instance (based on the data depicted in FIG. 17). The data indicate that in both ASN-RNAi transgenic lines and ASN mutant lines, the reduction of asparagine in cured lamina is concomitant with a subsequent reduction of acrylamide in combustible cigarette smoke and aerosol generated by heating. In other words, knocking-out ASN1 and ASN5 gene copies results in a decrease of asparagine within the tobacco matrix and a reduction of acrylamide formation in combustible cigarette smoke and aerosol generated by heating.

REFERENCES

Canales J, Rueda-López M, Craven-Bartle B, Avila C, Cánovas F M. (2012). Novel insights into regulation of asparagine synthetase in conifers. Front Plant Sci. 3:100

Lewis R S, Bowen S W, Keogh M R and Dewey R E. (2010) Three nicotine demethylase genes mediate nornicotine biosynthesis in *Nicotiana tabacum* L.: functional characterization of the CYP82E10 gene. Phytochemistry 71: 17-18.

Moldoveanu S C (2005) Analysis of Protein Amino Acids in Tobacco Using Microwave Digestion of Plant Material. Contributions to Tobacco Research 21: 451-465

Naufal Z S, Marano K M, Kathman S J, Wilson C L. (2011) Differential exposure biomarker levels among cigarette smokers and smokeless tobacco consumers in the National Health and Nutrition Examination Survey 1999-2008. Biomarkers 16:222-235

Onoa H, Chudab Y, Ohnishi-Kameyamaa M, H. Yadaa, M. Ishizakac, H. Kobayashia & M. Yoshidaa. 2003. Analysis of acrylamide by LC-MS/MS and GC-MS in processed Japanese foods. Food Additives & Contaminants, 20: 215-220.

Papousek et al., (2014) Determination of Acrylamide and Acrolein in Smoke from Tobacco and E-Cigarettes, Chromatographia 77: 1145-1151

Sierro N, Battey J N, Ouadi S, Bakaher N, Bovet L, Willig A, Goepfert S, Peitsch M C and Ivanov N V. (2014) The tobacco genome sequence and its comparison with those of tomato and potato. Nat Commun. 5:3833.

A further aspect relates to a mutant, non-naturally occurring or transgenic plant or part thereof having reduced expression or activity of asparagine synthetase, said asparagine synthetase comprising, consisting or consisting essentially of: (i) a polynucleotide sequence comprising, consisting or consisting essentially of a sequence having at least 72% sequence identity to SEQ ID NO:1 or SEQ ID NO:3 or SEQ ID NO:5 or SEQ ID NO:7; or (ii) a polypeptide encoded by the polynucleotide set forth in (i); or (iii) a polypeptide having at least 78% sequence identity to SEQ ID NO:2 or SEQ ID NO:4 or SEQ ID NO:6 or SEQ ID NO:8; wherein the expression or activity of the asparagine synthetase set forth in (i), (ii) or (iii) is reduced as compared to a control plant.

A further aspect relates to a method of preparing plant material with reduced levels of asparagine and reduced levels of acrylamide in aerosol derived from said plant material as compared to plant material from a control plant, said method comprising the steps of: (a) providing a plant or part thereof comprising a polynucleotide comprising, consisting or consisting essentially of a sequence encoding an asparagine synthetase and having at least 72% sequence identity to SEQ ID NO:1 or SEQ ID NO:3 or SEQ ID NO:5 or SEQ ID NO:7; (b) reducing the expression of the polynucleotide or the activity of the protein encoded thereby in the plant or part thereof; (c) harvesting plant material from the plant or part thereof; (d) drying or curing the plant material; (e) optionally, measuring the levels of asparagine in the plant or part thereof and/or measuring the levels of acrylamide in aerosol derived from the plant or part thereof; and (f) obtaining cured or dried plant material with reduced levels of asparagine and reduced levels of acrylamide in aerosol derived from said plant material, suitably, wherein the level of nicotine is substantially the same as the level of nicotine in the control plant; suitably, wherein the formation of glutamine, aspartic acid and glutamic acid is increased as compared to cured or dried leaf of the control plant.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

TABLE 1

Percentage of identical residues in ungapped alignment regions between Tobacco, Tomato and *Arabidopsis* asparagine synthetase (ASN) gene products.

| | AtASN1 | AtASN2 | AtASN3 | NtASN5-T | NtASN5-S | NtASN1-T |
|---|---|---|---|---|---|---|
| AtASN1 | 100 | 76.91 | 77.26 | 83.01 | 83.73 | 85.1 |
| AtASN2 | 76.91 | 100 | 91.33 | 77.22 | 76.99 | 78.03 |
| AtASN3 | 77.26 | 91.33 | 100 | 77.4 | 76.99 | 78.37 |
| NtASN5-T | 83.01 | 77.22 | 77.4 | 100 | 97.88 | 90.27 |
| NtASN5-S | 83.73 | 76.99 | 76.99 | 97.88 | 100 | 90.85 |
| NtASN1-T | 85.1 | 78.03 | 78.37 | 90.27 | 90.85 | 100 |
| NtASN1-S | 85.27 | 78.03 | 78.37 | 89.91 | 90.51 | 98.31 |
| NtASN3-T | 76.17 | 84.64 | 85.14 | 77.16 | 77.28 | 77.62 |
| NtASN3-S | 76.17 | 84.64 | 85.14 | 77.16 | 77.28 | 77.62 |
| Solyc06g007180 | 83.9 | 76.82 | 76.99 | 93.81 | 95.08 | 90.34 |
| Solyc04g055200 | 77.44 | 85.46 | 85.96 | 80.2 | 79.7 | 80.45 |

| | NtASN1-S | NtASN3-T | NtASN3-S | Solyc06g007180 | Solyc04g055200 |
|---|---|---|---|---|---|
| AtASN1 | 85.27 | 76.17 | 76.17 | 83.9 | 77.44 |
| AtASN2 | 78.03 | 84.64 | 84.64 | 76.82 | 85.46 |
| AtASN3 | 78.37 | 85.14 | 85.14 | 76.99 | 85.96 |
| NtASN5-T | 89.91 | 77.16 | 77.16 | 93.81 | 80.2 |
| NtASN5-S | 90.51 | 77.28 | 77.28 | 95.08 | 79.7 |
| NtASN1-T | 98.31 | 77.62 | 77.62 | 90.34 | 80.45 |
| NtASN1-S | 100 | 77.45 | 77.45 | 89.83 | 80.2 |
| NtASN3-T | 77.45 | 100 | 100 | 75.93 | 64.73 |
| NtASN3-S | 77.45 | 100 | 100 | 75.93 | 64.73 |
| Solyc06g007180 | 89.83 | 75.93 | 75.93 | 100 | 79.95 |
| Solyc04g055200 | 80.2 | 64.73 | 64.73 | 79.95 | 100 |

TABLE 2 qPCR analyses (relative gene expression units) to determine the degree of silencing of both ASN1 and ASN5 transcripts in ASN1-RNAi (ASN1-1, ASN1-2 and ASN1-3) and ASN5-RNAi (ASN5-1, ASN5-2 and ASN5-3) transgenic lines using the specific primers ASN1p and ASN5p.

| | ASN1p | ASN5p |
|---|---|---|
| Control | 1 | 1 |
| ASN1-1 | 0.35 | 0.88 |
| ASN1-2 | 0.54 | 0.74 |
| ASN1-3 | 0.10 | 0.40 |
| ASN5-1 | 0.31 | 0.24 |
| ASN5-2 | 0.50 | 0.34 |
| ASN5-3 | 0.16 | 0.35 |

TABLE 3

Analyses of asparagine (mg/g) in air-cured leaves harvested at bottom-/mid-stalk position in the four ASN variants: ASN1-S_W156* and its corresponding WT out-segregants ASN1-S_WT*, ASN1-T_W156* and its corresponding WT out-segregants ASN1-T_WT*, ASN5-S_Q66* and its WT out-segregants ASN5-S_WT*, ASN5-T_G59D and its corresponding WT out-segregants ASN5-T_WT*. Each variant and WT out-segregant were planted side by side in individual plots to prevent any undesired field effects (i.e. nitrate and soil variation).

| Plot | ASN1-S_WT# | ASN1-S_W156* | ASN1-T WT# | ASN1-T W156* | ASN5-S_WT# | ASN5-S_Q66* | ASN5-T_WT# | ASN5-T_G59D |
|---|---|---|---|---|---|---|---|---|
| 1 | 24.2 | 20.5 | 27.5 | 4.7 | 20.9 | 12.0 | 25.0 | 26.4 |
| 2 | 26.0 | 20.6 | | | 22.3 | 16.2 | 18.5 | 27.9 |

TABLE 3-continued

Analyses of asparagine (mg/g) in air-cured leaves harvested at bottom-/mid-stalk position in the four ASN variants: ASN1-S_W156* and its corresponding WT out-segregants ASN1-S_WT*, ASN1-T_W156* and its corresponding WT out-segregants ASN1-T_WT*, ASN5-S_Q66* and its WT out-segregants ASN5-S_WT*, ASN5-T_G59D and its corresponding WT out-segregants ASN5-T_WT*. Each variant and WT out-segregant were planted side by side in individual plots to prevent any undesired field effects (i.e. nitrate and soil variation).

| Plot | ASN1-S_WT# | ASN1-S_W156* | ASN1-T WT# | ASN1-T W156* | ASN5-S_WT# | ASN5-S_Q66* | ASN5-T_WT# | ASN5-T_G59D |
|---|---|---|---|---|---|---|---|---|
| 3 | 22.9 | 20.5 | | | 22.0 | 15.2 | 17.7 | 28.0 |
| 4 | 25.7 | 21.3 | | | | | 28.3 | 28.7 |
| 5 | 30.9 | 22.0 | | | | | 25.4 | 31.9 |
| 6 | 17.4 | 14.1 | | | | | | |
| 7 | 18.4 | 17.3 | | | | | | |
| % Reduction | 17 +/- 7 | | 83 | | 34 +/- 8 | | No | |

SEQUENCES

SEQ ID NO: 1 - NtASN1-S, genomic DNA sequence
atgtgcgggatcttggctgttttgggttgttctgatgattctcaggccaaaagggttcgtgttctcgagctctctcg
caggtaaattatatttcccttcttttctgtattgttaatgttattgtgttgcgttattatattgattctttttatga
gaaagtagtttcctgaacgtttgcattttagaataaaagaagactaaagcttaagatagattatatatttagatatt
cttgacgtggacctatatcttagattcacaatataattttctcggaccaactgttttagcatgacttgtaaatgatg
ttgatatgaaaagctgtgatttaattagtaggagtaattcatttccatgttacaattacttatctttctcctccttg
tgttcttgccactgctagaggcagatctataattcctacttagagtattgaacacattgtacttttgaaattgtaag
tgtgcagtttaatatttgttaaaattttgaaggtttttttaattacatgtatatcgtgacgttatatagcctctcta
cccgcataaggtaggggtaatgtctgcgtacaaataggctgatttcactctgtgttcagttgaatcaatatatgcgg
catccaccactgtttgcaaatgcatgggaatggaaaagtcatgcctcatcactgtcacacatgattttatttattt
atttattatatatgattctttaaatctattagtgggtactgaatcttgctaactgatcgattgatgaaacaggttga
agcatcgtggaccagattggagtgggctgtatcaacatggggactgttacttggcacatcagcgtctagctattgtt
gatcctgcttccggtgatcaacctctgtttaacgaagataagacgattgttgttacggtgggtgcttttaatttcat
gtttactctcatttcttgctcagtttactgatgaaaacgaaactaatgctgataactatcaaccaatcaaccacata
caagtaggggtcgactatatgattcattatatcctttcctctattcaaatagttgatgattaatttcatgccaaaaa
tttcaggtaaatggagagatctacaatcacgagcaacttcgtaagcaaatgcctaatcataagttccggactggcag
tgactgtgatgtcattgcacacctagtgagtactcatcttccaacttaggaaacatgtatgtatatgtaaaattatt
ccctgattatattatgtacattaatcagtatgaagaacatggagaagattttgtggacatgctggatgggatcttcg
cttttgtgttattggatactcgagataacagctttcttgttgctcgtgatgccattggaattacttccctttatatt
ggttggggacttgatggtaagattccatatgattttctcacttagatttgttattgcaaatgaatatgttgaatcc
ttatatgtactaattgttgtaattctgttccttctcagggtctgtatggatatcatctgagcttaagggcttgaatg
atgactgcgaacatttgaagttttcccaccagggcacttgtactctagcaagaatggcggctttaggaggtggtac
aatcctccttggttctctgaggccattccttccactcgttatgatcccttagttctcaggcgtgcctttgaaaatgt
gagttaatattgttgttgttgaaatggatccaacatgttggttttaaggctatatatcatttgcaggctgttatca
aaaggttgatgactgatgtcccctttggtgttctcctctccgggggactcgattcatccttggttgcttcgattact
gctcgctacttggctggtacaaaggctgccaagcagtggggagcacagcttcattccttctgtgttggccttgaggt
cagataatcttgagacttgtgtgattacaacattaataacgacaacacctcattcacaagctagtaaggtcagctat
atgaaatctgataccgatttgcttgctttcaccgaacagggctcaccggatctcaaggctgcaagagaagttgctga
ctacttgggaaccgttcaccacgagtttcacttcaccgttcaggttttgatggagcaactctattttcacttgatct
atcatcctcttcgtttctcctttgtttacctgatggcaaatgacatgtgttgtatttgcaggatggaattgatgcaa
ttgaagatgttatttaccatattgagacatacgatgtaacgacaatcagagcaagcactcctatgttccttatgtcg
cgtaagattaagtcactaggagtgaagatggtcatatctggggaaggatctgatgaagtgtttggtggctacttgta
ctttcacaaggctcccaacaaggaagagttccacaaggaaacatgtcgcaaggtataagaaagtgcttccagttcct
agtttaaataggacaaggagttgagaaaatgttgatttttccctatgcagattaaagcgcttcaccaatatgactg
cttaagagcaaataagtcaacatctgcatggggtttagaagctagagtccctttcctagataaggagttcatcaatg
ttgccatgagtattgatccagagtggaagttggtaagtagttgacccccaattgttgatcgaataaacaatcaactg
tccctaaaactatgtatttattcatttcagattaaaccagagcaaaggaggattgaaaagtgggctctaaggagggc
ctttgatgatgaggagcatccttatctcccaaaggtgtactaaatcgccattttcaaactgatttgcaaatgatttt
gaatgttatattattaatcaaactaacaatttactcattacattccttgcagcacatcctgtataggcaaaaagaac
aattcagtgatggcgtgggctatagttggatagatggactcaaagcacatgctgaacaacatgtgcgtttcaatgac
taatcaacgactttctactgctcttatttatcttccaatgcttgtttgttttaaagctgaccgaggaaacaaatttt
ttcctttaataggtgaccaataggatgatgtttaatgcttcacatatattccctcataacacacccattacaaagga
agcatactactataggatgattttcgagcgctttttcccacaggtaatttgttcagataatagtgagaatttatgat
aaatggactaatttacgtttgttgtcgattttgcaaccttccaacagtgtgagcaagctcacataatcggaatttt
tgttcaaataataatgcattggaaatcataatgctaaattgagatttacttttaaccatgttcctctaccattttg
gttctgcagaattcagctgggctaaccgttcctggaggagcaagtgtggcgtgtagcacagctaaagctgtagagtg
ggatgcttcttggtcaaagaaccttgatccttcaggcagggctgctattggtgtacataactcggcttatgagaatc
atgtacctgctatggctaatgggaatttgaccaaaaaaatcattggtcgtgtgccttctatggtagaagttggtgct
gctcccgagctcacaataaagagttag SEQ ID NO: 2 - NtASN1-S, deduced amino acid sequence
MCGILAVLGCSDDSQAKRVRVLELSRRLKHRGPDWSGLYQHGDCYLAHQRLAIVDPASGDQPLFNEDKTIVVTVNGE
IYNHEQLRKQMPNHKFRTGSDCDVIAHLYEEHGEDFVDMLDGIFAFVLLDTRDNSFLVARDAIGITSLYIGWGLDGS
VWISSELKGLNDDCEHFEVFPPGHLYSSKNGGFRRWYNPPWFSEAIPSTRYDPLVLRRAFENAVIKRLMTDVPFGVL
LSGGLDSSLVASITARYLAGTKAAKQWGAQLHSFCVGLEGSPDLKAAREVADYLGTVHHEFHFTVQDGIDAIEDVIY
HIETYDVTTIRASTPMFLMSRKIKSLGVKMVISGEGSDEVFGGYLYFHKAPNKEEFHKETCRKIKALHQYDCLRANK
STSAWGLEARVPFLDKEFINVAMSIDPEWKLIKPEQRRIEKWALRRAFDDEEHPYLPKHILYRQKEQFSDGVGYSWI -continued

SEQUENCES

DGLKAHAEQHVTNRMMFNASHIFPHNTPITKEAYYYRMIFERFFPQNSAGLTVPGGASVACSTAKAVEWDASWSKNL
DPSGRAAIGVHNSAYENHVPAMANGNLTKKIIGRVPSMVEVGAAPELTIKS

SEQ ID NO: 3 - NtASN1-T, genomic DNA sequence
atgtgcgggatcttggctgttttgggttgttctgatgattctcaggccaaaagggttcgtgttctcgagctctctcg
caggtaaattatattcccttcttttctctattgttaatgttattgtgttgcatgcgttattaattctttttatgaga
aagtagtttcctgagcgtttggagctgctactgattgcttgcattttagaataaaacttaagatggattatatattt
agatattcttgacgtggacctatatcttagattcacaattttctcggaccaactgttttagcatgacttgtatatga
tgttgatatgaaaagctgtggtttagtaattcatttccatgttacaattactaatctttctcctatctgtgttcttg
ccactgctagaggcagatctataattcgtaattagagtattgaacacattgtacttttcaaaattataagtgcgcaa
tttaatatttgttaaaattttgaaggctttttaattacatgtatatcgtgtctcgtatagcctctctacccatgta
aggtctgcgtacacattacccgccccatgccctcccgtgaaattttactggggtttgctgttgttgttggtatcgtg
tgtcgcatatactttgttctgttgaatcaatatatgcgtcatctgccactgtttgcaaatgcatggaatggaaaagt
catgcctcatcactgtcacacaggatttttatttatttatttatttattatatatgattctttttcttgatgtgaaa
tctattagtgggtactgaatctggctaactgactaatgaaacaggttgaagcatcgtggaccagattggagtgggct
gtatcaacatggggactgttacttggcacatcagcgtctagctattgttgatcctgcttccggtgatcaacctctgt
ttaacgaagataagacgattgttgttacggtgggtgcttttaatttcatgtttactctcatttcttgctcagtttac
tgatgaacatgaaactaatgactatcaatcagccaatcaaccacgcttaattccatacaagtaggggtcgactatat
gattcattatatcctttcctctattccggttcctttttattcaaatagttgatgattaatttcatgccaaaaatttc
aggtaaatggagagatctacaatcacgagcaacttcgcaagcaaatgcctgatcataagttccggactggaagtgac
tgtgatgtcattgcacacctagtgagtaatctagattactcatcttccaacttaggaaacatgtatgtattcccctg
attatttcatcatctttatgtacattaatcagtatgaagaacatggagaagattttgtggacatgctggatgggatc
ttcgcttttgtgttactggatactcgagataacagctttcttgttgctcgtgatgccattggaattacttcccttta
tattggttggggacttgatggtaagattccatattattttctcacttagattttgttattgcaaatgaatatgttga
atctttatatgtagtaactgttgtaatttggttccttctcagggtctgtatggatatcatctgagcttaagggcttg
aatgatgactgcgaacattttgaagttttcccaccaggacacttgtactctagcaagaatggcggctttaggaggtg
gtacaatcctctttggttctctgaggctattccttccactccttatgatcccttagttctcaggcgcgcctttgaaa
atgtgagttattattgttgttgttgaaatggatccaacatgttggttctaaggctggatatcattgtgcaggctgtt
atcaaaaggttgatgactgatgtcccttttggtgttctgctctccgggggactcgattcatccttggttgcttcgat
tactgcccgctacttggctggcacaaaggctgccaagcagtggggagcacagcttcattccttctgtgttggccttg
aggtcagataatcttgagatttctgtgattacaacattaataacgaccacacctcattcacaagctagtaaggtcag
ctatatgaatctgataccgatttgcttgctttcaaacgaacagggatcaccggatctcaaggctgcaagagaagttg
ctgactacttgggaaccgttcaccacgagtttcacttcaccgttcaggtattgatggagcaactctattttgacttg
atctatcatcctctgcgttccctttttgtttacctgatggcaaatgacatgtgtcgtatttgcaggatggaattgatg
caattgaagatgttatttaccatattgagacatacgatgtaacgacaatcagagcaagcactcctatgttccttatg
tcgcgtaagattaagtcactaggagtgaagatggttatatctggggaaggctctgatgaagtgtttggtggctactt
gtactttcacaaggctcccaacaaggaagagttccacaaggaaacatgtcgcaaggtataaaaaagtgtttccagtt
ccttgtttaaaaccttatttaaataggataagcaacaacaacaacaacaacccagtataatcccactagtggggtct
gaggagggtattgtgtatgcagaccttacccctaccctggggtagagaggctgtttcagatagaaactcgactccct
ccctccaaaaaccttatttaaataggacaaggagttgagaaaatgttgatctttttcctccatctctatgcagatta
aagcacttcaccaatatgactgtttaagagcaaataagtcaacatctgcatggggcttagaagctagagtgcctttc
ctagataaggagttcatcaatgttgccatgagtattgatccagagtggaagttggtaagtagttgaaccccaattgt
tgatcgaataaacgatcaactgtccctaaaaccttgtattctatccatttcagattaaaccagagcaaaggaggatt
gagaagtgggctctaaggagggcctttgatgatgaggagcatccctatctcccaaaggtggtactaaatcgcccttt
tcaaactgatttgcaagtgatttcgaatgttatattgttaaccaaactaacaatttnaaggctctgatgaagtgttt
ggtggctacttgtactttcacaaggctcccaacaaagaagagttccacaaggaaacatgtcgcaaggtataaaaaag
tgtttccagttccttgtttaaaaccttatttaaataggataagcaacaacaacaacaacaacccagtataatcccac
tagtggggtctgaggagggtattgtgtatgcagaccttacccctaccctggggtagagaggctgtttcagatagaaa
ctcgactccctccctccaaaaaccttatttaaataggacaaggagttgagaaaatgttgatctttttcctccatctc
tatgcagattaaagcacttcaccaatatgactgtttaagagcaaataagtcaacatctgcatggggcttagaagcta
gagtgcctttcctagataaggagttcatcaatgttgccatgagtattgatccagagtggaagttggtaagtagttga
accccaattgttgatcgaataaacgatcaactgtccctaaaaccttgtattctatccatttcagattaaaccagagc
aaaggaggattgagaagtgggctctaaggagggcctttgatgatgaggagcatccctatctcccaaaggtggtacta
aatcgcccttttcaaactgatttgcaagtgatttcgaatgttatattgttaaccaaactaacaatttactcattaca
tttcctgcagcacatcctatacaggcagaaagaacaattcagtgatggcgtaggctatagttggatagatggactca
aagcacatgctgaacaacatgtgcgtttcaatgactaatcaacaactttctaatgttcttatttatcttccaatgtt
tgtttgttttaaagctgacttggaatttttttgtttcctttaataggtgaccaataggatgatgcttaatgcttcac
atatattccctcataacacaccgattacaaaggaagcatactattataggatgattttcgagcgcttttttcccacag
gtaatttgttcatgtattgtgaggattcatgataaattagctaacttatgctggttttcaaccttgcaaccttccga
taagtcacattgttggagtttgttgttcaaatgcgagatttacttttaaccatgttcctctggtatttttggttctg
cagaattcagctgggctaaccgttcctggaggagcgagtgtggcgtgtagcacagctaaagctgtagagtgggatgc
ttcttggtcaaagaaccttgatccttcaggaagggctgctattggtgtacataactcagcttatgagaatcatgaac
ctgctatggctaatgggaatttggccacaaaaatcattggccgtgcgccgtctatggtagaagttggtgctgctcat
gagctcacaataaggagttag SEQ ID NO:4 - NtASN1-T, deduced amino acid sequence
MCGILAVLGCSDDSQAKRVRVLELSRRLKHRGPDWSGLYQHGDCYLAHQRLAIVDPASGDQPLFNEDKTIVVTVNGE
IYNHEQLRKQMPDHKFRTGSDCDVIAHLYEEHGEDFVDMLDGIFAFVLLDTRDNSFLVARDAIGITSLYIGWGLDGS
VWISSELKGLNDDCEHFEVFPPGHLYSSKNGGFRRWYNPLWFSEAIPSTPYDPLVLRRAFENAVIKRLMTDVPFGVL
LSGGLDSSLVASITARYLAGTKAAKQWGAQLHSFCVGLEGSPDLKAAREVADYLGTVHHEFHFTVQDGIDAIEDVIY
HIETYDVTTIRASTPMFLMSRKIKSLGVKMVISGEGSDEVFGGYLYFHKAPNKEEFHKETCRKIKALHQYDCLRANK
STSAWGLEARVPFLDKEFINVAMSIDPEWKLIKPEQRRIEKWALRRAFDDEEHPYLPKHILYRQKEQFSDGVGYSWI
DGLKAHAEQHVTNRMMLNASHIFPHNTPITKEAYYYRMIFERFFPQNSAGLTVPGGASVACSTAKAVEWDASWSKNL
DPSGRAAIGVHNSAYENHEPAMANGNLATKIIGRAPSMVEVGAAHELTIRS -continued

SEQUENCES

SEQ ID NO: 5 - NtASN5-S, genomic DNA sequence
atgtgtggaatcttggctttgttgggttgttcagatgattctcaggccaaaagggttcgagttcttgagctctctcg
caggcaatttcccctttcttttctcttttattttattactccatcatataattattctactttcacctttttttgttt
tttaatttcgatttgtttgctttttgctttcttcatttaatgttcttgcattgctctagctcctatacgaataatag
gagctaaagtaatagagtgaaggattattttggagcaacggtaaagttattttttgtatagttcacaggttggagccg
taaaagcagttactagtgtttgcattagggtaagttgtctatcaggaaagatatttgtagcaattgaccaccctttg
gcaaaaaattatgcgtaaaatattactacttgttattgattcaaaaaatatgactttgaacatccttgtatagccta
gtggcaaagggtgttcaaaattttgaacacctttattgaattttctggtttcgtcgttgctgtctacaacacactc
tcgaagtgcggccttccctcaaaccctacgtgaatatggaacgcctagtgtgccgggatgccctttaggctgagtaa
tagagtactatgttgatatacctaaaatacggaactggcacgagagataaattcagaatttatagcttaattattta
aaatttatcatttgatttatttcaaccagagttcattctagtagagtttatgttgcatatttgtctgatttgcacca
tttgttttaatgttcttgcattactctaatttatttatgaataataagctaaactaattgagtttatgttgatgtaa
ctgacctgagttggcagtgatgtttggctacttgaatttaaaacaagattaagacttgtgagttggcagtaattgtt
tggatacttgaatttagaacaagaataaaacaagattaattaaggatacattattcctaacccggaccctaattcta
tagattgattattaaattttcttggaccaaccgtcaccgtgacctgttcatgatggtgatggcaaaagccataata
cacttgatttctgttttcaattttaaggttcttattattatacttattatatactttgaaaattatgggtcaaaat
tttaatatttgttattccttccgtatgtttgactcaacttggagttcatgaaaaaaaaaaaaaatttttttaaactt
gtggtcttaaacaagtcatcgatatatgtgtggttgtgaatcgcctcgttaggataaagtagaaattttaaagttaa
actatttcgaaataaaaaagtatgatagtgtttttgggacatactaaaaaggaaataacacataaaatggaacaaag
aagtatatttagtgatttttcacatatatatcagtattttgtatcaaaaatgctggttcagttgaactcattgaac
tgggtgctccatccacctccgagtactgcaacatgtgaccggtggcagatgcaacccttacgtaccagggtcatctg
aacctagtataaatatatttgtgaaaaatccctaaaatttcaataattagtagatttaaaaccttaattttaaaact
acaatgagttcagttttaaaatctttatatgtcaaacctatcaagattaaatcctggatccaccttttgcatgtgac
agtacaatagccttttgtaattgaaacaaatatttgaattttggtaactatttgatcacataggttgaagcatcgtg
gaccagattggagtgggatatatcaacatggtgatttttacttagcacatcaacgtttagcaattatcgatcctgct
tctggtgatcagcctctgtttaatcaagataagacgattgttgttacagtgagtgcctctaatttacctcttttttt
tttcttttttttttttacgatcgcgttgtttagattatttatggatgaaaatttgtatatttgattattgattgtgtg
ctaaattttgcaggtcaatggagagatttacaatcatgagaaacttcgtaatcttatgcctaatcacaagttcagaa
ctggaagtgattgtgatgttattgcacatcttgtgagttagtttacttttctcattgaccaacttaggccagtgaat
tatattaggaatttcgggtgtttggatatggtcaaattagcttataagcacttattatcaattttaacattttatc
catacacgtaactgttcattcataaagtcattttagcacttgatgctcatcaacctatgttgttgggactcttcgaa
aatgtcagcccgatagcatttcggagagtccgagcaacatagcaatcaactacttttaatcagttaaacgaacatgc
tcatagtgataacctctggaaaatatgttatagtaaattagaaaaatttatacgatgtctcactatcggtatgtatt
gatcagtatgaagaatatggagaaaattttgtggacatgttggatggggtgttctcttttgtattgttggatacgcg
cgataacagctttcttgctgctcgtgatgcaattggaattactcccctatatattggttggggacttgatggtaaga
ttttctatacaattttccagttagaaattaaaactgaagctattcctatttactattgaagaatcttgatacatgtt
atttggtatttcgtcgtgttgttatgtctcaggctctgtgtggatttcatctgagctaaaaggattaaatggtgact
gtgaacattttgaagttttccctcccggtcacttgtactcgagcaagaatggcgggtttaggagatggtacaatcct
caatggttctctgaggctattccatcaaatccttacgaccccttagttttgagacgtgccttcgaaaatgtgaggct
tgttaatgaatctagtgtacaatcttggatgtttttctctcgactttggttttagcactcaaaaagttgtctgtaca
aacgatcttggctataaggagtggtggttaattttgcaggctgttatcaaacgattgatgaccgatgtcccctttgg
tgttctgctctccggggacttgattcgtctttggttgcttctgtcactgctcgctacttggctggaacaaaagctg
ctaagcaatggggagcacagcttcattccttctgtgttggtctcgaggtcagactatcaatcctgagcggagacata
tttggggcgggttctgtgggttcaactgaacccattgcttttggttcgaaccatatatacaaatccaagaaaatata
agatgtgtacatataatatgacactcattctgagcctactgacgctagatactggactcgcctttggtcttgagact
ttataatagaaaatagatattcaataccaatttctgtttttcttttctgactgacagggctcaccagatctcaaggc
tgcaagagaagttgctgactatttgggaaccgttcaccacgagttcaccttcacagttcaggtttgtaaatcgtgtt
gctactccgatttattcatgtgagtctcttctgttttcctcctagaaagcaacaagtgttcatgttttgcaggatgg
aattgatgctattgaagatgttatttaccatatcgagacatacgatgtaacaacgatcagagcaagcactcctatgt
tccttatgtcgcgtaagattaaatcactgggagttaagatggtcatatcaggggaaggctcagatgaactgtttggc
ggctatttgtacttccacaaggctccgaacaaggaagaattccatgtggagacatgtcacaaggtaataaaacacgt
cggctcccttggcaagtctgattctccttgtcattgtttgtctcgggttggaataaattgctataattcgagaagaa
atgttaatcctgctctttcactcgcatgcagataaaagcgcttcaccaatacgactgtttgagagcaaataaggcaa
catcagcatggggcttagaagctagagtaccatttctggataaagagttcatcaacgttgctatgagtatcgatcct
gaatggaagatggtaacaaaactgagctccaattgtcaatgagatgagaagcataactgaatatgcacgttctctaa
aacttgtttttcatccgtttcagattaaacacgatcatggtaggatcgagaagtgggttcttaggaaggcttttgat
gatgaggagcaaccctatctcccaaaggtccacaaagtcatgtttttcctactgatttgccgattagtatggatcaa
aactaacatgttttgttcttttatgtactctgcagcatattctgtaccggcagaaagaacaattcagtgatggcgta
ggctatagttggatcgatggactcaaagcacatgctgaacaacatgtgagcttctaaataaatccagaactattaca
tcgttatcgtccaattttcgtttgttttgctgtcagctgatcttggaaacaattcttttctctcaggtgactgatag
gatgatgcttaatgctgcacatatcttccctcacaacactccaactacaaaggaagcatactattacaggatgattt
tcgagaggttcttcccacaggtacttatagcgcgagactagaatcatatatctcttaaatggaaacatgaaaaataa
aggaggtgtttttttctccttggaaaaagtatttactactgattaaagcaccttcattcacccatcttgctacttcgc
gtactttactaagttgtggttctaaaaaagaagatttagcttggtatattccatcacgaggaagccacaaaaagatt
ctacttataagaagttggatacttttaatggtgtgagaccttttgggaaaaaccatgcgggcttggcccaaagccga
caatatcacaccatgttaagagtatctttgcttcgttttagccaaacagtacaataagtcaatttttaaaccatgtt
gttactattgttggatttgcagaattcagcaaggctaactgttcctggaggaccgagtatagcttgcagcacagcta
aagctattgagtgggatgcttcgtggtcgaacaaccttgatccttccggtagggctgcaatcggtgtacataactcg
gcttatgacgatcatctccccgatgttggtaatgggaatttggacacaacgatcatcgataatgtgccgaggatggt
aggagtgggtgctgctgcagagctcacaataaggagctag SEQ ID NO: 6 - NtASN5-s, deduced amino acid sequence
MCGILALLGCSDDSQAKRVRVLELSRRLKHRGPDWSGIYQHGDFYLAHQRLAIIDPASGDQPLFNQDKTIVVTVNGE
IYNHEKLRNLMPNHKFRTGSDCDVIAHLYEEYGENFVDMLDGVFSFVLLDTRDNSFLAARDAIGITPLYIGWGLDGS
VWISSELKGLNGDCEHFEVFPPGHLYSSKNGGFRRWYNPQWFSEAIPSNPYDPLVLRRAFENAVIKRLMTDVPFGVL
LSGGLDSSLVASVTARYLAGTKAAKQWGAQLHSFCVGLEGSPDLKAAREVADYLGTVHHEFTFTVQDGIDAIEDVIY -continued

| SEQUENCES |
| --- |

HIETYDVTTIRASTPMFLMSRKIKSLGVKMVISGEGSDELFGGYLYFHKAPNKEEFHVETCHKIKALHQYDCLRANK
ATSAWGLEARVPFLDKEFINVAMSIDPEWKMIKHDHGRIEKWVLRKAFDDEEQPYLPKHILYRQKEQFSDGVGYSWI
DGLKAHAEQHVTDRMMLNAAHIFPHNTPTTKEAYYYRMIFERFFPQNSARLTVPGGPSIACSTAKAIEWDASWSNNL
DPSGRAAIGVHNSAYDDHLPDVGNGNLDTTIIDNVPRMVGVGAAAELTIRS

SEQ ID NO: 7 - NtASN5-T, genomic DNA sequence
atgacgtagtttagcttgttcgtccacggcataaaaacgcctataaattcggtggtcattttggttcatttacagaa
tcccacgatcatcttttgtgtattatcatttgccttctttacgtgttcttctctcccaaaatcctgcaaatcttta
actatcttcccatatttctctccctctttctctttctttttgttatctactttactacttctattagtagagcttta
tccaattaaagtcatctatattggatatagtttttactactactttatcttgtttgggaaagaaaagaataaaaaat
tagagtgtctatattaagtataaaaaggtgaaaaataaaaaagtagtgatcaatcatgtgtgggatcttggctttgt
tgggttgtccagatgattctcaagccaaaagggttcgagttcttgagctctctcgcaggcaattcccctttcttttc
tcttttatttattactccatcatattattcaactataatttcaccttttttgtttttcaattaatatttgtctgct
tttgctttcttcatttaatgttcttgcattgctctagttcctttatgaataataggctaaagtaatagagtgaagga
gtagagtcggagcaacggtgaagctgtctttacatgatctatagctcacgggttcaccatagaagcagccaatggcg
aagctagaaaattcaataagggtgttctttcctttgccagtgggctatgcaagggtgttcaaagtctatttttaatc
aataacaagtaatattttatcttatagtgaaagcaaccactaatacttgcatttaggtaattagctgtctatcaagg
gaagttatgtgtggtaagtagtggcggagccagaattttcgttaaggggtgtcaaaatatataaaagtaaacatacc
aggaaattaaggggagtcaatacatagtatatatacatataatttatttttttacctagctatacagtatattttttt
ccgcgaagtgacacccccttcctataaggtggctccgccactggtggtaagggtggtcaattgaacacccttcgccga
aaaattatactctggatggtgtaaaatattactacttgttactgattcaataaataaattttgaaaacccttgcata
gtctagtagcaaagagtgttcaaaattttgaacacatttattgaattctctggtttcgccactgctgtctacatcac
atcccttaaggtgcgatctttttttcgaatcatgtgtgaatacgggatgccttgtgttccaggctgcccctttaggct
aaagtaatagagtacgtcttaattcttatgttgatcatatacctgaaactcggaactggcacgagagatataaattc
agaatttatagcaaatttatcattatgttgcatttgttttaatgttcttgcattactctaatttttttatgaataat
aagctaaactaattgagtttatgttgatgtaactgacctgagtttggctacttgaaagttaaaacaagattaagact
tgtgagttggcagcgattgtttggatacttgaacacgtttaaaacaagattaagacattatgatggatacattattc
ctaacctgggtgggacctaattctatggattcattattaaaatttcttggacaaaccatcaccatgatctgttcatg
atgtttatggcaaaagccataatacactttatttctgtatcacaactactttatacacatgttatagagttttaaaa
ttattttaatatttgttattccttgagtctcctgatatttgactccgcatgaaattcaagaaaaaaaaaagaagatt
tttaaaatttatagtcgaaaacaagccatcgatatatgtgtggttgttaataacctcgttaggcgtaaagtagaaat
tttaaagttaaactatttctaaataagaaaatatgatattgtttttgcatagactaataaggaaagtatgacaagta
aaataaaacaaagaagtatattttaatgatttttccgtgtcaaaaatgtcagtttagttgaacttgaactcattga
aactggtgaccagtggtggatgcaaaccttaggtacggaggtcatccgaacctagtatagttatatttgtgaaaaat
cactaaaatttcaataattactagatatgaaaccttaattttaaaactacaatgagtgcagttttaaaatctttaaa
tgtcaaaccgatcaagattaaattatggatccacctttaaatgtcaaaccgacagtacaatagccttttgcaattga
aacaaatataaacattacatttattaaactagttttaattttggttactatttgattacataggttgaagcatcgtg
gaccagattggagtgggatatatcaacatggtgatttttacttagcacatcaacgtttagcaattatcgatcctact
tctggtgatcagcctctgtttaatcaagataagactattgttgttacagtgagtgcctctaatttaccctttttttt
gtggacgaatgcgttgtttagattactttaattatggctgaaaatttgtatatttgattattgattgtgtgccaaat
gttgcaggtcaatggagaaatttacaatcatgagaaacttcgtaatcttatgcctaatcacaagttcagaaccggaa
gtgattgtgatgttattgcacatcttgtgagttagtttactttactcatcaaccaacttaggctagtgaattcaaag
gcggagctagaattttgagtatatgagttctggaatttaggacaagataagttactgggttcggatagattatttag
acatattaagtagatttcttaacacaaatacacggcccgagccgaagctattgggttctgccgaacccgtagctaga
cttgtagctccgccattgagtgaattatataaggaatttcgggtgtttgggtaaacttataagctggtcaaattagc
ttataagcacttattatcaatttcaacatttctatccaaacacgtaactattcattcgattttagcacttgatgctt
atcgactacttttaatcagttaaacgaacaggctcatagtgacaaactctagaaaatatggtattgtaaattagtag
aagaatttatacgatgtctcactatcgatatgtattgatcagtatgaagaatatggagaaaattttgtggacatgtt
ggatggggtgttctcttttgtattgttggatacgcgcgataacagctttcttgctgctcgtgatgcgattggaatta
ctcccctctatattggttggggacttgatggtaagattttctatacaattttccaagtagaaattaaaactgaagcc
attccaatttgctattgtagaatcttgatatatgttatttggtatttcaggctctgtgtggatttcatctgagttaa
agggcttaaatgatgattgtgaacattttgaagttttccctcccgggcacttgtactcgagcaagaatggcgggttt
aggagatggtacaatcctcaatggttctctgaggctgttccatcaaatccttatgaccccttagttctgaggcgtgc
cttcgaaaatgtgagaaatgaatctaggaggtttccctctcgactttggacttagcactctaaaaatttgtctgtac
aaacgatcttggctataaggagtggttgttaatttcgcaggctgttattaaacggttgatgaccgatgtaccctttg
gtgttctgctctccgggggacttgattcgtctttggttgcttctgtcactgctcgctacttggctggaacaaaagct
gctaagcaatggggagcgcagcttcattccttctgtgttggtctcgaggtcagtcaatcaatcttgagtagaaaaaa
tttagggtcggttctgtgggtttaacttaactcattgcttttggctcgaaccatatatgcaaatccaaaaagattta
agatgtatacatataatataacactcattctgagcctactgacgctagatactggactgtgcctttggtcttgagac
ttttgtaatagaaaattgatattcaataccaatttctgttcttttgtgactaacagggctcaccagatctcaaggct
gcaagagaagttgctgactatttgggaaccgttcaccacgagttcaccttcacagttcaggtttgtaaatcgcgatg
ctacttcaatttattcatgtgaggctcttctgttttcctactagaaagcaacatgtgtgcatgttttggcaggacgg
aattgatgctattgaagatgttatttaccatatcgagacgtatgatgtaacaacgatcagagcaagcacccctatgt
tccttatgtcgcgtaagattaaatcacttggagtgaagatggtcatatcaggggaaggctcagatgaactgtttggt
ggctacttgtacttccacaaggctcccaacaaggaagaattccacacggagacatgtcacaaggtaataaaacacat
cggcaagtctgattctccttgtcattgtttgtctcgggttggaataaattgctataattcgagatatggaatgagtt
aagaaatgttaatcatgtttttccattcgcatgcagataaaagcgcttcaccaatacgactgtttgagagcaaataa
ggcaacatcagcatggggcttagaagctagagtaccatttctggataaagagttcatcaatattgctatgagtatcg
atcctgaatggaagatggtaagaaaactgagctccaattgtcaatgagacgagaagcataactgaatatgcgcgttc
tctaaaacctgtttttcatccgtttcagattaaacacgatcaaggtaggatcgagaagtgggttcttaggaaggctt
ttgatgatgaggagcacccctatctcccaaaggtccacaaactcatatttttcctactgatttgccaataattatgg
atcaaaactaacatgtttgttctgttatgtgctctgcagcatattttgtaccggcagaaagaacaattcagcgatgg
tgtaggctatagttggatcgatgggctcaaagcacatgctgaacaacatgtgagcttccttaataaatccagaacta
atgcagcgttatcgtccaatttttgtttgttttactatcaactaattttagtcatgttagtatgtttaccttaggta
ctatgtttttaaggagtttttagtcgtgtcaagaatttattcgctggtaaaaaatagattgaacttccagtattttc
tacttttattatgcatatgattggactgagatgaggttaaatggaacaacatggttgaggattaatataaccaattc
caacttggttggaattgaggcgtcgtagttgttgttagatctcagaaacaattcttttctctcaggtgactgatagg -continued

SEQUENCES atgatgcttaatgcttcacatatcttccctcacaacactccaactacaaaggaagcatactattacaggatgatttt
tgagaggttctttccacaggtaatattagtgagagattaaaatctatagattttgtttatggctgaggtttaaatca
tagatttcttaagctcaaaaactaaaaccatgtccctgctactgttggatttgcagaattcagcaaggctaactgtt
cctggaggaccgagtatagcttgcagcacggctaaagctattgagtgggacgcttcttggtcgaacaaccttgatcc
ttccggtagggctgctatcggtgtacataactcagcttatgacgatcatctacccgatgttagtaatgggaatttgg
acacaacgatcatcgataatgtgccaaggatggtaggagtgggtgcttctgcagagctcacaataaggagctag SEQ ID NO: 8 - NtASN5-T, deduced amino acid sequence
MTLKHRGPDWSGIYQHGDFYLAHQRLAIIDPTSGDQPLFNQDKTIVVTVNGEIYNHEKLRNLMPNHKFRTGSDCDVI
AHLYEEYGENFVDMLDGVFSFVLLDTRDNSFLAARDAIGITPLYIGWGLDGSVWISSELKGLNDDCEHFEVFPPGHL
YSSKNGGFRRWYNPQWFSEAVPSNPYDPLVLRRAFENAVIKRLMTDVPFGVLLSGGLDSSLVASVTARYLAGTKAAK
QWGAQLHSFCVGLEGSPDLKAAREVADYLGTVHHEFTFTVQDGIDAIEDVIYHIETYDVTTIRASTPMFLMSRKIKS
LGVKMVISGEGSDELFGGYLYFHKAPNKEEFHTETCHKIKALHQYDCLRANKATSAWGLEARVPFLDKEFINIAMSI
DPEWKMIKHDQGRIEKWVLRKAFDDEEHPYLPKHILYRQKEQFSDGVGYSWIDGLKAHAEQHVTDRMMLNASHIFPH
NTPTTKEAYYYRMIFERFFPQNSARLTVPGGPSIACSTAKAIEWDASWSNNLDPSGRAAIGVHNSAYDDHLPDVSNG
NLDTTIIDNVPRMVGVGASAELTIRS SEQ ID NO: 9 - NtASN3-S, genomic DNA sequence
atgtgtggaatactagctgtttttggttgcattgataactctcaggccaagcgttcccgaatcatcgaactttccag
aaggtttcttctttttattgctttccgattttctacagcattcttattcttctggggtgtcaatggtatgcatgtgt
tttggatttgctattcgtgaacttgttcgctttctcgtggtcttcgatttatttttgtcaatttataatcagcgttt
tttgtatggatttctcttttgaatctctcaaatatatgacatttgatttcctcgagaaaatttggcatttttatggt
tcttatgatatgtggttaacccctcgctctgcatcgcttcagcgctttaaaacacgaagtgatggctattagtaata
ctgctagagtggttattgaattacattaaataacgggttgctagtagatcaaattcagaatgacagtgaaatatctc
tggaaacttgaatccccgttcgattcgctggtaaaacctggctaaaaaatagctttatctcaaaggagagtatgtca
ctgtgaaattggtggtatgtgttgtttaaggcatgatatgctgctcttaggtgatgtcaagatgataataccatcct
tttcacactagactcagctttgtagcacttacatctcagttaatcgatggaggaaaatctagtctgctttggggcat
attataccaaatgtcttccttttgttttctagtgttgtttctcaagaattgaaaaaccaatctacaatatagtgata
taattaactagttaactcttcctgtgttttctgaaaatttccaataattgagaagtgtttactggtcaattagtaaa
gggagaacggaatatttttttcctctaaagaacttctctttttccatacagaatgactttctatacaaggcctaagt
ctaatttagtgtctgcgattaagcatcttctgggaacttcacacttgaaagaagtagaactaggagggggcaggtct
agaaagataattgcttcagtcatttctcataaaaaacattgcttcagtcattatgtgcattcatatagagttggtca
agctgctaagctgagctaatagtatgatagctgtgactctcgacaaagtaggttgcctcttagggctttatcctttg
gctccgtaaagaatttctttgggagggctccagagtgggtaggattgttctcatggtaagctgtaacaccaacgaaa
caagcctttgtagctgtggaagtccgagggggtggtggtggtggtggtggtgtgagagttagagtggtggaggagag
gggaggagtgaagagaagtttatatttaaagaatagggccttgagaacttttagtagtgagcatgcattattatta
ttgttattgttattattattattattattattattattattatattattattattattatattattgttatgtaatt
acttagctaatgaggttttccaactgtttccaaattaggaaatgtgttgaaagcatagttaagtatataaaagcgt
gttctttctaatatccttagcttttagagcagataatcacaaaatttatcatgataatatagcagacaatttttcct
agttcaaatctcatgccacccttcataaaaaatttccacgtgcttggctggcatgttaggggacgtcttggcataat
taaacaaatagaattgtccctttctaacagcttaagcttttagatgaggcggtcaacaattcaacaatttgcatttg
tttgataagaagatattaaaagaaccttaaaaggtgtcagtatgtgaacaaactcaaggggtagactaactagaagt
caatttaaatttctgcttgtctgtgttttacttcttttgcactatagaaattgcatttccagcattccgaaagctg
cttcctttgcatatagacttcacatttccagcgtttctgataagcgttcttgcttattcctgtccttctacttggtt
gattctcctctcacttagttcactatcttcttgcacgcattttcaaattgttttatcaattctcttgctttcttttc
atctgaccccacaaaatacctcccaaaagcctttctgcttttccgagtctgaaattatctgcttattactgcctttc
aagtattctgatgcgttgactgtttttttcccttgtagtaatgcatggttcgctgtccaatctctatttttgtttttt
gtgaaccactattctttgttgcttctgtttcgtcatcctcagttccccatcttctcagtttgatttcctcatttaa
aaagcgtgtgccccttttcttgtgctaccctctaaaaaatcagttgctgtcatctcgtttgatctgtcatgatccca
gttgatgccacatgtttagttctttacctctggacaacttttacttcctgagaaccacgatttcttttcctgaagaa
attcttagaaattggttatgtaaaggaaattcccagcaatcaccatttggcctctacctggcttgcttttcaactta
ccgacacgtgttcatccccttttaacagatgctgaccattatcttctgcttgttggggcatacttcttacccatggt
gttaaccctgatctttcgtatcacatttttcaactcttaattctcacatgtaaagtgcctatctttgcctctttagt
tgatcttgggttgggctgttaatccaaattctctgggctttgctttgaagtatgataagcggtagctttactacagt
accatattctacattgctacagacgtgaaattatcctgatttgtctttgatgtgatgtctggcaagtgtagattacg
ccacagaggacctgattggagtggattgcatagccatgatgactgttatcttgctcatcaacggttggcaatagtag
acccaacttctggagatcagccactttacaacgaggacaagaccattgttgtcgcggtatggaaatatttattatat
tttttcttagatattaccggtacatggactttggacaatatttgtgcgttttgatcttctatagtacaaacttttct
cgtaggataaatttcctctactttgaatggatcttaacaggaaaatcggaataaacaatttgtgatttcgaaatttt
tagttcttacatatttggaacatatgcggtaaagtaactaggcgattgactaggtgaatacggagaatttcctctac
tgttatcaatatttactcagctcatttgaaagatctctgggtcgtctagcagtacagctatttaggcaacttaacca
aatccccttcccatgtgtttcactttcttgacttattttatatttgacattttgcaatgccgaaaataaattgttt
ttccattttatgacctttaaaatgttgaggtgaagggctaggcggtactttaattgacttatcagcaacaatgtatt
agatacagagcacaaacttgtttgggtgcctaatttggtatttttttgagaacgatggagtaaatggaaatatgaatt
agcaaaatattgaaatagtagatctgaaaaatgaatgactgaatttagaggaggaccttttcttctttccttgctga
agtggttataagagaattatgtgaagaacatgtaagctttagggtagtgttacaccataacagtcatgctttccctc
aactattagtgtagctgatgaatgctttcagaaatgtggctgtttttttgctgcgtattttatgtctttcatcatct
caaaatttattgtgttttaacactgcttggaaggcctagagtcttccgaaaatagtaggttgagaaaacatgagtaa
gcaaatttcttcctgctggcaattaatcgttttatatgaggtgaagccacacaatctaacatggtcttagacataaa
aatattattttgacatagagcagacagaaatcttgggtctagttgctatctcccttcctaataagatgccctctat
cctcattgctatatcccaaaacagattcacactagaatgaataaatctctccttgcagccacatttatattaataag
tagtgtaacaccaaaacatttgtgcttctgcaaagtctgttgaagtggacgattaagtaataaattgtgtgagtttg
actgaagagaaagtaataaattgggtgagcttctcacattttcaggataatgtcaattcatctgattgaactttt
gaaggacatctccttttctaaaagtttttgttcacttcctgaaaatggttgctttcccaaatttattctcctgtatt
ttccttgtgctttttttttttaccaggatgactctggccttccctttttgcaaatagtgacttcattaccttttaaca
aaagaccaaatagcctttgtatgcttgaaatcgaagcagaatttacggctcaatttctctaggagatgtgtagcagt
aacataaaacgtggttaaagcaacttgtaagcactgccactgtccaatttgacatgactctattactatttagagtg -continued

| SEQUENCES |
| --- |
| tcaaatagtgtttcttttgactaccaatttttcaatttctttttttatacctttttctttgactgtgacttatagta<br>tattttatgtagtttcagaatatatattttagtttttaaagaattgatgtctgaaagtacagccaattagatggttt<br>caccctcgtactttaaatcttataagttgtcttaggttaaaggaataatatgcatgattacattgtttggattgata<br>ttcagaagatcaaatgtgccggacaaaagcttgcagaagatataattctgtcattttgttgtttagataaactaccc<br>ttgtcaaatacctaaaactaattcatacttttcaggatccttcttgattggactactctgatcttcttccatatatt<br>gatatcctattctttttgcttttaggttaacggggagatatataaccatagagacttacgggaaaagctgaagtccc<br>accagtttcgaactggcagtgactgtgaagttattgcacatcttgtaagtactttcagaatatatttagataactat<br>acatgacttctcagtttctgtgcgcagaatgatttcaaaataccatgactcaaatttttcatcaaaagcgaaaaagg<br>tggattgtagtaggagaatgagatttttttgtcataatttctttcttatggtacttgaactccgcaatctacctatcg<br>cagtatgaagactatggagaagacttcgttcacatgttggatggaatgttctcctttgtgcttcttgacacccgtga<br>taaaagtttcattgctgctcgggatgcaattggcattacacccctttatatgggatggggtcttgatggtatgtaat<br>tgttccatttcataattttggtatattgtccttttaataaatagcccgtgagctatatgaagttcctttgttgttt<br>ccttgtttttatttgactgatgtatctttgttgttttgcctactattaggggtgtcaatggttcggttcggccggt<br>tattttataaaatttgtaccataccaatttttaggttattctattatgtataaccaaaattagacttttttgaaaccg<br>tcccaatcatgtcggtttctcttcggtatcggtacggttcggttaattttcggtatttttttaatatcatgtaaaatt<br>caccagtagaagtagaattgcaataacatacattcttttataggacttagcaaaactctctagatatttttactgtt<br>taaagggtgatgaattaaaaaaaaagaaaagaaagatggctagaatatagatccatcaactattatacaacagcgta<br>aaagaaatcaaacaaagacaaagaaaatattaatcacacgagttgaaagatataccaaggtaggactcaagaataaa<br>gtctatagaagattaaatattcaaaaagataaatctaaattatatgaaaggaaacatattcaattcattgtagtttg<br>ctactcataatcgctagaatactttgtgtcttgctaataaagatacttgaaataatttagtttaagtagaagtagca<br>taataggttttatgaattagtattttgagtttaattacttgttggcttgtaataattttcataattccaaggctcaa<br>agaaaatttattgcattattatttttaaacttactaaataaatatattttctacatgtaaaatttattcggtatggt<br>tctgtatttttttcggtttatttttataaaataaaaaacctaccctaattatcggtgcggttgtagatttatataaaa<br>acctacggtttcttaaaaagaaagctaaaaatcggttcggtgcggtacggttcggtcggtttagtcgattttcgaat<br>atccattgacacccctacctactataatgctggtctcatgctgttgttacaaacaaatgatgtataatagtgcatag<br>tacatgttttcttgccgctgtagatcaacaatgtaccaagaacatctgtcttagctagttcaacctaatcttcagtt<br>atctatcattccagtgaataacacatatagagttaggccgacattacctaaggccaactatacaacattgtgaggtg<br>cgactaaggaactctgaacactgatcgggagaaaaagcaacttatccgtgtttgttttgaagtactatgaggaggca<br>gcaaccttgctggatttatcacttgacagtaaatgtcaatggttgaggaacatttttaatgaccggaggagaaacag<br>agaagagaagaaataattgattttaaaaaagcagaatagaaaattttgtgaagtcgtatgttaatttcaatgaagag<br>gatcaacaggtgcaatatttgacttggcacctagcatgtagaagtttctggttggggttgagcatggtaggcactgt<br>tgcttttacaactgtcattagagtcggaaacatattgtattcttgagggagcgttgctatggataaaaaaggcctat<br>ctactacttgatatttgggcattcagaactagttgtctaggaggaagaaaaggatttaaaatggtgagtattgtagg<br>ctttctttgccgtccaggatgcctgggctagttccctgaattgggatactggtggaggatttcctgaaattgatcat<br>ggccctgatatgttaggggataagaacattgaaggatcgaaggaaggtgccggcgctaagttttgctagaaatgaac<br>agttccattatggcttttgtcaaagatgggaatggaattggccccaacttctaggcatctccatccatcgtcaggtg<br>aactaaagtaaggttacactggtagaatttttcattatttcatattaagtaaggtgaagccgtcaacaatcattgcg<br>tgagaaggaaccaggaacaaaatctagaagatgtctactaaagtgctaatagataatctgcaaaatttagcacggta<br>aggctagtgtagatctggttcaaattttaaattggtccaaaatgcgttaataaatgtcgggcctcgttttggtcccc<br>cgaaaggttgctaaataaagacttgacaaagaaacaggtgaaggagaagcccaaacatttgaacaaactacacctag<br>cctaaacaaagtgattgtttgcgaggaggaaaagcgagcatgcggagagagcctcaaacacaaaaaatggcctagtc<br>ttgtaatgagtctagccaaatcatgtaagctccgactttcaagagagatcaacagaaaacttcgtcaatccggataa<br>atcaagaaaattatgataatggaaaggaggctggacattctactgccgacgcaacccctggttttggagtcagtgag<br>acaagtggaactaaagaagaatatggatcaaaagagtttatccagttgacacctgatagactcactacatcagtttt<br>cagttcaagaacatttcaattcttgctgataaagatagttgccgataaagataggcaaactgttacctaccaatcaa<br>aggaggttgtttcaattgagttagaggtatcaaaggaggagccagtatatatagagcaagttttgatgaagggagtt<br>gcctctatttgagaccaccaggtactcaagtgcttcccgtagttcctaggcattttatgatggatatgatagagaaa<br>tgtcttattgacaagaatatactagggctacagggataatagggttgggaaggtgaggacttctttggttgctgtca<br>ggaacttggaaacaaagggagaaaggggttggaatcaaaggttttgatttcgtttttgatttataaggaaataatgg<br>gtagtggatggagtcgaggataggaaagaggtttaccagttgcaccattgaatatgtaattagagacactatcctct<br>tgttagggaacacgactatcacaagcacgtaagggtgagtgaaagctccgacatggacgtggtttattcgggtatgt<br>tggcacgaagccttcgtgtctaggtttggtgttgggttaagtgcaactccttaggaaggcaaataaacttgggacag<br>atttgatagttgtcggaagttgcacaatgatgatatttctttatccaaacgctacgaatgattgcacatatagtaa<br>ctagagttatttctcatttgagcttttatatgtaagaatcaaataaaatgattgatgaaatgcatgaaagctcaaat<br>gagaaataactagttgtgagaatgcacgggggaaaaatatattatattgattaaagtgttgtacaaccctatttaga<br>tacagtaattacataataataggtatctacttcccgatgtgggacactagacatgactaactacttaacaatccccc<br>tcaagccggtgcatataaatcatatgtatcgagcttgttacagatgtaactaatacgagaaccagtaagagacttag<br>tgaaaatatctgctagctaatcattcgactttacaaactttgtaacaatatctcttgagagtatttttctctaaca<br>aagtgacagtcgatctcaatgtgtttagtcctttcatagaacaccggatttgacgcaatatgaagagcagcttgatt<br>atcacacaccagttccatcttgctgatttctccgaacttcaactccttgagcaactgcttgatccaaactagaatca<br>cacgttgccacaaccatggcccgatattcggcttcggcgctagatcgagcaactacattctgtttcttgctcttcca<br>agagactaaattacctcctactagaacacaatatccagacgtagaacgtcaatcagcaggtaatcctgcccaatcag<br>catctgtgtacccaacaatctgctcgtggcctcgatcctcaaatcgtaaccctttgcctggagctgactttatatac<br>cgaagaatgcgaacaactgcatcccagtgactatcacagggagaaaccataaactaacttgcaacactcaccggaaa<br>agaaatattaggtctagtcactgtgtggtaatttaatttgccaaccaacctcctctatctcgtaggatctctaagat<br>gctccccctgtccatgcagaagcttagcattcggatccatagaagtgtcaactggtctacaacccatcattccagtc<br>tcctcaagaatgtctaaggcatatttccgctgtgaaataacaatacctgagctagactgagcgacctcaatacctag<br>aaaatacttcaatctgcccagatccttagtctggaagtgctgaaagagatgctgcttcagattagtaataccatctt<br>gatcattgccaataataataatatcatcaacataccactcaactttggcatttctatctcaatttggctggaatatc<br>ctggacaatgcccaataacactgcgtctcttctcagtagctggaacaatggaggggcaaatattaaacagaagaaat<br>ggtggaaagtagttcctgcttgtatctggtgggtcatgtggaaggaaaagaatgcagagtttttgaagataggccta<br>gctcttagcctcttaccagaaaattaagcttaattgtttttttgttatttcatttttggtgcaaagagagctataggg<br>aggatgtacattctttactagatttgctagaagaaatgtaatcgattagaataggcaaggcagttgcagatcttttg<br>gggtctgattgtggcttacactatctcctgtaaatatttttaatcttttatataatttgttaccattctaaaaaaaa<br>acataaaccaccagataaatatacagattaggagcagaatgtcgataaagcacagagtgatccgcttcactacgagt<br>catgccgaactcctgaataattatgctgaacttaccaaaccaagctcgagggaactgtttcaaaccatatagtgacc<br>tgcgcaatcggcatacaagaccactagacttcccttaagcaacaaaaccaggtgattgctccatataaatttcttcc |

-continued

| SEQUENCES |
| --- |
| tcaagatcaccgtggaggaaagcattcttagtgtctaactgataaagaggtcattgacgtacaacaaccatgaacaa<br>gaagagacaaccgatgctactttagccacgggagagagtgtcactataatcaagcccaaaaatctgagtgtatcctt<br>ttgcaacaagacgagccttaagacgatcaacttggccatccgggctgactttgactgcataaacccaacgataacca<br>acaatagacttacttgaaggaagaggaacaagcttccaagtgccactcacatgtaaagcagacatctcctcaatcat<br>agtttgtcgccatcctggatgagatagtgcctcacctgtagactttgggatagaaacaattgacaaagatgatataa<br>aagcataatgaggtgatgacagacgatgataacttaaatcgacataatgaggattaagattaagagtggatcataca<br>cctttccgaagtgcaatcggtgtactaggaagagacaagtccgcagtaggagcagggtcaagtgtaggatgtgaatc<br>agttgggcctgatgctgggtgcggacgacgatgatatgtcaagagtggtgttccggtggcggggaatctaggaggag<br>ccacactagactccccaacggttggaatgggtaagacttatgtggcggaaggtgaaggaggagctatagtaagctct<br>ttaaaggtcggtataggtaagacctcagatatatcaaggtggtcagaagaggtaaagaaaggtttagactcaaaaaa<br>tgtgacgtcagatgacataaagtaattacgaaaatcaagtgagtaacaacgatatccctttttgaacacgagaataac<br>caaggaagacatacttgagagtacgaggagctaacttatctttcctaggggctaaattatgaacgaaacaagagctc<br>cccaaaacacgaggaggaacagagtataagggtgactgggaaacaatactgcatacggaatctgattctggatggga<br>gatgaaggcattcgattaaccaaataacaagctgtgagaactgtatcgcctaaaaaacgcaacggaacatgagattc<br>aaagagaagtgtgcgagcagtttcaatgatgtgcctattctttctctctgcaaccccattttgctgaggggtataag<br>gacaagaggtctgatgaataattccttgagaagtcataaagtgctaaaattgagaggataactattctaaggcatta<br>tcactgcgaaaagtgcgaatagaaacaccaaattgattttttaatttcatcacaaaaattctggaatatagaaaacaa<br>ctcagaacgatctttcattaagaaaatccaagtacatcttgaatgatcatcaatgaaactatcaaactaacgaaatc<br>ccaaggttgagttgactctactatgaccctatatatcagaatgaactaaagaaaaaacagactatgcatgactctca<br>atactacgaggaaaggaggctcaggtatgtttcccgagctgacatgactcacactctaatgtagataaactaggcac<br>tatcttctgaagcttggatgtcctaaacatctgtgaattaggtccggaggatctgtaactagacatgccttggagga<br>attgagtgggttaaggtagtaaaggccttctaattcaagtcctgttccaatcgtctgtccgtactgcggtcctgcat<br>aataaaagaatcattaataaaatatataccacaatggagggcacaagtcaaacgactaacagatgcaagattaaaag<br>gacaaccagggacataaagaacggaatctagagtgacagagggtaggggattcgcttgtccaactccttttgcttca<br>gtttgagacccgttggctaaagtaacagtggaaagagactgtgaatacgcaatatttgacaaaagtgatttattacc<br>agagatatgatcagaagcggttgagtccacaacccattgtccaagagtactagactgggaaacacaagcaaaagaat<br>taccagcaacaaaagcatcagtctgagcaacagaggctacttgtggagatgtctgcttacttgctcgatactgaagg<br>aacttattatactccccttccgataaagaaaatacccggttacctatagtctcggtctgagcaacataagcattttt<br>gggtggacgaccatgtaaagaatagcacacgtcacgagtgtgtccaagtttatgacaataagagcacttgggtctag<br>atcttccaaaacgacctcctcctcgtctattctccatagtttgagatgcccgattgttcacttactgggatacgaga<br>acagatgagtcaggtctctgtgatgagctcactgggtgacttggtgctgcagcaaggcgaagtaatcgagagaataa<br>ttcatcaactgtggggacagtcggactagccaaaatctggtcacgtactgaatcaaggtcattagggagtccatcaa<br>gtgtaagaactagaaacatcttctgtcgttgctcttgttgcttttttaatactagcagaaactggcatcaacgtctca<br>aattcttccatgattgcctgtacttgtcccctagtaagtagacatatccaattcctgtttcttcaagcttgtcattc<br>gcgatattacatcatagaaacgagatatgtcattagtgtataaattacgagccttttcccaaactaaataacatgtc<br>tggaatggacggaacaagggcatcaacttggaatcaatagatcgccacaggatactacataactgagcatcgacctt<br>cttcaaaagtgttttggccttttcatcaccttcgctagcctttttttgttaaatgatcttgaactccttgacctttac<br>aacacaactcgacagacgaagcccaagctaagtagtttgaacttctcattaaaggttctgaggtaatcataatagca<br>gaacttccagaactcgtgtttttagacccaaatacatccactcccaaagacattattggattgaaaagagatctagc<br>aaattagcaccaaataaaacaaagaatcaactgtggttgcccaaaaactgccggaaaactactgtagttgccggaaa<br>attttcaaagtgctcggaatcaaaaaataaaaatatgggcaggctcggaatggtagagcgatcagactaacctaaag<br>gagtttttctgaaaaaattgacggaacgggctccatgcgctggtgcgtggagtagatctcgccggagaagactgtct<br>ccgatcggcgcgtggcggtgcgtgaggcggcttatgacggaggtgttcgctggggtttggtcgccggaagttggggg<br>accttgtggtggtgttggttttttgcacaacaccgatggaattggttttgacgaaaaatagccctaaaaggtcaccgg<br>aattgaagcacggcgacggctggtttttttttttccccggatgttttctcactgccgctctgataccatgtgagaatg<br>cacgggagaaaaatatattatattgattaaagtgttgtacaaccctatttatatacagtaattacataataataggt<br>atctacttcccgatgtgggacactaaacatgactaactacttaacactagtaacctcatggttctcatcctacttca<br>ttgaccacttggccacatccttgggtgcctgcactgtagttgtagctgtaatgaagatagtttttttttcttttctgg<br>atactcttatattgtgacaatttttctctatttgctgttaatggatgaggttatgtgactctccggtggtgagaatg<br>ttaatgaacatcaagctcacatgtcatttcattttctgattgatcttgctcttcactctttacgagtttaatgtgtt<br>agtccttccaagttctgtccatctatctttctggtgtgcttaacccatgtatattggaccacactttgtattcatgc<br>tgattgcaacaaagcctgactgatcctgaactcctccttttatgccttaggtagaaattttgtgtgtttagtgttaca<br>tgtttcgcttcaaaggaaaaagggagaaacttaaggtagaatcctgctccttgacctttggatccttgcacattgaa<br>gtggacagacatgtttgctttgctttgatgagttgttttagtagtcggtctaaacaactgctgatgtattctgcttt<br>attgtaagtgtctataatttttatctttccacaatttgctttcagctctttctgcatgtagagaaaataacagaagc<br>ttctatttgatcatgtaatattgactgcgcaagttcagttttaaacaactttggctatgcatatgcaagcaatgacc<br>tgaaataaatattatttttttatgcagggtctgtatggtttcttcagagatgaaagccttaagtgatgactgtgaac<br>gatttgttagtttccttcccggtcacatttattcaagcaaaaatggtatgcccatacgaagctcatttctgagcttg<br>tgcttcatttatgttgatagttgatcatgtttcctatacgatcagcgtacttttgctatttatttcagatttacttt<br>aggaccctgtcggaaacagtcttgaaacccttattgatggtgtaattgttatctcttgatcaaccaaaggagtaatt<br>acatgtaattattacaaatttgcaataaaataacttttaggataaccagtggagcttaatgaatcttttaggatatt<br>tgggatgctagagtgatgtacttttgataatgtcggttaatataaaatcctctgactttgtactgatgtactggctg<br>agcagattttatattactttctagtccctctgcaaataaaaaaaattgtgagactgcaatataacaccatttttttaat<br>gcatttacaatgtttaaacttgatgtagcagtgaagaacatgtcgaccttaaacagaggttctatttgtcctagata<br>aaggaacatcagcgtaatgaaacattacaggagagaagctctattgagtttttgttaatctagagggagcccgtaaa<br>tagaacaccaattcatctgttatatgacttctttttcatttggaacgttttaaaagtttgacaacatttttttgatc<br>tccgtacactaaactttttgatgtattaaactaactatttccactactttaatattttcttccttaaacaactcatg<br>ttagcatcttaaactgtgtgtgttcaataccctcataaaaaattaaacgagtatttttttatatttgcttatgccct<br>tggagattgggatggggaagttcatcatttgaggtgaaaggtaaattcttttggatggacaaaaagtgaacctcgtc<br>tttggcatggagggactatttaaatcgtcatcattaccaaagtcatcctttcaaatgtttactttcaagaactattc<br>atgctatttctcaagtatattatgggtgcaggaggactcagaagatggtacaacccaccatggtactcagaaaccat<br>tccttctactccatatgatcaccttgtcttacggaaagcttttgagaaggtcattctattttggatgtcgcttgttt<br>ctgagttgtacataatatttaggtgccactttgttatattttgaacttcatcaaaagcctttggtttttttgaggaca<br>catatccccttgactgactgggcgctgaatttccttgatgtattgtgcttattttgattgtcctcttctttgtaata<br>ctcttgcctataaataaaccttctttatcaaaagaaaatgataaaatgttaataacactttgtgatatatgttgaag<br>gggagtcttggcataactggtaaagttgctgccatgtgaccaggaggtcacgggttcaagccgtggaaacagcctct<br>tgcagaaatgtagggtaaggctgcatacaatcgacccttgtggtccgacccttccccggaccccgcgcataacggga |

-continued

SEQUENCES gcttagtgcaccgggctgtcctttttttttgcatagactttacatgatattttatttcaatctttatcaattctttt
ttaccttcacatgcaaattatactaccgtatgtgaaatatgcaatagtttttcccgcaattttcatctttcatgtac
ctctctctactatccttgtattactactgatttggtgcattagatgttaattttattcccaacctttactttatgca
ggctgtagtcaagcgacttatgacggatgtaccatttggtgtgcttctctcaggtggactagattcttcacttgttg
ctgcagtggccaaccgttatttggctgatactgaagctgcgcgacaatggggatcacagttgcatacctttgcgta
ggcttgaaggtggtgatgctccctttgtaaacttgctctgattagggaattgctagctgtatcatcccaattcaca
tggaagttctagaccattattgctgtttcttttccatatatagggattttctgaaaatagtaaaaaggaaatggaat
ttctcattattaaagataccaaatgccttttgggaaatgatcttacagttgaatctgaaatttccttttgacattg
tgattaattctgatatgaatttggtccatcctggctttccttctcttgattgtagatttttttctctttttgcaat
tatatgcctttgtatttcatatctcttattatgctattattttattatgcatttttatggtactaatatatcggctc
ctgttgctttttttgagccgagatttgtttatttctgctatcacgtcctcctgaaaaagtgctactatcttgtatt
catgcgggagtttgaaatttgcaagtgtataactttacaaaatgattcgaactgatcacagttcattgctaataaac
ttttataaaaagcaggtattgttgtgatataatgtgacacttaaataaatttaaacctacatcctttcgaaatctct
aatagcttcactaatatttcttgtgctaaattcttccaacacctcttatcgatgccaaatttggcagaccttagtgc
aattgaaagtgtttagtgttctttatgcagtaggtatgttattgtccaaaatgacagaaataaagttagagatttgt
tgaaaagccacttggtgtgattgagcagttcggagatgagtgatttatccatctttttatacttttagtgttttgtt
ttcttttatattgtttctcttttgcttttgtcattgtaattaaggttgtcttttgtttgactttagggttctcctg
atctgaaagctgccagagaggtggcagactaccttggaactcgtcaccatgagtttcactttactgtgcaggtaact
ttcttcataaagacatcctatgctgattttccttataggagtataactgcttaagtcaaattggctatctacttctt
tctattgctacatcaggaaggaattgatgcactagatgaagtcatttatcatgttgaaacatatgatgtgaccacta
tcagagccagtacaccaatgtttctcatgtctcggaagataaagtccttgggtgtgaaaatggttctatctggtgaa
ggttctgatgaaattttggcggttatttatatttccacaaggcacccaacaantttacacaaaaatgacacaagtt
atgcagaaaaaatagtcctcaatgtcatgggagaccagggttcaaatctgaggttaaaaaaaatactaggtgaactc
ttctaatccgtttaagccttggtagatagagttaactagtatatgagctagttagagctagcaggtacctggtagat
tagtgcaggtgcacacgagctgactcaaaaccaccattattaaaaaataagaaagttttcaatgttgttccaccgtg
aattcatgatgtgccgactttcctgtgtttatctctggatagatgaagagtgtttttggatcttgattaattctgtt
tggcccctttgaggttctgcaagctatttctagactcaaacttgctgcgatctatgttaggtctagagaatatctgc
caaataaaacaatggaaggtacactcaagtattttatctccatattacaagtcagtgttagttgaatgggtctgata
tatgggacagaaaatggcttcatacccataacctcattaaaatgttgctgatgtgctgatctcatctgtacatctag
tataatcctaattacaaattaatgcatctctttgcggtgactatagtatgctgaagaacttttcttgaaacattgca
gatcagacctgatctcggaagaatagaaaagtgggttctacgcaatgcttttgacgatgatcagaatccttatctgc
caaaggtttgtttgttttcttgtatcaggtccaaaatcaaaatctttgtttattcatttgcataaacaggcagtaga
ctcccaatacattgtgtacacttatgcacaaatgtatgagatgtgtattatatgtgtcacatataagggtatttcca
catggtgtttattgatctagagaaagcgtacgacagggttcctagggaggtcctatggagatgcctagaggttaaag
gggtcccggttgactgcattagggtgattaaagacatgtatgatggagctaagactcgaattaggacagtaggaggc
aactccgaccattttccggttgttacggggttgcatcaagggtctgcgttcaaccctttcctatttgccttggtgat
ggatgctataaccgcatcatattcaaggggaggtgccatggtgcatgttatttgctgatgacatagtcctaattgac
gagacacgacgcggcgtcaacgagaggctagaggtttggagacatgcccttgagtctaaaggtttcaggctgagcag
gacgaagacggaatatctcgagtgcaannnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnatcgtatatgggtagggtg
gatgaagtggaggttagcaacgggagtcttgtgtgacaagaaagtgtcaccgttactaantctcgagtgcaactttg
gggccgagccgatggaagcatgagtggaagtgaggctcgactcacaagtcatccctaagaggggtagtttcaagtac
cttgggtcagttattcaggggaccggggagatcgacgaggatgtcacacatcgtataggggtggggtggatgaagtg
gnnnnnnnnnnnnnnnnnnnnnnnnnnnnnnnnnnnnnnnnnnnnnnnnnnnnnnnnnnnnnnnnnnnnnnnnnata
ggggtagggtggatgaagtggaggttagcaacgggagtcttgtgtgacaagaaagtgtcaccgttactaaaggtaa
gttttacagagcagtggttaggcctgctatgttgcatgggaccgagtgttggccggttaaaaattcacacatctaga
agatgaaagtagcagagatgaggatgctgaggtggatgtgcgggcatacaaggatggacaagattaggaatgaagtt
attcgagagaaggtnttgagccgagggtctcctggaaacagcctctctgcccctcggggtaggggtaaggtctgcgt
acatactaccctccccagaccccattggtgggattatactgggatgttgttgttgttgttgttgttgttgtacatat
aagggtattatatgtacacactcctcccacctttcacttatatattcacgtaaaacacatgcatgtgtaaaacctat
atatgtgtgtgtgatatatataataaaatgatgtttgaaaagacattatgatcaagtagttgatcttcatctgcttt
ccgtttttagcatatcttgtataggcagaaggaacagttcagtgatggagttggctacagttggattgatggtttga
aggatcacgcaagcagactggtgagctttttagttgttttctcttccctcctcttccattctttatcccttcctttg
tggttttgttgaacacatctcgtatatttggtccaggtttctgattctatgttagcgaatgcaagtttcgtttaccc
gcataacacacccacgacaaaggaaggatactactatagaactatttttgagcgatatttccccaaggtgggtctta
gatagtcttcttttccttgttattcatgttcaattttgatattttgtcccaaacaatgtttcttttttcttccttc
tgttaacaaggtcgcttctatcttcatatttgttgataaaggtaatcacattgataactattatttggagcagaatg
ctgcgagggaaacagttccaggtggtccaagtgtggcatgcagcactgcaaaagcagtagaatgggacgcagcttgg
tccaagaatctagatccatctggacgagctgcactcggtgttcatgcagctgcttatgaggatgcatcagaggttaa
aaccacagtcgcaacagataccccctcagaaacttgaagttgataaagctgcagtagctgtttga SEQ ID NO: 10 - NtASN3-S, deduced amino acid sequence
MCGILAVFGCIDNSQAKRSRIIELSRRLRHRGPDWSGLHSHDDCYLAHQRLAIVDPTSGDQPLYNEDKTIVVAVNGE
IYNHRDLREKLKSHQFRTGSDCEVIAHLYEDYGEDFVHMLDGMFSFVLLDTRDKSFIAARDAIGITPLYMGWGLDGS
VWFSSEMKALSDDCERFVSFLPGHIYSSKNGGLRRWYNPPWYSETIPSTPYDHLVLRKAFEKAVVKRLMTDVPFGVL
LSGGLDSSLVAAVANRYLADTEAARQWGSQLHTFCVGLKGSPDLKAAREVADYLGTRHHEFHFTVQEGIDALDEVIY
HVETYDVTTIRASTPMFLMSRKIKSLGVKMVLSGEGSDEIFGGYLYFHKAPNKEEFHQETCRKIKALHLYDCLRANK
STSAWGVEARVPFLDKEFVNVAMNMDPESKMIRPDLGRIEKWVLRNAFDDDQNPYLPKHILYRQKEQFSDGVGYSWI
DGLKDHASRLVSDSMLANASFVYPHNTPTTKEGYYYRTIFERYFPKNAARETVPGGPSVACSTAKAVEWDAAWSKNL
DPSGRAALGVHAAAYEDASEVKTTVATDTPQKLEVDKAAVAV SEQ ID NO: 11 - NtASN3-T, genomic DNA sequence
atgtgtggaatactagcagttttcggttgcattgataattctcaggccaagcgttcccgaatcatcgaactttctag
aaggtagaatttttttaaaaaaaa
aattgcattccaatttttctacagcattcttattctttggggtgacaatggtatgcatgt
gttttggatttgctattcgtggacttgttcgctttctcgtggtcttcgatttgtttttgt
taatttataatcagtgtttttatatggatttctttttttgaatctctcaaatatatgacat -continued

| SEQUENCES |
| --- |
| ttgatttccacgagaaaatttggcatttttatggttcttatgatatgcggttaacccttc |
| gccttgcatcgcttcagcgctttaaaagacgaaatgatggctattagtaatactgctaga |
| gtggttattgaattacattaaataacagattgctagtagatcaaattcagaatgacagtg |
| aaatatctctggaaacttgaatccccgttcaattcgctggtaaaacctggcaaaaaaata |
| gctttatctcaaaggagagtatgtcactgtgaaattggtggtatgtgttgtttaagcttt |
| aaggcatgatatgctgctcttaggtgatgtcaggatgataataccatccttttcacacta |
| gactcagctttgaagcactttcatctcagttaatcggtggaggaaaatctagtttgcttt |
| gggcataatataccaaatgtcttcctttttgttttctagtgttgtttctcaagaattgaaa |
| aaccaacctacaatatagtgatataattaactagttagctcttcctgtttttctgaaaat |
| ttccaataattgagaagcgtttacaggtcaattagtaaagggagaacggaacattttttt |
| cctctaaagaacttctcttttttccatacagaatgactttctatacaaggcctaagtctgc |
| tttagtgtctgcgattaagcatcttctgggaaacttcacacttgaaagaagtagaactag |
| gagggggcaggtctagcaagataattgcttcagtcatttctcataaaaaaacattgtttc |
| attcattatgtgcattcatatagagttggttaagctgctaagctgagctaatagtatgat |
| agctatgaatctcgacaaagtaggttgcttcttagggctttattctttggctccgtaaag |
| aatttcttttggaagggcttcagagtgggtaggactgttctgatgataagctgtaacacc |
| aacgaaacaagcctttgtagctgtggaagtccgagggggtggtggtggtggtggtggtgt |
| gagagttagagtggtggaggagaggggaggagtgaagagaagtttatattttaaagaata |
| gggccttgagaacttttagtagtgagcngggggggggggggggcagaggggaggagtgaa |
| gagaagtatatattttaaagaatagggccttgagaacttatagtagtaagcatgcattat |
| tattattgttgttattattattattattattatttttattattatgtaagatgtaattac |
| ttagctaatgaggtttttccaactatttccaaattgtgaaatgtgttgaaagcataatta |
| agtatataaaagcgtgttctttctaatatctttagctttaagaggagataatcacaaaat |
| ttatcttgataatatagcagacaattttttcctagttcaaatctcacgtcacccttcataa |
| aaaatttccacgtgcttggcttgcatgttaggggacgtcttgacataattaaacaaatat |
| aattgtccctctctaacagcttaagcttttagatgaggcggtcaacaattcaacaatttg |
| catttgtttgataagaagttatattaaaagaacacttaaaaggtgtcagtatgtgcacaa |
| actcaaggtgtagactaactagaagtcaattcaaattttctgcttgttctctctgtttta |
| cttcttttgcactatagaaattgcatttccagcattcccgaaagctgcttcctttgcata |
| tagacatcacatttccagcgtgtctgataagcgttcttgcttattcctgtccctctactt |
| ggttgatttcctctcacttagttcactgtcttcttgcacgcattatcaaattgtgttct |
| caattctcttgccttcttttcatctgaccccacaaaatacctcccaaaaagcctttagtt |
| tctgcttttccgagtctgaaattatctgcttattactgcctttcaagtattctgatacgt |
| tgaccattgttttccccagtagtaatgcattgttctctgtccaatctctatttttttttt |
| tgtgaaccactattctttgttgcttctgtttcgtcatcctcagttccccatcttctcaat |
| ttgattttcctcatttaaaaagcgtgtgccccttttcttgtgctaccctctcaaaaatca |
| gttgctgtcatctcgtttgatctgtcatgaacccagttgatgccacatgtttagttcttt |
| acctctggacaacttttacttcctgagaaccacaattccctttccttaagaaattcttag |
| aaattggttatgtaaactgtaaagggaaaatttcccagcaatcaccatttggcctctacg |
| tggcttgcttttcaacttaccgacacgtgttcatccccttttaacaaatgctgaccatta |
| tcttctgcttgttggggcatgcttcttacccatggtgttaaccctgatctttcgtatcac |
| atttttcaactcttaattctcatcttataaagtgcatatccttgcctctttagttgatct |
| tgggttgggctgttaatccaaattccatgggctttgctttgaagtatgataagcattagc |
| tttactacagtagcatattctacgttgctacagacatgaaattttcctgatttgtctttg |
| atgtgatgtctggcaagtgtagattacgccacagaggacctgactggagtggattgcata |
| gccatgatgactgttatcttgctcatcaacggttggcaatagtagacccaacttctggag |
| atcagccactttacaatgaggacaagaccattgttgtcgcggtagggaaatatttattat |
| atcatttcttagatagttaagtattttaccagtacatggactttggacaatatttgtgcg |
| ttttgatcttctatagcacaaactttttctcgtaggataaatttcctctactttgagtgaa |
| tcttaacaggaaaatcggaataaacaatttgtgatttcgaaatttttagttcttacatat |
| ttgaaacatgtgcggtgaagtaactaggcgcttgactaggtgaatacggagaatttcctc |
| tactgttatcgatattttctcagttcatttgaaagatctctgggtcgtctagcagtacaa |
| ctatttaggcaacttaatcaaatccccttcccatgagtttcactttcttgacttgtttta |
| tattttgacattttgcaatgccgaaaataaattgtttttccattttatgacctttaaaat |
| gttgaggtgaagggctaggcggtactttaatcgacttatcggcaacaatgtattagatac |
| agagcacaaacttgtttgggtgcctaaattgatatttttgaaaagtcgatggagtaaatg |
| gaaatatggattagcaaaaatattgaaatagtagatctaaacaatggatgactgaattta |
| gaggaggaccttttcttctttccttgttgaagtggttataagagaattattggaagaaaa |
| tgtaagctttagggtagtgttgcaccataacagtcatgctttccctcaattattagtgta |
| gctgatgaatgcttttggaaaggtggctgatttttttgctgcgtattttatgtctttcatc |
| atctcaaaatttgttgtgttttaacagtgcttggaaggcctagagtcttctgaaaaaagt |
| aggctgagaaaacatgagtaagcaaatttcttcctgctggcaattaatctttgtatatga |
| ggtgaagccacataatctaacatggtattagacatataaatattatttttgacatagagc |
| agacagaaatcttgggtctagttgctatctcccttcctaataagatgccctcattgctat |
| atcccaaaacagattcaccctagaacgaataaatctctccttgcagccacatatatatta |
| ataagtagtgtaacactaaaacatttgtgcttctgcaaagtctgttgaagtgggcgatta |
| agtaataaattgtgtgagtttgactgaagagaaagtaataaattgtgtgagcttctcaca |
| ttttcatgataatgtcaattcatctgattgaactttttgaaggacatctccttttctaaa |
| agtttttgttcacttcctgaaaatggttgctttcccaaatgtattctcctgtattttcct |
| tgtgctttatgttgaccaggatgactctggccttcccttttttcaaatggtgacttcatta |
| ccttttaacaaaagatcaaatagcctttgtatgcttgaaatcgaagcagaatttagggct |
| caatttctctaggagatgtgtagcagtaacataacacgtggttaaagcaacttttaagca |
| ctgccactgtcaaatttgatatgacgctattactatttagagtgtcaaatagtatttctt |
| ttgactaccaattttttcaatatctttttttatacctttttttctttgactgtgacttatagt |
| atattttatgtagtttcagaatatatattttagtttttaaagaattgatgtctgaaagta |
| cagccaattagatggtttcacccttgtacttcaaatcttataagttgtttaggttaaagg |
| aataatatgcatgattacattgtttggattgaaattcagaagatcaaatgtgcaggcaaa |

-continued

| SEQUENCES |
|---|
| aagcttgcggaagatataattctgtcattttgttgtttagattaacttcccctgtcaaat<br>agctaaaactaattcatactttctcaggatccttcttgattggactactctgatcttctt<br>ccatatattgatatatcatattccttttgcttttaggttaacggggagatatataaccat<br>agagaattacgggaaaagctgaagtcccaccagtttcgaactggcagtgactgtgaagtt<br>attgcacatcttgtaagtactttcagaatatattcaaataaatatacatgacttctcagt<br>ttctgtgcgaagaatgatttcaaaataccatgactcaaatttctcatcaaaagagaaaaa<br>ggtggattgtagtaagagaatgagatttttgtcataatttctttcttatggtatttgaa<br>ctccacgatctacctatcgcagtatgaagactttggagaagacttcgttcacatgttgga<br>tggaatgttctcctttgtgcttcttaacacccgtgataaaagtttcattgctgctcggga<br>tgcaattggcattacgcccctttatatgggatggggtcttgatggtatgtaatttttcca<br>tttcataatttttggtatattgcccttttaataaatagcctgtgagttatgtgaagttcc<br>tttgttgtttccttgtttttttatttgcctgatgcatctttgttgttttgcctactataat<br>gctggtttcatgctgttgttacaaacaaatgatgtataatagtgaacagtacatgttttc<br>ttgccgctgtagatcaacaatgtaccaagaacatctgtcttaagctagttcaacctaatc<br>ttcagttatctatcattccagcgaataacacatgtagagttaaccggacattacctaagg<br>ccagctatacaacattgtgaggtgtgactaaggaactctgaacactgtttggagaaatgg<br>aaagcaacatatccgtgtttgttttgaagtactataaggaggcagcaaccttgctggatt<br>tatcacttgacagcaaatgtcaatggttgaggaacatttttttatggctggaggagaaaca<br>gagaagagaaaaaataattgattttaaaaaacagaggagaaaattttgtgaagtcgtatg<br>ttaatttcaatggctggaggtgcaatatttgacttggcaactagcgtgtagaagtttctg<br>gttggggttgagcatggaagacactgttgcttttacaactgtcattagagtcggaaacat<br>attgtattcttgagggagcgttgcaatggataaaaaagtcctacctactacttgatattt<br>gggcattcagaactggttgtctaaagctgagaaggaagaaaaggatttaaaatggtgagt<br>attgtaggctttcttttctgtccagggtgcctggactagttccctgaattgggatactgg<br>tggaggatttcctgaaattgatcatggccaaagagatatgtcaggggataagaacattga<br>aggatcaaaggaaggtgctgcgctaagttttgctagaaatgaacagttccactatggctt<br>ttgtcaaagatgggaattgaattggccccaacttctgggcatctccatccatcgtcaggt<br>gaacaaaagtaaggttacaatggtagaattttcattatttcaaacaagtaaggtgaagt<br>cgtcagcaatcattgcctgagaaggaaccaggaacaaaatctagaagatgtctgctaaag<br>tgctaatagataatctgccaaatttagcacggtaaggctagtgcagatctggttcaaatt<br>ttaaattggtccaaaatgctttaataaatgtcggacctcgttttggtcccccaaaaggtt<br>gctatataaagacttgacaaagaaacaggtgaaggagaagcccaaacaattgaacaaact<br>acacctagcctaaagaaagtggttgatagtttggtcggaggaggaagagcgagcctgcgg<br>agagagcctcaaacataaaaaatgacctagtcttgtaatgagtctggccaaatcaagtaa<br>gctctgactttcaagagagatcaacagaaaacttcgtcagtctagataaatcaagaaaat<br>tatgataatgaaaaggaggctggacattctactgccgaccaaccctggttttggtgtcag<br>tgagacaagtggaactaaagaagaatatggatcaaaagagtttatccggttgacacctga<br>taaactcactacatcagttttcagttcaaaaacatttcaattcttgctgataaagacagg<br>caaactgtcacctaccaatcaaaggaggttgtttcaattgagttagaggtatcaaaggag<br>gcggcagtatatatggagcaagttttgatgaagggagttgcttctattggagaccaccag<br>gtactcaagtgcttcccgtagttcctaggcattttataattgatatgacagagaaatgtc<br>ttattgacaagaatagactaggactacagggataatagtgttgggaaggtgaggacttct<br>ttggttgctgtcaggaacttggaaacaaagggagaaaggggttggaatcaaaggttttga<br>tttcattttgatttatgaggaaataatgggtagtggatggagtcgaggatgggaaagag<br>gtttaccaattgcaccattgaatatgtaattagagacactatcctcttatttgggaacac<br>gactagggtgagggaacgctccgacagggatgtggtttattcgggtatgttggcacgaag<br>cttttgtgtctaggtttggtgttggcttaagtgcaacaccttaggaagacaaacaaactt<br>aggacagatttgatagttgtcggaaattgcacagtgatgatattttcttcttccaaacgt<br>tgggaatgattgcacatgtagtaactagagttatttctcatttaagcttttatatgtaag<br>aatcaaataaaataattgatgaaatgcatgaaagcaactgtcttacgcctgaatgctttt<br>aaaaggcatgctttacaaagtttttggtacatctatctgacatgacacactaacattcac<br>tcttatatgtgtacatatttaactaagtccaagcctaactatctaactggagatatcaaa<br>gttcttagctctttaaagctttcttaactttaggaagatcctgcagtgttgtttttttat<br>aaccgtggtatccaggctagcttgcacacatctcgactaattccaccgggtgcttgctat<br>ctcccaccaacacagattacctggtaactcatgggaagaaatcacctattgttttgagtc<br>tgctggcatttgaagttttggactactaacctcatggttctcatcccacttcattgacca<br>cttggccacatccttgggtgcctgcactgtagctgtaacgaagatagtttttttttccgg<br>gatactcttatattgtgataatttttttgtattcgctgttaatggatgaggttatgtgac<br>tctccggtggtgagagtgttaatgaacatcaagctcatatgtcatttcattttctgattg<br>atcttgctcttcactctttacgagtttaatgtgttagtccttcccagtttttttttaagag<br>cgagaagcgcaaaaaagcgacaagggctcgcctcgcttcaaaagcgaagcgcaaagcgaa<br>gcgcacactttattaaagtgaagcgcaattcttaaaaaacataatgtaaaccttgcaaag<br>acacaatataaaattataaataatcaaaaagttcaaattgtcaaaatcaaagctactaaa<br>ttactagaatcaacctcttattcttctactcttcttgttcttcttcaagattgtcaaaat<br>cttgaattcctctattatcttcatattgctcgtcatcttcctcctcccccctcctcttcct<br>cttcatgatcactttcatcttcatcaattagggatagggatcgacttgtagtagccacac<br>tttttcccttcctaatcgagcttgaacttgaagtattccccccttaaaccataaggattct<br>ccccaactccactagcaaccgcaacatcaccccaagtgaaattagaatcgccttcaaata<br>cttcttcatcttcacaattttcggggactccggttagccactcattagcctcatcaatat<br>tgtccaaaagaattggatcaattagattgcggtggttgtagcgacgcctcaatgctctat<br>tgtattttatgaacactagattatggaggcgcttcaaggttagtcgattcctcttctttg<br>tatgaatctgcaaacaagatgtgtcaactaattagtaggagttgggacaattgagatata<br>atttactttatctcaaaacacgaaataattctttttatttctcacgtgttcaaaaacgct<br>ccagttcctttcacatccggatgagctacaagttaaacttagaactctgatggcgaaagt<br>ctgtaaattcggagtctctacaccatattggtcccaccactcaactatagaagtgaaaaa<br>aaaaaattcaagagttaataagtataaaaaatacattaaagttagagctataaaatatag<br>aagcacttggtcacctggcgatttcgtctttctttgtttaatagcaagtcggagcttaaa |

-continued

| SEQUENCES |
| --- |
| aagtccctcagctgccttgtaaatagcaagctgatctactatcttttcttgcatgtcttc<br>atctggggtcaacttgataacaacctcatggaatcctgtccacacttctctagccaatga<br>attattctcatgctgatcataaaagagtgacgggttcagaataagtccagctgcatgcaa<br>aggtctatgaagttgctcactccatcttgcatcaatgatctgaaagacctttgcatattt<br>ctgctcatcagtgaatgatgcttgaatagcctccttggccctatccatagcttcatagag<br>gtagcccattggtggttttgctccccatccaccaaacggagtactttaaccaaagggcc<br>accaattttaagagcatgaaggacattattccaaaaagaataagaaagaataatgcgtgc<br>aacatctttccctgcactttcctttgcaaatttactcttgctccattcctctgaagtgaa<br>caactttctcaaattggattttgcaagtggatactatgtaaagtcaagaaagcagtggc<br>gaaccttgtcttgcccggtttcaccaaatttttttgtccggtgaatcttctcatcatatt<br>caataacaagggccgctgagaaatataagaatgtaccctaacgccctggccaaaaactgt<br>agagaagggttttccttgaaaatgtccccgaagattaagttgatacaatgagccgcaca<br>tggagtccaatagacattcttgtacgctccttccaccatgccacccgctttcacattttc<br>actcgcattatcagtgaccacttgaacaactttgcttgggccaatcttttcaatggtgtt<br>ctgaaacaaggtgaacattttgatgtggtcagtggatgagtcgctagcatcaatggactc<br>aagaaacaaacttcccttgggagaattcaccaacacgttaataatcattttcccagttct<br>tgccgtccacttatccatcataatggagcagccatacttgttccacgcaactttatgttc<br>ctccacaattttattagtctcctccacttccttatttagataaggacctctgatttcatg<br>ataagtgggaggcttcattccaggtccgtattgaccaacggcctcaataaagtctccaaa<br>agtgtcagtatagttgacacaattgaaggggagcccagcatcatagacccatcgtgcaaa<br>agctctaactgcacgatccctcaaaatgtccttagcaatttttttgtacatcttttccacc<br>gctctttccttccggcttctttgggaaatagcaatctataggacctttagtcctactcgt<br>acccgtcgatccatggcttgaagagattgcatctcttccccgttttgttggaagtgacaa<br>ttcttcaatatcatcatcaccatcatcatcaagattggtcaccaatggttgatgactcat<br>ttgatttttttgctccttcttcttctcaacaaaattctttatttcatccctcacctccgg<br>tggacatttcggacaacttgtgacgtttctatcgccaccaataagatggaatttaaagcg<br>ataaattccacccgttgtaatcttgttacaaaacttgcatacaatatttgtattcttctc<br>attaactctatcgccatatcgccaagccgggtctttatctttcgatctttgagacatttt<br>gaaatccctattaagatataagaaaatacataatcaaataaactgaaaatacatataata<br>tatataataattaattttataaaccgaaatacacattaaaaaaatcaaataaactaaaat<br>ataacatatataattttctaaattgaaatacatataaaattaatcaaataaactgaaaac<br>ataacatatatataataattaattttatatactgaaaaatgcattaagaaaatcaaataa<br>actgaaaaatataacatatataaataataattaattttatatactgaaataaaaatcaaa<br>taaactaaaatataacatatatatataataattaatttctaaaatgaaatacatataaa<br>attaatcaaataaactgaaaatataacatatataaataataattaatattatatactgaa<br>atatacattaaaaaatcaaataaactgaaaaatataacatatataaataataattaattt<br>tatatgctgaaatatacattaaaaaaatcaaataaactgaaaaatataacatatataaat<br>aataattaattttataaactaaaatacatattaaaagtaataaataagaagaataaaggg<br>gggaaaaaaacaaaatgggttagagataaaaggaagaagaagacgctgaagtctgaacag<br>tgcaaactggactgtcagagtctcagagataaacgaagaagaagaaggaagaaagaagga<br>aaaagaaagaaaaaaaagcagaatctgacgggaccaagaagaagaaagaaagaagaaaga<br>aaaaaaagagaagaagaaaattacctggactggtcagcaatgtcaatgaagttgaaccct<br>aggctttggtcgacctcgatcgaagaagagagaagaagaaatggccatttttttgtcaatt<br>tagggtctgttttgtataatagaaaaacagacccaaagttttttttaaaaaaaaaagggc<br>ctgcgctttttttaacaaaagcgatcgcttcgtcgcttcctccgttgaagcgtgcgcttcc<br>ctcggtcgagtcgcctcaggcagctagaagcgacactgagtcgcgtcgcgtcgcttcgcg<br>ctttaagcgcgaagcgatcgcttttctaaacactggtccttccaagttctgtccatcttt<br>ctggtgtgcttaacccatgtatattggaccacactttgtattcatgctgattgcaacaaa<br>gcctgactgatcctgaactcctccttttttgccttgggtagaattatttttgtgtttttag<br>tgttacatatttcaatttaaaggaaaaagggagaagcttaaggtagaatcctgctccttg<br>acctttggatccttacacattgaagtggacagacatgtttgctttgctttgctttgatga<br>gttgttttagtagtcagtctaagcaactgctgatgtattctgctttattgtaagtgtcta<br>taatttttatctttccacaatttgctttcagctctttctgcatataagagaaaataacag<br>aagcttctattcgatcatgtaatattgactgcacaagtgcatatttaaacaactttggct<br>atgcgtatgcaagcaataataaatattacttttttatgcagggtctgtatggttttcttca<br>gagatgaaagccttaagtgatgactgtgaacgatttgttagtttccttcccggtcatatt<br>tattcaagcaaaaatggtatgcccatacgaagctcatttctgagcttgcgcttcatttat<br>gatcagcgtacttttcctatttatttcagatttactttaggaccctgttggaaacagtct<br>tgaacccttattgatggtgtaattattatctcttgatcaaccaaaggagtaattacatgt<br>aattattacaaatttgcaacaaaatcttttaggataatcagtggagcttcatgaatcttt<br>taggatagttgggatgctagagtgatgtacttttgataatgtcggttaacataaatcctc<br>tgactttgtactgatgtactggctgagcagattttatattactttctaatccctctacaa<br>ataaaaaaattgtgagactgcaatataacaccatttttttaatgcatttacaatgtttaa<br>acttgatttagcaacgtagaacatgtcgaccttaaacagaggttctatttgtcctagata<br>aaggaagatcagcataatgaaacattacaggagaggagctctattgagtttttgttaatc<br>tagagggagcccgtaaatagtacaccaattcatctcttatatgacttctttttcattttg<br>gaacgttttaaaagtttgactacatttttttgatctccgtacactaaacttttttgatgtat<br>taaactaactatttccactactttaatattttcttccttaaacaactcctgttagcatct<br>taaactctgtgtgttcaataccctcatataaaattatacgagtatttttttttatatttgc<br>ttatgtccttggagtttgggatggggaagctcatcatttgaggcgaaaggtaaattcttt<br>tgaatggacaaaaagtgaacctcggtctttggcatggagggactatttaagtcgccatca<br>ttaccaaagtcatcctttcaagtgtttgctttcaagaactattcatgctatgtctcaagt<br>atattatgtgtgcaggaggactcagaagatggtacaacccaccatggtactcagaaacca<br>ttccttctactccatatgatcaccttgtcttacggaaagcttttgagaaggtcattctat<br>tttggaagtcgcttgtttctgagttgtatataatatttaggtgccactttgttatatttt<br>aaacttcatcaaaagcctttggattctttgaggacacatatccccttgactgactgggag<br>ctgaatttccttgatgtatagtgcttattttgattgtcctctcctttgtaatactcttgc |

-continued

SEQUENCES ctataaataaaccttccttatcaaaagaaaatgataaaatgttaaaaatactttgtgata
gatgttgactatagactttaaatgatattttatctcaatctttatcaattctttttttacc
ttcacatgcaaattatactacagtatgtgaaatatgcaatagtttgtcctgcaattttca
tctttcatgtacctctctctactatccgtgtattactactgatttgatgcattaaatgct
aattttattcccaacctttactttatgcaggctgtagtcaagcgacttatgacggatgta
ccatttggtgtgcttctctcaggcggactagattcttcacttgttgctgcagtggccaac
cgctatttggctgatactgaagctgcgcgacaatggggatcacagttgcataccttttgc
gtaggcttgaaggtggtgatgctcctttttgtaaacttgctctgatttgggaattgctag
ctgtatcatcccaatttacatggaagttctagaccattattgctgtttcttttccatata
tagggattttctgaaaatagtaaaaaggaaatggaatttctctttattaaagataccgaa
tgcctttttgggaaatgatcttacagttctgaatcgaaaatttccttttgacattgtgat
taattctgatatgaatttggtccatcctggctttccttctcttgattgtagattttcctt
ctcttgttacaattatatgcctgtctttttgtcttactctctgagacaggcaatgtaact
ccagttgcaaggtttggtaatattgacttgtttatttctgttatcacatcctcctgaaaa
agtgctactagcttgtattcatgcgggaatttgaaattttcaagtgtatagctttacaaa
atgatcagaactgatcacagtcattgctctaaataaaattttctaaaaagcaggtattgt
tgtgatataatgtgacacttaaataaatttaaacctacatcctttcgaaatctgtaatag
ctccactaatatttcttgtgctaaactattccaacacctcttatcgatgccaattttgac
agaccttagtgcacttaaaagtgtttagtgttctttatgcagtaggtatgttattgtcca
aaatgacagaaataaagttagagatttgttgaaagccacttggtgtgattgagcagttcg
gagatgagtgatttatccattttatatacttgtagtgttttgttttcttttgcttttgtc
attgtaattaaggttgtcttttgtttgacattagggttctcctgatctgaaagctgccag
agaggtggcagactaccttggaacccgtcaccatgagtttcactttacagtgcaggtaac
tttccacaaagacatcctaccatgtgaccaggaggtcacgggtttgagctgtggaaacaa
ccttttgcagaaatgcagcgtaaggttgcgtacaatagacccttgtggtccggcccttcc
ccgaccccgcacatagcgggagcttagtgcaccgggctgcccatcctaagctgattttcc
ttataggagtataaccgcttaagtcaaattggctatctacttctttctattgctacatca
ggaaggaattgatgcactagatgaagtcatttatcatgttgaaacatatgatgtgaccac
tatcagagccagtacaccaatgtttctcatgtctcggaagataaagtctttgggtgtgaa
aatggttctatctggtgaaggttctgatgaaattttggcggttatttatatttccacaa
gggacccaacaaagaggagtttcaccaagaaacttgtagaaaggtggatctcattgtcat
ttcttcagtcattcaggattattggaagtaactgtatttttactagaatacttctttgaa
ctatttctagctctgatggacgctttgatgttaatccagattaaagcacttcatctttat
gattgcttgagggccaacaaatctacttcagcttggggtgttgaagctcgtgtacctttc
ttggataaagaatttatcaatgttgcaatgaacattgatccagagtggaaaatggtaacc
tacagtgcttccgtctcatttctccacccccaccccccaaaaaaaagaacagaaaaga
attgaaaagagagattcttttcttccttcaaggaagaaggggtaacaaaagaatagctg
caagttatgcagaaaaaatagtcttccatgtcatgggagaccagggttcaaatctgattg
ttaaaaaaaacactaggtgaactcttctaatctgtttaagccttggtggacatagttaac
tagtatatgagctagttagagctgactcgaaaccaccattattcaaaaaattaagaaagt
cttcaatgttgttccaccgtgaattcatgatgtgtcgactttcatgtgtttatctctgga
tagatgaagagtttttttggatcttgattaattctgtttggcccctttgaggttctgcac
gctatttctagactcaaacttgctgcgacctatgttaggtctagagaatatctgcctaat
aaaacaatggaagttacattcaagtattttacctccatattacaagtcagtgttagttaa
atgggtctgatatatgggatagaaaatggcttcatacccataacctcgttaaaatgttgc
tgatgtgctgatctcatctgtacatctagtataatcctaattacaaattaatgcatctct
ttgcggtgactatagtatgctgaagaacctgtcttgaaacattgcagatcagacctgatc
tcggaagaatagaaaagtgggttctacgcaatgcttttgacgatgatcagaatccttatc
tgccaaaggtttgtttgttttcttgtatcaggtccaataatcataatctttgtttattca
tttgcataaaaggcagtagactcccaatacattgtgtacgcttatgcacaaatgtatgag
atgtgtattatatgtgtcacatataagggtattatatgtacacactcctcccaccttcca
catatattatgtgtgtgtgtgtgtgtgtataatgaaatgatgtttgaaaagacattatga
tcaagtagttgatcctcatctgctttctgtttttagcatatcttgtataggcagaaggaa
cagttcagtgatggagttggctacagttggattgatggcttgaaggatcacgcaagcagt
ctggtgagctctttagttgttttctcttccctcctcttccattctttatcccttcctttt
gtggttttgttgaacacatctcatatacttggtccaggtttctgattctatgttagcgaa
tgcaagttttgtttacccgcataacacacccacgacaaaggaaggatactattatagaac
tatttttgagcgatatttccccaaggtgggtcttacatagtcttcttttccttgttattc
atgttcagtttatgatattttgtcccaaacaatgttttctttttcttcctttttctgtta
acaagatcgcttctatcttcgtatttgttgataaagttaatcacattgttaactattatt
tggagcagaatgctgcgagggaaacagttccaggtggtccaagtgtggcatgcagcactg
caaaagcagtagaatgggacgcagcttggtccaagaatctagatccatctggtcgagctg
cactcggtgttcatgcagctgcttatgaggatgcatcagaggttaaaaccacagtcgcga
cagatactgctcagaaacttgacgttgataaagctgcagtagctgtttga SEQ ID NO: 12 - NtASN3-T, deduced amino acid sequence
MCGILAVFGCIDNSQAKRSRIIELSRRLRHRGPDWSGLHSHDDCYLAHQRLAIVDPTSGDQPLYNEDKTIVVAVNGE
IYNHRDLREKLKSHQFRTGSDCEVIAHLYEDYGEDFVHMLDGMFSFVLLDTRDKSFIAARDAIGITPLYMGWGLDGS
VWFSSEMKALSDDCERFVSFLPGHIYSSKNGGLRRWYNPPWYSETIPSTPYDHLVLRKAFEKAVVKRLMTDVPFGVL
LSGGLDSSLVAAVANRYLADTEAARQWGSQLHTFCVGLKGSPDLKAAREVADYLGTRHHEFHFTVQEGIDALDEVIY
HVETYDVTTIRASTPMFLMSRKIKSLGVKMVLSGEGSDEIFGGYLYFHKAPNKEEFHQETCRKIKALHLYDCLRANK
STSAWGVEARVPFLDKEFVNVAMNMDPESKMIRPDLGRIEKWVLRNAFDDDQNPYLPKHILYRQKEQFSDGVGYSWI
DGLKDHASRLVSDSMLANASFVYPHNTPTTKEGYYYRTIFERYFPKNAARETVPGGPSVACSTAKAVEWDAAWSKNL
DPSGRAALGVHAAAYEDASEVKTTVATDTPQKLEVDKAAVAV -continued

| SEQUENCES |
|---|

SEQ ID NO: 13 - DNA sequence of NtASN1 primer, ASN1-f
tcacatatattccctcataacacac

SEQ ID NO: 14 - DNA sequence of NtASN1 primer, ASN1-r
aagaagcatcccactctacagctt

SEQ ID NO: 15 - DNA sequence of NtASN5 primer, ASN5-f
atatcttccctcacaacactccaact SEQ ID NO: 16 - DNA sequence of NtASN5 primer, ASN5-r
Ctaccggaaggatcaaggttgt SEQ ID NO: 17 - DNA coding sequence from NtASN1-S used to silence both NtASN1-S and NtASN1-T copies
tcacatatattccctcataacacacccattacaaaggaagcatactactataggatgattttcgagcgctttttccc
acagaattcagctgggctaaccgttcctggaggagcaagtgtggcgtgtagcacagctaaagctgtagagtgggatg
cttcttggtcaaagaaccttgatccttcaggcagggctgctattggtgtacataactcggcttatgagaatcatgta
cctgctatggctaatgggaatttgaccaaaaaaatcattggtcgtgtgccttctatggtagaagttggtgctgctcc
cgagctcacaataaagagttag SEQ ID NO: 18 - DNA coding sequence from NtASN5-T used to silence both NtASN5-S and NtASN5-T copies
gaccagattggagtgggatatatcaacatggtgattttacttagcacatcaacgtttagcaattatcgatcctact
tctggtgatcagcctctgtttaatcaagataagactattgttgttacagtcaatggagaaatttacaatcatgagaa
acttcgtaatcttatgcctaatcacaagttcagaaccggaagtgattgtgatgttattgcacatctttatgaagaat
atggagaaaattttgtggacatgttggatggggtgttctcttttgtattgttggatacgcgcgataacagctttctt
gctgctcgtgatgcgattggaattactcccctctatattggttggggacttgatgg SEQ ID NO: 19- DNA sequence of ASN1-S stop mutant: ASN1-S_W156*
atgtgcgggatcttggctgttttgggttgttctgatgattctcaggccaaaagggttcgtgttctcgagctctctcg
caggtaggttgaagcatcgtggaccagattggagtgggctgtatcaacatggggactgttacttggcacatcagcgt
ctagctattgttgatcctgcttccggtgatcaacctctgtttaacgaagataagacgattgttgttacggtaggtaa
atggagagatctacaatcacgagcaacttcgtaagcaaatgcctaatcataagttccggactggcagtgactgtgat
gtcattgcacacctagtagtatgaagaacatggagaagattttgtggacatgctggatgggatcttcgcttttgtgt
tattggatactcgagataacagctttcttgttgctcgtgatgccattggaattacttccctttatattggttggga
cttgatggtagggtctgtatgaatatcatctgagcttaagggcttgaatgatgactgcgaacattttgaagttttcc
caccagggcacttgtactctagcaagaatggcggctttaggaggtggtacaatcctccttggttctctgaggccatt
ccttccactcgttatgatcccttagttctcaggcgtgcctttgaaaatgtaggctgttatcaaaaggttgatgactg
atgtcccctttggtgttctcctctccgggggactcgattcatccttggttgcttcgattactgctcgctacttggct
ggtacaaaggctgccaagcagtggggagcacagcttcattccttctgtgttggccttgaggtagggctcaccggatc
tcaaggctgcaagagaagttgctgactacttgggaaccgttcaccacgagtttcacttcaccgttcaggtaggatgg
aattgatgcaattgaagatgttatttaccatattgagacatacgatgtaacgacaatcagagcaagcactcctatgt
tccttatgtcgcgtaagattaagtcactaggagtgaagatggtcatatctggggaaggatctgatgaagtgtttggt
ggctacttgtactttcacaaggctcccaacaaggaagagttccacaaggaaacatgtcgcaaggtagattaaagcgc
ttcaccaatatgactgcttaagagcaaataagtcaacatctgcatggggtttagaagctagagtccctttcctagat
aaggagttcatcaatgttgccatgagtattgatccagagtggaagttgagattaaaccagagcaaaggaggattgaa
aagtgggctctaaggagggcctttgatgatgaggagcatccttatctcccaaaggtagcacatcctgtataggcaaa
aagaacaattcagtgatggcgtgggcatagttggatagatggactcaaagcacatgctgaacaacatgtaggtgacc
aataggatgatgtttaatgcttcacatatattccctcataacacacccattacaaaggaagcatactactataggat
gattttcgagcgctttttcccacaggtagaattcagctgggctaaccgttcctggaggagcaagtgtggcgtgtagc
acagctaaagctgtagagtgggatgcttcttggtcaaagaaccttgatccttcaggcagggctgctattggtgtaca
taactcggcttatgagaatcatgtacctgctatggctaatgggaatttgaccaaaaaaatcattggtcgtgtgcctt
ctatggtagaagttggtgctgctcccgagctcacaataaagagt SEQ ID NO: 20 - amino acid sequence of ASN1-S stop mutant: ASN1-S_W156*
MetCysGlyIleLeuAlaValLeuGlyCysSerAspAspSerGlnAlaLysArgValArgValLeuGluLeuSerArg
ArgLeuLysHisArgGlyProAspTrpSerGlyLeuTyrGlnHisGlyAspCysTyrLeuAlaHisGlnArgLeuAla
IleValAspProAlaSerGlyAspGlnProLeuPheAsnGluAspLysThrIleValValThrValAsnGlyGluIle
TyrAsnHisGluGlnLeuArgLysGlnMetProAsnHisLysPheArgThrGlySerAspCysAspValIleAlaHis
LeuTyrGluGluHisGlyGluAspPheValAspMetLeuAspGlyIlePheAlaPheValLeuLeuAspThrArgAsp
AsnSerPheLeuValAlaArgAspAlaIleGlyIleThrSerLeuTyrIleGlyTrpGlyLeuAspGlySer
ValSTOP

SEQ ID NO: 21 - DNA sequence of ASN1-T stop mutant: ASN1-T_W156*
atgtgcgggatcttggctgttttgggttgttctgatgattctcaggccaaaagggttcgtgttctcgagctctctcg
caggtaggttgaagcatcgtggaccagattggagtgggctgtatcaacatggggactgttacttggcacatcagcgt
ctagctattgttgatcctgcttccggtgatcaacctctgtttaacgaagataagacgattgttgttacggtaggtaa
atggagagatctacaatcacgagcaacttcgcaagcaaatgcctgatcataagttccggactggaagtgactgtgat
gtcattgcacacctagtagtatgaagaacatggagaagattttgtggacatgctggatgggatcttcgcttttgtgt
tactggatactcgagataacagctttcttgttgctcgtgatgccattggaattacttccctttatattggttggga
cttgatggtagggtctgtatgaatatcatctgagcttaagggcttgaatgatgactgcgaacattttgaagttttcc
caccaggacacttgtactctagcaagaatggcggctttaggaggtggtacaatcctctttggttctctgaggctatt
ccttccactccttatgatcccttagttctcaggcgcgcctttgaaaatgtaggctgttatcaaaaggttgatgactg
atgtcccttttggtgttctgctctccgggggactcgattcatccttggttgcttcgattactgcccgctacttggct
ggcacaaaggctgccaagcagtggggagcacagcttcattccttctgtgttggccttgaggtagggatcaccggatc
tcaaggctgcaagagaagttgctgactacttgggaaccgttcaccacgagtttcacttcaccgttcaggtaggatgg -continued

SEQUENCES aattgatgcaattgaagatgttatttaccatattgagacatacgatgtaacgacaatcagagcaagcactcctatgt
tccttatgtcgcgtaagattaagtcactaggagtgaagatggttatatctggggaaggctctgatgaagtgtttggt
ggctacttgtactttcacaaggctcccaacaaggaagagttccacaaggaaacatgtcgcaaggtagattaaagcac
ttcaccaatatgactgtttaagagcaaataagtcaacatctgcatggggcttagaagctagagtgcctttcctagat
aaggagttcatcaatgttgccatgagtattgatccagagtggaagttggtagattaaaccagagcaaaggaggattg
agaagtgggctctaaggagggcctttgatgatgaggagcatccctatctcccaaaggtagcacatcctatacaggca
gaaagaacaattcagtgatggcgtaggctatagttggatagatggactcaaagcacatgctgaacaacatgtaggtg
accaataggatgatgcttaatgcttcacatatattccctcataacacaccgattacaaaggaagcatactattatag
gatgattttcgagcgctttttcccacaggtagaattcagctgggctaaccgttcctggaggagcgagtgtggcgtgt
agcacagctaaagctgtagagtgggatgcttcttggtcaaagaaccttgatccttcaggaagggctgctattggtgt
acataactcagcttatgagaatcatgaacctgctatggctaatgggaatttggccacaaaaatcattggccgtgcgc
cgtctatggtagaagttggtgctgctcatgagctcacaataaggagt SEQ ID NO: 22 - Amino acid sequence ASN1-T stop mutant: ASN1-T_W156*
MetCysGlyIleLeuAlaValLeuGlyCysSerAspAspSerGlnAlaLysArgValArgValLeuGluLeuSerArg
ArgLeuLysHisArgGlyProAspTrpSerGlyLeuTyrGlnHisGlyAspCysTyrLeuAlaHisGlnArgLeu
AlaIleValAspProAlaSerGlyAspGlnProLeuPheAsnGluAspLysThrIleValValThrValAsnGlyGlu
IleTyrAsnHisGluGlnLeuArgLysGlnMetProAspHisLysPheArgThrGlySerAspCysAspValIleAla
HisLeuTyrGluGluHisGlyGluAspPheValAspMetLeuAspGlyIlePheAlaPheValLeuLeuAspThr
ArgAspAsnSerPheLeuValAlaArgAspAlaIleGlyIleThrSerLeuTyrIleGlyTrpGlyLeuAspGlySer
ValSTOP

SEQ ID NO: 23 - DNA sequence of ASN5-S stop mutant: ASN5-S_Q66*
atgtgtggaatcttggctttgttgggttgttcagatgattctcaggccaaaagggttcgagttcttgagctctctcg
caggcaggttgaagcatcgtggaccagattggagtgggatatatcaacatggtgatttttacttagcacatcaacgt
ttagcaattatcgatcctgcttctggtgatcagcctctgtttaattaagataagacgattgttgttacagtaggtca
atggagagatttacaatcatgagaaacttcgtaatcttatgcctaatcacaagttcagaactggaagtgattgtgat
gttattgcacatcttgtagtatgaagaatatggagaaaatttgtggacatgttggatggggtgttctcttttgtat
tgttggatacgcgcgataacagctttcttgctgctcgtgatgcaattggaattactcccctatatattggttgggga
cttgatggtaggctctgtgtggatttcatctgagctaaaaggattaaatggtgactgtgaacattttgaagttttcc
ctcccggtcacttgtactcgagcaagaatggcgggtttaggagatggtacaatcctcaatggttctctgaggctatt
ccatcaaatccttacgaccccttagttttgagacgtgccttcgaaaatgtaggctgttatcaaacgattgatgaccg
atgtcccctttggtgttctgctctccgggggacttgattcgtctttggttgcttctgtcactgctcgctacttggct
ggaacaaaagctgctaagcaatggggagcacagcttcattccttctgtgttggtctcgaggtagggctcaccagatc
tcaaggctgcaagagaagttgctgactatttgggaaccgttcaccacgagttcaccttcacagttcaggtaggatgg
aattgatgctattgaagatgttatttaccatatcgagacatacgatgtaacaacgatcagagcaagcactcctatgt
tccttatgtcgcgtaagattaaatcactgggagttaagatggtcatatcaggggaaggctcagatgaactgtttggc
ggctatttgtacttccacaaggctccgaacaaggaagaattccatgtggagacatgtcacaaggtagataaaagcgc
ttcaccaatacgactgtttgagagcaaataaggcaacatcagcatggggcttagaagctagagtaccatttctggat
aaagagttcatcaacgttgctatgagtatcgatcctgaatggaagatggtagattaaacacgatcatggtaggatcg
agaagtgggttcttaggaaggcttttgatgatgaggagcaaccctatctcccaaaggtagcatattctgtaccggca
gaaagaacaattcagtgatggcgtaggctatagttggatcgatggactcaaagcacatgctgaacaacatgtaggtg
actgataggatgatgcttaatgctgcacatatcttccctcacaacactccaactacaaaggaagcatactattacag
gatgattttcgagaggttcttcccacaggtagaattcagcaaggctaactgttcctggaggaccgagtatagcttgc
agcacagctaaagctattgagtgggatgcttcgtggtcgaacaaccttgatccttccggtagggctgcaatcggtgt
acataactcggcttatgacgatcatctccccgatgttggtaatgggaatttggacacaacgatcatcgataatgtgc
cgaggatggtaggagtgggtgctgctgcagagctcacaataaggagc SEQ ID NO: 24 - Amino acid sequence of ASN5-S stop mutant: ASN5-S_Q66*
MetCysGlyIleLeuAlaLeuLeuGlyCysSerAspAspSerGlnAlaLysArgValArgValLeuGluLeuSerArg
ArgLeuLysHisArgGlyProAspTrpSerGlyIleTyrGlnHisGlyAspPheTyrLeuAlaHisGlnArgLeuAla
IleIleAspProAlaSerGlyAspGlnProLeuPheAsnSTOP

The invention claimed is:

1. A mutant, non-naturally occurring or transgenic tobacco plant or part thereof having reduced expression or activity of asparagine synthetase, said asparagine synthetase comprising:

(i) a polynucleotide sequence having at least 95% sequence identity to SEQ ID NO:1 or SEQ ID NO:3 or SEQ ID NO:5 or SEQ ID NO:7; or (ii) a polypeptide encoded by the polynucleotide set forth in (i); or (iii) a polypeptide having at least 90% sequence identity to SEQ ID NO:2 or SEQ ID NO:4 or SEQ ID NO:6 or SEQ ID NO:8;

wherein the expression or activity of the asparagine synthetase set forth in (i), (ii) or (iii) is reduced as compared to a control plant.

2. The mutant, non-naturally occurring or transgenic plant or part thereof according to claim 1, wherein the plant comprises at least one genetic alteration in a regulatory region or in the coding sequence of the polynucleotide encoding the asparagine synthetase.

3. The mutant, non-naturally occurring or transgenic plant or part thereof according to claim 1, wherein the reduced expression or activity of the asparagine synthetase confers a reduction in a level of asparagine in cured or dried leaf derived from the mutant, non-naturally occurring or transgenic plant or part thereof as compared to the level of asparagine in cured or dried leaf derived from the control plant; and/or wherein the reduced expression or activity of the asparagine synthetase confers a reduction in a level of acrylamide in aerosol produced upon heating or combusting the cured or dried leaf derived from the mutant, non-naturally occurring or transgenic plant or part thereof as compared to cured or dried leaf derived from the control plant; and/or wherein a level of asparagine in cured or dried leaf derived from the mutant, non-naturally occurring or transgenic plant or part thereof is at least about 22% lower and the amount of acrylamide in aerosol produced upon heating or combusting the cured or dried leaf derived from the mutant, non-naturally occurring or transgenic plant or part thereof is at least 24% lower than cured or dried leaf and aerosol of the control plant.

4. The mutant, non-naturally occurring or transgenic plant or part thereof according to claim 1, wherein a level of nicotine in cured or dried leaf from the mutant, non-naturally occurring or transgenic plant or part thereof is substantially the same as the level of nicotine in cured or dried leaf of the control plant; and/or wherein the formation of glutamine, aspartic acid and glutamic acid is increased in cured or dried leaf derived from the mutant, non-naturally occurring or transgenic plant or part thereof as compared to cured or dried leaf of the control plant.

5. The mutant, non-naturally occurring or transgenic plant or part thereof according to claim 1, wherein the plant comprises at least one mutation in each copy of the polynucleotide sequence encoding the asparagine synthetase set forth in (i), (ii) or (iii).

6. The mutant, non-naturally occurring or transgenic plant or part thereof according to claim 1, wherein the asparagine synthetase nucleotide sequence comprises a nucleotide sequence encoding a stop mutation at a position equivalent to the location of the nucleotide sequence encoding the stop mutation in SEQ ID Nos. 19, 21 and 23, or wherein the asparagine synthetase comprises a nucleotide sequence encoding a stop codon at a position equivalent to the location of the stop codon in SEQ ID Nos. 20, 22 and 24.

7. The mutant, non-naturally occurring or transgenic plant or part thereof according to claim 1, wherein the asparagine synthetase comprises a nucleotide sequence selected from the group consisting of SEQ ID Nos. 19, 21 and 23, or is encoded by the nucleotide sequence selected from the group consisting of SEQ ID Nos. 19, 21 and 23, or comprises the polypeptide sequence set forth in SEQ ID Nos. 20, 22 and 24; and/or wherein the amount of leaf biomass from the mutant, non-naturally occurring or transgenic plant or part thereof plant is substantially the same as the amount of leaf biomass from the control plant.

8. The mutant, non-naturally occurring or transgenic plant or part thereof according to claim 3, wherein the leaf is air cured.

9. Plant material or cured or dried plant material from the plant of claim 1.

10. A plant product comprising at least a part of the plant of claim 1.

11. A method of preparing tobacco plant material with reduced levels of asparagine and reduced levels of acrylamide in aerosol derived from said tobacco plant material as compared to plant material from a control tobacco plant, said method comprising the steps of:

(a) providing a tobacco plant or part thereof comprising a polynucleotide comprising a sequence encoding an asparagine synthetase and having at least 95% sequence identity to SEQ ID NO:1 or SEQ ID NO:3 or SEQ ID NO:5 or SEQ ID NO:7;

(b) reducing the expression of the polynucleotide or the activity of the protein encoded thereby in the tobacco plant or part thereof;

(c) harvesting plant material from the tobacco plant or part thereof;

(d) drying or curing the tobacco plant material;

(e) optionally, measuring a level of asparagine in the tobacco plant or part thereof and/or measuring a level of acrylamide in aerosol derived from the tobacco plant or part thereof; and (f) obtaining cured or dried plant material with reduced levels of asparagine and reduced levels of acrylamide in aerosol derived from said tobacco plant material.

12. The method according to claim 11, wherein the plant material is cured or dried for at least about 3 days after harvesting; and/or wherein the plant material is air cured.

13. Plant material obtained or obtainable by the method of claim 11.

14. A method for producing plant material with reduced levels of asparagine and reduced levels of acrylamide in aerosol derived from cured or dried plant material as compared to a control plant, said method comprising the steps of:

(a) providing a plant according to claim 8;

(b) harvesting plant material from the plant;

(c) curing or drying the plant material for a period of time; and (d) obtaining cured or dried plant material that has reduced levels of asparagine and reduced levels of acrylamide in aerosol derived from the cured or dried plant material.

15. A tobacco product or a smoking article comprising the plant material of claim 9.

16. A tobacco product or a smoking article comprising the plant material of claim 13.

17. A plant product comprising at least a part of the plant of claim 9.

18. A method for producing plant material with reduced levels of asparagine and reduced levels of acrylamide in aerosol derived from cured or dried plant material as compared to a control plant, said method comprising the steps of:

(a) providing the plant material according to claim 9;

(b) harvesting plant material from the plant;

(c) curing or drying the plant material for a period of time; and (d) obtaining cured or dried plant material that has reduced levels of asparagine and reduced levels of acrylamide in aerosol derived from the cured or dried plant material.

19. A mutant, non-naturally occurring, or transgenic tobacco plant, or part thereof having asparagine synthetase comprising:

(i) a polynucleotide sequence having at least 90% sequence identity to SEQ ID NO:1 or at least 72% sequence identity to SEQ ID NO:3 or SEQ ID NO:5 or SEQ ID NO:7, wherein a control plant does not comprise the polynucleotide; or (ii) a polypeptide encoded by the polynucleotide set forth in (i), wherein the control plant does not comprise the polypeptide; or (iii) a polypeptide having at least 78% sequence identity to SEQ ID NO:2 or SEQ ID NO:4 or SEQ ID NO:6 or SEQ ID NO:8, wherein a control plant does not comprise the polypeptide, and wherein the mutant, non-naturally occurring, or transgenic tobacco plant comprises substantially the same amount of nicotine as the control plant or contains higher amounts of nicotine than the control plant.

20. A method comprising altering a tobacco plant to comprise a polynucleotide comprising a sequence encoding an asparagine synthetase having at least 90% sequence identity to SEQ ID NO:1 or at least 72% sequence identity to SEQ ID NO:3 or SEQ ID NO:5 or SEQ ID NO:7, wherein a control plant does not comprise the polynucleotide, and wherein the altered tobacco plant comprises substantially the same amount of nicotine as the control plant or contains higher amounts of nicotine than the control plant.

21. The mutant, non-naturally occurring or transgenic plant or part thereof according to claim 3, wherein the level of asparagine in the cured or dried leaf derived from the mutant, non-naturally occurring or transgenic plant or part thereof is reduced by at least about 17% as compared to the control plant; and/or wherein the level of acrylamide in aerosol produced upon heating or combusting the cured or dried leaf derived from the mutant, non-naturally occurring or transgenic plant or part thereof is reduced by at least 20% as compared to cured or dried leaf of the control plant; and/or wherein the level of asparagine in cured or dried leaf derived from the mutant, non-naturally occurring or transgenic plant or part thereof is at least about 44% lower and the amount of acrylamide in aerosol produced upon heating or combusting the cured or dried leaf derived from the mutant, non-naturally occurring or transgenic plant or part thereof is at least 66% lower as compared to cured or dried leaf and aerosol of the control plant.

22. The mutant, non-naturally occurring or transgenic plant or part thereof according to claim 3, wherein the level of asparagine in cured or dried leaf derived from the mutant, non-naturally occurring or transgenic plant or part thereof is at least about 70% lower and the amount of acrylamide in aerosol produced upon heating or combusting the cured or dried leaf derived from the mutant, non-naturally occurring or transgenic plant or part thereof is at least about 88% lower as compared to cured or dried leaf and aerosol of the control plant.

23. The mutant, non-naturally occurring or transgenic plant or part thereof according to claim 1, wherein the plant is a *Nicotiana tabacum* tobacco plant.

24. The mutant, non-naturally occurring or transgenic plant or part thereof according to claim 1, wherein the plant is a Burley type *Nicotiana tabacum* tobacco plant.

25. The mutant, non-naturally occurring or transgenic plant or part thereof according to claim 5, wherein the plant comprises a stop mutation(s) and/or a gene fragment(s) that interferes with the translation of an RNA transcript encoding the asparagine synthetase in each copy of the polynucleotide sequence encoding the asparagine synthetase set forth in (i), (ii) or (iii).

26. The mutant, non-naturally occurring or transgenic plant or part thereof according to claim 8, wherein the air cured leaf is sun cured or fire cured; or wherein the leaf is air dried.

27. The mutant, non-naturally occurring or transgenic plant or part thereof according to claim 26, wherein the air dried leaf is sun dried or fire dried.

28. The method according to claim 11, wherein a level of nicotine in the plant material with reduced a level of asparagine and reduced levels of acrylamide in aerosol derived from said plant material is substantially the same as a level of nicotine in the control plant.

29. The method according to claim 11, wherein the formation of glutamine, aspartic acid and glutamic acid is increased in the plant material with reduced levels of asparagine and reduced levels of acrylamide in aerosol derived from said plant material compared to cured or dried leaf of the control plant.

30. The method according to claim 12, wherein the air cured leaf is sun cured or fire cured, or wherein the plant material is air dried or sun dried or fire dried.

31. The method according to claim 14, wherein a level of nicotine in the plant material with reduced levels of asparagine and reduced levels of acrylamide in aerosol derived from cured or dried plant material is substantially the same as in the control plant.

32. The method according to claim 14, wherein the formation of glutamine, aspartic acid and glutamic acid is increased in the plant material with reduced levels of asparagine and reduced levels of acrylamide in aerosol derived from cured or dried plant material as compared to the control plant.

33. The method according to claim 18, wherein a level of nicotine in the plant material with reduced levels of asparagine and reduced levels of acrylamide in aerosol derived from cured or dried plant material is substantially the same as in the control plant.

34. The method according to claim 18, wherein the formation of glutamine, aspartic acid and glutamic acid in the plant material with reduced levels of asparagine and reduced levels of acrylamide in aerosol derived from cured or dried plant material is increased as compared to the control plant.

35. The mutant, non-naturally occurring or transgenic plant or part thereof according to claim 1, wherein the asparagine synthetase comprises a nucleotide sequence selected from the group consisting of SEQ ID Nos. 19, 21 and 23, or is encoded by the nucleotide sequence selected from the group consisting of SEQ ID Nos. 19, 21 and 23, or comprises the polypeptide sequence set forth in SEQ ID Nos. 20, 22 and 24.

36. The method of claim 11, wherein a level of nicotine in the dried or cured tobacco plant material is substantially the same as, or higher than, in the plant material from the control tobacco plant.

37. The mutant, non-naturally occurring or transgenic plant or part thereof according to claim 1, wherein a level of nicotine in the non-naturally occurring or transgenic plant or part thereof is substantially the same as, or higher than, in the control tobacco plant or part thereof.

* * * * *